(12) United States Patent
Wang

(10) Patent No.: US 6,660,838 B1
(45) Date of Patent: Dec. 9, 2003

(54) COMPOUNDS AND METHODS FOR THERAPY AND DIAGNOSIS OF LUNG CANCER

(75) Inventor: Tongtong Wang, Medina, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/221,107

(22) Filed: Dec. 22, 1998

Related U.S. Application Data

(63) Continuation-in-part of application No. 09/123,912, filed on Jul. 27, 1998, now Pat. No. 6,312,695, which is a continuation-in-part of application No. 09/040,802, filed on Mar. 18, 1998, now abandoned.

(51) Int. Cl.⁷ .......................... C07K 1/00; A61K 38/00; G01N 33/53
(52) U.S. Cl. .......................... 530/350; 530/300; 435/7.1
(58) Field of Search ................................ 530/300, 350; 435/7.1; 514/2

(56) References Cited

U.S. PATENT DOCUMENTS

| | | | |
|---|---|---|---|
| 5,705,159 A | * 1/1998 | Irie et al. | 424/185.1 |
| 5,783,422 A | 7/1998 | Suminami et al. | 435/69.3 |
| 6,309,857 B1 | * 10/2001 | Pauli et al. | 435/69.1 |
| 2002/0119463 A1 | 8/2002 | Faris et al. | 435/6 |

FOREIGN PATENT DOCUMENTS

| | | |
|---|---|---|
| EP | 0695760 A1 | 2/1996 |
| EP | 1033401 A2 | 9/2000 |
| WO | WO 91/18926 | 12/1991 |
| WO | WO 94/06929 | 3/1994 |
| WO | WO 95/21862 | 8/1995 |
| WO | WO 96/02552 | 2/1996 |
| WO | WO 96/13610 | 5/1996 |
| WO | WO 96/28473 | 9/1996 |
| WO | WO 96/30389 | 10/1996 |
| WO | WO 97/07244 | 2/1997 |
| WO | WO 98/35985 | 8/1998 |
| WO | WO 98/46788 | 10/1998 |
| WO | WO 99/06550 | 2/1999 |
| WO | WO 99/38973 | 8/1999 |
| WO | WO 99/44620 | 9/1999 |
| WO | WO 99/47674 | 9/1999 |
| WO | WO 00/12711 | 3/2000 |
| WO | WO 02/10449 | 2/2002 |
| WO | WO 02/14366 | 2/2002 |

OTHER PUBLICATIONS

Cunningham et al., The Journal of Biological Chemistry, vol. 270, No. 52, pp. 31016–31026, 1995.*
Genbank Accession No. 018741 (Jan 1, 1998).*
Database EMBLest17 Accession No. W22264:Human retina cDNA Tsp509I–cleaved *Homo sapiens* cDNA not directional, May 9, 1996.

Database EMBLest17 Accession No. AA340797: EST46165 Fetal Kidney II Homo Sapiens cDNA 3' end, Apr. 18, 1997.

Brass et al., "Translation initiation factor eIF–4gamma is encoded by an amplified gene and induces an immune response in squamous cell lung carcinoma," *Human Molecular Genetics* 6(1):33–39, 1997.

Finch et al., "Identification of a cloned sequence activated during multi–stage carcinogenesis in mouse skin," *Carcinogenesis* 12(8):1519–1522, 1991.

GenBank Accession No. AF043977, Jun. 23, 1999.

GenBank Accession No. U85946, Jul. 30, 1999.

Geneseq Accession No. AAZ24653, Dec. 7, 1999.

Gruber et al., "Molecular cloning and transmembrane structure of hCLCA2 from human lung, trachea, and mammary gland," *Am. J. Physiol.* 276(Cell Physiol. 45):C1261–C1270, 1999.

Guo et al., "Identification and characterization of homologues of the Exocyst component Sec 10p," *FEBS Letters* 404(2–3):135–139, 1997.

Gerhold and Caskey, "It's the genes! EST access to human genome content," *BioEssays* 18(12):973–981, 1996.

Russell and Barton, "Structural features can be unconserved in proteins with similar folds," *J. Mol. Biol.* 244:332–350, 1994.

Wells and Peitsch, "The chemokine information source: identification and characterization of novel chemokines using the WorldWideWeb and expressed sequence tag databases," *Journal of Leukocyte Biology* 61:545–550, May 1997.

Baldi et al., "Differential expression of Rb2/p130 and p107 in normal human tissues and in primary lung cancer," *Clinical Cancer Research* 3(10):1691–1697, Oct. 1997.

Database EMBL Nucleotide and Protein Sequence, Accession No. AI468638, Mar. 17, 1999.

Hara et al., "Characterization of cell phenotype by a novel cDNA library subtraction system: expression of CD8α in a mast cell–derived interleukin–4–dependent cell line," *Blood* 84(1):189–1999, Jul. 1, 1994.

Henderson et al., "Identification of lung tumor antigens for cancer immunotherapy: immunological and molecular approaches," *Immunological Investigation* 29(2):87–91, May 2000.

(List continued on next page.)

*Primary Examiner*—Ardin H. Marschel
(74) *Attorney, Agent, or Firm*—Seed IP Law Group PLLC

(57) ABSTRACT

Compounds and methods for the treatment and diagnosis of lung cancer are provided. The inventive compounds include polypeptides containing at least a portion of a lung tumor protein. Vaccines and pharmaceutical compositions for immunotherapy of lung cancer comprising such polypeptides, or DNA molecules encoding such polypeptides, are also provided, together with DNA molecules for preparing the inventive polypeptides.

5 Claims, No Drawings

OTHER PUBLICATIONS

Hogan et al., "The peptide recognized by HLA–A68.2–restricted, squamous cell carcinoma of the lung–specific cytotoxic T lymphocytes is derived from a mutated elongation factor 2 gene," *Cancer Research* 58(22):5144–5150, Nov. 15, 1998.

Lelievre et al., "Structural properties of chimeric peptides containing a T–cell epitope linked to a fusion peptide and their importance for in vivo induction of cytotoxic T–cell responses," *European Journal of Biochemistry* 249(3):895–904, 1997.

Marshall and Hodgson, "DNA chips: an array of possibilities," *Nature Biotechnology* 16:27 Jan. 31, 1998.

Ramsay, G., "DNA chips: state–of the art," *Nature Biotechnology* 16:40–44, Jan. 1998.

Visseren et al., "Identification of HLA–A *0201–restricted CTL epitopes encoded by the tumor–specific MAGE–2 gene product," *International Journal of Cancer* 73(1): 125–130, 1997.

Wang et al., "Identification of genes differentially over–expressed in lung squamous cell carcinoma using combination of cDNA subtraction and microarray analysis,"*Oncogene* 19(12):1519–1528, Mar. 16, 2000.

GenBank Database, Accession No. AAD48397, Aug. 11, 1999.

GenBank Database, Accession No. AB026833, May 26, 1999.

GenBank Database, Accession No. AF114429, Jan. 1, 2000.

GenBank Database, Accession No. AF127980, Aug. 11, 1999.

GenBank Database, Accession No. NM_006536, Aug. 10, 1999.

GenBank Database, Accession No. NP_006527, Aug. 10, 1999.

GenBank Database, Accession No. BAA77810, May 26, 1999.

Genseq Database (Derwent), Accession No. AAB45904, Mar. 21, 2001.

Genseq Database (Derwent), Accession No. AAC82881, Mar. 21, 2001.

Genseq Database (Derwent), Accession No. AAC82886, Mar. 21, 2001.

Genseq Database (Derwent), Accession No. AAC82887, Mar. 21, 2001.

Genseq Database (Derwent), Accession No. AAC82890, Mar. 21, 2001.

Genseq Database (Derwent), Accession No. AAC82893, Mar. 21, 2001.

Genseq Database (Derwent), Accession No. AAC82895, Mar. 21, 2001.

Genseq Database (Derwent), Accession No. AAC82896, Mar. 21, 2001.

Genseq Database (Derwent), Accession No. AAC82897, Mar. 21, 2001.

Genseq Database (Derwent), Accession No. AAC82898, Mar. 21, 2001.

Genseq Database (Derwent), Accession No. AAX40511, Jun. 18, 1999.

Genseq Database (Derwent), Accession No. AAY11789, Jun. 18, 1999.

* cited by examiner

SEQUENCE LISTING

<160> NUMBER OF SEQ ID NOS: 161

<210> SEQ ID NO 1
<211> LENGTH: 315
<212> TYPE: DNA
<213> ORGANISM: Homo sapiens
<220> FEATURE:
<221> NAME/KEY: modified_base
<222> LOCATION: (236)
<223> OTHER INFORMATION: Where n is a, c, g or t
<220> FEATURE:
<221> NAME/KEY: modified_base
<222> LOCATION: (241)
<223> OTHER INFORMATION: Where n is a, c, g or t

<400> SEQUENCE: 1

```
gcagagacag actggtggtt gaacctggag gtgccaaaaa agccagctgc gggcccagga      60
cagctgccgt gagactcccg atgtcacagg cagtctgtgt ggttacagcg cccctcagtg     120
ttcatctcca gcagagacaa cggaggaggc tcccaccagg acggttctca ttatttatat     180
gttaatatgt ttgtaaactc atgtacagtt tttttggggg gggaagcaat gggaanggta     240
naaattacaa atagaatcat ttgctgtaat ccttaaatgg caaacggtca ggccacgtga     300
aaaaaaaaaa aaaaa                                                       315
```

<210> SEQ ID NO 2
<211> LENGTH: 380
<212> TYPE: DNA
<213> ORGANISM: Homo sapiens

<400> SEQUENCE: 2

```
atttaggctt aagattttgt ttaccttgt tactaaggag caaattagta ttaaagtata       60
atatatataa acaaatacaa aaagttttga gtggttcagc ttttttattt tttttaatgg     120
cataactttt aacaacactg ctctgtaatg ggttgaactg tggtactcag actgagataa    180
ctgaaatgag tggatgtata gtgttattgc ataattatcc cactatgaag caaagggact    240
ggataaattc ccagtctaga ttattagcct ttgttaacca tcaagcacct agaagaagaa    300
ttattggaaa ttttgtcctc tgtaactggc actttggggt gtgacttatc ttttgccttt   360
gtaaaaaaaa aaaaaaaaaa                                                  380
```

<210> SEQ ID NO 3
<211> LENGTH: 346
<212> TYPE: DNA
<213> ORGANISM: Homo sapiens
<220> FEATURE:
<221> NAME/KEY: modified_base
<222> LOCATION: (316)
<223> OTHER INFORMATION: Where n is a, c, g or t
<220> FEATURE:
<221> NAME/KEY: modified_base
<222> LOCATION: (317)
<223> OTHER INFORMATION: Where n is a, c, g or t
<220> FEATURE:
<221> NAME/KEY: modified_base
<222> LOCATION: (318)
<223> OTHER INFORMATION: Where n is a, c, g or t
<220> FEATURE:
<221> NAME/KEY: modified_base
<222> LOCATION: (322)
<223> OTHER INFORMATION: Where n is a, c, g or t
<220> FEATURE:
<221> NAME/KEY: modified_base
<222> LOCATION: (323)
<223> OTHER INFORMATION: Where n is a, c, g or t

```
<220> FEATURE:
<221> NAME/KEY: modified_base
<222> LOCATION: (326)
<223> OTHER INFORMATION: Where n is a, c, g or t
<220> FEATURE:
<221> NAME/KEY: modified_base
<222> LOCATION: (329)
<223> OTHER INFORMATION: Where n is a, c, g or t
<220> FEATURE:
<221> NAME/KEY: modified_base
<222> LOCATION: (330)
<223> OTHER INFORMATION: Where n is a, c, g or t
<220> FEATURE:
<221> NAME/KEY: modified_base
<222> LOCATION: (331)
<223> OTHER INFORMATION: Where n is a, c, g or t
<220> FEATURE:
<221> NAME/KEY: modified_base
<222> LOCATION: (336)
<223> OTHER INFORMATION: Where n is a, c, g or t
<220> FEATURE:
<221> NAME/KEY: modified_base
<222> LOCATION: (337)
<223> OTHER INFORMATION: Where n is a, c, g or t
<220> FEATURE:
<221> NAME/KEY: modified_base
<222> LOCATION: (339)
<223> OTHER INFORMATION: Where n is a, c, g or t
<220> FEATURE:
<221> NAME/KEY: modified_base
<222> LOCATION: (340)
<223> OTHER INFORMATION: Where n is a, c, g or t
<220> FEATURE:
<221> NAME/KEY: modified_base
<222> LOCATION: (342)
<223> OTHER INFORMATION: Where n is a, c, g or t
<220> FEATURE:
<221> NAME/KEY: modified_base
<222> LOCATION: (343)
<223> OTHER INFORMATION: Where n is a, c, g or t

<400> SEQUENCE: 3
ttgtaagtat acaattttag aaaggattaa atgttattga tcattttact gaatactgca      60
catcctcacc atacaccatc cactttccaa taacatttaa tcctttctaa aattgtaagt     120
atacaattgt actttctttg gattttcata acaaatatac catagactgt taattttatt     180
gaagtttcct taatggaatg agtcattttt gtcttgtgct tttgaggtta cctttgcttt     240
gacttccaac aatttgatca tatagtgttg agctgtggaa atctttaagt ttattctata     300
gcaataattt ctattnnnag annccnggnn naaaannann annaaa                    346

<210> SEQ ID NO 4
<211> LENGTH: 372
<212> TYPE: DNA
<213> ORGANISM: Homo sapiens
<220> FEATURE:
<221> NAME/KEY: modified_base
<222> LOCATION: (296)
<223> OTHER INFORMATION: Where n is a, c, g or t
<220> FEATURE:
<221> NAME/KEY: modified_base
<222> LOCATION: (306)
<223> OTHER INFORMATION: Where n is a, c, g or t
<220> FEATURE:
<221> NAME/KEY: modified_base
<222> LOCATION: (332)
<223> OTHER INFORMATION: Where n is a, c, g or t

<400> SEQUENCE: 4
actagtctca ttactccaga attatgctct tgtacctgtg tggctgggtt tcttagtcgt      60
tggtttggtt tggttttttg aactggtatg tagggtggtt cacagttcta atgtaagcac     120
```

-continued

| | |
|---|---|
| tctcttctcc aagttgtgct ttgtggggac aatcattctt tgaacattag agaggaaggc | 180 |
| agttcaagct gttgaaaaga ctattgctta tttttgtttt taaagaccta cttgacgtca | 240 |
| tgtggacagt gcacgtgcct tacgctacat cttgttttct aggaagaagg ggatgcnggg | 300 |
| aaggantggg tgctttgtga tggataaaac gnctaaataa cacacccttta cattttgaaa | 360 |
| aaaacaaaac aa | 372 |

```
<210> SEQ ID NO 5
<211> LENGTH: 698
<212> TYPE: DNA
<213> ORGANISM: Homo sapiens
<220> FEATURE:
<221> NAME/KEY: modified_base
<222> LOCATION: (8)
<223> OTHER INFORMATION: Where n is a, c, g or t
<220> FEATURE:
<221> NAME/KEY: modified_base
<222> LOCATION: (345)
<223> OTHER INFORMATION: Where n is a, c, g or t
<220> FEATURE:
<221> NAME/KEY: modified_base
<222> LOCATION: (422)
<223> OTHER INFORMATION: Where n is a, c, g or t
<220> FEATURE:
<221> NAME/KEY: modified_base
<222> LOCATION: (430)
<223> OTHER INFORMATION: Where n is a, c, g or t
<220> FEATURE:
<221> NAME/KEY: modified_base
<222> LOCATION: (433)
<223> OTHER INFORMATION: Where n is a, c, g or t
<220> FEATURE:
<221> NAME/KEY: modified_base
<222> LOCATION: (436)
<223> OTHER INFORMATION: Where n is a, c, g or t
<220> FEATURE:
<221> NAME/KEY: modified_base
<222> LOCATION: (438)
<223> OTHER INFORMATION: Where n is a, c, g or t
<220> FEATURE:
<221> NAME/KEY: modified_base
<222> LOCATION: (472)
<223> OTHER INFORMATION: Where n is a, c, g or t
<220> FEATURE:
<221> NAME/KEY: modified_base
<222> LOCATION: (481)
<223> OTHER INFORMATION: Where n is a, c, g or t
<220> FEATURE:
<221> NAME/KEY: modified_base
<222> LOCATION: (486)
<223> OTHER INFORMATION: Where n is a, c, g or t
<220> FEATURE:
<221> NAME/KEY: modified_base
<222> LOCATION: (515)
<223> OTHER INFORMATION: Where n is a, c, g or t
<220> FEATURE:
<221> NAME/KEY: modified_base
<222> LOCATION: (521)
<223> OTHER INFORMATION: Where n is a, c, g or t
<220> FEATURE:
<221> NAME/KEY: modified_base
<222> LOCATION: (526)
<223> OTHER INFORMATION: Where n is a, c, g or t
<220> FEATURE:
<221> NAME/KEY: modified_base
<222> LOCATION: (549)
<223> OTHER INFORMATION: Where n is a, c, g or t
<220> FEATURE:
<221> NAME/KEY: modified_base
<222> LOCATION: (553)
<223> OTHER INFORMATION: Where n is a, c, g or t
<220> FEATURE:
<221> NAME/KEY: modified_base
<222> LOCATION: (556)
<223> OTHER INFORMATION: Where n is a, c, g or t
```

-continued

```
<220> FEATURE:
<221> NAME/KEY: modified_base
<222> LOCATION: (557)
<223> OTHER INFORMATION: Where n is a, c, g or t
<220> FEATURE:
<221> NAME/KEY: modified_base
<222> LOCATION: (559)
<223> OTHER INFORMATION: Where n is a, c, g or t
<220> FEATURE:
<221> NAME/KEY: modified_base
<222> LOCATION: (568)
<223> OTHER INFORMATION: Where n is a, c, g or t
<220> FEATURE:
<221> NAME/KEY: modified_base
<222> LOCATION: (593)
<223> OTHER INFORMATION: Where n is a, c, g or t
<220> FEATURE:
<221> NAME/KEY: modified_base
<222> LOCATION: (597)
<223> OTHER INFORMATION: Where n is a, c, g or t
<220> FEATURE:
<221> NAME/KEY: modified_base
<222> LOCATION: (605)
<223> OTHER INFORMATION: Where n is a, c, g or t
<220> FEATURE:
<221> NAME/KEY: modified_base
<222> LOCATION: (611)
<223> OTHER INFORMATION: Where n is a, c, g or t
<220> FEATURE:
<221> NAME/KEY: modified_base
<222> LOCATION: (613)
<223> OTHER INFORMATION: Where n is a, c, g or t
<220> FEATURE:
<221> NAME/KEY: modified_base
<222> LOCATION: (616)
<223> OTHER INFORMATION: Where n is a, c, g or t
<220> FEATURE:
<221> NAME/KEY: modified_base
<222> LOCATION: (618)
<223> OTHER INFORMATION: Where n is a, c, g or t
<220> FEATURE:
<221> NAME/KEY: modified_base
<222> LOCATION: (620)
<223> OTHER INFORMATION: Where n is a, c, g or t
<220> FEATURE:
<221> NAME/KEY: modified_base
<222> LOCATION: (628)
<223> OTHER INFORMATION: Where n is a, c, g or t
<220> FEATURE:
<221> NAME/KEY: modified_base
<222> LOCATION: (630)
<223> OTHER INFORMATION: Where n is a, c, g or t
<220> FEATURE:
<221> NAME/KEY: modified_base
<222> LOCATION: (632)
<223> OTHER INFORMATION: Where n is a, c, g or t
<220> FEATURE:
<221> NAME/KEY: modified_base
<222> LOCATION: (634)
<223> OTHER INFORMATION: Where n is a, c, g or t
<220> FEATURE:
<221> NAME/KEY: modified_base
<222> LOCATION: (635)
<223> OTHER INFORMATION: Where n is a, c, g or t
<220> FEATURE:
<221> NAME/KEY: modified_base
<222> LOCATION: (639)
<223> OTHER INFORMATION: Where n is a, c, g or t
<220> FEATURE:
<221> NAME/KEY: modified_base
<222> LOCATION: (643)
<223> OTHER INFORMATION: Where n is a, c, g or t
<220> FEATURE:
<221> NAME/KEY: modified_base
<222> LOCATION: (647)
<223> OTHER INFORMATION: Where n is a, c, g or t
<220> FEATURE:
<221> NAME/KEY: modified_base
<222> LOCATION: (648)
```

<223> OTHER INFORMATION: Where n is a, c, g or t
<220> FEATURE:
<221> NAME/KEY: modified_base
<222> LOCATION: (649)
<223> OTHER INFORMATION: Where n is a, c, g or t
<220> FEATURE:
<221> NAME/KEY: modified_base
<222> LOCATION: (652)
<223> OTHER INFORMATION: Where n is a, c, g or t
<220> FEATURE:
<221> NAME/KEY: modified_base
<222> LOCATION: (654)
<223> OTHER INFORMATION: Where n is a, c, g or t
<220> FEATURE:
<221> NAME/KEY: modified_base
<222> LOCATION: (658)
<223> OTHER INFORMATION: Where n is a, c, g or t
<220> FEATURE:
<221> NAME/KEY: modified_base
<222> LOCATION: (664)
<223> OTHER INFORMATION: Where n is a, c, g or t
<220> FEATURE:
<221> NAME/KEY: modified_base
<222> LOCATION: (690)
<223> OTHER INFORMATION: Where n is a, c, g or t

<400> SEQUENCE: 5

| | | | | | |
|---|---|---|---|---|---|
| actagtanga | tagaaacact | gtgtcccgag | agtaaggaga | gaagctacta | ttgattagag | 60 |
| cctaacccag | gttaactgca | agaagaggcg | ggatactttc | agctttccat | gtaactgtat | 120 |
| gcataaagcc | aatgtagtcc | agtttctaag | atcatgttcc | aagctaactg | aatcccactt | 180 |
| caatacacac | tcatgaactc | ctgatggaac | aataacaggc | ccaagcctgt | ggtatgatgt | 240 |
| gcacacttgc | tagactcaga | aaaaatacta | ctctcataaa | tgggtgggag | tattttgggt | 300 |
| gacaacctac | tttgcttggc | tgagtgaagg | aatgatattc | atatnttcat | ttattccatg | 360 |
| gacatttagt | tagtgctttt | tatataccag | gcatgatgct | gagtgacact | cttgtgtata | 420 |
| tntccaaatn | ttngtncngt | cgctgcacat | atctgaaatc | ctatattaag | antttcccaa | 480 |
| natgangtcc | ctggtttttc | cacgccactt | gatcngtcaa | ngatctcacc | tctgtntgtc | 540 |
| ctaaaaccnt | ctnctnnang | gttagacngg | acctctcttc | tcccttcccg | aanaataagg | 600 |
| tgtgngaaga | nanccncncn | ccccccctncn | tncnnnctng | ccngctnnnc | cncntgtngg | 660 |
| gggngccgcc | cccgcggggg | gaccccccn | ttttcccc | | | 698 |

<210> SEQ ID NO 6
<211> LENGTH: 740
<212> TYPE: DNA
<213> ORGANISM: Homo sapiens
<220> FEATURE:
<221> NAME/KEY: modified_base
<222> LOCATION: (82)
<223> OTHER INFORMATION: Where n is a, c, g or t
<220> FEATURE:
<221> NAME/KEY: modified_base
<222> LOCATION: (406)
<223> OTHER INFORMATION: Where n is a, c, g or t
<220> FEATURE:
<221> NAME/KEY: modified_base
<222> LOCATION: (426)
<223> OTHER INFORMATION: Where n is a, c, g or t
<220> FEATURE:
<221> NAME/KEY: modified_base
<222> LOCATION: (434)
<223> OTHER INFORMATION: Where n is a, c, g or t
<220> FEATURE:
<221> NAME/KEY: modified_base
<222> LOCATION: (462)
<223> OTHER INFORMATION: Where n is a, c, g or t
<220> FEATURE:
<221> NAME/KEY: modified_base -continued

```
<222> LOCATION: (536)
<223> OTHER INFORMATION: Where n is a, c, g or t
<220> FEATURE:
<221> NAME/KEY: modified_base
<222> LOCATION: (551)
<223> OTHER INFORMATION: Where n is a, c, g or t
<220> FEATURE:
<221> NAME/KEY: modified_base
<222> LOCATION: (558)
<223> OTHER INFORMATION: Where n is a, c, g or t
<220> FEATURE:
<221> NAME/KEY: modified_base
<222> LOCATION: (563)
<223> OTHER INFORMATION: Where n is a, c, g or t
<220> FEATURE:
<221> NAME/KEY: modified_base
<222> LOCATION: (567)
<223> OTHER INFORMATION: Where n is a, c, g or t
<220> FEATURE:
<221> NAME/KEY: modified_base
<222> LOCATION: (582)
<223> OTHER INFORMATION: Where n is a, c, g or t
<220> FEATURE:
<221> NAME/KEY: modified_base
<222> LOCATION: (584)
<223> OTHER INFORMATION: Where n is a, c, g or t
<220> FEATURE:
<221> NAME/KEY: modified_base
<222> LOCATION: (592)
<223> OTHER INFORMATION: Where n is a, c, g or t
<220> FEATURE:
<221> NAME/KEY: modified_base
<222> LOCATION: (638)
<223> OTHER INFORMATION: Where n is a, c, g or t
<220> FEATURE:
<221> NAME/KEY: modified_base
<222> LOCATION: (651)
<223> OTHER INFORMATION: Where n is a, c, g or t
<220> FEATURE:
<221> NAME/KEY: modified_base
<222> LOCATION: (660)
<223> OTHER INFORMATION: Where n is a, c, g or t
<220> FEATURE:
<221> NAME/KEY: modified_base
<222> LOCATION: (664)
<223> OTHER INFORMATION: Where n is a, c, g or t
<220> FEATURE:
<221> NAME/KEY: modified_base
<222> LOCATION: (673)
<223> OTHER INFORMATION: Where n is a, c, g or t
<220> FEATURE:
<221> NAME/KEY: modified_base
<222> LOCATION: (675)
<223> OTHER INFORMATION: Where n is a, c, g or t
<220> FEATURE:
<221> NAME/KEY: modified_base
<222> LOCATION: (697)
<223> OTHER INFORMATION: Where n is a, c, g or t
<220> FEATURE:
<221> NAME/KEY: modified_base
<222> LOCATION: (706)
<223> OTHER INFORMATION: Where n is a, c, g or t
<220> FEATURE:
<221> NAME/KEY: modified_base
<222> LOCATION: (711)
<223> OTHER INFORMATION: Where n is a, c, g or t
<220> FEATURE:
<221> NAME/KEY: modified_base
<222> LOCATION: (715)
<223> OTHER INFORMATION: Where n is a, c, g or t
<220> FEATURE:
<221> NAME/KEY: modified_base
<222> LOCATION: (716)
<223> OTHER INFORMATION: Where n is a, c, g or t
<220> FEATURE:
<221> NAME/KEY: modified_base
<222> LOCATION: (717)
<223> OTHER INFORMATION: Where n is a, c, g or t
<220> FEATURE:
```

<221> NAME/KEY: modified_base
<222> LOCATION: (723)
<223> OTHER INFORMATION: Where n is a, c, g or t
<220> FEATURE:
<221> NAME/KEY: modified_base
<222> LOCATION: (724)
<223> OTHER INFORMATION: Where n is a, c, g or t
<220> FEATURE:
<221> NAME/KEY: modified_base
<222> LOCATION: (725)
<223> OTHER INFORMATION: Where n is a, c, g or t
<220> FEATURE:
<221> NAME/KEY: modified_base
<222> LOCATION: (733)
<223> OTHER INFORMATION: Where n is a, c, g or t

<400> SEQUENCE: 6

```
actagtcaaa aatgctaaaa taatttggga gaaatatttt tttaagtagt gttatagttt      60
catgtttatc tttttattatg tnttgtgaag ttgtgtcttt tcactaatta cctatactat    120
gccaatattt ccttatatct atccataaca tttatactac atttgtaaga gaatatgcac    180
gtgaaactta acactttata aggtaaaaat gaggtttcca agatttaata atctgatcaa    240
gttcttgtta tttccaaata gaatggactt ggtctgttaa ggggctaagg gagaagaaga    300
agataaggtt aaaagttgtt aatgaccaaa cattctaaaa gaaatgcaaa aaaaaattta    360
ttttcaagcc ttcgaactat ttaaggaaag caaaatcatt tcctanatgc atatcatttg    420 tgaganttc tcantaatat cctgaatcat tcatttcagc tnaggcttca tgttgactcg    480
atatgtcatc tagggaaagt ctatttcatg gtccaaacct gttgccatag ttggtnaggc    540
tttcctttaa ntgtgaanta ttnacangaa attttctctt tnanagttct tnatagggtt    600
aggggtgtgg gaaaagcttc taacaatctg tagtgttncg tgttatctgt ncagaaccan    660
aatnacggat cgnangaagg actgggtcta tttacangaa cgaatnatct ngttnnntgt    720
gtnnncaact ccngggagcc                                                 740
```

<210> SEQ ID NO 7
<211> LENGTH: 670
<212> TYPE: DNA
<213> ORGANISM: Homo sapiens
<220> FEATURE:
<221> NAME/KEY: modified_base
<222> LOCATION: (265)
<223> OTHER INFORMATION: Where n is a, c, g or t
<220> FEATURE:
<221> NAME/KEY: modified_base
<222> LOCATION: (268)
<223> OTHER INFORMATION: Where n is a, c, g or t
<220> FEATURE:
<221> NAME/KEY: modified_base
<222> LOCATION: (457)
<223> OTHER INFORMATION: Where n is a, c, g or t
<220> FEATURE:
<221> NAME/KEY: modified_base
<222> LOCATION: (470)
<223> OTHER INFORMATION: Where n is a, c, g or t
<220> FEATURE:
<221> NAME/KEY: modified_base
<222> LOCATION: (485)
<223> OTHER INFORMATION: Where n is a, c, g or t
<220> FEATURE:
<221> NAME/KEY: modified_base
<222> LOCATION: (546)
<223> OTHER INFORMATION: Where n is a, c, g or t
<220> FEATURE:
<221> NAME/KEY: modified_base
<222> LOCATION: (553)
<223> OTHER INFORMATION: Where n is a, c, g or t
<220> FEATURE:
<221> NAME/KEY: modified_base
<222> LOCATION: (566)
<223> OTHER INFORMATION: Where n is a, c, g or t
<220> FEATURE:
<221> NAME/KEY: modified_base
<222> LOCATION: (590)
<223> OTHER INFORMATION: Where n is a, c, g or t
<220> FEATURE:
<221> NAME/KEY: modified_base
<222> LOCATION: (596)
<223> OTHER INFORMATION: Where n is a, c, g or t
<220> FEATURE:
<221> NAME/KEY: modified_base
<222> LOCATION: (613)
<223> OTHER INFORMATION: Where n is a, c, g or t
<220> FEATURE:
<221> NAME/KEY: modified_base
<222> LOCATION: (624)
<223> OTHER INFORMATION: Where n is a, c, g or t
<220> FEATURE:
<221> NAME/KEY: modified_base
<222> LOCATION: (639)
<223> OTHER INFORMATION: Where n is a, c, g or t
<220> FEATURE:
<221> NAME/KEY: modified_base
<222> LOCATION: (653)
<223> OTHER INFORMATION: Where n is a, c, g or t
<220> FEATURE:
<221> NAME/KEY: modified_base
<222> LOCATION: (659)
<223> OTHER INFORMATION: Where n is a, c, g or t
<220> FEATURE:
<221> NAME/KEY: modified_base
<222> LOCATION: (661)
<223> OTHER INFORMATION: Where n is a, c, g or t

<400> SEQUENCE: 7

```
gctggggagc tcggcatggc ggtccccgct gcagccatgg ggccctcggc gttgggccag      60
agcggccccg gctcgatggc cccgtggtgc tcagtgagca gcggcccgtc gcgctacgtg     120
cttgggatgc aggagctgtt ccggggccac agcaagaccg cgagttcctg gcgcacagcg     180
ccaaggtgca ctcggtggcc tggagttgcg acgggcgtcg cctacctcgg ggtcttcgac     240
aagacgccac gtcttcttgc tgganaanga ccgttggtca aagaaaacaa ttatcgggga     300
catggggata gtgtggacca cttttgttggc atccaagtaa tcctgaccta tttgttacgg     360
cgtctggaga taaaaccatt cgcatctggg atgtgaggac tacaaaatgc attgccactg     420
tgaacactaa aggggagaac attaatatct gctggantcc tgatgggcan accattgctg     480
tagcnacaag gatgatgtgg tgactttatt gatgccaaga aaccccgttc caaagcaaaa     540
aaacanttcc aanttcgaag tcaccnaaat ctcctggaac aatgaacatn aatatnttct     600
tcctgacaat ggnccttggg tgtntcacat cctcagctnc cccaaaactg aancctgtnc     660
natccacccc                                                             670
```

<210> SEQ ID NO 8
<211> LENGTH: 689
<212> TYPE: DNA
<213> ORGANISM: Homo sapiens
<220> FEATURE:
<221> NAME/KEY: modified_base
<222> LOCATION: (253)
<223> OTHER INFORMATION: Where n is a, c, g or t
<220> FEATURE:
<221> NAME/KEY: modified_base
<222> LOCATION: (335)
<223> OTHER INFORMATION: Where n is a, c, g or t
<220> FEATURE:
<221> NAME/KEY: modified_base
<222> LOCATION: (410)
<223> OTHER INFORMATION: Where n is a, c, g or t
<220> FEATURE:

```
<221> NAME/KEY: modified_base
<222> LOCATION: (428)
<223> OTHER INFORMATION: Where n is a, c, g or t
<220> FEATURE:
<221> NAME/KEY: modified_base
<222> LOCATION: (448)
<223> OTHER INFORMATION: Where n is a, c, g or t
<220> FEATURE:
<221> NAME/KEY: modified_base
<222> LOCATION: (458)
<223> OTHER INFORMATION: Where n is a, c, g or t
<220> FEATURE:
<221> NAME/KEY: modified_base
<222> LOCATION: (466)
<223> OTHER INFORMATION: Where n is a, c, g or t
<220> FEATURE:
<221> NAME/KEY: modified_base
<222> LOCATION: (479)
<223> OTHER INFORMATION: Where n is a, c, g or t
<220> FEATURE:
<221> NAME/KEY: modified_base
<222> LOCATION: (480)
<223> OTHER INFORMATION: Where n is a, c, g or t
<220> FEATURE:
<221> NAME/KEY: modified_base
<222> LOCATION: (482)
<223> OTHER INFORMATION: Where n is a, c, g or t
<220> FEATURE:
<221> NAME/KEY: modified_base
<222> LOCATION: (483)
<223> OTHER INFORMATION: Where n is a, c, g or t
<220> FEATURE:
<221> NAME/KEY: modified_base
<222> LOCATION: (485)
<223> OTHER INFORMATION: Where n is a, c, g or t
<220> FEATURE:
<221> NAME/KEY: modified_base
<222> LOCATION: (488)
<223> OTHER INFORMATION: Where n is a, c, g or t
<220> FEATURE:
<221> NAME/KEY: modified_base
<222> LOCATION: (491)
<223> OTHER INFORMATION: Where n is a, c, g or t
<220> FEATURE:
<221> NAME/KEY: modified_base
<222> LOCATION: (492)
<223> OTHER INFORMATION: Where n is a, c, g or t
<220> FEATURE:
<221> NAME/KEY: modified_base
<222> LOCATION: (495)
<223> OTHER INFORMATION: Where n is a, c, g or t
<220> FEATURE:
<221> NAME/KEY: modified_base
<222> LOCATION: (499)
<223> OTHER INFORMATION: Where n is a, c, g or t
<220> FEATURE:
<221> NAME/KEY: modified_base
<222> LOCATION: (500)
<223> OTHER INFORMATION: Where n is a, c, g or t
<220> FEATURE:
<221> NAME/KEY: modified_base
<222> LOCATION: (502)
<223> OTHER INFORMATION: Where n is a, c, g or t
<220> FEATURE:
<221> NAME/KEY: modified_base
<222> LOCATION: (503)
<223> OTHER INFORMATION: Where n is a, c, g or t
<220> FEATURE:
<221> NAME/KEY: modified_base
<222> LOCATION: (512)
<223> OTHER INFORMATION: Where n is a, c, g or t
<220> FEATURE:
<221> NAME/KEY: modified_base
<222> LOCATION: (516)
<223> OTHER INFORMATION: Where n is a, c, g or t
<220> FEATURE:
<221> NAME/KEY: modified_base
<222> LOCATION: (524)
<223> OTHER INFORMATION: Where n is a, c, g or t
```

-continued

```
<220> FEATURE:
<221> NAME/KEY: modified_base
<222> LOCATION: (525)
<223> OTHER INFORMATION: Where n is a, c, g or t
<220> FEATURE:
<221> NAME/KEY: modified_base
<222> LOCATION: (526)
<223> OTHER INFORMATION: Where n is a, c, g or t
<220> FEATURE:
<221> NAME/KEY: modified_base
<222> LOCATION: (527)
<223> OTHER INFORMATION: Where n is a, c, g or t
<220> FEATURE:
<221> NAME/KEY: modified_base
<222> LOCATION: (530)
<223> OTHER INFORMATION: Where n is a, c, g or t
<220> FEATURE:
<221> NAME/KEY: modified_base
<222> LOCATION: (540)
<223> OTHER INFORMATION: Where n is a, c, g or t
<220> FEATURE:
<221> NAME/KEY: modified_base
<222> LOCATION: (546)
<223> OTHER INFORMATION: Where n is a, c, g or t
<220> FEATURE:
<221> NAME/KEY: modified_base
<222> LOCATION: (550)
<223> OTHER INFORMATION: Where n is a, c, g or t
<220> FEATURE:
<221> NAME/KEY: modified_base
<222> LOCATION: (581)
<223> OTHER INFORMATION: Where n is a, c, g or t
<220> FEATURE:
<221> NAME/KEY: modified_base
<222> LOCATION: (593)
<223> OTHER INFORMATION: Where n is a, c, g or t
<220> FEATURE:
<221> NAME/KEY: modified_base
<222> LOCATION: (594)
<223> OTHER INFORMATION: Where n is a, c, g or t
<220> FEATURE:
<221> NAME/KEY: modified_base
<222> LOCATION: (601)
<223> OTHER INFORMATION: Where n is a, c, g or t
<220> FEATURE:
<221> NAME/KEY: modified_base
<222> LOCATION: (606)
<223> OTHER INFORMATION: Where n is a, c, g or t
<220> FEATURE:
<221> NAME/KEY: modified_base
<222> LOCATION: (609)
<223> OTHER INFORMATION: Where n is a, c, g or t
<220> FEATURE:
<221> NAME/KEY: modified_base
<222> LOCATION: (610)
<223> OTHER INFORMATION: Where n is a, c, g or t
<220> FEATURE:
<221> NAME/KEY: modified_base
<222> LOCATION: (620)
<223> OTHER INFORMATION: Where n is a, c, g or t
<220> FEATURE:
<221> NAME/KEY: modified_base
<222> LOCATION: (621)
<223> OTHER INFORMATION: Where n is a, c, g or t
<220> FEATURE:
<221> NAME/KEY: modified_base
<222> LOCATION: (622)
<223> OTHER INFORMATION: Where n is a, c, g or t
<220> FEATURE:
<221> NAME/KEY: modified_base
<222> LOCATION: (628)
<223> OTHER INFORMATION: Where n is a, c, g or t
<220> FEATURE:
<221> NAME/KEY: modified_base
<222> LOCATION: (641)
<223> OTHER INFORMATION: Where n is a, c, g or t
<220> FEATURE:
<221> NAME/KEY: modified_base
<222> LOCATION: (646)
```

<223> OTHER INFORMATION: Where n is a, c, g or t
<220> FEATURE:
<221> NAME/KEY: modified_base
<222> LOCATION: (656)
<223> OTHER INFORMATION: Where n is a, c, g or t
<220> FEATURE:
<221> NAME/KEY: modified_base
<222> LOCATION: (673)
<223> OTHER INFORMATION: Where n is a, c, g or t

<400> SEQUENCE: 8

```
actagtatct aggaatgaac agtaaaagag gagcagttgg ctacttgatt acaacagagt      60
aaatgaagta ctggatttgg gaaaacctgg ttttattaga acatatggaa tgaaagccta     120
cacctagcat tgcctactta gccccctgaa ttaacagagc ccaattgaga caaacccctg     180
gcaacaggaa attcaaggga gaaaagtaa gcaacttggg ctaggatgag ctgactccct      240
tagagcaaag ganagacagc ccccattacc aaataccatt tttgcctggg gcttgtgcag     300
ctggcagtgt tcctgcccca gcatggcacc ttatngtttt gatagcaact tcgttgaatt     360
ttcaccaact tattacttga aattataata tagcctgtcc gtttgctgtn tccaggctgt     420
gatatatntt cctagtggtt tgactttnaa aataaatnag gtttantttt ctcccccnn      480
cnntnctncc nntcnctcnn cnntcccccc cnctcngtcc tccnnnnttn gggggggccn     540
ccccncggn ggacccccct ttggtccctt agtggaggtt natggcccct ggnnttatcc     600
nggccntann tttccccgtn nnaaatgntt cccctccca ntcccnccac ctcaanccgg      660
aagcctaagt ttntaccctg ggggtcccc                                       689
```

<210> SEQ ID NO 9
<211> LENGTH: 674
<212> TYPE: DNA
<213> ORGANISM: Homo sapiens
<220> FEATURE:
<221> NAME/KEY: modified_base
<222> LOCATION: (602)
<223> OTHER INFORMATION: Where n is a, c, g or t
<220> FEATURE:
<221> NAME/KEY: modified_base
<222> LOCATION: (632)
<223> OTHER INFORMATION: Where n is a, c, g or t
<220> FEATURE:
<221> NAME/KEY: modified_base
<222> LOCATION: (639)
<223> OTHER INFORMATION: Where n is a, c, g or t
<220> FEATURE:
<221> NAME/KEY: modified_base
<222> LOCATION: (668)
<223> OTHER INFORMATION: Where n is a, c, g or t

<400> SEQUENCE: 9

```
gtccactctc ctttgagtgt actgtcttac tgtgcactct gttttcaac tttctagata      60
taaaaatgc ttgttctata gtggagtaag agctcacaca cccaaggcag caagataact     120
gaaaaagcg aggctttttt gccaccttgg taaaggccag ttcactgcta tagaactgct     180
ataagcctga agggaagtag ctatgagact ttccattttt cttagttctc caataggct    240
ccttcatgga aaaaggcttc ctgtaataat tttcacctaa tgaattagca gtgtgattat     300
ttctgaaata agagacaaat tgggccgcag agtcttcctg tgatttaaaa taaacaaccc     360
aaagttttgt ttggtcttca ccaaaggaca tactctaggg ggtatgttgt tgaagacatt     420
caaaaacatt agctgttctg tcttcaatt tcaagttatt ttggagactg cctccatgtg     480
agttaattac tttgctctgg aactagcatt attgtcatta tcatcacatt ctgtcatcat     540
catctgaata atattgtgga tttccccctc tgcttgcatc ttcttttgac tcctctggga     600
```

```
anaaatgtca aaaaaaaagg tcgatctact cngcaaggnc catctaatca ctgcgctgga    660
aggacccnct gccc                                                      674
```

<210> SEQ ID NO 10
<211> LENGTH: 346
<212> TYPE: DNA
<213> ORGANISM: Homo sapiens
<220> FEATURE:
<221> NAME/KEY: modified_base
<222> LOCATION: (320)
<223> OTHER INFORMATION: Where n is a, c, g or t
<220> FEATURE:
<221> NAME/KEY: modified_base
<222> LOCATION: (321)
<223> OTHER INFORMATION: Where n is a, c, g or t
<220> FEATURE:
<221> NAME/KEY: modified_base
<222> LOCATION: (322)
<223> OTHER INFORMATION: Where n is a, c, g or t
<220> FEATURE:
<221> NAME/KEY: modified_base
<222> LOCATION: (325)
<223> OTHER INFORMATION: Where n is a, c, g or t
<220> FEATURE:
<221> NAME/KEY: modified_base
<222> LOCATION: (326)
<223> OTHER INFORMATION: Where n is a, c, g or t
<220> FEATURE:
<221> NAME/KEY: modified_base
<222> LOCATION: (328)
<223> OTHER INFORMATION: Where n is a, c, g or t
<220> FEATURE:
<221> NAME/KEY: modified_base
<222> LOCATION: (329)
<223> OTHER INFORMATION: Where n is a, c, g or t
<220> FEATURE:
<221> NAME/KEY: modified_base
<222> LOCATION: (330)
<223> OTHER INFORMATION: Where n is a, c, g or t
<220> FEATURE:
<221> NAME/KEY: modified_base
<222> LOCATION: (332)
<223> OTHER INFORMATION: Where n is a, c, g or t
<220> FEATURE:
<221> NAME/KEY: modified_base
<222> LOCATION: (333)
<223> OTHER INFORMATION: Where n is a, c, g or t
<220> FEATURE:
<221> NAME/KEY: modified_base
<222> LOCATION: (334)
<223> OTHER INFORMATION: Where n is a, c, g or t
<220> FEATURE:
<221> NAME/KEY: modified_base
<222> LOCATION: (335)
<223> OTHER INFORMATION: Where n is a, c, g or t
<220> FEATURE:
<221> NAME/KEY: modified_base
<222> LOCATION: (342)
<223> OTHER INFORMATION: Where n is a, c, g or t

<400> SEQUENCE: 10

```
actagtctgc tgatagaaag cactatacat cctattgttt ctttctttcc aaaatcagcc    60
ttctgtctgt aacaaaaatg tactttatag agatggagga aaaggtctaa tactacatag   120
ccttaagtgt ttctgtcatt gttcaagtgt attttctgta acagaaacat atttggaatg   180
tttttctttt cccttataaa attgtaattc ctgaaatact gctgctttaa aaagtcccac   240
tgtcagatta tattatctaa caattgaata ttgtaaatat acttgtctta cctctcaata   300
aaagggtact tttctattan nnagnngnnn gnnnnataaa anaaaa                  346
```

<210> SEQ ID NO 11

```
<211> LENGTH: 602
<212> TYPE: DNA
<213> ORGANISM: Homo sapiens

<400> SEQUENCE: 11
actagtaaaa agcagcattg ccaaataatc cctaattttc cactaaaaat ataatgaaat      60
gatgttaagc tttttgaaaa gtttaggtta aacctactgt tgttagatta atgtatttgt     120
tgcttcccttt tatctggaat gtggcattag cttttttatt ttaaccctct ttaattctta    180
ttcaattcca tgacttaagg ttggagagct aaacactggg attttttggat aacagactga   240
cagttttgca taattataat cggcattgta catagaaagg atatggctac cttttgttaa    300
atctgcactt tctaaatatc aaaaaggga aatgaagtta taaatcaatt tttgtataat     360
ctgtttgaaa catgagtttt atttgcttaa tattagggct ttgccccttt tctgtaagtc    420
tcttgggatc ctgtgtagaa ctgttctcat taaacaccaa acagttaagt ccattctctg    480
gtactagcta caaattcggt ttcatattct acttaacaat ttaaataaac tgaaatattt    540
ctagatggtc tacttctgtt catataaaaa caaaacttga tttccaaaaa aaaaaaaaaa   600
aa                                                                    602

<210> SEQ ID NO 12
<211> LENGTH: 685
<212> TYPE: DNA
<213> ORGANISM: Homo sapiens
<220> FEATURE:
<221> NAME/KEY: modified_base
<222> LOCATION: (170)
<223> OTHER INFORMATION: Where n is a, c, g or t
<220> FEATURE:
<221> NAME/KEY: modified_base
<222> LOCATION: (279)
<223> OTHER INFORMATION: Where n is a, c, g or t
<220> FEATURE:
<221> NAME/KEY: modified_base
<222> LOCATION: (318)
<223> OTHER INFORMATION: Where n is a, c, g or t
<220> FEATURE:
<221> NAME/KEY: modified_base
<222> LOCATION: (321)
<223> OTHER INFORMATION: Where n is a, c, g or t
<220> FEATURE:
<221> NAME/KEY: modified_base
<222> LOCATION: (322)
<223> OTHER INFORMATION: Where n is a, c, g or t
<220> FEATURE:
<221> NAME/KEY: modified_base
<222> LOCATION: (422)
<223> OTHER INFORMATION: Where n is a, c, g or t
<220> FEATURE:
<221> NAME/KEY: modified_base
<222> LOCATION: (450)
<223> OTHER INFORMATION: Where n is a, c, g or t
<220> FEATURE:
<221> NAME/KEY: modified_base
<222> LOCATION: (453)
<223> OTHER INFORMATION: Where n is a, c, g or t
<220> FEATURE:
<221> NAME/KEY: modified_base
<222> LOCATION: (459)
<223> OTHER INFORMATION: Where n is a, c, g or t
<220> FEATURE:
<221> NAME/KEY: modified_base
<222> LOCATION: (467)
<223> OTHER INFORMATION: Where n is a, c, g or t
<220> FEATURE:
<221> NAME/KEY: modified_base
<222> LOCATION: (468)
<223> OTHER INFORMATION: Where n is a, c, g or t
<220> FEATURE:
<221> NAME/KEY: modified_base
```

-continued

```
<222> LOCATION: (470)
<223> OTHER INFORMATION: Where n is a, c, g or t
<220> FEATURE:
<221> NAME/KEY: modified_base
<222> LOCATION: (473)
<223> OTHER INFORMATION: Where n is a, c, g or t
<220> FEATURE:
<221> NAME/KEY: modified_base
<222> LOCATION: (475)
<223> OTHER INFORMATION: Where n is a, c, g or t
<220> FEATURE:
<221> NAME/KEY: modified_base
<222> LOCATION: (482)
<223> OTHER INFORMATION: Where n is a, c, g or t
<220> FEATURE:
<221> NAME/KEY: modified_base
<222> LOCATION: (485)
<223> OTHER INFORMATION: Where n is a, c, g or t
<220> FEATURE:
<221> NAME/KEY: modified_base
<222> LOCATION: (486)
<223> OTHER INFORMATION: Where n is a, c, g or t
<220> FEATURE:
<221> NAME/KEY: modified_base
<222> LOCATION: (491)
<223> OTHER INFORMATION: Where n is a, c, g or t
<220> FEATURE:
<221> NAME/KEY: modified_base
<222> LOCATION: (498)
<223> OTHER INFORMATION: Where n is a, c, g or t
<220> FEATURE:
<221> NAME/KEY: modified_base
<222> LOCATION: (503)
<223> OTHER INFORMATION: Where n is a, c, g or t
<220> FEATURE:
<221> NAME/KEY: modified_base
<222> LOCATION: (506)
<223> OTHER INFORMATION: Where n is a, c, g or t
<220> FEATURE:
<221> NAME/KEY: modified_base
<222> LOCATION: (509)
<223> OTHER INFORMATION: Where n is a, c, g or t
<220> FEATURE:
<221> NAME/KEY: modified_base
<222> LOCATION: (522)
<223> OTHER INFORMATION: Where n is a, c, g or t
<220> FEATURE:
<221> NAME/KEY: modified_base
<222> LOCATION: (526)
<223> OTHER INFORMATION: Where n is a, c, g or t
<220> FEATURE:
<221> NAME/KEY: modified_base
<222> LOCATION: (527)
<223> OTHER INFORMATION: Where n is a, c, g or t
<220> FEATURE:
<221> NAME/KEY: modified_base
<222> LOCATION: (528)
<223> OTHER INFORMATION: Where n is a, c, g or t
<220> FEATURE:
<221> NAME/KEY: modified_base
<222> LOCATION: (538)
<223> OTHER INFORMATION: Where n is a, c, g or t
<220> FEATURE:
<221> NAME/KEY: modified_base
<222> LOCATION: (542)
<223> OTHER INFORMATION: Where n is a, c, g or t
<220> FEATURE:
<221> NAME/KEY: modified_base
<222> LOCATION: (544)
<223> OTHER INFORMATION: Where n is a, c, g or t
<220> FEATURE:
<221> NAME/KEY: modified_base
<222> LOCATION: (551)
<223> OTHER INFORMATION: Where n is a, c, g or t
<220> FEATURE:
<221> NAME/KEY: modified_base
<222> LOCATION: (567)
<223> OTHER INFORMATION: Where n is a, c, g or t
<220> FEATURE:
```

-continued

```
<221> NAME/KEY: modified_base
<222> LOCATION: (568)
<223> OTHER INFORMATION: Where n is a, c, g or t
<220> FEATURE:
<221> NAME/KEY: modified_base
<222> LOCATION: (569)
<223> OTHER INFORMATION: Where n is a, c, g or t
<220> FEATURE:
<221> NAME/KEY: modified_base
<222> LOCATION: (574)
<223> OTHER INFORMATION: Where n is a, c, g or t
<220> FEATURE:
<221> NAME/KEY: modified_base
<222> LOCATION: (576)
<223> OTHER INFORMATION: Where n is a, c, g or t
<220> FEATURE:
<221> NAME/KEY: modified_base
<222> LOCATION: (582)
<223> OTHER INFORMATION: Where n is a, c, g or t
<220> FEATURE:
<221> NAME/KEY: modified_base
<222> LOCATION: (587)
<223> OTHER INFORMATION: Where n is a, c, g or t
<220> FEATURE:
<221> NAME/KEY: modified_base
<222> LOCATION: (588)
<223> OTHER INFORMATION: Where n is a, c, g or t
<220> FEATURE:
<221> NAME/KEY: modified_base
<222> LOCATION: (589)
<223> OTHER INFORMATION: Where n is a, c, g or t
<220> FEATURE:
<221> NAME/KEY: modified_base
<222> LOCATION: (590)
<223> OTHER INFORMATION: Where n is a, c, g or t
<220> FEATURE:
<221> NAME/KEY: modified_base
<222> LOCATION: (592)
<223> OTHER INFORMATION: Where n is a, c, g or t
<220> FEATURE:
<221> NAME/KEY: modified_base
<222> LOCATION: (593)
<223> OTHER INFORMATION: Where n is a, c, g or t
<220> FEATURE:
<221> NAME/KEY: modified_base
<222> LOCATION: (598)
<223> OTHER INFORMATION: Where n is a, c, g or t
<220> FEATURE:
<221> NAME/KEY: modified_base
<222> LOCATION: (599)
<223> OTHER INFORMATION: Where n is a, c, g or t
<220> FEATURE:
<221> NAME/KEY: modified_base
<222> LOCATION: (603)
<223> OTHER INFORMATION: Where n is a, c, g or t
<220> FEATURE:
<221> NAME/KEY: modified_base
<222> LOCATION: (605)
<223> OTHER INFORMATION: Where n is a, c, g or t
<220> FEATURE:
<221> NAME/KEY: modified_base
<222> LOCATION: (608)
<223> OTHER INFORMATION: Where n is a, c, g or t
<220> FEATURE:
<221> NAME/KEY: modified_base
<222> LOCATION: (633)
<223> OTHER INFORMATION: Where n is a, c, g or t
<220> FEATURE:
<221> NAME/KEY: modified_base
<222> LOCATION: (634)
<223> OTHER INFORMATION: Where n is a, c, g or t
<220> FEATURE:
<221> NAME/KEY: modified_base
<222> LOCATION: (635)
<223> OTHER INFORMATION: Where n is a, c, g or t
<220> FEATURE:
<221> NAME/KEY: modified_base
<222> LOCATION: (644)
<223> OTHER INFORMATION: Where n is a, c, g or t
```

```
<220> FEATURE:
<221> NAME/KEY: modified_base
<222> LOCATION: (646)
<223> OTHER INFORMATION: Where n is a, c, g or t
<220> FEATURE:
<221> NAME/KEY: modified_base
<222> LOCATION: (648)
<223> OTHER INFORMATION: Where n is a, c, g or t
<220> FEATURE:
<221> NAME/KEY: modified_base
<222> LOCATION: (651)
<223> OTHER INFORMATION: Where n is a, c, g or t
<220> FEATURE:
<221> NAME/KEY: modified_base
<222> LOCATION: (655)
<223> OTHER INFORMATION: Where n is a, c, g or t
<220> FEATURE:
<221> NAME/KEY: modified_base
<222> LOCATION: (660)
<223> OTHER INFORMATION: Where n is a, c, g or t
<220> FEATURE:
<221> NAME/KEY: modified_base
<222> LOCATION: (662)
<223> OTHER INFORMATION: Where n is a, c, g or t
<220> FEATURE:
<221> NAME/KEY: modified_base
<222> LOCATION: (663)
<223> OTHER INFORMATION: Where n is a, c, g or t
<220> FEATURE:
<221> NAME/KEY: modified_base
<222> LOCATION: (672)
<223> OTHER INFORMATION: Where n is a, c, g or t
<220> FEATURE:
<221> NAME/KEY: modified_base
<222> LOCATION: (674)
<223> OTHER INFORMATION: Where n is a, c, g or t
<220> FEATURE:
<221> NAME/KEY: modified_base
<222> LOCATION: (675)
<223> OTHER INFORMATION: Where n is a, c, g or t
<220> FEATURE:
<221> NAME/KEY: modified_base
<222> LOCATION: (682)
<223> OTHER INFORMATION: Where n is a, c, g or t
<220> FEATURE:
<221> NAME/KEY: modified_base
<222> LOCATION: (683)
<223> OTHER INFORMATION: Where n is a, c, g or t

<400> SEQUENCE: 12
actagtcctg tgaaagtaca actgaaggca gaaagtgtta ggattttgca tctaatgttc    60
attatcatgg tattgatgga cctaagaaaa taaaaattag actaagcccc caaataagct   120
gcatgcattt gtaacatgat tagtagattt gaatatatag atgtagtatn ttgggtatct   180
aggtgtttta tcattatgta aaggaattaa agtaaaggac tttgtagttg tttttattaa   240
atatgcatat agtagagtgc aaaaatatag caaaaatana aactaaaggt agaaaagcat   300
tttagatatg ccttaatnta nnaactgtgc caggtggccc tcggaataga tgccaggcag   360
agaccagtgc ctgggtggtg cctccccttg tctgcccccc tgaagaactt ccctcacgtg   420
angtagtgcc ctcgtaggtg tcacgtggan tantggganc aggccgnncn gtnanaagaa   480
ancanngtga nagtttcncc gtngangcng aactgtccct gngccnnnac gctcccanaa   540
cntntccaat ngacaatcga gtttccnnnc tccngnaacc tngccgnnnn cnngcccnnc   600
cantntgnta accccgcgcc cggatcgctc tcnnntcgtt ctcncncnaa ngggntttcn   660
cnnccgccgt cncnnccccg cnncc                                         685

<210> SEQ ID NO 13
<211> LENGTH: 694
<212> TYPE: DNA
```

```
<213> ORGANISM: Homo sapiens
<220> FEATURE:
<221> NAME/KEY: modified_base
<222> LOCATION: (503)
<223> OTHER INFORMATION: Where n is a, c, g or t
<220> FEATURE:
<221> NAME/KEY: modified_base
<222> LOCATION: (546)
<223> OTHER INFORMATION: Where n is a, c, g or t
<220> FEATURE:
<221> NAME/KEY: modified_base
<222> LOCATION: (599)
<223> OTHER INFORMATION: Where n is a, c, g or t
<220> FEATURE:
<221> NAME/KEY: modified_base
<222> LOCATION: (611)
<223> OTHER INFORMATION: Where n is a, c, g or t
<220> FEATURE:
<221> NAME/KEY: modified_base
<222> LOCATION: (636)
<223> OTHER INFORMATION: Where n is a, c, g or t
<220> FEATURE:
<221> NAME/KEY: modified_base
<222> LOCATION: (641)
<223> OTHER INFORMATION: Where n is a, c, g or t
<220> FEATURE:
<221> NAME/KEY: modified_base
<222> LOCATION: (643)
<223> OTHER INFORMATION: Where n is a, c, g or t
<220> FEATURE:
<221> NAME/KEY: modified_base
<222> LOCATION: (645)
<223> OTHER INFORMATION: Where n is a, c, g or t
<220> FEATURE:
<221> NAME/KEY: modified_base
<222> LOCATION: (656)
<223> OTHER INFORMATION: Where n is a, c, g or t
<220> FEATURE:
<221> NAME/KEY: modified_base
<222> LOCATION: (658)
<223> OTHER INFORMATION: Where n is a, c, g or t
<220> FEATURE:
<221> NAME/KEY: modified_base
<222> LOCATION: (662)
<223> OTHER INFORMATION: Where n is a, c, g or t
<220> FEATURE:
<221> NAME/KEY: modified_base
<222> LOCATION: (676)
<223> OTHER INFORMATION: Where n is a, c, g or t
<220> FEATURE:
<221> NAME/KEY: modified_base
<222> LOCATION: (679)
<223> OTHER INFORMATION: Where n is a, c, g or t
<220> FEATURE:
<221> NAME/KEY: modified_base
<222> LOCATION: (687)
<223> OTHER INFORMATION: Where n is a, c, g or t

<400> SEQUENCE: 13
cactagtcac tcattagcgt tttcaatagg gctcttaagt ccagtagatt acgggtagtc      60
agttgacgaa gatctggttt acaagaacta attaaatgtt tcattgcatt tttgtaagaa     120
cagaataatt ttataaaatg tttgtagttt ataattgccg aaaataattt aaagacactt    180
tttctctgtg tgtgcaaatg tgtgtttgtg atccattttt ttttttttttt taggacacct   240 gtttactagc tagctttaca atatgccaaa aaaggatttc tccctgaccc catccgtggt    300
tcaccctctt ttcccccccat gcttttttgcc ctagtttata acaaaggaat gatgatgatt  360
taaaaagtag ttctgtatct tcagtatctt ggtcttccag aaccctctgg ttgggaaggg    420
gatcattttt tactggtcat ttcccttttgg agtgtactac tttaacagat ggaaagaact   480
cattggccat ggaaacagcc gangtgttgg gagccagcag tgcatggcac cgtccggcat    540
ctggcntgat tggtctggct gccgtcattg tcagcacagt gccatgggac atggggaana   600
```
ctgactgcac ngccaatggt tttcatgaag aatacngcat ncncngtgat cacgtnancc    660
angacgctat gggggncana gggccanttg cttc    694

<210> SEQ ID NO 14
<211> LENGTH: 679
<212> TYPE: DNA
<213> ORGANISM: Homo sapiens
<220> FEATURE:
<221> NAME/KEY: modified_base
<222> LOCATION: (29)
<223> OTHER INFORMATION: Where n is a, c, g or t
<220> FEATURE:
<221> NAME/KEY: modified_base
<222> LOCATION: (68)
<223> OTHER INFORMATION: Where n is a, c, g or t
<220> FEATURE:
<221> NAME/KEY: modified_base
<222> LOCATION: (83)
<223> OTHER INFORMATION: Where n is a, c, g or t
<220> FEATURE:
<221> NAME/KEY: modified_base
<222> LOCATION: (87)
<223> OTHER INFORMATION: Where n is a, c, g or t
<220> FEATURE:
<221> NAME/KEY: modified_base
<222> LOCATION: (94)
<223> OTHER INFORMATION: Where n is a, c, g or t
<220> FEATURE:
<221> NAME/KEY: modified_base
<222> LOCATION: (104)
<223> OTHER INFORMATION: Where n is a, c, g or t
<220> FEATURE:
<221> NAME/KEY: modified_base
<222> LOCATION: (117)
<223> OTHER INFORMATION: Where n is a, c, g or t
<220> FEATURE:
<221> NAME/KEY: modified_base
<222> LOCATION: (142)
<223> OTHER INFORMATION: Where n is a, c, g or t
<220> FEATURE:
<221> NAME/KEY: modified_base
<222> LOCATION: (145)
<223> OTHER INFORMATION: Where n is a, c, g or t
<220> FEATURE:
<221> NAME/KEY: modified_base
<222> LOCATION: (151)
<223> OTHER INFORMATION: Where n is a, c, g or t
<220> FEATURE:
<221> NAME/KEY: modified_base
<222> LOCATION: (187)
<223> OTHER INFORMATION: Where n is a, c, g or t
<220> FEATURE:
<221> NAME/KEY: modified_base
<222> LOCATION: (201)
<223> OTHER INFORMATION: Where n is a, c, g or t
<220> FEATURE:
<221> NAME/KEY: modified_base
<222> LOCATION: (211)
<223> OTHER INFORMATION: Where n is a, c, g or t
<220> FEATURE:
<221> NAME/KEY: modified_base
<222> LOCATION: (226)
<223> OTHER INFORMATION: Where n is a, c, g or t
<220> FEATURE:
<221> NAME/KEY: modified_base
<222> LOCATION: (229)
<223> OTHER INFORMATION: Where n is a, c, g or t
<220> FEATURE:
<221> NAME/KEY: modified_base
<222> LOCATION: (239)
<223> OTHER INFORMATION: Where n is a, c, g or t
<220> FEATURE:
<221> NAME/KEY: modified_base
<222> LOCATION: (241)
<223> OTHER INFORMATION: Where n is a, c, g or t
<220> FEATURE:

```
<221> NAME/KEY: modified_base
<222> LOCATION: (245)
<223> OTHER INFORMATION: Where n is a, c, g or t
<220> FEATURE:
<221> NAME/KEY: modified_base
<222> LOCATION: (252)
<223> OTHER INFORMATION: Where n is a, c, g or t
<220> FEATURE:
<221> NAME/KEY: modified_base
<222> LOCATION: (255)
<223> OTHER INFORMATION: Where n is a, c, g or t
<220> FEATURE:
<221> NAME/KEY: modified_base
<222> LOCATION: (259)
<223> OTHER INFORMATION: Where n is a, c, g or t
<220> FEATURE:
<221> NAME/KEY: modified_base
<222> LOCATION: (303)
<223> OTHER INFORMATION: Where n is a, c, g or t
<220> FEATURE:
<221> NAME/KEY: modified_base
<222> LOCATION: (309)
<223> OTHER INFORMATION: Where n is a, c, g or t
<220> FEATURE:
<221> NAME/KEY: modified_base
<222> LOCATION: (359)
<223> OTHER INFORMATION: Where n is a, c, g or t
<220> FEATURE:
<221> NAME/KEY: modified_base
<222> LOCATION: (387)
<223> OTHER INFORMATION: Where n is a, c, g or t
<220> FEATURE:
<221> NAME/KEY: modified_base
<222> LOCATION: (400)
<223> OTHER INFORMATION: Where n is a, c, g or t
<220> FEATURE:
<221> NAME/KEY: modified_base
<222> LOCATION: (441)
<223> OTHER INFORMATION: Where n is a, c, g or t
<220> FEATURE:
<221> NAME/KEY: modified_base
<222> LOCATION: (446)
<223> OTHER INFORMATION: Where n is a, c, g or t
<220> FEATURE:
<221> NAME/KEY: modified_base
<222> LOCATION: (461)
<223> OTHER INFORMATION: Where n is a, c, g or t
<220> FEATURE:
<221> NAME/KEY: modified_base
<222> LOCATION: (492)
<223> OTHER INFORMATION: Where n is a, c, g or t
<220> FEATURE:
<221> NAME/KEY: modified_base
<222> LOCATION: (504)
<223> OTHER INFORMATION: Where n is a, c, g or t
<220> FEATURE:
<221> NAME/KEY: modified_base
<222> LOCATION: (505)
<223> OTHER INFORMATION: Where n is a, c, g or t
<220> FEATURE:
<221> NAME/KEY: modified_base
<222> LOCATION: (512)
<223> OTHER INFORMATION: Where n is a, c, g or t
<220> FEATURE:
<221> NAME/KEY: modified_base
<222> LOCATION: (525)
<223> OTHER INFORMATION: Where n is a, c, g or t
<220> FEATURE:
<221> NAME/KEY: modified_base
<222> LOCATION: (527)
<223> OTHER INFORMATION: Where n is a, c, g or t
<220> FEATURE:
<221> NAME/KEY: modified_base
<222> LOCATION: (533)
<223> OTHER INFORMATION: Where n is a, c, g or t
<220> FEATURE:
<221> NAME/KEY: modified_base
<222> LOCATION: (574)
<223> OTHER INFORMATION: Where n is a, c, g or t
```

```
<220> FEATURE:
<221> NAME/KEY: modified_base
<222> LOCATION: (592)
<223> OTHER INFORMATION: Where n is a, c, g or t
<220> FEATURE:
<221> NAME/KEY: modified_base
<222> LOCATION: (609)
<223> OTHER INFORMATION: Where n is a, c, g or t
<220> FEATURE:
<221> NAME/KEY: modified_base
<222> LOCATION: (610)
<223> OTHER INFORMATION: Where n is a, c, g or t
<220> FEATURE:
<221> NAME/KEY: modified_base
<222> LOCATION: (618)
<223> OTHER INFORMATION: Where n is a, c, g or t
<220> FEATURE:
<221> NAME/KEY: modified_base
<222> LOCATION: (620)
<223> OTHER INFORMATION: Where n is a, c, g or t
<220> FEATURE:
<221> NAME/KEY: modified_base
<222> LOCATION: (626)
<223> OTHER INFORMATION: Where n is a, c, g or t
<220> FEATURE:
<221> NAME/KEY: modified_base
<222> LOCATION: (627)
<223> OTHER INFORMATION: Where n is a, c, g or t
<220> FEATURE:
<221> NAME/KEY: modified_base
<222> LOCATION: (633)
<223> OTHER INFORMATION: Where n is a, c, g or t
<220> FEATURE:
<221> NAME/KEY: modified_base
<222> LOCATION: (639)
<223> OTHER INFORMATION: Where n is a, c, g or t
<220> FEATURE:
<221> NAME/KEY: modified_base
<222> LOCATION: (645)
<223> OTHER INFORMATION: Where n is a, c, g or t
<220> FEATURE:
<221> NAME/KEY: modified_base
<222> LOCATION: (654)
<223> OTHER INFORMATION: Where n is a, c, g or t

<400> SEQUENCE: 14
cagccgcctg catctgtatc cagcgccang tcccgccagt cccagctgcg cgcgccccc       60 agtcccgnac ccgttcggcc cangctnagt tagncctcac catnccggtc aaaggangca    120
ccaagtgcat caaatacctg cngtncggat ntaaattcat cttctggctt gccgggattg    180
ctgtccntgc cattggacta nggctccgat ncgactctca gaccanganc atcttcganc    240
naganactaa tnatnattnt tccagcttct acacaggagt ctatattctg atcggatccg    300
gcnccctcnt gatgctggtg ggcttcctga gctgctgcgg ggctgtgcaa gagtcccant    360
gcatgctggg actgttcttc ggcttcntct tggtgatatn cgccattgaa atacctgcgg    420
ccatctgggg atattccact ncgatnatgt gattaaggaa ntccacggag ttttacaagg    480
acacgtacaa cnacctgaaa accnnggatg ancccaccg ggaancnctg aangccatcc     540
actatgcgtt gaactgcaat ggtttggctg gggncttga acaatttaat cncatacatc     600 tggcccann aaaggacntn ctcgannect tncegtgna attcgttct gatnccatca       660 cagaagtctc gaacaatcc                                                  679

<210> SEQ ID NO 15
<211> LENGTH: 695
<212> TYPE: DNA
<213> ORGANISM: Homo sapiens
<220> FEATURE:
<221> NAME/KEY: modified_base
<222> LOCATION: (105)
```

-continued

```
<223> OTHER INFORMATION: Where n is a, c, g or t
<220> FEATURE:
<221> NAME/KEY: modified_base
<222> LOCATION: (172)
<223> OTHER INFORMATION: Where n is a, c, g or t
<220> FEATURE:
<221> NAME/KEY: modified_base
<222> LOCATION: (176)
<223> OTHER INFORMATION: Where n is a, c, g or t
<220> FEATURE:
<221> NAME/KEY: modified_base
<222> LOCATION: (179)
<223> OTHER INFORMATION: Where n is a, c, g or t
<220> FEATURE:
<221> NAME/KEY: modified_base
<222> LOCATION: (189)
<223> OTHER INFORMATION: Where n is a, c, g or t
<220> FEATURE:
<221> NAME/KEY: modified_base
<222> LOCATION: (203)
<223> OTHER INFORMATION: Where n is a, c, g or t
<220> FEATURE:
<221> NAME/KEY: modified_base
<222> LOCATION: (212)
<223> OTHER INFORMATION: Where n is a, c, g or t
<220> FEATURE:
<221> NAME/KEY: modified_base
<222> LOCATION: (219)
<223> OTHER INFORMATION: Where n is a, c, g or t
<220> FEATURE:
<221> NAME/KEY: modified_base
<222> LOCATION: (221)
<223> OTHER INFORMATION: Where n is a, c, g or t
<220> FEATURE:
<221> NAME/KEY: modified_base
<222> LOCATION: (229)
<223> OTHER INFORMATION: Where n is a, c, g or t
<220> FEATURE:
<221> NAME/KEY: modified_base
<222> LOCATION: (231)
<223> OTHER INFORMATION: Where n is a, c, g or t
<220> FEATURE:
<221> NAME/KEY: modified_base
<222> LOCATION: (238)
<223> OTHER INFORMATION: Where n is a, c, g or t
<220> FEATURE:
<221> NAME/KEY: modified_base
<222> LOCATION: (242)
<223> OTHER INFORMATION: Where n is a, c, g or t
<220> FEATURE:
<221> NAME/KEY: modified_base
<222> LOCATION: (261)
<223> OTHER INFORMATION: Where n is a, c, g or t
<220> FEATURE:
<221> NAME/KEY: modified_base
<222> LOCATION: (266)
<223> OTHER INFORMATION: Where n is a, c, g or t
<220> FEATURE:
<221> NAME/KEY: modified_base
<222> LOCATION: (270)
<223> OTHER INFORMATION: Where n is a, c, g or t
<220> FEATURE:
<221> NAME/KEY: modified_base
<222> LOCATION: (278)
<223> OTHER INFORMATION: Where n is a, c, g or t
<220> FEATURE:
<221> NAME/KEY: modified_base
<222> LOCATION: (285)
<223> OTHER INFORMATION: Where n is a, c, g or t
<220> FEATURE:
<221> NAME/KEY: modified_base
<222> LOCATION: (286)
<223> OTHER INFORMATION: Where n is a, c, g or t
<220> FEATURE:
<221> NAME/KEY: modified_base
<222> LOCATION: (298)
<223> OTHER INFORMATION: Where n is a, c, g or t
<220> FEATURE:
<221> NAME/KEY: modified_base
```

-continued

```
<222> LOCATION: (311)
<223> OTHER INFORMATION: Where n is a, c, g or t
<220> FEATURE:
<221> NAME/KEY: modified_base
<222> LOCATION: (324)
<223> OTHER INFORMATION: Where n is a, c, g or t
<220> FEATURE:
<221> NAME/KEY: modified_base
<222> LOCATION: (337)
<223> OTHER INFORMATION: Where n is a, c, g or t
<220> FEATURE:
<221> NAME/KEY: modified_base
<222> LOCATION: (350)
<223> OTHER INFORMATION: Where n is a, c, g or t
<220> FEATURE:
<221> NAME/KEY: modified_base
<222> LOCATION: (363)
<223> OTHER INFORMATION: Where n is a, c, g or t
<220> FEATURE:
<221> NAME/KEY: modified_base
<222> LOCATION: (384)
<223> OTHER INFORMATION: Where n is a, c, g or t
<220> FEATURE:
<221> NAME/KEY: modified_base
<222> LOCATION: (391)
<223> OTHER INFORMATION: Where n is a, c, g or t
<220> FEATURE:
<221> NAME/KEY: modified_base
<222> LOCATION: (395)
<223> OTHER INFORMATION: Where n is a, c, g or t
<220> FEATURE:
<221> NAME/KEY: modified_base
<222> LOCATION: (405)
<223> OTHER INFORMATION: Where n is a, c, g or t
<220> FEATURE:
<221> NAME/KEY: modified_base
<222> LOCATION: (411)
<223> OTHER INFORMATION: Where n is a, c, g or t
<220> FEATURE:
<221> NAME/KEY: modified_base
<222> LOCATION: (424)
<223> OTHER INFORMATION: Where n is a, c, g or t
<220> FEATURE:
<221> NAME/KEY: modified_base
<222> LOCATION: (427)
<223> OTHER INFORMATION: Where n is a, c, g or t
<220> FEATURE:
<221> NAME/KEY: modified_base
<222> LOCATION: (443)
<223> OTHER INFORMATION: Where n is a, c, g or t
<220> FEATURE:
<221> NAME/KEY: modified_base
<222> LOCATION: (448)
<223> OTHER INFORMATION: Where n is a, c, g or t
<220> FEATURE:
<221> NAME/KEY: modified_base
<222> LOCATION: (453)
<223> OTHER INFORMATION: Where n is a, c, g or t
<220> FEATURE:
<221> NAME/KEY: modified_base
<222> LOCATION: (455)
<223> OTHER INFORMATION: Where n is a, c, g or t
<220> FEATURE:
<221> NAME/KEY: modified_base
<222> LOCATION: (458)
<223> OTHER INFORMATION: Where n is a, c, g or t
<220> FEATURE:
<221> NAME/KEY: modified_base
<222> LOCATION: (463)
<223> OTHER INFORMATION: Where n is a, c, g or t
<220> FEATURE:
<221> NAME/KEY: modified_base
<222> LOCATION: (467)
<223> OTHER INFORMATION: Where n is a, c, g or t
<220> FEATURE:
<221> NAME/KEY: modified_base
<222> LOCATION: (470)
<223> OTHER INFORMATION: Where n is a, c, g or t
<220> FEATURE:
```

-continued

```
<221> NAME/KEY: modified_base
<222> LOCATION: (479)
<223> OTHER INFORMATION: Where n is a, c, g or t
<220> FEATURE:
<221> NAME/KEY: modified_base
<222> LOCATION: (481)
<223> OTHER INFORMATION: Where n is a, c, g or t
<220> FEATURE:
<221> NAME/KEY: modified_base
<222> LOCATION: (484)
<223> OTHER INFORMATION: Where n is a, c, g or t
<220> FEATURE:
<221> NAME/KEY: modified_base
<222> LOCATION: (493)
<223> OTHER INFORMATION: Where n is a, c, g or t
<220> FEATURE:
<221> NAME/KEY: modified_base
<222> LOCATION: (499)
<223> OTHER INFORMATION: Where n is a, c, g or t
<220> FEATURE:
<221> NAME/KEY: modified_base
<222> LOCATION: (505)
<223> OTHER INFORMATION: Where n is a, c, g or t
<220> FEATURE:
<221> NAME/KEY: modified_base
<222> LOCATION: (518)
<223> OTHER INFORMATION: Where n is a, c, g or t
<220> FEATURE:
<221> NAME/KEY: modified_base
<222> LOCATION: (520)
<223> OTHER INFORMATION: Where n is a, c, g or t
<220> FEATURE:
<221> NAME/KEY: modified_base
<222> LOCATION: (523)
<223> OTHER INFORMATION: Where n is a, c, g or t
<220> FEATURE:
<221> NAME/KEY: modified_base
<222> LOCATION: (531)
<223> OTHER INFORMATION: Where n is a, c, g or t
<220> FEATURE:
<221> NAME/KEY: modified_base
<222> LOCATION: (540)
<223> OTHER INFORMATION: Where n is a, c, g or t
<220> FEATURE:
<221> NAME/KEY: modified_base
<222> LOCATION: (584)
<223> OTHER INFORMATION: Where n is a, c, g or t
<220> FEATURE:
<221> NAME/KEY: modified_base
<222> LOCATION: (595)
<223> OTHER INFORMATION: Where n is a, c, g or t
<220> FEATURE:
<221> NAME/KEY: modified_base
<222> LOCATION: (597)
<223> OTHER INFORMATION: Where n is a, c, g or t
<220> FEATURE:
<221> NAME/KEY: modified_base
<222> LOCATION: (609)
<223> OTHER INFORMATION: Where n is a, c, g or t
<220> FEATURE:
<221> NAME/KEY: modified_base
<222> LOCATION: (611)
<223> OTHER INFORMATION: Where n is a, c, g or t
<220> FEATURE:
<221> NAME/KEY: modified_base
<222> LOCATION: (626)
<223> OTHER INFORMATION: Where n is a, c, g or t
<220> FEATURE:
<221> NAME/KEY: modified_base
<222> LOCATION: (628)
<223> OTHER INFORMATION: Where n is a, c, g or t
<220> FEATURE:
<221> NAME/KEY: modified_base
<222> LOCATION: (651)
<223> OTHER INFORMATION: Where n is a, c, g or t
<220> FEATURE:
<221> NAME/KEY: modified_base
<222> LOCATION: (652)
<223> OTHER INFORMATION: Where n is a, c, g or t
```

<220> FEATURE:
<221> NAME/KEY: modified_base
<222> LOCATION: (657)
<223> OTHER INFORMATION: Where n is a, c, g or t
<220> FEATURE:
<221> NAME/KEY: modified_base
<222> LOCATION: (661)
<223> OTHER INFORMATION: Where n is a, c, g or t
<220> FEATURE:
<221> NAME/KEY: modified_base
<222> LOCATION: (665)
<223> OTHER INFORMATION: Where n is a, c, g or t
<220> FEATURE:
<221> NAME/KEY: modified_base
<222> LOCATION: (669)
<223> OTHER INFORMATION: Where n is a, c, g or t
<220> FEATURE:
<221> NAME/KEY: modified_base
<222> LOCATION: (672)
<223> OTHER INFORMATION: Where n is a, c, g or t
<220> FEATURE:
<221> NAME/KEY: modified_base
<222> LOCATION: (681)
<223> OTHER INFORMATION: Where n is a, c, g or t
<220> FEATURE:
<221> NAME/KEY: modified_base
<222> LOCATION: (683)
<223> OTHER INFORMATION: Where n is a, c, g or t
<220> FEATURE:
<221> NAME/KEY: modified_base
<222> LOCATION: (691)
<223> OTHER INFORMATION: Where n is a, c, g or t
<220> FEATURE:
<221> NAME/KEY: modified_base
<222> LOCATION: (693)
<223> OTHER INFORMATION: Where n is a, c, g or t

<400> SEQUENCE: 15

```
actagtggat aaaggccagg gatgctgctc aacctcctac catgtacagg gacgtctccc      60
cattacaact acccaatccg aagtgtcaac tgtgtcagga ctaanaaacc ctggttttga     120
ttaaaaaagg gcctgaaaaa aggggagcca caaatctgtc tgcttcctca cnttantcnt     180
tggcaaatna gcattctgtc tcnttggctg cngcctcanc ncaaaaaanc ngaactcnat     240
cnggcccagg aatacatctc ncaatnaacn aaattganca aggcnntggg aaatgccnga     300
tgggattatc ntccgcttgt tgancttcta agtttcnttc ccttcattcn acccctgccag    360
ccnagttctg ttagaaaaat gccngaattc naacnccggt tttcntactc ngaatttaga    420
tctncanaaa cttcctggcc acnattcnaa ttnanggnca cgnacanatn ccttccatna    480
ancncacccc acntttgana gccangacaa tgactgcntn aantgaaggc ntgaaggaan    540
aactttgaaa ggaaaaaaaa ctttgtttcc ggcccccttcc aacncttctg tgttnancac   600
tgccttctng naaccctgga agcccngnga cagtgttaca tgttgttcta nnaaacngac    660
ncttnaatnt cnatcttccc nanaacgatt ncncc                               695
```

<210> SEQ ID NO 16
<211> LENGTH: 669
<212> TYPE: DNA
<213> ORGANISM: Homo sapiens
<220> FEATURE:
<221> NAME/KEY: modified_base
<222> LOCATION: (299)
<223> OTHER INFORMATION: Where n is a, c, g or t
<220> FEATURE:
<221> NAME/KEY: modified_base
<222> LOCATION: (354)
<223> OTHER INFORMATION: Where n is a, c, g or t
<220> FEATURE:
<221> NAME/KEY: modified_base
<222> LOCATION: (483)

<223> OTHER INFORMATION: Where n is a, c, g or t
<220> FEATURE:
<221> NAME/KEY: modified_base
<222> LOCATION: (555)
<223> OTHER INFORMATION: Where n is a, c, g or t
<220> FEATURE:
<221> NAME/KEY: modified_base
<222> LOCATION: (571)
<223> OTHER INFORMATION: Where n is a, c, g or t
<220> FEATURE:
<221> NAME/KEY: modified_base
<222> LOCATION: (573)
<223> OTHER INFORMATION: Where n is a, c, g or t
<220> FEATURE:
<221> NAME/KEY: modified_base
<222> LOCATION: (577)
<223> OTHER INFORMATION: Where n is a, c, g or t
<220> FEATURE:
<221> NAME/KEY: modified_base
<222> LOCATION: (642)
<223> OTHER INFORMATION: Where n is a, c, g or t
<220> FEATURE:
<221> NAME/KEY: modified_base
<222> LOCATION: (651)
<223> OTHER INFORMATION: Where n is a, c, g or t
<220> FEATURE:
<221> NAME/KEY: modified_base
<222> LOCATION: (662)
<223> OTHER INFORMATION: Where n is a, c, g or t
<220> FEATURE:
<221> NAME/KEY: modified_base
<222> LOCATION: (667)
<223> OTHER INFORMATION: Where n is a, c, g or t

<400> SEQUENCE: 16

| | | | | | |
|---|---|---|---|---|---|
| cgccgaagca | gcagcgcagg | ttgtccccgt | ttccctccc | ccttcccttc | tccggttgcc | 60 |
| ttcccgggcc | ccttacactc | cacagtcccg | gtccgccat | gtcccagaaa | caagaagaag | 120 |
| agaaccctgc | ggaggagacc | ggcgaggaga | agcaggacac | gcaggagaaa | gaaggtattc | 180 |
| tgcctgagag | agctgaagag | gcaaagctaa | aggccaaata | cccaagccta | ggacaaaagc | 240 |
| ctggaggctc | cgacttcctc | atgaagagac | tccagaaagg | gcaaaagtac | tttgactcng | 300 |
| gagactacaa | catggccaaa | gccaacatga | agaataagca | gctgccaagt | gcangaccag | 360 |
| acaagaacct | ggtgactggt | gatcacatcc | ccaccccaca | ggatctgccc | agagaaagtc | 420 |
| ctcgctcgtc | accagcaagc | ttgcgggtgg | ccaagttgaa | tgatgctgcc | ggggctctgc | 480 |
| canatctgag | acgcttccct | ccctgcccca | cccgggtcct | gtgctggctc | ctgcccttcc | 540 |
| tgcttttgca | gccangggtc | aggaagtggc | ncngtgtg | gctggaaagc | aaaaccctt | 600 |
| cctgttggtg | tcccacccat | ggagcccctg | gggcgagccc | angaacttga | nccttttgt | 660 |
| tntcttncc | | | | | | 669 |

<210> SEQ ID NO 17
<211> LENGTH: 697
<212> TYPE: DNA
<213> ORGANISM: Homo sapiens
<220> FEATURE:
<221> NAME/KEY: modified_base
<222> LOCATION: (33)
<223> OTHER INFORMATION: Where n is a, c, g or t
<220> FEATURE:
<221> NAME/KEY: modified_base
<222> LOCATION: (48)
<223> OTHER INFORMATION: Where n is a, c, g or t
<220> FEATURE:
<221> NAME/KEY: modified_base
<222> LOCATION: (50)
<223> OTHER INFORMATION: Where n is a, c, g or t
<220> FEATURE:
<221> NAME/KEY: modified_base -continued

```
<222> LOCATION: (58)
<223> OTHER INFORMATION: Where n is a, c, g or t
<220> FEATURE:
<221> NAME/KEY: modified_base
<222> LOCATION: (59)
<223> OTHER INFORMATION: Where n is a, c, g or t
<220> FEATURE:
<221> NAME/KEY: modified_base
<222> LOCATION: (60)
<223> OTHER INFORMATION: Where n is a, c, g or t
<220> FEATURE:
<221> NAME/KEY: modified_base
<222> LOCATION: (76)
<223> OTHER INFORMATION: Where n is a, c, g or t
<220> FEATURE:
<221> NAME/KEY: modified_base
<222> LOCATION: (77)
<223> OTHER INFORMATION: Where n is a, c, g or t
<220> FEATURE:
<221> NAME/KEY: modified_base
<222> LOCATION: (78)
<223> OTHER INFORMATION: Where n is a, c, g or t
<220> FEATURE:
<221> NAME/KEY: modified_base
<222> LOCATION: (90)
<223> OTHER INFORMATION: Where n is a, c, g or t
<220> FEATURE:
<221> NAME/KEY: modified_base
<222> LOCATION: (113)
<223> OTHER INFORMATION: Where n is a, c, g or t
<220> FEATURE:
<221> NAME/KEY: modified_base
<222> LOCATION: (118)
<223> OTHER INFORMATION: Where n is a, c, g or t
<220> FEATURE:
<221> NAME/KEY: modified_base
<222> LOCATION: (130)
<223> OTHER INFORMATION: Where n is a, c, g or t
<220> FEATURE:
<221> NAME/KEY: modified_base
<222> LOCATION: (135)
<223> OTHER INFORMATION: Where n is a, c, g or t
<220> FEATURE:
<221> NAME/KEY: modified_base
<222> LOCATION: (141)
<223> OTHER INFORMATION: Where n is a, c, g or t
<220> FEATURE:
<221> NAME/KEY: modified_base
<222> LOCATION: (143)
<223> OTHER INFORMATION: Where n is a, c, g or t
<220> FEATURE:
<221> NAME/KEY: modified_base
<222> LOCATION: (150)
<223> OTHER INFORMATION: Where n is a, c, g or t
<220> FEATURE:
<221> NAME/KEY: modified_base
<222> LOCATION: (156)
<223> OTHER INFORMATION: Where n is a, c, g or t
<220> FEATURE:
<221> NAME/KEY: modified_base
<222> LOCATION: (166)
<223> OTHER INFORMATION: Where n is a, c, g or t
<220> FEATURE:
<221> NAME/KEY: modified_base
<222> LOCATION: (167)
<223> OTHER INFORMATION: Where n is a, c, g or t
<220> FEATURE:
<221> NAME/KEY: modified_base
<222> LOCATION: (170)
<223> OTHER INFORMATION: Where n is a, c, g or t
<220> FEATURE:
<221> NAME/KEY: modified_base
<222> LOCATION: (172)
<223> OTHER INFORMATION: Where n is a, c, g or t
<220> FEATURE:
<221> NAME/KEY: modified_base
<222> LOCATION: (180)
<223> OTHER INFORMATION: Where n is a, c, g or t
<220> FEATURE:
```

-continued

```
<221> NAME/KEY: modified_base
<222> LOCATION: (181)
<223> OTHER INFORMATION: Where n is a, c, g or t
<220> FEATURE:
<221> NAME/KEY: modified_base
<222> LOCATION: (190)
<223> OTHER INFORMATION: Where n is a, c, g or t
<220> FEATURE:
<221> NAME/KEY: modified_base
<222> LOCATION: (192)
<223> OTHER INFORMATION: Where n is a, c, g or t
<220> FEATURE:
<221> NAME/KEY: modified_base
<222> LOCATION: (194)
<223> OTHER INFORMATION: Where n is a, c, g or t
<220> FEATURE:
<221> NAME/KEY: modified_base
<222> LOCATION: (199)
<223> OTHER INFORMATION: Where n is a, c, g or t
<220> FEATURE:
<221> NAME/KEY: modified_base
<222> LOCATION: (201)
<223> OTHER INFORMATION: Where n is a, c, g or t
<220> FEATURE:
<221> NAME/KEY: modified_base
<222> LOCATION: (209)
<223> OTHER INFORMATION: Where n is a, c, g or t
<220> FEATURE:
<221> NAME/KEY: modified_base
<222> LOCATION: (211)
<223> OTHER INFORMATION: Where n is a, c, g or t
<220> FEATURE:
<221> NAME/KEY: modified_base
<222> LOCATION: (224)
<223> OTHER INFORMATION: Where n is a, c, g or t
<220> FEATURE:
<221> NAME/KEY: modified_base
<222> LOCATION: (225)
<223> OTHER INFORMATION: Where n is a, c, g or t
<220> FEATURE:
<221> NAME/KEY: modified_base
<222> LOCATION: (226)
<223> OTHER INFORMATION: Where n is a, c, g or t
<220> FEATURE:
<221> NAME/KEY: modified_base
<222> LOCATION: (230)
<223> OTHER INFORMATION: Where n is a, c, g or t
<220> FEATURE:
<221> NAME/KEY: modified_base
<222> LOCATION: (233)
<223> OTHER INFORMATION: Where n is a, c, g or t
<220> FEATURE:
<221> NAME/KEY: modified_base
<222> LOCATION: (234)
<223> OTHER INFORMATION: Where n is a, c, g or t
<220> FEATURE:
<221> NAME/KEY: modified_base
<222> LOCATION: (236)
<223> OTHER INFORMATION: Where n is a, c, g or t
<220> FEATURE:
<221> NAME/KEY: modified_base
<222> LOCATION: (242)
<223> OTHER INFORMATION: Where n is a, c, g or t
<220> FEATURE:
<221> NAME/KEY: modified_base
<222> LOCATION: (244)
<223> OTHER INFORMATION: Where n is a, c, g or t
<220> FEATURE:
<221> NAME/KEY: modified_base
<222> LOCATION: (251)
<223> OTHER INFORMATION: Where n is a, c, g or t
<220> FEATURE:
<221> NAME/KEY: modified_base
<222> LOCATION: (253)
<223> OTHER INFORMATION: Where n is a, c, g or t
<220> FEATURE:
<221> NAME/KEY: modified_base
<222> LOCATION: (256)
<223> OTHER INFORMATION: Where n is a, c, g or t
```

-continued

```
<220> FEATURE:
<221> NAME/KEY: modified_base
<222> LOCATION: (268)
<223> OTHER INFORMATION: Where n is a, c, g or t
<220> FEATURE:
<221> NAME/KEY: modified_base
<222> LOCATION: (297)
<223> OTHER INFORMATION: Where n is a, c, g or t
<220> FEATURE:
<221> NAME/KEY: modified_base
<222> LOCATION: (305)
<223> OTHER INFORMATION: Where n is a, c, g or t
<220> FEATURE:
<221> NAME/KEY: modified_base
<222> LOCATION: (308)
<223> OTHER INFORMATION: Where n is a, c, g or t
<220> FEATURE:
<221> NAME/KEY: modified_base
<222> LOCATION: (311)
<223> OTHER INFORMATION: Where n is a, c, g or t
<220> FEATURE:
<221> NAME/KEY: modified_base
<222> LOCATION: (314)
<223> OTHER INFORMATION: Where n is a, c, g or t
<220> FEATURE:
<221> NAME/KEY: modified_base
<222> LOCATION: (315)
<223> OTHER INFORMATION: Where n is a, c, g or t
<220> FEATURE:
<221> NAME/KEY: modified_base
<222> LOCATION: (317)
<223> OTHER INFORMATION: Where n is a, c, g or t
<220> FEATURE:
<221> NAME/KEY: modified_base
<222> LOCATION: (322)
<223> OTHER INFORMATION: Where n is a, c, g or t
<220> FEATURE:
<221> NAME/KEY: modified_base
<222> LOCATION: (324)
<223> OTHER INFORMATION: Where n is a, c, g or t
<220> FEATURE:
<221> NAME/KEY: modified_base
<222> LOCATION: (327)
<223> OTHER INFORMATION: Where n is a, c, g or t
<220> FEATURE:
<221> NAME/KEY: modified_base
<222> LOCATION: (333)
<223> OTHER INFORMATION: Where n is a, c, g or t
<220> FEATURE:
<221> NAME/KEY: modified_base
<222> LOCATION: (337)
<223> OTHER INFORMATION: Where n is a, c, g or t
<220> FEATURE:
<221> NAME/KEY: modified_base
<222> LOCATION: (343)
<223> OTHER INFORMATION: Where n is a, c, g or t
<220> FEATURE:
<221> NAME/KEY: modified_base
<222> LOCATION: (362)
<223> OTHER INFORMATION: Where n is a, c, g or t
<220> FEATURE:
<221> NAME/KEY: modified_base
<222> LOCATION: (364)
<223> OTHER INFORMATION: Where n is a, c, g or t
<220> FEATURE:
<221> NAME/KEY: modified_base
<222> LOCATION: (367)
<223> OTHER INFORMATION: Where n is a, c, g or t
<220> FEATURE:
<221> NAME/KEY: modified_base
<222> LOCATION: (368)
<223> OTHER INFORMATION: Where n is a, c, g or t
<220> FEATURE:
<221> NAME/KEY: modified_base
<222> LOCATION: (373)
<223> OTHER INFORMATION: Where n is a, c, g or t
<220> FEATURE:
<221> NAME/KEY: modified_base
<222> LOCATION: (384)
```

-continued

```
<223> OTHER INFORMATION: Where n is a, c, g or t
<220> FEATURE:
<221> NAME/KEY: modified_base
<222> LOCATION: (388)
<223> OTHER INFORMATION: Where n is a, c, g or t
<220> FEATURE:
<221> NAME/KEY: modified_base
<222> LOCATION: (394)
<223> OTHER INFORMATION: Where n is a, c, g or t
<220> FEATURE:
<221> NAME/KEY: modified_base
<222> LOCATION: (406)
<223> OTHER INFORMATION: Where n is a, c, g or t
<220> FEATURE:
<221> NAME/KEY: modified_base
<222> LOCATION: (411)
<223> OTHER INFORMATION: Where n is a, c, g or t
<220> FEATURE:
<221> NAME/KEY: modified_base
<222> LOCATION: (413)
<223> OTHER INFORMATION: Where n is a, c, g or t
<220> FEATURE:
<221> NAME/KEY: modified_base
<222> LOCATION: (423)
<223> OTHER INFORMATION: Where n is a, c, g or t
<220> FEATURE:
<221> NAME/KEY: modified_base
<222> LOCATION: (429)
<223> OTHER INFORMATION: Where n is a, c, g or t
<220> FEATURE:
<221> NAME/KEY: modified_base
<222> LOCATION: (438)
<223> OTHER INFORMATION: Where n is a, c, g or t
<220> FEATURE:
<221> NAME/KEY: modified_base
<222> LOCATION: (449)
<223> OTHER INFORMATION: Where n is a, c, g or t
<220> FEATURE:
<221> NAME/KEY: modified_base
<222> LOCATION: (450)
<223> OTHER INFORMATION: Where n is a, c, g or t
<220> FEATURE:
<221> NAME/KEY: modified_base
<222> LOCATION: (473)
<223> OTHER INFORMATION: Where n is a, c, g or t
<220> FEATURE:
<221> NAME/KEY: modified_base
<222> LOCATION: (476)
<223> OTHER INFORMATION: Where n is a, c, g or t
<220> FEATURE:
<221> NAME/KEY: modified_base
<222> LOCATION: (479)
<223> OTHER INFORMATION: Where n is a, c, g or t
<220> FEATURE:
<221> NAME/KEY: modified_base
<222> LOCATION: (489)
<223> OTHER INFORMATION: Where n is a, c, g or t
<220> FEATURE:
<221> NAME/KEY: modified_base
<222> LOCATION: (491)
<223> OTHER INFORMATION: Where n is a, c, g or t
<220> FEATURE:
<221> NAME/KEY: modified_base
<222> LOCATION: (494)
<223> OTHER INFORMATION: Where n is a, c, g or t
<220> FEATURE:
<221> NAME/KEY: modified_base
<222> LOCATION: (499)
<223> OTHER INFORMATION: Where n is a, c, g or t
<220> FEATURE:
<221> NAME/KEY: modified_base
<222> LOCATION: (505)
<223> OTHER INFORMATION: Where n is a, c, g or t
<220> FEATURE:
<221> NAME/KEY: modified_base
<222> LOCATION: (507)
<223> OTHER INFORMATION: Where n is a, c, g or t
<220> FEATURE:
<221> NAME/KEY: modified_base
```

-continued

```
<222> LOCATION: (508)
<223> OTHER INFORMATION: Where n is a, c, g or t
<220> FEATURE:
<221> NAME/KEY: modified_base
<222> LOCATION: (522)
<223> OTHER INFORMATION: Where n is a, c, g or t
<220> FEATURE:
<221> NAME/KEY: modified_base
<222> LOCATION: (523)
<223> OTHER INFORMATION: Where n is a, c, g or t
<220> FEATURE:
<221> NAME/KEY: modified_base
<222> LOCATION: (527)
<223> OTHER INFORMATION: Where n is a, c, g or t
<220> FEATURE:
<221> NAME/KEY: modified_base
<222> LOCATION: (530)
<223> OTHER INFORMATION: Where n is a, c, g or t
<220> FEATURE:
<221> NAME/KEY: modified_base
<222> LOCATION: (533)
<223> OTHER INFORMATION: Where n is a, c, g or t
<220> FEATURE:
<221> NAME/KEY: modified_base
<222> LOCATION: (535)
<223> OTHER INFORMATION: Where n is a, c, g or t
<220> FEATURE:
<221> NAME/KEY: modified_base
<222> LOCATION: (538)
<223> OTHER INFORMATION: Where n is a, c, g or t
<220> FEATURE:
<221> NAME/KEY: modified_base
<222> LOCATION: (539)
<223> OTHER INFORMATION: Where n is a, c, g or t
<220> FEATURE:
<221> NAME/KEY: modified_base
<222> LOCATION: (545)
<223> OTHER INFORMATION: Where n is a, c, g or t
<220> FEATURE:
<221> NAME/KEY: modified_base
<222> LOCATION: (548)
<223> OTHER INFORMATION: Where n is a, c, g or t
<220> FEATURE:
<221> NAME/KEY: modified_base
<222> LOCATION: (550)
<223> OTHER INFORMATION: Where n is a, c, g or t
<220> FEATURE:
<221> NAME/KEY: modified_base
<222> LOCATION: (552)
<223> OTHER INFORMATION: Where n is a, c, g or t
<220> FEATURE:
<221> NAME/KEY: modified_base
<222> LOCATION: (555)
<223> OTHER INFORMATION: Where n is a, c, g or t
<220> FEATURE:
<221> NAME/KEY: modified_base
<222> LOCATION: (562)
<223> OTHER INFORMATION: Where n is a, c, g or t
<220> FEATURE:
<221> NAME/KEY: modified_base
<222> LOCATION: (563)
<223> OTHER INFORMATION: Where n is a, c, g or t
<220> FEATURE:
<221> NAME/KEY: modified_base
<222> LOCATION: (566)
<223> OTHER INFORMATION: Where n is a, c, g or t
<220> FEATURE:
<221> NAME/KEY: modified_base
<222> LOCATION: (568)
<223> OTHER INFORMATION: Where n is a, c, g or t
<220> FEATURE:
<221> NAME/KEY: modified_base
<222> LOCATION: (572)
<223> OTHER INFORMATION: Where n is a, c, g or t
<220> FEATURE:
<221> NAME/KEY: modified_base
<222> LOCATION: (577)
<223> OTHER INFORMATION: Where n is a, c, g or t
<220> FEATURE:
```

-continued

```
<221> NAME/KEY: modified_base
<222> LOCATION: (578)
<223> OTHER INFORMATION: Where n is a, c, g or t
<220> FEATURE:
<221> NAME/KEY: modified_base
<222> LOCATION: (580)
<223> OTHER INFORMATION: Where n is a, c, g or t
<220> FEATURE:
<221> NAME/KEY: modified_base
<222> LOCATION: (581)
<223> OTHER INFORMATION: Where n is a, c, g or t
<220> FEATURE:
<221> NAME/KEY: modified_base
<222> LOCATION: (591)
<223> OTHER INFORMATION: Where n is a, c, g or t
<220> FEATURE:
<221> NAME/KEY: modified_base
<222> LOCATION: (594)
<223> OTHER INFORMATION: Where n is a, c, g or t
<220> FEATURE:
<221> NAME/KEY: modified_base
<222> LOCATION: (622)
<223> OTHER INFORMATION: Where n is a, c, g or t
<220> FEATURE:
<221> NAME/KEY: modified_base
<222> LOCATION: (628)
<223> OTHER INFORMATION: Where n is a, c, g or t
<220> FEATURE:
<221> NAME/KEY: modified_base
<222> LOCATION: (632)
<223> OTHER INFORMATION: Where n is a, c, g or t
<220> FEATURE:
<221> NAME/KEY: modified_base
<222> LOCATION: (638)
<223> OTHER INFORMATION: Where n is a, c, g or t
<220> FEATURE:
<221> NAME/KEY: modified_base
<222> LOCATION: (642)
<223> OTHER INFORMATION: Where n is a, c, g or t
<220> FEATURE:
<221> NAME/KEY: modified_base
<222> LOCATION: (644)
<223> OTHER INFORMATION: Where n is a, c, g or t
<220> FEATURE:
<221> NAME/KEY: modified_base
<222> LOCATION: (653)
<223> OTHER INFORMATION: Where n is a, c, g or t
<220> FEATURE:
<221> NAME/KEY: modified_base
<222> LOCATION: (658)
<223> OTHER INFORMATION: Where n is a, c, g or t
<220> FEATURE:
<221> NAME/KEY: modified_base
<222> LOCATION: (662)
<223> OTHER INFORMATION: Where n is a, c, g or t
<220> FEATURE:
<221> NAME/KEY: modified_base
<222> LOCATION: (663)
<223> OTHER INFORMATION: Where n is a, c, g or t
<220> FEATURE:
<221> NAME/KEY: modified_base
<222> LOCATION: (665)
<223> OTHER INFORMATION: Where n is a, c, g or t
<220> FEATURE:
<221> NAME/KEY: modified_base
<222> LOCATION: (669)
<223> OTHER INFORMATION: Where n is a, c, g or t
<220> FEATURE:
<221> NAME/KEY: modified_base
<222> LOCATION: (675)
<223> OTHER INFORMATION: Where n is a, c, g or t
<220> FEATURE:
<221> NAME/KEY: modified_base
<222> LOCATION: (680)
<223> OTHER INFORMATION: Where n is a, c, g or t
<220> FEATURE:
<221> NAME/KEY: modified_base
<222> LOCATION: (686)
<223> OTHER INFORMATION: Where n is a, c, g or t
```

<220> FEATURE:
<221> NAME/KEY: modified_base
<222> LOCATION: (689)
<223> OTHER INFORMATION: Where n is a, c, g or t

<400> SEQUENCE: 17

| | | | | | |
|---|---|---|---|---|---|
| gcaagatatg | gacaactaag | tgagaaggta | atnctctact | gctctagntn | ctccnggcnn | 60 |
| gacgcgctga | ggagannnac | gctggcccan | ctgccggcca | cacacgggga | tcntggtnat | 120 |
| gcctgcccan | gggancccca | ncnctcggan | cccatntcac | acccgnnccn | tncgcccacn | 180 |
| ncctggctcn | cncngcccng | nccagctcnc | gnccccctcc | gccnnnctcn | ttnncntctc | 240 |
| cncnccctcc | ncnacnacct | cctacccncg | gctccctccc | cagccccccc | ccgcaancct | 300 |
| ccacnacncc | ntcnncncga | ancnccnctc | gcntcngcc | ccngccccct | gccccccgcc | 360 |
| cncnacnncg | cgntcccccg | cgcncgcngc | ctcnccccct | cccacnacag | ncnacccgc | 420 |
| agncacgcnc | tccgcccnct | gacgccccnn | cccgccgcgc | tcaccttcat | ggnccnacng | 480 |
| ccccgctcnc | nccnctgcnc | gccgncnngg | cgccccgccc | cnnccgngtn | ccncncgnng | 540 |
| ccccngcngn | angcngtgcg | cnncangncc | gngccgnncn | naccctccg | nccnccgccc | 600 |
| cgcccgctgg | gggctcccgc | cncgcggtc | antccccncc | cntncgccca | ctntccgntc | 660 |
| cnncnctcnc | gctcngcgcn | cgcccnccnc | ccccccc | | | 697 |

<210> SEQ ID NO 18
<211> LENGTH: 670
<212> TYPE: DNA
<213> ORGANISM: Homo sapiens
<220> FEATURE:
<221> NAME/KEY: modified_base
<222> LOCATION: (234)
<223> OTHER INFORMATION: Where n is a, c, g or t
<220> FEATURE:
<221> NAME/KEY: modified_base
<222> LOCATION: (292)
<223> OTHER INFORMATION: Where n is a, c, g or t
<220> FEATURE:
<221> NAME/KEY: modified_base
<222> LOCATION: (329)
<223> OTHER INFORMATION: Where n is a, c, g or t
<220> FEATURE:
<221> NAME/KEY: modified_base
<222> LOCATION: (437)
<223> OTHER INFORMATION: Where n is a, c, g or t
<220> FEATURE:
<221> NAME/KEY: modified_base
<222> LOCATION: (458)
<223> OTHER INFORMATION: Where n is a, c, g or t
<220> FEATURE:
<221> NAME/KEY: modified_base
<222> LOCATION: (478)
<223> OTHER INFORMATION: Where n is a, c, g or t
<220> FEATURE:
<221> NAME/KEY: modified_base
<222> LOCATION: (487)
<223> OTHER INFORMATION: Where n is a, c, g or t
<220> FEATURE:
<221> NAME/KEY: modified_base
<222> LOCATION: (524)
<223> OTHER INFORMATION: Where n is a, c, g or t
<220> FEATURE:
<221> NAME/KEY: modified_base
<222> LOCATION: (542)
<223> OTHER INFORMATION: Where n is a, c, g or t
<220> FEATURE:
<221> NAME/KEY: modified_base
<222> LOCATION: (549)
<223> OTHER INFORMATION: Where n is a, c, g or t
<220> FEATURE:
<221> NAME/KEY: modified_base
<222> LOCATION: (550)

```
<223> OTHER INFORMATION: Where n is a, c, g or t
<220> FEATURE:
<221> NAME/KEY: modified_base
<222> LOCATION: (557)
<223> OTHER INFORMATION: Where n is a, c, g or t
<220> FEATURE:
<221> NAME/KEY: modified_base
<222> LOCATION: (576)
<223> OTHER INFORMATION: Where n is a, c, g or t
<220> FEATURE:
<221> NAME/KEY: modified_base
<222> LOCATION: (597)
<223> OTHER INFORMATION: Where n is a, c, g or t
<220> FEATURE:
<221> NAME/KEY: modified_base
<222> LOCATION: (603)
<223> OTHER INFORMATION: Where n is a, c, g or t
<220> FEATURE:
<221> NAME/KEY: modified_base
<222> LOCATION: (604)
<223> OTHER INFORMATION: Where n is a, c, g or t
<220> FEATURE:
<221> NAME/KEY: modified_base
<222> LOCATION: (646)
<223> OTHER INFORMATION: Where n is a, c, g or t
<220> FEATURE:
<221> NAME/KEY: modified_base
<222> LOCATION: (665)
<223> OTHER INFORMATION: Where n is a, c, g or t

<400> SEQUENCE: 18
ctcgtgtgaa gggtgcagta cctaagccgg agcggggtag aggcgggccg gcacccsctt      60
ctgacctcca gtgccgccgg cctcaagatc agacatggcc cagaacttga acgacttggc     120
gggacggctg cccgccgggc cccgggcat gggcacggcc ctgaagctgt tgctgggggc     180
cggcgccgtg gcctacggtg tgcgcgaatc tgtgttcacc gtggaaggcg ggcncagagc    240
catcttcttc aatcggatcg gtggagtgca caggacacta tcctgggccg anggccttca    300
cttcaggatc cttggttcca gtaccccanc atctatgaca ttcgggccag acctcgaaaa    360
aatctcctcc ctacaggctc caaagaccta cagatggtga atatctccct gcgagtgttg    420
tctcgaccaa tgctcangaa cttcctaaca tgttccancg cctaagggct ggactacnaa    480
gaacgantgt tgccgtccat tgtcacgaag tgctcaagaa tttnggtggc caagttcaat    540
gncctcacnn ctgatcnccc agcggggcca agttacccct ggttgatccc cggggactg   600 acnnaaaagg gccaaggact tcccctcatc ctggataatg tggccntcac aaagctcaac   660 tttanccacc                                                            670

<210> SEQ ID NO 19
<211> LENGTH: 606
<212> TYPE: DNA
<213> ORGANISM: Homo sapiens
<220> FEATURE:
<221> NAME/KEY: modified_base
<222> LOCATION: (506)
<223> OTHER INFORMATION: Where n is a, c, g or t

<400> SEQUENCE: 19
actagtgcca acctcagctc ccaggccagt tctctgaatg tcgaggagtt ccaggatctc     60
tggcctcagt tgtccttggt tattgatggg ggacaaattg gggatggcca gagcccgag    120 tgtcgccttg gctcaactgt ggttgatttg tctgtgcccg gaaagtttgg catcattcgt    180
ccaggctgtg ccctggaaag tactacagcc atcctccaac agaagtacgg actgctcccc   240
tcacatgcgt cctacctgtg aaactctggg aagcaggaag gcccaagacc tggtgctgga   300
tactatgtgt ctgtccactg acgactgtca aggcctcatt tgcagaggcc accggagcta   360
```

```
gggcactagc ctgactttta aggcagtgtg tctttctgag cactgtagac caagcccttg    420
gagctgctgg tttagccttg cacctgggga aaggatgtat ttatttgtat tttcatatat    480
cagccaaaag ctgaatggaa aagttnagaa cattcctagg tggccttatt ctaataagtt    540
tcttctgtct gttttgtttt tcaattgaaa agttattaaa taacagattt agaatctagt    600
gagacc                                                              606

<210> SEQ ID NO 20
<211> LENGTH: 449
<212> TYPE: DNA
<213> ORGANISM: Homo sapiens

<400> SEQUENCE: 20
actagtaaac aacagcagca gaaacatcag tatcagcagc gtcgccagca ggagaatatg     60
cagcgccaga gccgaggaga accccgctc cctgaggagg acctgtccaa actcttcaaa    120
ccaccacagc cgcctgccag gatggactcg ctgctcattg caggccagat aaacacttac    180
tgccagaaca tcaaggagtt cactgcccaa aacttaggca agctcttcat ggcccaggct    240
cttcaagaat acaacaacta agaaaaggaa gtttccagaa aagaagttaa catgaactct    300
tgaagtcaca ccagggcaac tcttggaaga aatatatttg catattgaaa agcacagagg    360
atttctttag tgtcattgcc gattttggct ataacagtgt ctttctagcc ataataaaat    420
aaaacaaaat cttgactgct tgctcaaaa                                     449

<210> SEQ ID NO 21
<211> LENGTH: 409
<212> TYPE: DNA
<213> ORGANISM: Homo sapiens

<400> SEQUENCE: 21
tatcaatcaa ctggtgaata attaaacaat gtgtggtgtg atcatacaaa gggtaccact     60
caatgataaa aggaacaagc tgcctatatg tggaacaaca tggatgcatt tcagaaactt    120
tatgttgagt gaaagaacaa acacggagaa catactatgt ggttctcttt atgtaacatt    180
acagaaataa aaacagaggc aaccacctt gaggcagtat ggagtgagat agactggaaa    240
aaggaaggaa ggaaactcta cgctgatgga aatgtctgtg tcttcattgg gtggtagtta    300
tgtggggata tacatttgtc aaaatttatt gaactatata ctaaagaact ctgcatttta    360
ttgggatgta ataataacct caattaaaaa gacaaaaaaa aaaaaaaaa                409

<210> SEQ ID NO 22
<211> LENGTH: 649
<212> TYPE: DNA
<213> ORGANISM: Homo sapiens
<220> FEATURE:
<221> NAME/KEY: modified_base
<222> LOCATION: (263)
<223> OTHER INFORMATION: Where n is a, c, g or t
<220> FEATURE:
<221> NAME/KEY: modified_base
<222> LOCATION: (353)
<223> OTHER INFORMATION: Where n is a, c, g or t
<220> FEATURE:
<221> NAME/KEY: modified_base
<222> LOCATION: (610)
<223> OTHER INFORMATION: Where n is a, c, g or t
<220> FEATURE:
<221> NAME/KEY: modified_base
<222> LOCATION: (635)
<223> OTHER INFORMATION: Where n is a, c, g or t
<220> FEATURE:
```

<221> NAME/KEY: modified_base
<222> LOCATION: (646)
<223> OTHER INFORMATION: Where n is a, c, g or t

<400> SEQUENCE: 22

| acaattttca | ttatcttaag | cacattgtac | atttctacag | aacctgtgat | tattctcgca | 60 |
| tgataaggat | ggtacttgca | tatggtgaat | tactactgtt | gacagtttcc | gcagaaatcc | 120 |
| tatttcagtg | gaccaacatt | gtggcatggc | agcaaatgcc | acatttgt | ggaatagcag | 180 |
| caaatctaca | agagaccctg | gttggttttt | cgttttgttt | tctttgtttt | ttccccttc | 240 |
| tcctgaatca | gcagggatgg | aangagggta | gggaagttat | gaattactcc | ttccagtagt | 300 |
| agctctgaag | tgtcacattt | aatatcagtt | tttttaaac | atgattctag | ttnaatgtag | 360 |
| aagagagaag | aaagaggaag | tgttcacttt | tttaatacac | tgatttagaa | atttgatgtc | 420 |
| ttatatcagt | agttctgagg | tattgatagc | ttgctttatt | tctgccttta | cgttgacagt | 480 |
| gttgaagcag | ggtgaataac | tagggcata | tatatttttt | tttttgtaa | gctgtttcat | 540 |
| gatgttttct | ttggaatttc | cggataagtt | caggaaaaca | tctgcatgtt | gttatctagt | 600 |
| ctgaagttcn | tatccatctc | attacaacaa | aaacncccag | aacggnttg |  | 649 |

<210> SEQ ID NO 23
<211> LENGTH: 669
<212> TYPE: DNA
<213> ORGANISM: Homo sapiens
<220> FEATURE:
<221> NAME/KEY: modified_base
<222> LOCATION: (642)
<223> OTHER INFORMATION: Where n is a, c, g or t
<220> FEATURE:
<221> NAME/KEY: modified_base
<222> LOCATION: (661)
<223> OTHER INFORMATION: Where n is a, c, g or t

<400> SEQUENCE: 23

| actagtgccg | tactggctga | aatccctgca | ggaccaggaa | gagaaccagt | tcagactttg | 60 |
| tactctcagt | caccagctct | ggaattagat | aaattccttg | aagatgtcag | gaatgggatc | 120 |
| tatcctctga | cagcctttgg | gctgcctcgg | ccccagcagc | cacagcagga | ggaggtgaca | 180 |
| tcacctgtcg | tgcccccctc | tgtcaagact | ccgacacctg | aaccagctga | ggtggagact | 240 |
| cgcaaggtgg | tgctgatgca | gtgcaacatt | gagtcggtgg | aggagggagt | caaacaccac | 300 |
| ctgacacttc | tgctgaagtt | ggaggacaaa | ctgaaccggc | acctgagctg | tgacctgatg | 360 |
| ccaaatgaga | atatccccga | gttggcggct | gagctggtgc | agctgggctt | cattagtgag | 420 |
| gctgaccaga | gccggttgac | ttctctgcta | gaagagactt | gaacaagttc | aattttgcca | 480 |
| ggaacagtac | cctcaactca | gccgctgtca | ccgtctcctc | ttagagctca | ctcgggccag | 540 |
| gccctgatct | gcgctgtggc | tgtcctggac | gtgctgcacc | ctctgtcctt | cccccagtc | 600 |
| agtattacct | gtgaagccct | tccctccttt | attattcagg | anggctgggg | gggctccttg | 660 |
| nttctaacc |  |  |  |  |  | 669 |

<210> SEQ ID NO 24
<211> LENGTH: 442
<212> TYPE: DNA
<213> ORGANISM: Homo sapiens

<400> SEQUENCE: 24

| actagtacca | tcttgacaga | ggatacatgc | tcccaaaacg | tttgttacca | cacttaaaaa | 60 |
| tcactgccat | cattaagcat | cagtttcaaa | attatagcca | ttcatgattt | acttttcca | 120 |

```
gatgactatc attattctag tcctttgaat ttgtaagggg aaaaaaaaca aaaacaaaaa      180
cttacgatgc acttttctcc agcacatcag atttcaaatt gaaattaaa gacatgctat      240 ggtaatgcac ttgctagtac tacacacttt ggtacaacaa aaaacagagg caagaaacaa      300
cggaaagaga aaagccttcc tttgttggcc cttaaactga gtcaagatct gaaatgtaga      360
gatgatctct gacgatacct gtatgttctt attgtgtaaa taaaattgct ggtatgaaat      420
gacctaaaaa aaaaaaaga aa                                                442
```

<210> SEQ ID NO 25
<211> LENGTH: 656
<212> TYPE: DNA
<213> ORGANISM: Homo sapiens
<220> FEATURE:
<221> NAME/KEY: modified_base
<222> LOCATION: (330)
<223> OTHER INFORMATION: Where n is a, c, g or t
<220> FEATURE:
<221> NAME/KEY: modified_base
<222> LOCATION: (342)
<223> OTHER INFORMATION: Where n is a, c, g or t
<220> FEATURE:
<221> NAME/KEY: modified_base
<222> LOCATION: (418)
<223> OTHER INFORMATION: Where n is a, c, g or t
<220> FEATURE:
<221> NAME/KEY: modified_base
<222> LOCATION: (548)
<223> OTHER INFORMATION: Where n is a, c, g or t
<220> FEATURE:
<221> NAME/KEY: modified_base
<222> LOCATION: (579)
<223> OTHER INFORMATION: Where n is a, c, g or t
<220> FEATURE:
<221> NAME/KEY: modified_base
<222> LOCATION: (608)
<223> OTHER INFORMATION: Where n is a, c, g or t

<400> SEQUENCE: 25

```
tgcaagtacc acacactgtt tgaattttgc acaaaaagtg actgtaggat caggtgatag       60
ccccggaatg tacagtgtct tggtgcacca agatgccttc taaaggctga catagccttgg     120 accctaatgg ggcagagagt atagccctag cccagtggtg acatgaccac tcccttttggg    180 aggcctgagg tagaggggag tggtatgtgt tttctcagtg gaagcagcac atgagtgggt     240
gacaggatgt tagataaagg ctctagttag ggtgtcattg tcatttgaga gactgacaca     300
ctcctagcag ctggtaaagg ggtgctggan gccatggagg anctctagaa acattagcat    360
gggctgatct gattacttcc tggcatcccg ctcacttttta tgggaagtct tattagangg    420
atgggacagt tttccatatc cttgctgtgg agctctggaa cactctctaa atttccctct    480
attaaaaatc actgccctaa ctacacttcc tccttgaagg aatagaaatg gaactttctc    540
tgacatantt cttggcatgg ggagccagcc acaaatgana atctgaacgt gtccaggttt     600
ctcctganac tcatctacat agaattggtt aaaccctccc ttggaataag gaaaaa         656
```

<210> SEQ ID NO 26
<211> LENGTH: 434
<212> TYPE: DNA
<213> ORGANISM: Homo sapiens
<220> FEATURE:
<221> NAME/KEY: modified_base
<222> LOCATION: (395)
<223> OTHER INFORMATION: Where n is a, c, g or t

<400> SEQUENCE: 26

-continued

| | |
|---|---|
| actagttcag actgccacgc caaccccaga aaatacccca catgccagaa aagtgaagtc | 60 |
| ctaggtgttt ccatctatgt ttcaatctgt ccatctacca ggcctcgcga taaaaacaaa | 120 |
| acaaaaaaac gctgccaggt tttagaagca gttctggtct caaaaccatc aggatcctgc | 180 |
| caccagggtt cttttgaaat agtaccacat gtaaaaggga atttggcttt cacttcatct | 240 |
| aataactgaa ttgtcaggct ttgattgata attgtagaaa taagtagcct tctgttgtgg | 300 |
| gaataagtta taatcagtat tcatctcttt gttttttgtc actcttttct ctctaattgt | 360 |
| gtcatttgta ctgtttgaaa aatatttctt ctatnaaatt aaactaacct gccttaaaaa | 420 |
| aaaaaaaaaa aaaa | 434 |

<210> SEQ ID NO 27
<211> LENGTH: 654
<212> TYPE: DNA
<213> ORGANISM: Homo sapiens
<220> FEATURE:
<221> NAME/KEY: modified_base
<222> LOCATION: (505)
<223> OTHER INFORMATION: Where n is a, c, g or t
<220> FEATURE:
<221> NAME/KEY: modified_base
<222> LOCATION: (533)
<223> OTHER INFORMATION: Where n is a, c, g or t
<220> FEATURE:
<221> NAME/KEY: modified_base
<222> LOCATION: (563)
<223> OTHER INFORMATION: Where n is a, c, g or t
<220> FEATURE:
<221> NAME/KEY: modified_base
<222> LOCATION: (592)
<223> OTHER INFORMATION: Where n is a, c, g or t
<220> FEATURE:
<221> NAME/KEY: modified_base
<222> LOCATION: (613)
<223> OTHER INFORMATION: Where n is a, c, g or t
<220> FEATURE:
<221> NAME/KEY: modified_base
<222> LOCATION: (635)
<223> OTHER INFORMATION: Where n is a, c, g or t
<220> FEATURE:
<221> NAME/KEY: modified_base
<222> LOCATION: (638)
<223> OTHER INFORMATION: Where n is a, c, g or t

<400> SEQUENCE: 27

| | |
|---|---|
| actagtccaa cacagtcaga aacattgttt tgaatcctct gtaaaccaag gcattaatct | 60 |
| taataaacca ggatccattt aggtaccact tgatataaaa aggatatcca taatgaatat | 120 |
| tttatactgc atcctttaca ttagccacta aatacgttat tgcttgatga agacctttca | 180 |
| cagaatccta tggattgcag catttcactt ggctacttca tacccatgcc ttaaagaggg | 240 |
| gcagtttctc aaaagcagaa acatgccgcc agttctcaag ttttcctcct aactccattt | 300 |
| gaatgtaagg gcagctggcc cccaatgtgg ggaggtccga acattttctg aattcccatt | 360 |
| ttcttgttcg cggctaaatg acagtttctg tcattactta gattccgatc tttcccaaag | 420 |
| gtgttgattt acaaagaggc cagctaatag cagaaatcat gaccctgaaa gagagatgaa | 480 |
| attcaagctg tgagccaggc agganctcag tatggcaaag gtcttgagaa tcngccattt | 540 |
| ggtacaaaaa aaatttttaaa gcntttatgt tataccatgg aaccatagaa anggcaaggg | 600 |
| aattgttaag aanaatttta agtgtccaga cccanaanga aaaaaaaaa aaaa | 654 |

<210> SEQ ID NO 28
<211> LENGTH: 670
<212> TYPE: DNA
<213> ORGANISM: Homo sapiens -continued

```
<220> FEATURE:
<221> NAME/KEY: modified_base
<222> LOCATION: (101)
<223> OTHER INFORMATION: Where n is a, c, g or t
<220> FEATURE:
<221> NAME/KEY: modified_base
<222> LOCATION: (226)
<223> OTHER INFORMATION: Where n is a, c, g or t
<220> FEATURE:
<221> NAME/KEY: modified_base
<222> LOCATION: (274)
<223> OTHER INFORMATION: Where n is a, c, g or t
<220> FEATURE:
<221> NAME/KEY: modified_base
<222> LOCATION: (330)
<223> OTHER INFORMATION: Where n is a, c, g or t
<220> FEATURE:
<221> NAME/KEY: modified_base
<222> LOCATION: (385)
<223> OTHER INFORMATION: Where n is a, c, g or t
<220> FEATURE:
<221> NAME/KEY: modified_base
<222> LOCATION: (392)
<223> OTHER INFORMATION: Where n is a, c, g or t
<220> FEATURE:
<221> NAME/KEY: modified_base
<222> LOCATION: (397)
<223> OTHER INFORMATION: Where n is a, c, g or t
<220> FEATURE:
<221> NAME/KEY: modified_base
<222> LOCATION: (402)
<223> OTHER INFORMATION: Where n is a, c, g or t
<220> FEATURE:
<221> NAME/KEY: modified_base
<222> LOCATION: (452)
<223> OTHER INFORMATION: Where n is a, c, g or t
<220> FEATURE:
<221> NAME/KEY: modified_base
<222> LOCATION: (473)
<223> OTHER INFORMATION: Where n is a, c, g or t
<220> FEATURE:
<221> NAME/KEY: modified_base
<222> LOCATION: (476)
<223> OTHER INFORMATION: Where n is a, c, g or t
<220> FEATURE:
<221> NAME/KEY: modified_base
<222> LOCATION: (532)
<223> OTHER INFORMATION: Where n is a, c, g or t
<220> FEATURE:
<221> NAME/KEY: modified_base
<222> LOCATION: (534)
<223> OTHER INFORMATION: Where n is a, c, g or t
<220> FEATURE:
<221> NAME/KEY: modified_base
<222> LOCATION: (538)
<223> OTHER INFORMATION: Where n is a, c, g or t
<220> FEATURE:
<221> NAME/KEY: modified_base
<222> LOCATION: (550)
<223> OTHER INFORMATION: Where n is a, c, g or t
<220> FEATURE:
<221> NAME/KEY: modified_base
<222> LOCATION: (583)
<223> OTHER INFORMATION: Where n is a, c, g or t
<220> FEATURE:
<221> NAME/KEY: modified_base
<222> LOCATION: (595)
<223> OTHER INFORMATION: Where n is a, c, g or t
<220> FEATURE:
<221> NAME/KEY: modified_base
<222> LOCATION: (604)
<223> OTHER INFORMATION: Where n is a, c, g or t
<220> FEATURE:
<221> NAME/KEY: modified_base
<222> LOCATION: (613)
<223> OTHER INFORMATION: Where n is a, c, g or t
<220> FEATURE:
<221> NAME/KEY: modified_base
<222> LOCATION: (622)
```

<223> OTHER INFORMATION: Where n is a, c, g or t
<220> FEATURE:
<221> NAME/KEY: modified_base
<222> LOCATION: (643)
<223> OTHER INFORMATION: Where n is a, c, g or t
<220> FEATURE:
<221> NAME/KEY: modified_base
<222> LOCATION: (669)
<223> OTHER INFORMATION: Where n is a, c, g or t

<400> SEQUENCE: 28

| | | | | | |
|---|---|---|---|---|---|
| cgtgtgcaca | tactgggagg | atttccacag | ctgcacggtc | acagccctta | cggattgcca | 60 |
| ggaagggggcg | aaagatatgt | gggataaact | gagaaaagaa | nccaaaaacc | tcaacatcca | 120 |
| aggcagctta | ttcgaactct | gcggcagcgg | caacggggcg | gcggggtccc | tgctcccggc | 180 |
| gttcccggtg | ctcctggtgt | ctctctcggc | agctttagcg | acctgncttt | ccttctgagc | 240 |
| gtggggccag | ctcccccgc | ggcgcccacc | cacnctcact | ccatgctccc | ggaaatcgag | 300 |
| aggaagatca | ttagttcttt | ggggacgttn | gtgattctct | gtgatgctga | aaaacactca | 360 |
| tatagggaat | gtgggaaatc | ctganctctt | tnttatntcg | tntgatttct | tgtgttttat | 420 |
| ttgccaaaat | gttaccaatc | agtgaccaac | cnagcacagc | caaaaatcgg | acntcngctt | 480 |
| tagtccgtct | tcacacacag | aataagaaaa | cggcaaaccc | accccactttt | tnantttnat | 540 |
| tattactaan | ttttttctgt | tgggcaaaag | aatctcagga | acngcctgg | ggccnccgta | 600 |
| ctanagttaa | ccnagctagt | tncatgaaaa | atgatgggct | ccncctcaat | gggaaagcca | 660 |
| agaaaaagnc | | | | | | 670 |

<210> SEQ ID NO 29
<211> LENGTH: 551
<212> TYPE: DNA
<213> ORGANISM: Homo sapiens
<220> FEATURE:
<221> NAME/KEY: modified_base
<222> LOCATION: (336)
<223> OTHER INFORMATION: Where n is a, c, g or t
<220> FEATURE:
<221> NAME/KEY: modified_base
<222> LOCATION: (474)
<223> OTHER INFORMATION: Where n is a, c, g or t
<220> FEATURE:
<221> NAME/KEY: modified_base
<222> LOCATION: (504)
<223> OTHER INFORMATION: Where n is a, c, g or t
<220> FEATURE:
<221> NAME/KEY: modified_base
<222> LOCATION: (511)
<223> OTHER INFORMATION: Where n is a, c, g or t
<220> FEATURE:
<221> NAME/KEY: modified_base
<222> LOCATION: (522)
<223> OTHER INFORMATION: Where n is a, c, g or t
<220> FEATURE:
<221> NAME/KEY: modified_base
<222> LOCATION: (523)
<223> OTHER INFORMATION: Where n is a, c, g or t
<220> FEATURE:
<221> NAME/KEY: modified_base
<222> LOCATION: (524)
<223> OTHER INFORMATION: Where n is a, c, g or t
<220> FEATURE:
<221> NAME/KEY: modified_base
<222> LOCATION: (540)
<223> OTHER INFORMATION: Where n is a, c, g or t
<220> FEATURE:
<221> NAME/KEY: modified_base
<222> LOCATION: (547)
<223> OTHER INFORMATION: Where n is a, c, g or t

<400> SEQUENCE: 29

```
actagtcctc cacagcctgt gaatcccct agacctttca agcatagtga gcggagaaga      60
agatctcagc gtttagccac cttacccatg cctgatgatt ctgtagaaaa ggtttcttct     120
ccctctccag ccactgatgg gaaagtattc tccatcagtt ctcaaaatca gcaagaatct    180
tcagtaccag aggtgcctga tgttgcacat ttgccacttg agaagctggg accctgtctc    240
cctcttgact taagtcgtgg ttcagaagtt acagcaccgg tagcctcaga ttcctcttac    300
cgtaatgaat gtcccagggc agaaaaagag gatacncaga tgcttccaaa tccttcttcc    360
aaagcaatag ctgatgggaa gaggagctcc agcagcagca ggaatatcga aaacagaaaa    420
aaaagtgaaa ttgggaagac aaaagctcaa cagcatttgg taaggagaaa aganaagatg    480
aggaaggaag agagaagaga gacnaagatc nctacggacc gnnncggaag aagaagaagn    540
aaaaaanaaa a                                                         551

<210> SEQ ID NO 30
<211> LENGTH: 684
<212> TYPE: DNA
<213> ORGANISM: Homo sapiens
<220> FEATURE:
<221> NAME/KEY: modified_base
<222> LOCATION: (545)
<223> OTHER INFORMATION: Where n is a, c, g or t
<220> FEATURE:
<221> NAME/KEY: modified_base
<222> LOCATION: (570)
<223> OTHER INFORMATION: Where n is a, c, g or t
<220> FEATURE:
<221> NAME/KEY: modified_base
<222> LOCATION: (606)
<223> OTHER INFORMATION: Where n is a, c, g or t
<220> FEATURE:
<221> NAME/KEY: modified_base
<222> LOCATION: (657)
<223> OTHER INFORMATION: Where n is a, c, g or t
<220> FEATURE:
<221> NAME/KEY: modified_base
<222> LOCATION: (684)
<223> OTHER INFORMATION: Where n is a, c, g or t

<400> SEQUENCE: 30
actagttcta tctggaaaaa gcccggggtg gaagaagctg tggagagtgc gtgtgcaatg      60
cgagactcat ttcttggaag catccctggc aaaaatgcag ctgagtacaa ggttatcact    120
gtgatagaac ctggactgct ttttgagata atagagatgc tgcagtctga agagacttcc    180
agcacctctc agttgaatga attaatgatg gcttctgagt caactttact ggctcaggaa    240
ccacgagaga tgactgcaga tgtaatcgag cttaaaggga aattcctcat caacttagaa    300
ggtggtgata ttcgtgaaga gtcttcctat aaagtaattg tcatgccgac tacgaaagaa    360
aaatgccccc gttgttggaa gtatacagcg ggagtcttca gatacactgt gtcctcgatg    420
tgcagaagtt gtcagtggga aaatagtatt aacagctcac tcgagcaaga accctcctga    480
cagtactggg ctagaagttt ggatggatta tttacaatat aggaaagaaa gccaagaatt    540
aggtnatgag tggatgagta atggtggan gatgggaat tcaaatcaga attatggaag    600
aagttnttcc tgttactata gaaggaatt atgtttattt acatgcagaa aatatanatg    660
tgtggtgtgt accgtggatg gaan                                          684

<210> SEQ ID NO 31
<211> LENGTH: 654
<212> TYPE: DNA
<213> ORGANISM: Homo sapiens
<220> FEATURE:
```

```
<221> NAME/KEY: modified_base
<222> LOCATION: (326)
<223> OTHER INFORMATION: Where n is a, c, g or t
<220> FEATURE:
<221> NAME/KEY: modified_base
<222> LOCATION: (582)
<223> OTHER INFORMATION: Where n is a, c, g or t
<220> FEATURE:
<221> NAME/KEY: modified_base
<222> LOCATION: (651)
<223> OTHER INFORMATION: Where n is a, c, g or t

<400> SEQUENCE: 31
gcgcagaaaa ggaaccaata tttcagaaac aagcttaata ggaacagctg cctgtacatc      60
aacatcttct cagaatgacc cagaagttat catcgtggga gctggcgtgc ttggctctgc     120
tttggcagct gtgctttcca gagatggaag aaaggtgaca gtcattgaga gagacttaaa     180
agagcctgac agaatagttg gagaattcct gcagccgggt ggttatcatg ttctcaaaga     240
ccttggtctt ggagatacag tggaaggtct tgatgcccag gttgtaaatg gttacatgat     300
tcatgatcag ggaaagcaaa tcagangttc agattcctta ccctctgtca gaaacaatc     360 aagtgcagag tggaagagct ttccatcacg gaagattcat catgagtctc cggaaagcag     420
ctatggcaga gcccaatgca aagtttattg aaggtgttgt gttacagtta ttagaggaag     480
atgatgttgt gatgggagtt cagtacaagg ataaagagac tgggagatat caaggaactc     540
catgctccac tgactgttgt tgcagatggg cttttctcca anttcaggaa aagcctggtc     600
tcaataaagt ttctgtatca ctcatttggt tggcttctta tgaagaatgc nccc          654

<210> SEQ ID NO 32
<211> LENGTH: 673
<212> TYPE: DNA
<213> ORGANISM: Homo sapiens
<220> FEATURE:
<221> NAME/KEY: modified_base
<222> LOCATION: (376)
<223> OTHER INFORMATION: Where n is a, c, g or t
<220> FEATURE:
<221> NAME/KEY: modified_base
<222> LOCATION: (545)
<223> OTHER INFORMATION: Where n is a, c, g or t
<220> FEATURE:
<221> NAME/KEY: modified_base
<222> LOCATION: (627)
<223> OTHER INFORMATION: Where n is a, c, g or t

<400> SEQUENCE: 32
actagtgaag aaaagaaat tctgatacgg gacaaaaatg ctcttcaaaa catcattctt       60
tatcacctga caccaggagt tttcattgga aaaggatttg aacctggtgt tactaacatt     120
ttaaagacca cacaaggaag caaatctctt ctgaaagaag taaatgatac acttctggtg     180
aatgaattga atcaaaaga atctgacatc atgacaacaa atggtgtaat tcatgttgta     240
gataaactcc tctatccagc agacacacct gttggaaatg atcaactgct ggaaatactt     300
aataaattaa tcaaatacat ccaaattaag tttgttcgtg gtagcacctt caaagaaatc     360
cccgtgactg tctatnagcc aattattaaa aaatacacca aaatcattga tgggagtgcc     420
tgtgggaaat aactgaaaaa gagaccgaga agaacgaatc attacaggtc ctgaaataaa     480
atacctagga tttctactgg aggtggagaa acagaagaac tctgaagaaa ttgttacaag     540
aagangtccc aaggtcacca aattcattga aggtggtgat ggtctttatt tgaagatgaa     600
gaaattaaaa gacgcttcag ggagacnccc catgaaggaa ttgccagcca caaaaaaatt     660
cagggattag aaa                                                        673
```

<210> SEQ ID NO 33
<211> LENGTH: 673
<212> TYPE: DNA
<213> ORGANISM: Homo sapiens
<220> FEATURE:
<221> NAME/KEY: modified_base
<222> LOCATION: (325)
<223> OTHER INFORMATION: Where n is a, c, g or t
<220> FEATURE:
<221> NAME/KEY: modified_base
<222> LOCATION: (419)
<223> OTHER INFORMATION: Where n is a, c, g or t
<220> FEATURE:
<221> NAME/KEY: modified_base
<222> LOCATION: (452)
<223> OTHER INFORMATION: Where n is a, c, g or t
<220> FEATURE:
<221> NAME/KEY: modified_base
<222> LOCATION: (532)
<223> OTHER INFORMATION: Where n is a, c, g or t
<220> FEATURE:
<221> NAME/KEY: modified_base
<222> LOCATION: (538)
<223> OTHER INFORMATION: Where n is a, c, g or t
<220> FEATURE:
<221> NAME/KEY: modified_base
<222> LOCATION: (542)
<223> OTHER INFORMATION: Where n is a, c, g or t
<220> FEATURE:
<221> NAME/KEY: modified_base
<222> LOCATION: (571)
<223> OTHER INFORMATION: Where n is a, c, g or t
<220> FEATURE:
<221> NAME/KEY: modified_base
<222> LOCATION: (600)
<223> OTHER INFORMATION: Where n is a, c, g or t
<220> FEATURE:
<221> NAME/KEY: modified_base
<222> LOCATION: (616)
<223> OTHER INFORMATION: Where n is a, c, g or t
<220> FEATURE:
<221> NAME/KEY: modified_base
<222> LOCATION: (651)
<223> OTHER INFORMATION: Where n is a, c, g or t
<220> FEATURE:
<221> NAME/KEY: modified_base
<222> LOCATION: (653)
<223> OTHER INFORMATION: Where n is a, c, g or t
<220> FEATURE:
<221> NAME/KEY: modified_base
<222> LOCATION: (672)
<223> OTHER INFORMATION: Where n is a, c, g or t

<400> SEQUENCE: 33

```
actagttatt tactttcctc cgcttcagaa ggtttttcag actgagagcc taagcatact      60
ggatctgttg tttcttttgg gtctcacctc atcagtgtgc atagtggcag aaattataaa     120
gaaggttgaa aggagcaggg aaaagatcca gaagcatgtt agttcgacat catcatcttt     180
tcttgaagta tgatgcatat tgcattattt tatttgcaaa ctaggaattg cagtctgagg     240
atcatttaga agggcaagtt caagaggata tgaagatttg agaactttt aactattcat      300
tgactaaaaa tgaacattaa tgttnaagac ttaagacttt aacctgctgg cagtcccaaa     360
tgaaattatg caactttgat atcatattcc ttgatttaaa ttgggctttt gtgattgant     420
gaaactttat aaagcatatg gtcagttatt tnattaaaaa ggcaaaacct gaaccacctt     480
ctgcacttaa agaagtctaa cagtacaaat acctatctat cttagatgga tntatttntt     540
tntattttta aatattgtac tatttatggt nggtggggct ttcttactaa tacacaaatn     600
aatttatcat ttcaaggca ttctatttgg gtttagaagt tgattccaag nantgcatat      660
```
ttcgctactg tnt                                                          673

<210> SEQ ID NO 34
<211> LENGTH: 684
<212> TYPE: DNA
<213> ORGANISM: Homo sapiens
<220> FEATURE:
<221> NAME/KEY: modified_base
<222> LOCATION: (414)
<223> OTHER INFORMATION: Where n is a, c, g or t
<220> FEATURE:
<221> NAME/KEY: modified_base
<222> LOCATION: (472)
<223> OTHER INFORMATION: Where n is a, c, g or t
<220> FEATURE:
<221> NAME/KEY: modified_base
<222> LOCATION: (480)
<223> OTHER INFORMATION: Where n is a, c, g or t
<220> FEATURE:
<221> NAME/KEY: modified_base
<222> LOCATION: (490)
<223> OTHER INFORMATION: Where n is a, c, g or t
<220> FEATURE:
<221> NAME/KEY: modified_base
<222> LOCATION: (503)
<223> OTHER INFORMATION: Where n is a, c, g or t
<220> FEATURE:
<221> NAME/KEY: modified_base
<222> LOCATION: (507)
<223> OTHER INFORMATION: Where n is a, c, g or t
<220> FEATURE:
<221> NAME/KEY: modified_base
<222> LOCATION: (508)
<223> OTHER INFORMATION: Where n is a, c, g or t
<220> FEATURE:
<221> NAME/KEY: modified_base
<222> LOCATION: (513)
<223> OTHER INFORMATION: Where n is a, c, g or t
<220> FEATURE:
<221> NAME/KEY: modified_base
<222> LOCATION: (523)
<223> OTHER INFORMATION: Where n is a, c, g or t
<220> FEATURE:
<221> NAME/KEY: modified_base
<222> LOCATION: (574)
<223> OTHER INFORMATION: Where n is a, c, g or t
<220> FEATURE:
<221> NAME/KEY: modified_base
<222> LOCATION: (575)
<223> OTHER INFORMATION: Where n is a, c, g or t
<220> FEATURE:
<221> NAME/KEY: modified_base
<222> LOCATION: (598)
<223> OTHER INFORMATION: Where n is a, c, g or t
<220> FEATURE:
<221> NAME/KEY: modified_base
<222> LOCATION: (659)
<223> OTHER INFORMATION: Where n is a, c, g or t
<220> FEATURE:
<221> NAME/KEY: modified_base
<222> LOCATION: (662)
<223> OTHER INFORMATION: Where n is a, c, g or t
<220> FEATURE:
<221> NAME/KEY: modified_base
<222> LOCATION: (675)
<223> OTHER INFORMATION: Where n is a, c, g or t

<400> SEQUENCE: 34
actagtttat tcaagaaaag aacttactga ttcctctgtt cctaaagcaa gagtggcagg      60
tgatcagggc tggtgtagca tccggttcct ttagtgcagc taactgcatt tgtcactgat    120
gaccaaggag gaaatcacta agacatttga gaagcagtgg tatgaacgtt cttggacaag    180
ccacagttct gagccttaac cctgtagttt gcacacaaga acgagctcca cctcccttc    240 ttcaggagga atctgtgcgg atagattggc tggactttc aatggttctg ggttgcaagt    300

```
gggcactgtt atggctgggt atggagcgga cagccccagg aatcagagcc tcagcccggc    360
tgcctggttg gaaggtacag gtgttcagca ccttcggaaa aagggcataa agtngtgggg    420
gacaattctc agtccaagaa gaatgcattg accattgctg gctatttgct tncctagtan    480
gaattggatn catttttgac cangatnntt ctnctatgct ttnttgcaat gaaatcaaat    540
cccgcattat ctacaagtgg tatgaagtcc tgcnncccccc agagaggctg ttcaggcnat   600
gtcttccaag ggcagggtgg gttacaccat tttacctccc ctctccccccc agattatgna  660 cncagaagga atttntttcc tccc                                          684
```

<210> SEQ ID NO 35
<211> LENGTH: 614
<212> TYPE: DNA
<213> ORGANISM: Homo sapiens
<220> FEATURE:
<221> NAME/KEY: modified_base
<222> LOCATION: (17)
<223> OTHER INFORMATION: Where n is a, c, g or t
<220> FEATURE:
<221> NAME/KEY: modified_base
<222> LOCATION: (20)
<223> OTHER INFORMATION: Where n is a, c, g or t
<220> FEATURE:
<221> NAME/KEY: modified_base
<222> LOCATION: (152)
<223> OTHER INFORMATION: Where n is a, c, g or t
<220> FEATURE:
<221> NAME/KEY: modified_base
<222> LOCATION: (223)
<223> OTHER INFORMATION: Where n is a, c, g or t
<220> FEATURE:
<221> NAME/KEY: modified_base
<222> LOCATION: (267)
<223> OTHER INFORMATION: Where n is a, c, g or t
<220> FEATURE:
<221> NAME/KEY: modified_base
<222> LOCATION: (287)
<223> OTHER INFORMATION: Where n is a, c, g or t
<220> FEATURE:
<221> NAME/KEY: modified_base
<222> LOCATION: (304)
<223> OTHER INFORMATION: Where n is a, c, g or t
<220> FEATURE:
<221> NAME/KEY: modified_base
<222> LOCATION: (306)
<223> OTHER INFORMATION: Where n is a, c, g or t
<220> FEATURE:
<221> NAME/KEY: modified_base
<222> LOCATION: (316)
<223> OTHER INFORMATION: Where n is a, c, g or t
<220> FEATURE:
<221> NAME/KEY: modified_base
<222> LOCATION: (319)
<223> OTHER INFORMATION: Where n is a, c, g or t
<220> FEATURE:
<221> NAME/KEY: modified_base
<222> LOCATION: (321)
<223> OTHER INFORMATION: Where n is a, c, g or t
<220> FEATURE:
<221> NAME/KEY: modified_base
<222> LOCATION: (355)
<223> OTHER INFORMATION: Where n is a, c, g or t
<220> FEATURE:
<221> NAME/KEY: modified_base
<222> LOCATION: (365)
<223> OTHER INFORMATION: Where n is a, c, g or t
<220> FEATURE:
<221> NAME/KEY: modified_base
<222> LOCATION: (382)
<223> OTHER INFORMATION: Where n is a, c, g or t
<220> FEATURE:
<221> NAME/KEY: modified_base
<222> LOCATION: (391)

-continued

```
<223> OTHER INFORMATION: Where n is a, c, g or t
<220> FEATURE:
<221> NAME/KEY: modified_base
<222> LOCATION: (407)
<223> OTHER INFORMATION: Where n is a, c, g or t
<220> FEATURE:
<221> NAME/KEY: modified_base
<222> LOCATION: (419)
<223> OTHER INFORMATION: Where n is a, c, g or t
<220> FEATURE:
<221> NAME/KEY: modified_base
<222> LOCATION: (428)
<223> OTHER INFORMATION: Where n is a, c, g or t
<220> FEATURE:
<221> NAME/KEY: modified_base
<222> LOCATION: (434)
<223> OTHER INFORMATION: Where n is a, c, g or t
<220> FEATURE:
<221> NAME/KEY: modified_base
<222> LOCATION: (464)
<223> OTHER INFORMATION: Where n is a, c, g or t
<220> FEATURE:
<221> NAME/KEY: modified_base
<222> LOCATION: (467)
<223> OTHER INFORMATION: Where n is a, c, g or t
<220> FEATURE:
<221> NAME/KEY: modified_base
<222> LOCATION: (477)
<223> OTHER INFORMATION: Where n is a, c, g or t
<220> FEATURE:
<221> NAME/KEY: modified_base
<222> LOCATION: (480)
<223> OTHER INFORMATION: Where n is a, c, g or t
<220> FEATURE:
<221> NAME/KEY: modified_base
<222> LOCATION: (495)
<223> OTHER INFORMATION: Where n is a, c, g or t
<220> FEATURE:
<221> NAME/KEY: modified_base
<222> LOCATION: (499)
<223> OTHER INFORMATION: Where n is a, c, g or t
<220> FEATURE:
<221> NAME/KEY: modified_base
<222> LOCATION: (505)
<223> OTHER INFORMATION: Where n is a, c, g or t
<220> FEATURE:
<221> NAME/KEY: modified_base
<222> LOCATION: (515)
<223> OTHER INFORMATION: Where n is a, c, g or t
<220> FEATURE:
<221> NAME/KEY: modified_base
<222> LOCATION: (516)
<223> OTHER INFORMATION: Where n is a, c, g or t
<220> FEATURE:
<221> NAME/KEY: modified_base
<222> LOCATION: (522)
<223> OTHER INFORMATION: Where n is a, c, g or t
<220> FEATURE:
<221> NAME/KEY: modified_base
<222> LOCATION: (524)
<223> OTHER INFORMATION: Where n is a, c, g or t
<220> FEATURE:
<221> NAME/KEY: modified_base
<222> LOCATION: (527)
<223> OTHER INFORMATION: Where n is a, c, g or t
<220> FEATURE:
<221> NAME/KEY: modified_base
<222> LOCATION: (542)
<223> OTHER INFORMATION: Where n is a, c, g or t
<220> FEATURE:
<221> NAME/KEY: modified_base
<222> LOCATION: (547)
<223> OTHER INFORMATION: Where n is a, c, g or t
<220> FEATURE:
<221> NAME/KEY: modified_base
<222> LOCATION: (549)
<223> OTHER INFORMATION: Where n is a, c, g or t
<220> FEATURE:
<221> NAME/KEY: modified_base
```

```
<222> LOCATION: (567)
<223> OTHER INFORMATION: Where n is a, c, g or t
<220> FEATURE:
<221> NAME/KEY: modified_base
<222> LOCATION: (572)
<223> OTHER INFORMATION: Where n is a, c, g or t
<220> FEATURE:
<221> NAME/KEY: modified_base
<222> LOCATION: (576)
<223> OTHER INFORMATION: Where n is a, c, g or t
<220> FEATURE:
<221> NAME/KEY: modified_base
<222> LOCATION: (578)
<223> OTHER INFORMATION: Where n is a, c, g or t

<400> SEQUENCE: 35
actagtccaa cgcgttngcn aatattcccc tggtagccta cttccttacc cccgaatatt    60
ggtaagatcg agcaatggct tcaggacatg ggttctcttc tcctgtgatc attcaagtgc   120
tcactgcatg aagactggct tgtctcagtg tntcaacctc accagggctg tctcttggtc   180
cacacctcgc tccctgttag tgccgtatga cagcccccat canatgacct tggccaagtc   240
acggtttctc tgtggtcaat gttggtnggc tgattggtgg aaagtanggt ggaccaaagg   300
aagncncgtg agcagncanc nccagttctg caccagcagc gcctccgtcc tactngggtg   360
ttccngtttc tcctggccct gngtgggcta nggcctgatt cgggaanatg cctttgcang   420
gaaggganga taantgggat ctaccaattg attctggcaa aacnatntct aagattnttn   480
tgctttatgt ggganacana tctanctctc atttnntgct gnanatnaca ccctactcgt   540
gntcgancnc gtcttcgatt ttcgganaca cnccantnaa tactggcgtt ctgttgttaa   600
aaaaaaaaaa aaaa                                                     614

<210> SEQ ID NO 36
<211> LENGTH: 686
<212> TYPE: DNA
<213> ORGANISM: Homo sapiens
<220> FEATURE:
<221> NAME/KEY: modified_base
<222> LOCATION: (222)
<223> OTHER INFORMATION: Where n is a, c, g or t
<220> FEATURE:
<221> NAME/KEY: modified_base
<222> LOCATION: (224)
<223> OTHER INFORMATION: Where n is a, c, g or t
<220> FEATURE:
<221> NAME/KEY: modified_base
<222> LOCATION: (237)
<223> OTHER INFORMATION: Where n is a, c, g or t
<220> FEATURE:
<221> NAME/KEY: modified_base
<222> LOCATION: (264)
<223> OTHER INFORMATION: Where n is a, c, g or t
<220> FEATURE:
<221> NAME/KEY: modified_base
<222> LOCATION: (285)
<223> OTHER INFORMATION: Where n is a, c, g or t
<220> FEATURE:
<221> NAME/KEY: modified_base
<222> LOCATION: (548)
<223> OTHER INFORMATION: Where n is a, c, g or t
<220> FEATURE:
<221> NAME/KEY: modified_base
<222> LOCATION: (551)
<223> OTHER INFORMATION: Where n is a, c, g or t
<220> FEATURE:
<221> NAME/KEY: modified_base
<222> LOCATION: (628)
<223> OTHER INFORMATION: Where n is a, c, g or t
<220> FEATURE:
<221> NAME/KEY: modified_base
<222> LOCATION: (643)
```

-continued

<223> OTHER INFORMATION: Where n is a, c, g or t
<220> FEATURE:
<221> NAME/KEY: modified_base
<222> LOCATION: (645)
<223> OTHER INFORMATION: Where n is a, c, g or t
<220> FEATURE:
<221> NAME/KEY: modified_base
<222> LOCATION: (665)
<223> OTHER INFORMATION: Where n is a, c, g or t
<220> FEATURE:
<221> NAME/KEY: modified_base
<222> LOCATION: (674)
<223> OTHER INFORMATION: Where n is a, c, g or t

<400> SEQUENCE: 36

```
gtggctggcc cggttctccg cttctcccca tcccctactt tcctccctcc ctcccttcc      60
ctccctcgtc gactgttgct tgctggtcgc agactccctg acccctccct caccctccc     120
taacctcggt gccaccggat tgcccttctt ttcctgttgc ccagcccagc cctagtgtca    180
gggcggggc ctggagcagc ccgaggcact gcagcagaag ananaaaaga cacgacnaac     240
ctcagctcgc cagtccggtc gctngcttcc cgccgcatgg caatnagaca gacgccgctc    300
acctgctctg ggcacacgcg acccgtggtt gatttggcct tcagtggcat caccttatg    360
ggtatttctt aatcagcgct tgcaaagatg gttaacctat gctacgccag ggagatacag    420
gagactggat tggaacattt ttgggggtcta aaggtctgtt tggggtgcaa cactgaataa    480
ggatgccacc aaagcagcta cagcagctgc agatttcaca gcccaagtgt gggatgctgt    540
ctcagganat naattgataa cctggctcat aacacattgt caagaatgtg gatttcccca    600
ggatattatt atttgtttac cgggggganag gataactgtt tcncntattt taattgaaca    660
aactnaaaca aaanctaagg aaatcc                                          686
```

<210> SEQ ID NO 37
<211> LENGTH: 681
<212> TYPE: DNA
<213> ORGANISM: Homo sapiens
<220> FEATURE:
<221> NAME/KEY: modified_base
<222> LOCATION: (7)
<223> OTHER INFORMATION: Where n is a, c, g or t
<220> FEATURE:
<221> NAME/KEY: modified_base
<222> LOCATION: (10)
<223> OTHER INFORMATION: Where n is a, c, g or t
<220> FEATURE:
<221> NAME/KEY: modified_base
<222> LOCATION: (11)
<223> OTHER INFORMATION: Where n is a, c, g or t
<220> FEATURE:
<221> NAME/KEY: modified_base
<222> LOCATION: (19)
<223> OTHER INFORMATION: Where n is a, c, g or t
<220> FEATURE:
<221> NAME/KEY: modified_base
<222> LOCATION: (25)
<223> OTHER INFORMATION: Where n is a, c, g or t
<220> FEATURE:
<221> NAME/KEY: modified_base
<222> LOCATION: (32)
<223> OTHER INFORMATION: Where n is a, c, g or t
<220> FEATURE:
<221> NAME/KEY: modified_base
<222> LOCATION: (46)
<223> OTHER INFORMATION: Where n is a, c, g or t
<220> FEATURE:
<221> NAME/KEY: modified_base
<222> LOCATION: (53)
<223> OTHER INFORMATION: Where n is a, c, g or t
<220> FEATURE:
<221> NAME/KEY: modified_base -continued

```
<222> LOCATION: (77)
<223> OTHER INFORMATION: Where n is a, c, g or t
<220> FEATURE:
<221> NAME/KEY: modified_base
<222> LOCATION: (93)
<223> OTHER INFORMATION: Where n is a, c, g or t
<220> FEATURE:
<221> NAME/KEY: modified_base
<222> LOCATION: (101)
<223> OTHER INFORMATION: Where n is a, c, g or t
<220> FEATURE:
<221> NAME/KEY: modified_base
<222> LOCATION: (103)
<223> OTHER INFORMATION: Where n is a, c, g or t
<220> FEATURE:
<221> NAME/KEY: modified_base
<222> LOCATION: (109)
<223> OTHER INFORMATION: Where n is a, c, g or t
<220> FEATURE:
<221> NAME/KEY: modified_base
<222> LOCATION: (115)
<223> OTHER INFORMATION: Where n is a, c, g or t
<220> FEATURE:
<221> NAME/KEY: modified_base
<222> LOCATION: (123)
<223> OTHER INFORMATION: Where n is a, c, g or t
<220> FEATURE:
<221> NAME/KEY: modified_base
<222> LOCATION: (128)
<223> OTHER INFORMATION: Where n is a, c, g or t
<220> FEATURE:
<221> NAME/KEY: modified_base
<222> LOCATION: (139)
<223> OTHER INFORMATION: Where n is a, c, g or t
<220> FEATURE:
<221> NAME/KEY: modified_base
<222> LOCATION: (157)
<223> OTHER INFORMATION: Where n is a, c, g or t
<220> FEATURE:
<221> NAME/KEY: modified_base
<222> LOCATION: (175)
<223> OTHER INFORMATION: Where n is a, c, g or t
<220> FEATURE:
<221> NAME/KEY: modified_base
<222> LOCATION: (180)
<223> OTHER INFORMATION: Where n is a, c, g or t
<220> FEATURE:
<221> NAME/KEY: modified_base
<222> LOCATION: (192)
<223> OTHER INFORMATION: Where n is a, c, g or t
<220> FEATURE:
<221> NAME/KEY: modified_base
<222> LOCATION: (193)
<223> OTHER INFORMATION: Where n is a, c, g or t
<220> FEATURE:
<221> NAME/KEY: modified_base
<222> LOCATION: (194)
<223> OTHER INFORMATION: Where n is a, c, g or t
<220> FEATURE:
<221> NAME/KEY: modified_base
<222> LOCATION: (212)
<223> OTHER INFORMATION: Where n is a, c, g or t
<220> FEATURE:
<221> NAME/KEY: modified_base
<222> LOCATION: (218)
<223> OTHER INFORMATION: Where n is a, c, g or t
<220> FEATURE:
<221> NAME/KEY: modified_base
<222> LOCATION: (226)
<223> OTHER INFORMATION: Where n is a, c, g or t
<220> FEATURE:
<221> NAME/KEY: modified_base
<222> LOCATION: (227)
<223> OTHER INFORMATION: Where n is a, c, g or t
<220> FEATURE:
<221> NAME/KEY: modified_base
<222> LOCATION: (233)
<223> OTHER INFORMATION: Where n is a, c, g or t
<220> FEATURE:
```

-continued

```
<221> NAME/KEY: modified_base
<222> LOCATION: (240)
<223> OTHER INFORMATION: Where n is a, c, g or t
<220> FEATURE:
<221> NAME/KEY: modified_base
<222> LOCATION: (241)
<223> OTHER INFORMATION: Where n is a, c, g or t
<220> FEATURE:
<221> NAME/KEY: modified_base
<222> LOCATION: (259)
<223> OTHER INFORMATION: Where n is a, c, g or t
<220> FEATURE:
<221> NAME/KEY: modified_base
<222> LOCATION: (260)
<223> OTHER INFORMATION: Where n is a, c, g or t
<220> FEATURE:
<221> NAME/KEY: modified_base
<222> LOCATION: (267)
<223> OTHER INFORMATION: Where n is a, c, g or t
<220> FEATURE:
<221> NAME/KEY: modified_base
<222> LOCATION: (288)
<223> OTHER INFORMATION: Where n is a, c, g or t
<220> FEATURE:
<221> NAME/KEY: modified_base
<222> LOCATION: (296)
<223> OTHER INFORMATION: Where n is a, c, g or t
<220> FEATURE:
<221> NAME/KEY: modified_base
<222> LOCATION: (297)
<223> OTHER INFORMATION: Where n is a, c, g or t
<220> FEATURE:
<221> NAME/KEY: modified_base
<222> LOCATION: (298)
<223> OTHER INFORMATION: Where n is a, c, g or t
<220> FEATURE:
<221> NAME/KEY: modified_base
<222> LOCATION: (312)
<223> OTHER INFORMATION: Where n is a, c, g or t
<220> FEATURE:
<221> NAME/KEY: modified_base
<222> LOCATION: (313)
<223> OTHER INFORMATION: Where n is a, c, g or t
<220> FEATURE:
<221> NAME/KEY: modified_base
<222> LOCATION: (314)
<223> OTHER INFORMATION: Where n is a, c, g or t
<220> FEATURE:
<221> NAME/KEY: modified_base
<222> LOCATION: (320)
<223> OTHER INFORMATION: Where n is a, c, g or t
<220> FEATURE:
<221> NAME/KEY: modified_base
<222> LOCATION: (325)
<223> OTHER INFORMATION: Where n is a, c, g or t
<220> FEATURE:
<221> NAME/KEY: modified_base
<222> LOCATION: (330)
<223> OTHER INFORMATION: Where n is a, c, g or t
<220> FEATURE:
<221> NAME/KEY: modified_base
<222> LOCATION: (337)
<223> OTHER INFORMATION: Where n is a, c, g or t
<220> FEATURE:
<221> NAME/KEY: modified_base
<222> LOCATION: (345)
<223> OTHER INFORMATION: Where n is a, c, g or t
<220> FEATURE:
<221> NAME/KEY: modified_base
<222> LOCATION: (346)
<223> OTHER INFORMATION: Where n is a, c, g or t
<220> FEATURE:
<221> NAME/KEY: modified_base
<222> LOCATION: (352)
<223> OTHER INFORMATION: Where n is a, c, g or t
<220> FEATURE:
<221> NAME/KEY: modified_base
<222> LOCATION: (353)
<223> OTHER INFORMATION: Where n is a, c, g or t
```

```
-continued

<220> FEATURE:
<221> NAME/KEY: modified_base
<222> LOCATION: (356)
<223> OTHER INFORMATION: Where n is a, c, g or t
<220> FEATURE:
<221> NAME/KEY: modified_base
<222> LOCATION: (382)
<223> OTHER INFORMATION: Where n is a, c, g or t
<220> FEATURE:
<221> NAME/KEY: modified_base
<222> LOCATION: (385)
<223> OTHER INFORMATION: Where n is a, c, g or t
<220> FEATURE:
<221> NAME/KEY: modified_base
<222> LOCATION: (400)
<223> OTHER INFORMATION: Where n is a, c, g or t
<220> FEATURE:
<221> NAME/KEY: modified_base
<222> LOCATION: (427)
<223> OTHER INFORMATION: Where n is a, c, g or t
<220> FEATURE:
<221> NAME/KEY: modified_base
<222> LOCATION: (481)
<223> OTHER INFORMATION: Where n is a, c, g or t
<220> FEATURE:
<221> NAME/KEY: modified_base
<222> LOCATION: (484)
<223> OTHER INFORMATION: Where n is a, c, g or t
<220> FEATURE:
<221> NAME/KEY: modified_base
<222> LOCATION: (485)
<223> OTHER INFORMATION: Where n is a, c, g or t
<220> FEATURE:
<221> NAME/KEY: modified_base
<222> LOCATION: (491)
<223> OTHER INFORMATION: Where n is a, c, g or t
<220> FEATURE:
<221> NAME/KEY: modified_base
<222> LOCATION: (505)
<223> OTHER INFORMATION: Where n is a, c, g or t
<220> FEATURE:
<221> NAME/KEY: modified_base
<222> LOCATION: (515)
<223> OTHER INFORMATION: Where n is a, c, g or t
<220> FEATURE:
<221> NAME/KEY: modified_base
<222> LOCATION: (533)
<223> OTHER INFORMATION: Where n is a, c, g or t
<220> FEATURE:
<221> NAME/KEY: modified_base
<222> LOCATION: (542)
<223> OTHER INFORMATION: Where n is a, c, g or t
<220> FEATURE:
<221> NAME/KEY: modified_base
<222> LOCATION: (544)
<223> OTHER INFORMATION: Where n is a, c, g or t
<220> FEATURE:
<221> NAME/KEY: modified_base
<222> LOCATION: (554)
<223> OTHER INFORMATION: Where n is a, c, g or t
<220> FEATURE:
<221> NAME/KEY: modified_base
<222> LOCATION: (557)
<223> OTHER INFORMATION: Where n is a, c, g or t
<220> FEATURE:
<221> NAME/KEY: modified_base
<222> LOCATION: (560)
<223> OTHER INFORMATION: Where n is a, c, g or t
<220> FEATURE:
<221> NAME/KEY: modified_base
<222> LOCATION: (561)
<223> OTHER INFORMATION: Where n is a, c, g or t
<220> FEATURE:
<221> NAME/KEY: modified_base
<222> LOCATION: (564)
<223> OTHER INFORMATION: Where n is a, c, g or t
<220> FEATURE:
<221> NAME/KEY: modified_base
<222> LOCATION: (575)
```

<223> OTHER INFORMATION: Where n is a, c, g or t
<220> FEATURE:
<221> NAME/KEY: modified_base
<222> LOCATION: (583)
<223> OTHER INFORMATION: Where n is a, c, g or t
<220> FEATURE:
<221> NAME/KEY: modified_base
<222> LOCATION: (589)
<223> OTHER INFORMATION: Where n is a, c, g or t
<220> FEATURE:
<221> NAME/KEY: modified_base
<222> LOCATION: (595)
<223> OTHER INFORMATION: Where n is a, c, g or t
<220> FEATURE:
<221> NAME/KEY: modified_base
<222> LOCATION: (607)
<223> OTHER INFORMATION: Where n is a, c, g or t
<220> FEATURE:
<221> NAME/KEY: modified_base
<222> LOCATION: (619)
<223> OTHER INFORMATION: Where n is a, c, g or t
<220> FEATURE:
<221> NAME/KEY: modified_base
<222> LOCATION: (628)
<223> OTHER INFORMATION: Where n is a, c, g or t
<220> FEATURE:
<221> NAME/KEY: modified_base
<222> LOCATION: (634)
<223> OTHER INFORMATION: Where n is a, c, g or t
<220> FEATURE:
<221> NAME/KEY: modified_base
<222> LOCATION: (640)
<223> OTHER INFORMATION: Where n is a, c, g or t
<220> FEATURE:
<221> NAME/KEY: modified_base
<222> LOCATION: (645)
<223> OTHER INFORMATION: Where n is a, c, g or t
<220> FEATURE:
<221> NAME/KEY: modified_base
<222> LOCATION: (657)
<223> OTHER INFORMATION: Where n is a, c, g or t
<220> FEATURE:
<221> NAME/KEY: modified_base
<222> LOCATION: (670)
<223> OTHER INFORMATION: Where n is a, c, g or t

<400> SEQUENCE: 37

```
gagacanacn naacgtcang agaanaaaag angcatggaa cacaanccag gcncgatggc      60
caccttccca ccagcancca gcgccccca gcngccccca ngccggang accangactc      120 cancctgnat caatctganc tctattcctg gcccatncct acctcggagg tggangccgn      180
aaaggtcgca cnnncagaga agctgctgcc ancaccancc gccccnnccc tgncgggctn      240
nataggaaac tggtgaccnn gctgcanaat tcatacagga gcacgcgang ggcacnnnct      300
cacactgagt tnnngatgan gcctnaccan ggacctnccc cagcnnattg annacnggac      360
tgcggaggaa ggaagacccc gnacnggatc ctggccggcn tgccacccc ccacccctag      420 gattatnccc cttgactgag tctctgaggg gctacccgaa cccgcctcca ttccctacca      480
natnntgctc natcgggact dacangctgg ggatnggagg ggctatcccc cancatcccc      540
tnanaccaac agcnacngan natngggct cccngggtc ggngcaacnc tcctncaccc      600
cggcgcnggc cttcggtgnt gtcctccntc aacnaattcc naaanggcgg gccccccngt      660
ggactcctcn ttgttccctc c                                             681
```

<210> SEQ ID NO 38
<211> LENGTH: 687
<212> TYPE: DNA
<213> ORGANISM: Homo sapiens
<220> FEATURE:
<221> NAME/KEY: modified_base -continued

```
<222> LOCATION: (3)
<223> OTHER INFORMATION: Where n is a, c, g or t
<220> FEATURE:
<221> NAME/KEY: modified_base
<222> LOCATION: (30)
<223> OTHER INFORMATION: Where n is a, c, g or t
<220> FEATURE:
<221> NAME/KEY: modified_base
<222> LOCATION: (132)
<223> OTHER INFORMATION: Where n is a, c, g or t
<220> FEATURE:
<221> NAME/KEY: modified_base
<222> LOCATION: (151)
<223> OTHER INFORMATION: Where n is a, c, g or t
<220> FEATURE:
<221> NAME/KEY: modified_base
<222> LOCATION: (203)
<223> OTHER INFORMATION: Where n is a, c, g or t
<220> FEATURE:
<221> NAME/KEY: modified_base
<222> LOCATION: (226)
<223> OTHER INFORMATION: Where n is a, c, g or t
<220> FEATURE:
<221> NAME/KEY: modified_base
<222> LOCATION: (228)
<223> OTHER INFORMATION: Where n is a, c, g or t
<220> FEATURE:
<221> NAME/KEY: modified_base
<222> LOCATION: (233)
<223> OTHER INFORMATION: Where n is a, c, g or t
<220> FEATURE:
<221> NAME/KEY: modified_base
<222> LOCATION: (252)
<223> OTHER INFORMATION: Where n is a, c, g or t
<220> FEATURE:
<221> NAME/KEY: modified_base
<222> LOCATION: (264)
<223> OTHER INFORMATION: Where n is a, c, g or t
<220> FEATURE:
<221> NAME/KEY: modified_base
<222> LOCATION: (279)
<223> OTHER INFORMATION: Where n is a, c, g or t
<220> FEATURE:
<221> NAME/KEY: modified_base
<222> LOCATION: (306)
<223> OTHER INFORMATION: Where n is a, c, g or t
<220> FEATURE:
<221> NAME/KEY: modified_base
<222> LOCATION: (308)
<223> OTHER INFORMATION: Where n is a, c, g or t
<220> FEATURE:
<221> NAME/KEY: modified_base
<222> LOCATION: (320)
<223> OTHER INFORMATION: Where n is a, c, g or t
<220> FEATURE:
<221> NAME/KEY: modified_base
<222> LOCATION: (340)
<223> OTHER INFORMATION: Where n is a, c, g or t
<220> FEATURE:
<221> NAME/KEY: modified_base
<222> LOCATION: (347)
<223> OTHER INFORMATION: Where n is a, c, g or t
<220> FEATURE:
<221> NAME/KEY: modified_base
<222> LOCATION: (400)
<223> OTHER INFORMATION: Where n is a, c, g or t
<220> FEATURE:
<221> NAME/KEY: modified_base
<222> LOCATION: (407)
<223> OTHER INFORMATION: Where n is a, c, g or t
<220> FEATURE:
<221> NAME/KEY: modified_base
<222> LOCATION: (4029)
<223> OTHER INFORMATION: Where n is a, c, g or t
<220> FEATURE:
<221> NAME/KEY: modified_base
<222> LOCATION: (437)
<223> OTHER INFORMATION: Where n is a, c, g or t
<220> FEATURE:
```

-continued

```
<221> NAME/KEY: modified_base
<222> LOCATION: (440)
<223> OTHER INFORMATION: Where n is a, c, g or t
<220> FEATURE:
<221> NAME/KEY: modified_base
<222> LOCATION: (445)
<223> OTHER INFORMATION: Where n is a, c, g or t
<220> FEATURE:
<221> NAME/KEY: modified_base
<222> LOCATION: (448)
<223> OTHER INFORMATION: Where n is a, c, g or t
<220> FEATURE:
<221> NAME/KEY: modified_base
<222> LOCATION: (491)
<223> OTHER INFORMATION: Where n is a, c, g or t
<220> FEATURE:
<221> NAME/KEY: modified_base
<222> LOCATION: (559)
<223> OTHER INFORMATION: Where n is a, c, g or t
<220> FEATURE:
<221> NAME/KEY: modified_base
<222> LOCATION: (567)
<223> OTHER INFORMATION: Where n is a, c, g or t
<220> FEATURE:
<221> NAME/KEY: modified_base
<222> LOCATION: (586)
<223> OTHER INFORMATION: Where n is a, c, g or t
<220> FEATURE:
<221> NAME/KEY: modified_base
<222> LOCATION: (589)
<223> OTHER INFORMATION: Where n is a, c, g or t
<220> FEATURE:
<221> NAME/KEY: modified_base
<222> LOCATION: (593)
<223> OTHER INFORMATION: Where n is a, c, g or t
<220> FEATURE:
<221> NAME/KEY: modified_base
<222> LOCATION: (596)
<223> OTHER INFORMATION: Where n is a, c, g or t
<220> FEATURE:
<221> NAME/KEY: modified_base
<222> LOCATION: (603)
<223> OTHER INFORMATION: Where n is a, c, g or t
<220> FEATURE:
<221> NAME/KEY: modified_base
<222> LOCATION: (605)
<223> OTHER INFORMATION: Where n is a, c, g or t
<220> FEATURE:
<221> NAME/KEY: modified_base
<222> LOCATION: (606)
<223> OTHER INFORMATION: Where n is a, c, g or t
<220> FEATURE:
<221> NAME/KEY: modified_base
<222> LOCATION: (609)
<223> OTHER INFORMATION: Where n is a, c, g or t
<220> FEATURE:
<221> NAME/KEY: modified_base
<222> LOCATION: (626)
<223> OTHER INFORMATION: Where n is a, c, g or t
<220> FEATURE:
<221> NAME/KEY: modified_base
<222> LOCATION: (639)
<223> OTHER INFORMATION: Where n is a, c, g or t
<220> FEATURE:
<221> NAME/KEY: modified_base
<222> LOCATION: (655)
<223> OTHER INFORMATION: Where n is a, c, g or t
<220> FEATURE:
<221> NAME/KEY: modified_base
<222> LOCATION: (674)
<223> OTHER INFORMATION: Where n is a, c, g or t
<220> FEATURE:
<221> NAME/KEY: modified_base
<222> LOCATION: (682)
<223> OTHER INFORMATION: Where n is a, c, g or t

<400> SEQUENCE: 38
canaaaaaaa aaaacatggc cgaaaccagn aagctgcgcg atggcgccac ggcccctctt      60
```
ctcccggcct gtgtccggaa ggtttccctc cgaggcgccc cggctcccgc aagcggagga      120
gagggcggga cntgccgggg ccggagctca naggccctgg ggccgctctg ctctcccgcc      180
atcgcaaggg cggcgctaac ctnaggcctc cccgcaaagg tccccnangc ggnggcggcg      240
gggggctgtg anaaccgcaa aaanaacgct gggcgcgcng cgaacccgtc cacccccgcg      300
aaggananac ttccacagan gcagcgtttc cacagcccan agccacnttt ctagggtgat      360 gcacccagt aagttcctgn cggggaagct caccgctgtc aaaaaanctc ttcgctccac       420
cggcgcacna aggggangan ggcangangc tgccgcccgc acaggtcatc tgatcacgtc      480
gcccgcccta ntctgctttt gtgaatctcc actttgttca accccacccg ccgttctctc      540
ctccttgcgc cttcctctna ccttaanaac cagcttcctc tacccnatng tanttnctct      600
gcncnngtng aaattaattc ggtccnccgg aacctcttnc ctgtggcaac tgctnaaaga      660
aactgctgtt ctgnttactg cngtccc                                          687

<210> SEQ ID NO 39
<211> LENGTH: 695
<212> TYPE: DNA
<213> ORGANISM: Homo sapiens
<220> FEATURE:
<221> NAME/KEY: modified_base
<222> LOCATION: (300)
<223> OTHER INFORMATION: Where n is a, c, g or t
<220> FEATURE:
<221> NAME/KEY: modified_base
<222> LOCATION: (401)
<223> OTHER INFORMATION: Where n is a, c, g or t
<220> FEATURE:
<221> NAME/KEY: modified_base
<222> LOCATION: (423)
<223> OTHER INFORMATION: Where n is a, c, g or t
<220> FEATURE:
<221> NAME/KEY: modified_base
<222> LOCATION: (429)
<223> OTHER INFORMATION: Where n is a, c, g or t
<220> FEATURE:
<221> NAME/KEY: modified_base
<222> LOCATION: (431)
<223> OTHER INFORMATION: Where n is a, c, g or t
<220> FEATURE:
<221> NAME/KEY: modified_base
<222> LOCATION: (437)
<223> OTHER INFORMATION: Where n is a, c, g or t
<220> FEATURE:
<221> NAME/KEY: modified_base
<222> LOCATION: (443)
<223> OTHER INFORMATION: Where n is a, c, g or t
<220> FEATURE:
<221> NAME/KEY: modified_base
<222> LOCATION: (448)
<223> OTHER INFORMATION: Where n is a, c, g or t
<220> FEATURE:
<221> NAME/KEY: modified_base
<222> LOCATION: (454)
<223> OTHER INFORMATION: Where n is a, c, g or t
<220> FEATURE:
<221> NAME/KEY: modified_base
<222> LOCATION: (466)
<223> OTHER INFORMATION: Where n is a, c, g or t
<220> FEATURE:
<221> NAME/KEY: modified_base
<222> LOCATION: (492)
<223> OTHER INFORMATION: Where n is a, c, g or t
<220> FEATURE:
<221> NAME/KEY: modified_base
<222> LOCATION: (515)
<223> OTHER INFORMATION: Where n is a, c, g or t
<220> FEATURE:
<221> NAME/KEY: modified_base
<222> LOCATION: (523)

<223> OTHER INFORMATION: Where n is a, c, g or t
<220> FEATURE:
<221> NAME/KEY: modified_base
<222> LOCATION: (524)
<223> OTHER INFORMATION: Where n is a, c, g or t
<220> FEATURE:
<221> NAME/KEY: modified_base
<222> LOCATION: (536)
<223> OTHER INFORMATION: Where n is a, c, g or t
<220> FEATURE:
<221> NAME/KEY: modified_base
<222> LOCATION: (538)
<223> OTHER INFORMATION: Where n is a, c, g or t
<220> FEATURE:
<221> NAME/KEY: modified_base
<222> LOCATION: (541)
<223> OTHER INFORMATION: Where n is a, c, g or t
<220> FEATURE:
<221> NAME/KEY: modified_base
<222> LOCATION: (552)
<223> OTHER INFORMATION: Where n is a, c, g or t
<220> FEATURE:
<221> NAME/KEY: modified_base
<222> LOCATION: (561)
<223> OTHER INFORMATION: Where n is a, c, g or t
<220> FEATURE:
<221> NAME/KEY: modified_base
<222> LOCATION: (566)
<223> OTHER INFORMATION: Where n is a, c, g or t
<220> FEATURE:
<221> NAME/KEY: modified_base
<222> LOCATION: (581)
<223> OTHER INFORMATION: Where n is a, c, g or t
<220> FEATURE:
<221> NAME/KEY: modified_base
<222> LOCATION: (583)
<223> OTHER INFORMATION: Where n is a, c, g or t
<220> FEATURE:
<221> NAME/KEY: modified_base
<222> LOCATION: (619)
<223> OTHER INFORMATION: Where n is a, c, g or t
<220> FEATURE:
<221> NAME/KEY: modified_base
<222> LOCATION: (635)
<223> OTHER INFORMATION: Where n is a, c, g or t
<220> FEATURE:
<221> NAME/KEY: modified_base
<222> LOCATION: (636)
<223> OTHER INFORMATION: Where n is a, c, g or t
<220> FEATURE:
<221> NAME/KEY: modified_base
<222> LOCATION: (641)
<223> OTHER INFORMATION: Where n is a, c, g or t
<220> FEATURE:
<221> NAME/KEY: modified_base
<222> LOCATION: (649)
<223> OTHER INFORMATION: Where n is a, c, g or t
<220> FEATURE:
<221> NAME/KEY: modified_base
<222> LOCATION: (661)
<223> OTHER INFORMATION: Where n is a, c, g or t
<220> FEATURE:
<221> NAME/KEY: modified_base
<222> LOCATION: (694)
<223> OTHER INFORMATION: Where n is a, c, g or t

<400> SEQUENCE: 39
actagtctgg cctacaatag tgtgattcat gtaggacttc tttcatcaat tcaaaacccc      60
tagaaaaacg tatacagatt atataagtag ggataagatt tctaacatttt ctgggctctc    120 tgacccctgc gctagactgt ggaaagggag tattattata gtatacaaca ctgctgttgc    180
cttattagtt ataacatgat aggtgctgaa ttgtgattca caatttaaaa acactgtaat    240
ccaaactttt ttttttaact gtagatcatg catgtgaatg ttaatgttaa tttgttcaan    300
gttgttatgg gtagaaaaaa ccacatgcct taaaatttta aaaagcaggg cccaaactta    360

```
ttagtttaaa attaggggta tgtttccagt ttgttattaa ntggttatag ctctgtttag      420
aanaaatcna ngaacangat ttngaaantt aagntgacat tatttnccag tgacttgtta      480
atttgaaatc anacacggca ccttccgttt tggtnctatt ggnntttgaa tccaancngg      540
ntccaaatct tnttggaaac ngtccnttta actttttac nanatcttat tttttattt       600 tggaatggcc ctatttaang ttaaaagggg ggggnnccac naccattcnt gaataaaact     660
naatatatat ccttggtccc ccaaaattta aggng                                695
```

<210> SEQ ID NO 40
<211> LENGTH: 674
<212> TYPE: DNA
<213> ORGANISM: Homo sapiens
<220> FEATURE:
<221> NAME/KEY: modified_base
<222> LOCATION: (403)
<223> OTHER INFORMATION: Where n is a, c, g or t
<220> FEATURE:
<221> NAME/KEY: modified_base
<222> LOCATION: (428)
<223> OTHER INFORMATION: Where n is a, c, g or t
<220> FEATURE:
<221> NAME/KEY: modified_base
<222> LOCATION: (432)
<223> OTHER INFORMATION: Where n is a, c, g or t
<220> FEATURE:
<221> NAME/KEY: modified_base
<222> LOCATION: (507)
<223> OTHER INFORMATION: Where n is a, c, g or t
<220> FEATURE:
<221> NAME/KEY: modified_base
<222> LOCATION: (530)
<223> OTHER INFORMATION: Where n is a, c, g or t
<220> FEATURE:
<221> NAME/KEY: modified_base
<222> LOCATION: (543)
<223> OTHER INFORMATION: Where n is a, c, g or t
<220> FEATURE:
<221> NAME/KEY: modified_base
<222> LOCATION: (580)
<223> OTHER INFORMATION: Where n is a, c, g or t
<220> FEATURE:
<221> NAME/KEY: modified_base
<222> LOCATION: (583)
<223> OTHER INFORMATION: Where n is a, c, g or t
<220> FEATURE:
<221> NAME/KEY: modified_base
<222> LOCATION: (591)
<223> OTHER INFORMATION: Where n is a, c, g or t
<220> FEATURE:
<221> NAME/KEY: modified_base
<222> LOCATION: (604)
<223> OTHER INFORMATION: Where n is a, c, g or t
<220> FEATURE:
<221> NAME/KEY: modified_base
<222> LOCATION: (608)
<223> OTHER INFORMATION: Where n is a, c, g or t
<220> FEATURE:
<221> NAME/KEY: modified_base
<222> LOCATION: (621)
<223> OTHER INFORMATION: Where n is a, c, g or t
<220> FEATURE:
<221> NAME/KEY: modified_base
<222> LOCATION: (624)
<223> OTHER INFORMATION: Where n is a, c, g or t
<220> FEATURE:
<221> NAME/KEY: modified_base
<222> LOCATION: (626)
<223> OTHER INFORMATION: Where n is a, c, g or t
<220> FEATURE:
<221> NAME/KEY: modified_base
<222> LOCATION: (639)
<223> OTHER INFORMATION: Where n is a, c, g or t
<220> FEATURE:

<221> NAME/KEY: modified_base
<222> LOCATION: (672)
<223> OTHER INFORMATION: Where n is a, c, g or t

<400> SEQUENCE: 40

```
actagtagtc agttgggagt ggttgctata ccttgacttc atttatatga atttccactt    60
tattaaataa tagaaaagaa aatcccggtg cttgcagtag agttatagga cattctatgc   120
ttacagaaaa tatagccatg attgaaatca aatagtaaag gctgttctgg cttttttatct  180
tcttagctca tcttaaataa gtagtacact tgggatgcag tgcgtctgaa gtgctaatca   240
gttgtaacaa tagcacaaat cgaacttagg atgtgtttct tctcttctgt gtttcgattt   300
tgatcaattc tttaattttg ggaacctata atacagtttt cctattcttg gagataaaaa   360
ttaaatggat cactgatatt taagtcattc tgcttctcat ctnaatattc catattctgt   420
attagganaa antacctccc agcacagccc cctctcaaac cccacccaaa accaagcatt   480
tggaatgagt ctcctttatt tccgaantgt ggatggtata acccatatcn ctccaatttc   540
tgnttgggtt gggtattaat ttgaactgtg catgaaaagn ggnaatcttt ncttgggtc    600
aaantttncc ggttaatttg nctngncaaa tccaatttnc tttaagggtg tctttataaa   660
atttgctatt cngg                                                     674
```

<210> SEQ ID NO 41
<211> LENGTH: 657
<212> TYPE: DNA
<213> ORGANISM: Homo sapiens
<220> FEATURE:
<221> NAME/KEY: modified_base
<222> LOCATION: (243)
<223> OTHER INFORMATION: Where n is a, c, g or t
<220> FEATURE:
<221> NAME/KEY: modified_base
<222> LOCATION: (247)
<223> OTHER INFORMATION: Where n is a, c, g or t
<220> FEATURE:
<221> NAME/KEY: modified_base
<222> LOCATION: (251)
<223> OTHER INFORMATION: Where n is a, c, g or t
<220> FEATURE:
<221> NAME/KEY: modified_base
<222> LOCATION: (261)
<223> OTHER INFORMATION: Where n is a, c, g or t
<220> FEATURE:
<221> NAME/KEY: modified_base
<222> LOCATION: (267)
<223> OTHER INFORMATION: Where n is a, c, g or t
<220> FEATURE:
<221> NAME/KEY: modified_base
<222> LOCATION: (272)
<223> OTHER INFORMATION: Where n is a, c, g or t
<220> FEATURE:
<221> NAME/KEY: modified_base
<222> LOCATION: (298)
<223> OTHER INFORMATION: Where n is a, c, g or t
<220> FEATURE:
<221> NAME/KEY: modified_base
<222> LOCATION: (312)
<223> OTHER INFORMATION: Where n is a, c, g or t
<220> FEATURE:
<221> NAME/KEY: modified_base
<222> LOCATION: (315)
<223> OTHER INFORMATION: Where n is a, c, g or t
<220> FEATURE:
<221> NAME/KEY: modified_base
<222> LOCATION: (421)
<223> OTHER INFORMATION: Where n is a, c, g or t
<220> FEATURE:
<221> NAME/KEY: modified_base
<222> LOCATION: (432)
<223> OTHER INFORMATION: Where n is a, c, g or t
<220> FEATURE:
<221> NAME/KEY: modified_base
<222> LOCATION: (434)
<223> OTHER INFORMATION: Where n is a, c, g or t
<220> FEATURE:
<221> NAME/KEY: modified_base
<222> LOCATION: (501)
<223> OTHER INFORMATION: Where n is a, c, g or t
<220> FEATURE:
<221> NAME/KEY: modified_base
<222> LOCATION: (524)
<223> OTHER INFORMATION: Where n is a, c, g or t
<220> FEATURE:
<221> NAME/KEY: modified_base
<222> LOCATION: (569)
<223> OTHER INFORMATION: Where n is a, c, g or t
<220> FEATURE:
<221> NAME/KEY: modified_base
<222> LOCATION: (594)
<223> OTHER INFORMATION: Where n is a, c, g or t
<220> FEATURE:
<221> NAME/KEY: modified_base
<222> LOCATION: (607)
<223> OTHER INFORMATION: Where n is a, c, g or t
<220> FEATURE:
<221> NAME/KEY: modified_base
<222> LOCATION: (650)
<223> OTHER INFORMATION: Where n is a, c, g or t

<400> SEQUENCE: 41
gaaacatgca agtaccacac actgtttgaa ttttgcacaa aaagtgactg tagggatcag    60
gtgatagccc cggaatgtac agtgtcttgg tgcaccaaga tgccttctaa aggctgacat   120
accttgggac cctaatgggg cagagagtat agccctagcc cagtggtgac atgaccactc   180
cctttgggag gctgaagtta aagggaatgg tatgtgtttt ctcatggaag cagcacatga   240
atnggtnaca ngatgttaaa ntaaggntct antttgggtg tcttgtcatt tgaaaaantg   300
acacactcct ancanctggt aaagggggtgc tggaagccat ggaagaactc taaaaacatt   360
agcatgggct gatctgatta cttcctggca tcccgctcac ttttatggga agtcttatta   420
naaggatggg ananttttcc atatccttgc tgttggaact ctggaacact ctctaaattt   480
ccctctatta aaaatcactg nccttactac acttcctcct tganggaata gaaatggacc   540
tttctctgac ttagttcttg gcatgggganc cagcccaaat taaaatctga cttntccggt   600
ttctccngaa ctcacctact tgaattggta aaacctcctt tggaattagn aaaaacc     657

<210> SEQ ID NO 42
<211> LENGTH: 389
<212> TYPE: DNA
<213> ORGANISM: Homo sapiens
<220> FEATURE:
<221> NAME/KEY: modified_base
<222> LOCATION: (179)
<223> OTHER INFORMATION: Where n is a, c, g or t
<220> FEATURE:
<221> NAME/KEY: modified_base
<222> LOCATION: (317)
<223> OTHER INFORMATION: Where n is a, c, g or t
<220> FEATURE:
<221> NAME/KEY: modified_base
<222> LOCATION: (320)
<223> OTHER INFORMATION: Where n is a, c, g or t

<400> SEQUENCE: 42
actagtgctg aggaatgtaa acaagtttgc tgggccttgc gagacttcac caggttgttt    60
cgatagctca cactcctgca ctgtgcctgt cacccaggaa tgtctttttt aattagaaga   120
caggaagaaa acaaaaacca gactgtgtcc cacaatcaga aacctccgtt gtggcagang   180

```
ggccttcacc gccaccaggg tgtcccgcca gacagggaga gactccagcc ttctgaggcc      240
atcctgaaga attcctgttt gggggttgtg aaggaaaatc acccggattt aaaaagatgc      300
tgttgcctgc ccgcgtngtn gggaagggac tggtttcctg gtgaatttct taaaagaaaa      360
atattttaag ttaagaaaaa aaaaaaaaa                                        389

<210> SEQ ID NO 43
<211> LENGTH: 279
<212> TYPE: DNA
<213> ORGANISM: Homo sapiens

<400> SEQUENCE: 43
actagtgaca agctcctggt cttgagatgt cttctcgtta aggagatggg ccttttggag       60
gtaaaggata aaatgaatga gttctgtcat gattcactat tctagaactt gcatgacctt      120
tactgtgtta gctctttgaa tgttcttgaa attttagact ttctttgtaa acaaataata      180
tgtccttatc attgtataaa agctgttatg tgcaacagtg tggagatcct tgtctgattt      240
aataaaatac ttaaacactg aaaaaaaaaa aaaaaaaa                              279

<210> SEQ ID NO 44
<211> LENGTH: 449
<212> TYPE: DNA
<213> ORGANISM: Homo sapiens
<220> FEATURE:
<221> NAME/KEY: modified_base
<222> LOCATION: (245)
<223> OTHER INFORMATION: Where n is a, c, g or t
<220> FEATURE:
<221> NAME/KEY: modified_base
<222> LOCATION: (256)
<223> OTHER INFORMATION: Where n is a, c, g or t
<220> FEATURE:
<221> NAME/KEY: modified_base
<222> LOCATION: (264)
<223> OTHER INFORMATION: Where n is a, c, g or t
<220> FEATURE:
<221> NAME/KEY: modified_base
<222> LOCATION: (266)
<223> OTHER INFORMATION: Where n is a, c, g or t
<220> FEATURE:
<221> NAME/KEY: modified_base
<222> LOCATION: (273)
<223> OTHER INFORMATION: Where n is a, c, g or t
<220> FEATURE:
<221> NAME/KEY: modified_base
<222> LOCATION: (281)
<223> OTHER INFORMATION: Where n is a, c, g or t
<220> FEATURE:
<221> NAME/KEY: modified_base
<222> LOCATION: (323)
<223> OTHER INFORMATION: Where n is a, c, g or t
<220> FEATURE:
<221> NAME/KEY: modified_base
<222> LOCATION: (325)
<223> OTHER INFORMATION: Where n is a, c, g or t
<220> FEATURE:
<221> NAME/KEY: modified_base
<222> LOCATION: (337)
<223> OTHER INFORMATION: Where n is a, c, g or t
<220> FEATURE:
<221> NAME/KEY: modified_base
<222> LOCATION: (393)
<223> OTHER INFORMATION: Where n is a, c, g or t

<400> SEQUENCE: 44
actagtagca tcttttctac aacgttaaaa ttgcagaagt agcttatcat taaaaaacaa       60
caacaacaac aataacaata aatcctaagt gtaaatcagt tattctaccc cctaccaagg      120
atatcagcct gttttttccc ttttttctcc tgggaataat tgtgggcttc ttcccaaatt      180
```

```
tctacagcct ctttcctctt ctcatgcttg agcttccctg tttgcacgca tgcgttgtgc    240
aagantgggc tgtttngctt ggantncggt ccnagtggaa ncatgctttc ccttgttact    300
gttggaagaa actcaaacct tcnaccccta ggtgttncca ttttgtcaag tcatcactgt    360
atttttgtac tggcattaac aaaaaaagaa atnaaatatt gttccattaa actttaataa    420
aactttaaaa gggaaaaaaa aaaaaaaaa                                       449

<210> SEQ ID NO 45
<211> LENGTH: 559
<212> TYPE: DNA
<213> ORGANISM: Homo sapiens
<220> FEATURE:
<221> NAME/KEY: modified_base
<222> LOCATION: (263)
<223> OTHER INFORMATION: Where n is a, c, g or t

<400> SEQUENCE: 45
actagtgtgg gggaatcacg gacacttaaa gtcaatctgc gaaataattc ttttattaca     60
cactcactga agtttttgag tcccagagag ccattctatg tcaaacattc caagtactct    120
ttgagagccc agcattacat caacatgccc gtgcagttca aaccgaagtc cgcaggcaaa    180
tttgaagctt tgcttgtcat tcaaacagat gaaggcaaga gtattgctat tcgactaatt    240
ggtgaagctc ttggaaaaaa ttnactagaa tactttttgt gttaagttaa ttacataagt    300
tgtattttgt taactttatc tttctacact acaattatgc ttttgtatat atattttgta    360
tgatggatat ctataattgt agattttgtt tttacaagct aatactgaag actcgactga    420
aatattatgt atctagccca tagtattgta cttaacttt acagggtgaa aaaaaaattc     480
tgtgtttgca ttgattatga tattctgaat aaatatggga atatatttta atgtgggtaa    540
aaaaaaaaaa aaaaggaa                                                   559

<210> SEQ ID NO 46
<211> LENGTH: 731
<212> TYPE: DNA
<213> ORGANISM: Homo sapiens
<220> FEATURE:
<221> NAME/KEY: modified_base
<222> LOCATION: (270)
<223> OTHER INFORMATION: Where n is a, c, g or t
<220> FEATURE:
<221> NAME/KEY: modified_base
<222> LOCATION: (467)
<223> OTHER INFORMATION: Where n is a, c, g or t
<220> FEATURE:
<221> NAME/KEY: modified_base
<222> LOCATION: (477)
<223> OTHER INFORMATION: Where n is a, c, g or t
<220> FEATURE:
<221> NAME/KEY: modified_base
<222> LOCATION: (502)
<223> OTHER INFORMATION: Where n is a, c, g or t
<220> FEATURE:
<221> NAME/KEY: modified_base
<222> LOCATION: (635)
<223> OTHER INFORMATION: Where n is a, c, g or t
<220> FEATURE:
<221> NAME/KEY: modified_base
<222> LOCATION: (660)
<223> OTHER INFORMATION: Where n is a, c, g or t
<220> FEATURE:
<221> NAME/KEY: modified_base
<222> LOCATION: (671)
<223> OTHER INFORMATION: Where n is a, c, g or t
<220> FEATURE:
<221> NAME/KEY: modified_base
<222> LOCATION: (688)
```

<223> OTHER INFORMATION: Where n is a, c, g or t
<220> FEATURE:
<221> NAME/KEY: modified_base
<222> LOCATION: (695)
<223> OTHER INFORMATION: Where n is a, c, g or t
<220> FEATURE:
<221> NAME/KEY: modified_base
<222> LOCATION: (697)
<223> OTHER INFORMATION: Where n is a, c, g or t
<220> FEATURE:
<221> NAME/KEY: modified_base
<222> LOCATION: (725)
<223> OTHER INFORMATION: Where n is a, c, g or t

<400> SEQUENCE: 46

```
actagttcta gtaccatggc tgtcatagat gcaaccatta tattccattt agtttcttcc      60
tcaggttccc taacaattgt ttgaaactga atatatatgt ttatgtatgt gtgtgtgttc     120
actgtcatgt atatggtgta tatgggatgt gtgcagtttt cagttatata tatattcata     180
tatacatatg catatatatg tataatatac atatatacat gcatacactt gtataatata     240
catatatata cacatatatg cacacatatn atcactgagt tccaaagtga gtctttattt     300
ggggcaattg tattctctcc ctctgtctgc tcactgggcc tttgcaagac atagcaattg     360
cttgatttcc tttggataag agtcttatct tcggcactct tgactctagc cttaacttta     420
gatttctatt ccagaatacc tctcatatct atcttaaaac ctaaganggg taaagangtc     480
ataagattgt agtatgaaag antttgctta gttaaattat atctcaggaa actcattcat     540
ctacaaatta aattgtaaaa tgatggtttg ttgtatctga aaaaatgttt agaacaagaa     600
atgtaactgg gtacctgtta tatcaaagaa cctcnattta ttaagtctcc tcatagccan     660
atccttatat ngccctctct gacctgantt aatananact tgaataatga atagttaatt     720
taggnttggg c                                                          731
```

<210> SEQ ID NO 47
<211> LENGTH: 640
<212> TYPE: DNA
<213> ORGANISM: Homo sapiens
<220> FEATURE:
<221> NAME/KEY: modified_base
<222> LOCATION: (5)
<223> OTHER INFORMATION: Where n is a, c, g or t
<220> FEATURE:
<221> NAME/KEY: modified_base
<222> LOCATION: (28)
<223> OTHER INFORMATION: Where n is a, c, g or t
<220> FEATURE:
<221> NAME/KEY: modified_base
<222> LOCATION: (106)
<223> OTHER INFORMATION: Where n is a, c, g or t
<220> FEATURE:
<221> NAME/KEY: modified_base
<222> LOCATION: (153)
<223> OTHER INFORMATION: Where n is a, c, g or t
<220> FEATURE:
<221> NAME/KEY: modified_base
<222> LOCATION: (158)
<223> OTHER INFORMATION: Where n is a, c, g or t
<220> FEATURE:
<221> NAME/KEY: modified_base
<222> LOCATION: (173)
<223> OTHER INFORMATION: Where n is a, c, g or t
<220> FEATURE:
<221> NAME/KEY: modified_base
<222> LOCATION: (176)
<223> OTHER INFORMATION: Where n is a, c, g or t
<220> FEATURE:
<221> NAME/KEY: modified_base
<222> LOCATION: (182)
<223> OTHER INFORMATION: Where n is a, c, g or t

```
<220> FEATURE:
<221> NAME/KEY: modified_base
<222> LOCATION: (189)
<223> OTHER INFORMATION: Where n is a, c, g or t
<220> FEATURE:
<221> NAME/KEY: modified_base
<222> LOCATION: (205)
<223> OTHER INFORMATION: Where n is a, c, g or t
<220> FEATURE:
<221> NAME/KEY: modified_base
<222> LOCATION: (210)
<223> OTHER INFORMATION: Where n is a, c, g or t
<220> FEATURE:
<221> NAME/KEY: modified_base
<222> LOCATION: (214)
<223> OTHER INFORMATION: Where n is a, c, g or t
<220> FEATURE:
<221> NAME/KEY: modified_base
<222> LOCATION: (225)
<223> OTHER INFORMATION: Where n is a, c, g or t
<220> FEATURE:
<221> NAME/KEY: modified_base
<222> LOCATION: (226)
<223> OTHER INFORMATION: Where n is a, c, g or t
<220> FEATURE:
<221> NAME/KEY: modified_base
<222> LOCATION: (229)
<223> OTHER INFORMATION: Where n is a, c, g or t
<220> FEATURE:
<221> NAME/KEY: modified_base
<222> LOCATION: (237)
<223> OTHER INFORMATION: Where n is a, c, g or t
<220> FEATURE:
<221> NAME/KEY: modified_base
<222> LOCATION: (260)
<223> OTHER INFORMATION: Where n is a, c, g or t
<220> FEATURE:
<221> NAME/KEY: modified_base
<222> LOCATION: (263)
<223> OTHER INFORMATION: Where n is a, c, g or t
<220> FEATURE:
<221> NAME/KEY: modified_base
<222> LOCATION: (269)
<223> OTHER INFORMATION: Where n is a, c, g or t
<220> FEATURE:
<221> NAME/KEY: modified_base
<222> LOCATION: (277)
<223> OTHER INFORMATION: Where n is a, c, g or t
<220> FEATURE:
<221> NAME/KEY: modified_base
<222> LOCATION: (281)
<223> OTHER INFORMATION: Where n is a, c, g or t
<220> FEATURE:
<221> NAME/KEY: modified_base
<222> LOCATION: (282)
<223> OTHER INFORMATION: Where n is a, c, g or t
<220> FEATURE:
<221> NAME/KEY: modified_base
<222> LOCATION: (322)
<223> OTHER INFORMATION: Where n is a, c, g or t
<220> FEATURE:
<221> NAME/KEY: modified_base
<222> LOCATION: (337)
<223> OTHER INFORMATION: Where n is a, c, g or t
<220> FEATURE:
<221> NAME/KEY: modified_base
<222> LOCATION: (338)
<223> OTHER INFORMATION: Where n is a, c, g or t
<220> FEATURE:
<221> NAME/KEY: modified_base
<222> LOCATION: (354)
<223> OTHER INFORMATION: Where n is a, c, g or t
<220> FEATURE:
<221> NAME/KEY: modified_base
<222> LOCATION: (365)
<223> OTHER INFORMATION: Where n is a, c, g or t
<220> FEATURE:
<221> NAME/KEY: modified_base
<222> LOCATION: (428)
```

```
<223> OTHER INFORMATION: Where n is a, c, g or t
<220> FEATURE:
<221> NAME/KEY: modified_base
<222> LOCATION: (441)
<223> OTHER INFORMATION: Where n is a, c, g or t
<220> FEATURE:
<221> NAME/KEY: modified_base
<222> LOCATION: (443)
<223> OTHER INFORMATION: Where n is a, c, g or t
<220> FEATURE:
<221> NAME/KEY: modified_base
<222> LOCATION: (456)
<223> OTHER INFORMATION: Where n is a, c, g or t
<220> FEATURE:
<221> NAME/KEY: modified_base
<222> LOCATION: (467)
<223> OTHER INFORMATION: Where n is a, c, g or t
<220> FEATURE:
<221> NAME/KEY: modified_base
<222> LOCATION: (476)
<223> OTHER INFORMATION: Where n is a, c, g or t
<220> FEATURE:
<221> NAME/KEY: modified_base
<222> LOCATION: (484)
<223> OTHER INFORMATION: Where n is a, c, g or t
<220> FEATURE:
<221> NAME/KEY: modified_base
<222> LOCATION: (503)
<223> OTHER INFORMATION: Where n is a, c, g or t
<220> FEATURE:
<221> NAME/KEY: modified_base
<222> LOCATION: (508)
<223> OTHER INFORMATION: Where n is a, c, g or t
<220> FEATURE:
<221> NAME/KEY: modified_base
<222> LOCATION: (554)
<223> OTHER INFORMATION: Where n is a, c, g or t
<220> FEATURE:
<221> NAME/KEY: modified_base
<222> LOCATION: (567)
<223> OTHER INFORMATION: Where n is a, c, g or t
<220> FEATURE:
<221> NAME/KEY: modified_base
<222> LOCATION: (575)
<223> OTHER INFORMATION: Where n is a, c, g or t
<220> FEATURE:
<221> NAME/KEY: modified_base
<222> LOCATION: (579)
<223> OTHER INFORMATION: Where n is a, c, g or t
<220> FEATURE:
<221> NAME/KEY: modified_base
<222> LOCATION: (588)
<223> OTHER INFORMATION: Where n is a, c, g or t
<220> FEATURE:
<221> NAME/KEY: modified_base
<222> LOCATION: (601)
<223> OTHER INFORMATION: Where n is a, c, g or t
<220> FEATURE:
<221> NAME/KEY: modified_base
<222> LOCATION: (606)
<223> OTHER INFORMATION: Where n is a, c, g or t
<220> FEATURE:
<221> NAME/KEY: modified_base
<222> LOCATION: (609)
<223> OTHER INFORMATION: Where n is a, c, g or t
<220> FEATURE:
<221> NAME/KEY: modified_base
<222> LOCATION: (611)
<223> OTHER INFORMATION: Where n is a, c, g or t
<220> FEATURE:
<221> NAME/KEY: modified_base
<222> LOCATION: (621)
<223> OTHER INFORMATION: Where n is a, c, g or t
<220> FEATURE:
<221> NAME/KEY: modified_base
<222> LOCATION: (636)
<223> OTHER INFORMATION: Where n is a, c, g or t

<400> SEQUENCE: 47
```

```
tgcgngccgg tttggcccctt ctttgtanga cactttcatc cgccctgaaa tcttcccgat    60
cgttaataac tcctcaggtc cctgcctgca cagggttttt tcttantttg ttgcctaaca   120
gtacaccaaa tgtgacatcc tttcaccaat atngattnct tcataccaca tcntcnatgg   180
anacgactnc aacaattttt tgatnacccn aaanactggg ggctnnaana agtacantct   240
ggagcagcat ggacctgtcn gcnactaang gaacaanagt nntgaacatt tacacaacct   300
ttggtatgtc ttactgaaag anagaaacat gcttctnncc ctagaccacg aggncaaccg   360
caganattgc caatgccaag tccgagcggt tagatcaggt aatacattcc atggatgcat   420
tacatacntt gtccccgaaa nanaagatgc cctaanggct tcttcanact ggtccngaaa   480
acanctacac ctggtgcttg ganaacanac tctttggaag atcatctggc acaagttccc   540
cccagtgggt tttnccttgg cacctancttt accanatcna ttcggaancc attctttgcc   600
ntggcnttnt nttgggacca ntcttctcac aactgnaccc                         640
```

<210> SEQ ID NO 48
<211> LENGTH: 257
<212> TYPE: DNA
<213> ORGANISM: Homo sapiens

<400> SEQUENCE: 48

```
actagtatat gaaaatgtaa atatcacttg tgtactcaaa caaaagttgg tcttaagctt    60
ccaccttgag cagccttgga aacctaacct gcctctttta gcataatcac attttctaaa   120
tgattttctt tgttcctgaa aaagtgattt gtattagttt tacatttgtt ttttggaaga   180
ttatatttgt atatgtatca tcataaaata tttaaataaa aagtatcttt agagtgaaaa   240
aaaaaaaaaa aaaaaaa                                                  257
```

<210> SEQ ID NO 49
<211> LENGTH: 652
<212> TYPE: DNA
<213> ORGANISM: Homo sapiens
<220> FEATURE:
<221> NAME/KEY: modified_base
<222> LOCATION: (410)
<223> OTHER INFORMATION: Where n is a, c, g or t
<220> FEATURE:
<221> NAME/KEY: modified_base
<222> LOCATION: (428)
<223> OTHER INFORMATION: Where n is a, c, g or t
<220> FEATURE:
<221> NAME/KEY: modified_base
<222> LOCATION: (496)
<223> OTHER INFORMATION: Where n is a, c, g or t
<220> FEATURE:
<221> NAME/KEY: modified_base
<222> LOCATION: (571)
<223> OTHER INFORMATION: Where n is a, c, g or t
<220> FEATURE:
<221> NAME/KEY: modified_base
<222> LOCATION: (647)
<223> OTHER INFORMATION: Where n is a, c, g or t

<400> SEQUENCE: 49

```
actagttcag atgagtggct gctgaagggg ccccccttgtc attttcatta tacccccaatt    60 tccacttatt tgaactctta agtcataaat gtataatgac ttatgaatta gcacagttaa   120
gttgacacta gaaactgccc atttctgtat tacactatca aataggaaac attggaaaga   180
tggggaaaaa aatcttattt taaaatggct tagaaagttt tcagattact ttgaaaattc   240
taaacttctt tctgtttcca aaacttgaaa atatgtagat ggactcatgc attaagactg   300
```

| | | |
|---|---|---|
| ttttcaaagc tttcctcaca tttttaaagt gtgatttttcc ttttaatata catatttatt | 360 | |
| ttctttaaag cagctatatc ccaacccatg actttggaga tatacctatn aaaccaatat | 420 | |
| aacagcangg ttattgaagc agctttctca aatgttgctt cagatgtgca agttgcaaat | 480 | |
| tttattgtat ttgtanaata caatttttgt tttaaactgt atttcaatct atttctccaa | 540 | |
| gatgcttttc atatagagtg aaatatccca ngataactgc ttctgtgtcg tcgcatttga | 600 | |
| cgcataactg cacaaatgaa cagtgtatac ctcttggttg tgcattnacc cc | 652 | |

<210> SEQ ID NO 50
<211> LENGTH: 650
<212> TYPE: DNA
<213> ORGANISM: Homo sapiens
<220> FEATURE:
<221> NAME/KEY: modified_base
<222> LOCATION: (237)
<223> OTHER INFORMATION: Where n is a, c, g or t
<220> FEATURE:
<221> NAME/KEY: modified_base
<222> LOCATION: (270)
<223> OTHER INFORMATION: Where n is a, c, g or t
<220> FEATURE:
<221> NAME/KEY: modified_base
<222> LOCATION: (311)
<223> OTHER INFORMATION: Where n is a, c, g or t
<220> FEATURE:
<221> NAME/KEY: modified_base
<222> LOCATION: (443)
<223> OTHER INFORMATION: Where n is a, c, g or t
<220> FEATURE:
<221> NAME/KEY: modified_base
<222> LOCATION: (454)
<223> OTHER INFORMATION: Where n is a, c, g or t
<220> FEATURE:
<221> NAME/KEY: modified_base
<222> LOCATION: (488)
<223> OTHER INFORMATION: Where n is a, c, g or t
<220> FEATURE:
<221> NAME/KEY: modified_base
<222> LOCATION: (520)
<223> OTHER INFORMATION: Where n is a, c, g or t
<220> FEATURE:
<221> NAME/KEY: modified_base
<222> LOCATION: (535)
<223> OTHER INFORMATION: Where n is a, c, g or t
<220> FEATURE:
<221> NAME/KEY: modified_base
<222> LOCATION: (539)
<223> OTHER INFORMATION: Where n is a, c, g or t
<220> FEATURE:
<221> NAME/KEY: modified_base
<222> LOCATION: (556)
<223> OTHER INFORMATION: Where n is a, c, g or t
<220> FEATURE:
<221> NAME/KEY: modified_base
<222> LOCATION: (567)
<223> OTHER INFORMATION: Where n is a, c, g or t
<220> FEATURE:
<221> NAME/KEY: modified_base
<222> LOCATION: (594)
<223> OTHER INFORMATION: Where n is a, c, g or t
<220> FEATURE:
<221> NAME/KEY: modified_base
<222> LOCATION: (603)
<223> OTHER INFORMATION: Where n is a, c, g or t
<220> FEATURE:
<221> NAME/KEY: modified_base
<222> LOCATION: (634)
<223> OTHER INFORMATION: Where n is a, c, g or t

<400> SEQUENCE: 50

| | | |
|---|---|---|
| ttgcgctttg atttttttag ggcttgtgcc ctgtttcact tatagggtct agaatgcttg | 60 | |
| tgttgagtaa aaaggagatg cccaatattc aaagctgcta aatgttctct ttgccataaa | 120 | |

```
gactccgtgt aactgtgtga acacttggga tttttctcct ctgtcccgag gtcgtcgtct      180
gctttctttt ttgggttctt tctagaagat tgagaaatgc atatgacagg ctgagancac      240
ctccccaaac acacaagctc tcagccacan gcagcttctc cacagcccca gcttcgcaca      300
ggctcctgga nggctgcctg ggggaggcag acatgggagt gccaaggtgg ccagatggtt      360
ccaggactac aatgtcttta tttttaactg tttgccactg ctgccctcac ccctgcccgg      420
ctctggagta ccgtctgccc canacaagtg ggantgaaat gggggtgggg gggaacactg      480
attcccantt aggggtgcc  taactgaaca gtagggatan aagtgtgaa  cctgngaant       540 gcttttataa attatnttcc ttgttanatt tattttttaa tttaatctct gttnaactgc      600
ccngggaaaa gggaaaaaa  aaaaaaaaat tctntttaaa cacatgaaca                 650
```

<210> SEQ ID NO 51
<211> LENGTH: 545
<212> TYPE: DNA
<213> ORGANISM: Homo sapiens
<220> FEATURE:
<221> NAME/KEY: modified_base
<222> LOCATION: (66)
<223> OTHER INFORMATION: Where n is a, c, g or t
<220> FEATURE:
<221> NAME/KEY: modified_base
<222> LOCATION: (159)
<223> OTHER INFORMATION: Where n is a, c, g or t
<220> FEATURE:
<221> NAME/KEY: modified_base
<222> LOCATION: (195)
<223> OTHER INFORMATION: Where n is a, c, g or t
<220> FEATURE:
<221> NAME/KEY: modified_base
<222> LOCATION: (205)
<223> OTHER INFORMATION: Where n is a, c, g or t
<220> FEATURE:
<221> NAME/KEY: modified_base
<222> LOCATION: (214)
<223> OTHER INFORMATION: Where n is a, c, g or t
<220> FEATURE:
<221> NAME/KEY: modified_base
<222> LOCATION: (243)
<223> OTHER INFORMATION: Where n is a, c, g or t
<220> FEATURE:
<221> NAME/KEY: modified_base
<222> LOCATION: (278)
<223> OTHER INFORMATION: Where n is a, c, g or t
<220> FEATURE:
<221> NAME/KEY: modified_base
<222> LOCATION: (298)
<223> OTHER INFORMATION: Where n is a, c, g or t
<220> FEATURE:
<221> NAME/KEY: modified_base
<222> LOCATION: (306)
<223> OTHER INFORMATION: Where n is a, c, g or t
<220> FEATURE:
<221> NAME/KEY: modified_base
<222> LOCATION: (337)
<223> OTHER INFORMATION: Where n is a, c, g or t
<220> FEATURE:
<221> NAME/KEY: modified_base
<222> LOCATION: (366)
<223> OTHER INFORMATION: Where n is a, c, g or t
<220> FEATURE:
<221> NAME/KEY: modified_base
<222> LOCATION: (375)
<223> OTHER INFORMATION: Where n is a, c, g or t
<220> FEATURE:
<221> NAME/KEY: modified_base
<222> LOCATION: (382)
<223> OTHER INFORMATION: Where n is a, c, g or t
<220> FEATURE:
<221> NAME/KEY: modified_base
<222> LOCATION: (405)

```
<223> OTHER INFORMATION: Where n is a, c, g or t
<220> FEATURE:
<221> NAME/KEY: modified_base
<222> LOCATION: (446)
<223> OTHER INFORMATION: Where n is a, c, g or t
<220> FEATURE:
<221> NAME/KEY: modified_base
<222> LOCATION: (477)
<223> OTHER INFORMATION: Where n is a, c, g or t
<220> FEATURE:
<221> NAME/KEY: modified_base
<222> LOCATION: (492)
<223> OTHER INFORMATION: Where n is a, c, g or t
<220> FEATURE:
<221> NAME/KEY: modified_base
<222> LOCATION: (495)
<223> OTHER INFORMATION: Where n is a, c, g or t
<220> FEATURE:
<221> NAME/KEY: modified_base
<222> LOCATION: (503)
<223> OTHER INFORMATION: Where n is a, c, g or t
<220> FEATURE:
<221> NAME/KEY: modified_base
<222> LOCATION: (507)
<223> OTHER INFORMATION: Where n is a, c, g or t
<220> FEATURE:
<221> NAME/KEY: modified_base
<222> LOCATION: (508)
<223> OTHER INFORMATION: Where n is a, c, g or t
<220> FEATURE:
<221> NAME/KEY: modified_base
<222> LOCATION: (521)
<223> OTHER INFORMATION: Where n is a, c, g or t
<220> FEATURE:
<221> NAME/KEY: modified_base
<222> LOCATION: (537)
<223> OTHER INFORMATION: Where n is a, c, g or t

<400> SEQUENCE: 51
tggcgtgcaa ccagggtagc tgaagtttgg gtctgggact ggagattggc cattaggcct      60
cctganattc cagctccctt ccaccaagcc cagtcttgct acgtggcaca gggcaaacct     120
gactcccttt gggcctcagt ttcccctccc cttcatgana tgaaaagaat actactttt     180 cttgttggtc taacnttgct ggacncaaag tgtngtcatt attgttgtat tgggtgatgt     240
gtncaaaact gcagaagctc actgcctatg agaggaanta agagagatag tggatganag     300
ggacanaagg agtcattatt tggtatagat ccacccntcc caacctttct ctcctcagtc     360 cctgcnccttc atgntctgg tntggtgagt cctttgtgcc accanccatc atgctttgca     420
ttgctgccat cctgggaagg gggtgnatcg tctcacaact tgttgtcatc gtttganatg     480
catgctttct tnatnaaaca aanaaannaa tgtttgacag ngtttaaaat aaaaaanaaa     540
caaaa                                                                 545

<210> SEQ ID NO 52
<211> LENGTH: 678
<212> TYPE: DNA
<213> ORGANISM: Homo sapiens
<220> FEATURE:
<221> NAME/KEY: modified_base
<222> LOCATION: (98)
<223> OTHER INFORMATION: Where n is a, c, g or t
<220> FEATURE:
<221> NAME/KEY: modified_base
<222> LOCATION: (119)
<223> OTHER INFORMATION: Where n is a, c, g or t
<220> FEATURE:
<221> NAME/KEY: modified_base
<222> LOCATION: (121)
<223> OTHER INFORMATION: Where n is a, c, g or t
<220> FEATURE:
<221> NAME/KEY: modified_base
```

```
<222> LOCATION: (131)
<223> OTHER INFORMATION: Where n is a, c, g or t
<220> FEATURE:
<221> NAME/KEY: modified_base
<222> LOCATION: (136)
<223> OTHER INFORMATION: Where n is a, c, g or t
<220> FEATURE:
<221> NAME/KEY: modified_base
<222> LOCATION: (139)
<223> OTHER INFORMATION: Where n is a, c, g or t
<220> FEATURE:
<221> NAME/KEY: modified_base
<222> LOCATION: (140)
<223> OTHER INFORMATION: Where n is a, c, g or t
<220> FEATURE:
<221> NAME/KEY: modified_base
<222> LOCATION: (142)
<223> OTHER INFORMATION: Where n is a, c, g or t
<220> FEATURE:
<221> NAME/KEY: modified_base
<222> LOCATION: (143)
<223> OTHER INFORMATION: Where n is a, c, g or t
<220> FEATURE:
<221> NAME/KEY: modified_base
<222> LOCATION: (163)
<223> OTHER INFORMATION: Where n is a, c, g or t
<220> FEATURE:
<221> NAME/KEY: modified_base
<222> LOCATION: (168)
<223> OTHER INFORMATION: Where n is a, c, g or t
<220> FEATURE:
<221> NAME/KEY: modified_base
<222> LOCATION: (172)
<223> OTHER INFORMATION: Where n is a, c, g or t
<220> FEATURE:
<221> NAME/KEY: modified_base
<222> LOCATION: (176)
<223> OTHER INFORMATION: Where n is a, c, g or t
<220> FEATURE:
<221> NAME/KEY: modified_base
<222> LOCATION: (184)
<223> OTHER INFORMATION: Where n is a, c, g or t
<220> FEATURE:
<221> NAME/KEY: modified_base
<222> LOCATION: (189)
<223> OTHER INFORMATION: Where n is a, c, g or t
<220> FEATURE:
<221> NAME/KEY: modified_base
<222> LOCATION: (190)
<223> OTHER INFORMATION: Where n is a, c, g or t
<220> FEATURE:
<221> NAME/KEY: modified_base
<222> LOCATION: (191)
<223> OTHER INFORMATION: Where n is a, c, g or t
<220> FEATURE:
<221> NAME/KEY: modified_base
<222> LOCATION: (200)
<223> OTHER INFORMATION: Where n is a, c, g or t
<220> FEATURE:
<221> NAME/KEY: modified_base
<222> LOCATION: (201)
<223> OTHER INFORMATION: Where n is a, c, g or t
<220> FEATURE:
<221> NAME/KEY: modified_base
<222> LOCATION: (205)
<223> OTHER INFORMATION: Where n is a, c, g or t
<220> FEATURE:
<221> NAME/KEY: modified_base
<222> LOCATION: (207)
<223> OTHER INFORMATION: Where n is a, c, g or t
<220> FEATURE:
<221> NAME/KEY: modified_base
<222> LOCATION: (221)
<223> OTHER INFORMATION: Where n is a, c, g or t
<220> FEATURE:
<221> NAME/KEY: modified_base
<222> LOCATION: (223)
<223> OTHER INFORMATION: Where n is a, c, g or t
<220> FEATURE:
```

```
<221> NAME/KEY: modified_base
<222> LOCATION: (229)
<223> OTHER INFORMATION: Where n is a, c, g or t
<220> FEATURE:
<221> NAME/KEY: modified_base
<222> LOCATION: (230)
<223> OTHER INFORMATION: Where n is a, c, g or t
<220> FEATURE:
<221> NAME/KEY: modified_base
<222> LOCATION: (237)
<223> OTHER INFORMATION: Where n is a, c, g or t
<220> FEATURE:
<221> NAME/KEY: modified_base
<222> LOCATION: (240)
<223> OTHER INFORMATION: Where n is a, c, g or t
<220> FEATURE:
<221> NAME/KEY: modified_base
<222> LOCATION: (241)
<223> OTHER INFORMATION: Where n is a, c, g or t
<220> FEATURE:
<221> NAME/KEY: modified_base
<222> LOCATION: (255)
<223> OTHER INFORMATION: Where n is a, c, g or t
<220> FEATURE:
<221> NAME/KEY: modified_base
<222> LOCATION: (264)
<223> OTHER INFORMATION: Where n is a, c, g or t
<220> FEATURE:
<221> NAME/KEY: modified_base
<222> LOCATION: (266)
<223> OTHER INFORMATION: Where n is a, c, g or t
<220> FEATURE:
<221> NAME/KEY: modified_base
<222> LOCATION: (267)
<223> OTHER INFORMATION: Where n is a, c, g or t
<220> FEATURE:
<221> NAME/KEY: modified_base
<222> LOCATION: (276)
<223> OTHER INFORMATION: Where n is a, c, g or t
<220> FEATURE:
<221> NAME/KEY: modified_base
<222> LOCATION: (280)
<223> OTHER INFORMATION: Where n is a, c, g or t
<220> FEATURE:
<221> NAME/KEY: modified_base
<222> LOCATION: (288)
<223> OTHER INFORMATION: Where n is a, c, g or t
<220> FEATURE:
<221> NAME/KEY: modified_base
<222> LOCATION: (289)
<223> OTHER INFORMATION: Where n is a, c, g or t
<220> FEATURE:
<221> NAME/KEY: modified_base
<222> LOCATION: (291)
<223> OTHER INFORMATION: Where n is a, c, g or t
<220> FEATURE:
<221> NAME/KEY: modified_base
<222> LOCATION: (297)
<223> OTHER INFORMATION: Where n is a, c, g or t
<220> FEATURE:
<221> NAME/KEY: modified_base
<222> LOCATION: (301)
<223> OTHER INFORMATION: Where n is a, c, g or t
<220> FEATURE:
<221> NAME/KEY: modified_base
<222> LOCATION: (306)
<223> OTHER INFORMATION: Where n is a, c, g or t
<220> FEATURE:
<221> NAME/KEY: modified_base
<222> LOCATION: (308)
<223> OTHER INFORMATION: Where n is a, c, g or t
<220> FEATURE:
<221> NAME/KEY: modified_base
<222> LOCATION: (314)
<223> OTHER INFORMATION: Where n is a, c, g or t
<220> FEATURE:
<221> NAME/KEY: modified_base
<222> LOCATION: (315)
<223> OTHER INFORMATION: Where n is a, c, g or t
```

```
-continued

<220> FEATURE:
<221> NAME/KEY: modified_base
<222> LOCATION: (326)
<223> OTHER INFORMATION: Where n is a, c, g or t
<220> FEATURE:
<221> NAME/KEY: modified_base
<222> LOCATION: (332)
<223> OTHER INFORMATION: Where n is a, c, g or t
<220> FEATURE:
<221> NAME/KEY: modified_base
<222> LOCATION: (335)
<223> OTHER INFORMATION: Where n is a, c, g or t
<220> FEATURE:
<221> NAME/KEY: modified_base
<222> LOCATION: (337)
<223> OTHER INFORMATION: Where n is a, c, g or t
<220> FEATURE:
<221> NAME/KEY: modified_base
<222> LOCATION: (339)
<223> OTHER INFORMATION: Where n is a, c, g or t
<220> FEATURE:
<221> NAME/KEY: modified_base
<222> LOCATION: (341)
<223> OTHER INFORMATION: Where n is a, c, g or t
<220> FEATURE:
<221> NAME/KEY: modified_base
<222> LOCATION: (343)
<223> OTHER INFORMATION: Where n is a, c, g or t
<220> FEATURE:
<221> NAME/KEY: modified_base
<222> LOCATION: (344)
<223> OTHER INFORMATION: Where n is a, c, g or t
<220> FEATURE:
<221> NAME/KEY: modified_base
<222> LOCATION: (345)
<223> OTHER INFORMATION: Where n is a, c, g or t
<220> FEATURE:
<221> NAME/KEY: modified_base
<222> LOCATION: (347)
<223> OTHER INFORMATION: Where n is a, c, g or t
<220> FEATURE:
<221> NAME/KEY: modified_base
<222> LOCATION: (350)
<223> OTHER INFORMATION: Where n is a, c, g or t
<220> FEATURE:
<221> NAME/KEY: modified_base
<222> LOCATION: (355)
<223> OTHER INFORMATION: Where n is a, c, g or t
<220> FEATURE:
<221> NAME/KEY: modified_base
<222> LOCATION: (356)
<223> OTHER INFORMATION: Where n is a, c, g or t
<220> FEATURE:
<221> NAME/KEY: modified_base
<222> LOCATION: (358)
<223> OTHER INFORMATION: Where n is a, c, g or t
<220> FEATURE:
<221> NAME/KEY: modified_base
<222> LOCATION: (362)
<223> OTHER INFORMATION: Where n is a, c, g or t
<220> FEATURE:
<221> NAME/KEY: modified_base
<222> LOCATION: (363)
<223> OTHER INFORMATION: Where n is a, c, g or t
<220> FEATURE:
<221> NAME/KEY: modified_base
<222> LOCATION: (372)
<223> OTHER INFORMATION: Where n is a, c, g or t
<220> FEATURE:
<221> NAME/KEY: modified_base
<222> LOCATION: (379)
<223> OTHER INFORMATION: Where n is a, c, g or t
<220> FEATURE:
<221> NAME/KEY: modified_base
<222> LOCATION: (395)
<223> OTHER INFORMATION: Where n is a, c, g or t
<220> FEATURE:
<221> NAME/KEY: modified_base
<222> LOCATION: (397)
```

-continued

```
<223> OTHER INFORMATION: Where n is a, c, g or t
<220> FEATURE:
<221> NAME/KEY: modified_base
<222> LOCATION: (398)
<223> OTHER INFORMATION: Where n is a, c, g or t
<220> FEATURE:
<221> NAME/KEY: modified_base
<222> LOCATION: (400)
<223> OTHER INFORMATION: Where n is a, c, g or t
<220> FEATURE:
<221> NAME/KEY: modified_base
<222> LOCATION: (403)
<223> OTHER INFORMATION: Where n is a, c, g or t
<220> FEATURE:
<221> NAME/KEY: modified_base
<222> LOCATION: (412)
<223> OTHER INFORMATION: Where n is a, c, g or t
<220> FEATURE:
<221> NAME/KEY: modified_base
<222> LOCATION: (414)
<223> OTHER INFORMATION: Where n is a, c, g or t
<220> FEATURE:
<221> NAME/KEY: modified_base
<222> LOCATION: (421)
<223> OTHER INFORMATION: Where n is a, c, g or t
<220> FEATURE:
<221> NAME/KEY: modified_base
<222> LOCATION: (423)
<223> OTHER INFORMATION: Where n is a, c, g or t
<220> FEATURE:
<221> NAME/KEY: modified_base
<222> LOCATION: (431)
<223> OTHER INFORMATION: Where n is a, c, g or t
<220> FEATURE:
<221> NAME/KEY: modified_base
<222> LOCATION: (435)
<223> OTHER INFORMATION: Where n is a, c, g or t
<220> FEATURE:
<221> NAME/KEY: modified_base
<222> LOCATION: (438)
<223> OTHER INFORMATION: Where n is a, c, g or t
<220> FEATURE:
<221> NAME/KEY: modified_base
<222> LOCATION: (439
<223> OTHER INFORMATION: Where n is a, c, g or t
<220> FEATURE:
<221> NAME/KEY: modified_base
<222> LOCATION: (457)
<223> OTHER INFORMATION: Where n is a, c, g or t
<220> FEATURE:
<221> NAME/KEY: modified_base
<222> LOCATION: (463)
<223> OTHER INFORMATION: Where n is a, c, g or t
<220> FEATURE:
<221> NAME/KEY: modified_base
<222> LOCATION: (467)
<223> OTHER INFORMATION: Where n is a, c, g or t
<220> FEATURE:
<221> NAME/KEY: modified_base
<222> LOCATION: (471)
<223> OTHER INFORMATION: Where n is a, c, g or t
<220> FEATURE:
<221> NAME/KEY: modified_base
<222> LOCATION: (474)
<223> OTHER INFORMATION: Where n is a, c, g or t
<220> FEATURE:
<221> NAME/KEY: modified_base
<222> LOCATION: (480)
<223> OTHER INFORMATION: Where n is a, c, g or t
<220> FEATURE:
<221> NAME/KEY: modified_base
<222> LOCATION: (483)
<223> OTHER INFORMATION: Where n is a, c, g or t
<220> FEATURE:
<221> NAME/KEY: modified_base
<222> LOCATION: (484)
<223> OTHER INFORMATION: Where n is a, c, g or t
<220> FEATURE:
<221> NAME/KEY: modified_base
```

-continued

```
<222> LOCATION: (487)
<223> OTHER INFORMATION: Where n is a, c, g or t
<220> FEATURE:
<221> NAME/KEY: modified_base
<222> LOCATION: (490)
<223> OTHER INFORMATION: Where n is a, c, g or t
<220> FEATURE:
<221> NAME/KEY: modified_base
<222> LOCATION: (491)
<223> OTHER INFORMATION: Where n is a, c, g or t
<220> FEATURE:
<221> NAME/KEY: modified_base
<222> LOCATION: (492)
<223> OTHER INFORMATION: Where n is a, c, g or t
<220> FEATURE:
<221> NAME/KEY: modified_base
<222> LOCATION: (493)
<223> OTHER INFORMATION: Where n is a, c, g or t
<220> FEATURE:
<221> NAME/KEY: modified_base
<222> LOCATION: (499)
<223> OTHER INFORMATION: Where n is a, c, g or t
<220> FEATURE:
<221> NAME/KEY: modified_base
<222> LOCATION: (500)
<223> OTHER INFORMATION: Where n is a, c, g or t
<220> FEATURE:
<221> NAME/KEY: modified_base
<222> LOCATION: (504)
<223> OTHER INFORMATION: Where n is a, c, g or t
<220> FEATURE:
<221> NAME/KEY: modified_base
<222> LOCATION: (508)
<223> OTHER INFORMATION: Where n is a, c, g or t
<220> FEATURE:
<221> NAME/KEY: modified_base
<222> LOCATION: (518)
<223> OTHER INFORMATION: Where n is a, c, g or t
<220> FEATURE:
<221> NAME/KEY: modified_base
<222> LOCATION: (536)
<223> OTHER INFORMATION: Where n is a, c, g or t
<220> FEATURE:
<221> NAME/KEY: modified_base
<222> LOCATION: (538)
<223> OTHER INFORMATION: Where n is a, c, g or t
<220> FEATURE:
<221> NAME/KEY: modified_base
<222> LOCATION: (549)
<223> OTHER INFORMATION: Where n is a, c, g or t
<220> FEATURE:
<221> NAME/KEY: modified_base
<222> LOCATION: (551)
<223> OTHER INFORMATION: Where n is a, c, g or t
<220> FEATURE:
<221> NAME/KEY: modified_base
<222> LOCATION: (552)
<223> OTHER INFORMATION: Where n is a, c, g or t
<220> FEATURE:
<221> NAME/KEY: modified_base
<222> LOCATION: (554)
<223> OTHER INFORMATION: Where n is a, c, g or t
<220> FEATURE:
<221> NAME/KEY: modified_base
<222> LOCATION: (556)
<223> OTHER INFORMATION: Where n is a, c, g or t
<220> FEATURE:
<221> NAME/KEY: modified_base
<222> LOCATION: (557)
<223> OTHER INFORMATION: Where n is a, c, g or t
<220> FEATURE:
<221> NAME/KEY: modified_base
<222> LOCATION: (562)
<223> OTHER INFORMATION: Where n is a, c, g or t
<220> FEATURE:
<221> NAME/KEY: modified_base
<222> LOCATION: (563)
<223> OTHER INFORMATION: Where n is a, c, g or t
<220> FEATURE:
```

-continued

```
<221> NAME/KEY: modified_base
<222> LOCATION: (567)
<223> OTHER INFORMATION: Where n is a, c, g or t
<220> FEATURE:
<221> NAME/KEY: modified_base
<222> LOCATION: (571)
<223> OTHER INFORMATION: Where n is a, c, g or t
<220> FEATURE:
<221> NAME/KEY: modified_base
<222> LOCATION: (572)
<223> OTHER INFORMATION: Where n is a, c, g or t
<220> FEATURE:
<221> NAME/KEY: modified_base
<222> LOCATION: (576)
<223> OTHER INFORMATION: Where n is a, c, g or t
<220> FEATURE:
<221> NAME/KEY: modified_base
<222> LOCATION: (579)
<223> OTHER INFORMATION: Where n is a, c, g or t
<220> FEATURE:
<221> NAME/KEY: modified_base
<222> LOCATION: (590)
<223> OTHER INFORMATION: Where n is a, c, g or t
<220> FEATURE:
<221> NAME/KEY: modified_base
<222> LOCATION: (592)
<223> OTHER INFORMATION: Where n is a, c, g or t
<220> FEATURE:
<221> NAME/KEY: modified_base
<222> LOCATION: (595)
<223> OTHER INFORMATION: Where n is a, c, g or t
<220> FEATURE:
<221> NAME/KEY: modified_base
<222> LOCATION: (598)
<223> OTHER INFORMATION: Where n is a, c, g or t
<220> FEATURE:
<221> NAME/KEY: modified_base
<222> LOCATION: (606)
<223> OTHER INFORMATION: Where n is a, c, g or t
<220> FEATURE:
<221> NAME/KEY: modified_base
<222> LOCATION: (609)
<223> OTHER INFORMATION: Where n is a, c, g or t
<220> FEATURE:
<221> NAME/KEY: modified_base
<222> LOCATION: (613)
<223> OTHER INFORMATION: Where n is a, c, g or t
<220> FEATURE:
<221> NAME/KEY: modified_base
<222> LOCATION: (620)
<223> OTHER INFORMATION: Where n is a, c, g or t
<220> FEATURE:
<221> NAME/KEY: modified_base
<222> LOCATION: (622)
<223> OTHER INFORMATION: Where n is a, c, g or t
<220> FEATURE:
<221> NAME/KEY: modified_base
<222> LOCATION: (624)
<223> OTHER INFORMATION: Where n is a, c, g or t
<220> FEATURE:
<221> NAME/KEY: modified_base
<222> LOCATION: (626)
<223> OTHER INFORMATION: Where n is a, c, g or t
<220> FEATURE:
<221> NAME/KEY: modified_base
<222> LOCATION: (631)
<223> OTHER INFORMATION: Where n is a, c, g or t
<220> FEATURE:
<221> NAME/KEY: modified_base
<222> LOCATION: (634)
<223> OTHER INFORMATION: Where n is a, c, g or t
<220> FEATURE:
<221> NAME/KEY: modified_base
<222> LOCATION: (638)
<223> OTHER INFORMATION: Where n is a, c, g or t
<220> FEATURE:
<221> NAME/KEY: modified_base
<222> LOCATION: (641)
<223> OTHER INFORMATION: Where n is a, c, g or t
```

<220> FEATURE:
<221> NAME/KEY: modified_base
<222> LOCATION: (647)
<223> OTHER INFORMATION: Where n is a, c, g or t
<220> FEATURE:
<221> NAME/KEY: modified_base
<222> LOCATION: (654)
<223> OTHER INFORMATION: Where n is a, c, g or t
<220> FEATURE:
<221> NAME/KEY: modified_base
<222> LOCATION: (660)
<223> OTHER INFORMATION: Where n is a, c, g or t
<220> FEATURE:
<221> NAME/KEY: modified_base
<222> LOCATION: (661)
<223> OTHER INFORMATION: Where n is a, c, g or t
<220> FEATURE:
<221> NAME/KEY: modified_base
<222> LOCATION: (664)
<223> OTHER INFORMATION: Where n is a, c, g or t

<400> SEQUENCE: 52

```
actagtagaa gaactttgcc gcttttgtgc ctctcacagg cgcctaaagt cattgccatg      60
ggaggaagac gatttggggg gggaggggggg gggggcanngg tccgtggggc tttccctant    120
ntatctccat ntccantgnn cnntgtcgcc tcttccctcg tcncattnga anttantccc     180
tggncccnn ncctctccn nctncncct cccccctccg ncncctccnn cttttttntan      240
ncttccccat ctccntcccc cctnanngtc ccaacnccgn cagcaatnnc ncacttnctc     300
nctccncncc tccnnccgtt cttctnttct cnacntntnc ncnnntnccn tgccnntnaa     360
annctctccc cnctgcaanc gattctctcc ctccncnnan ctntccactc cntncttctc    420
ncncgctcct nttcntcnnc ccacctctcn ccttcgnccc cantacnctc nccnccttn     480
cgnntcnttn nnntcctcnn accncccncc tcccttcncc cctcttctcc ccggtntntc    540
tctctcccnc nncncnncct cnncccntcc nngcgnccnt ttccgccccn cnccnccntt    600
ccttcntcnc cantccatcn cntntnccat nctcctncc nctcacnccc gctncccccn     660
ntctctttca cacngtcc                                                  678
```

<210> SEQ ID NO 53
<211> LENGTH: 502
<212> TYPE: DNA
<213> ORGANISM: Homo sapiens
<220> FEATURE:
<221> NAME/KEY: modified_base
<222> LOCATION: (139)
<223> OTHER INFORMATION: Where n is a, c, g or t
<220> FEATURE:
<221> NAME/KEY: modified_base
<222> LOCATION: (146)
<223> OTHER INFORMATION: Where n is a, c, g or t
<220> FEATURE:
<221> NAME/KEY: modified_base
<222> LOCATION: (215)
<223> OTHER INFORMATION: Where n is a, c, g or t
<220> FEATURE:
<221> NAME/KEY: modified_base
<222> LOCATION: (217)
<223> OTHER INFORMATION: Where n is a, c, g or t
<220> FEATURE:
<221> NAME/KEY: modified_base
<222> LOCATION: (257)
<223> OTHER INFORMATION: Where n is a, c, g or t
<220> FEATURE:
<221> NAME/KEY: modified_base
<222> LOCATION: (263)
<223> OTHER INFORMATION: Where n is a, c, g or t
<220> FEATURE:
<221> NAME/KEY: modified_base
<222> LOCATION: (289)

```
<223> OTHER INFORMATION: Where n is a, c, g or t
<220> FEATURE:
<221> NAME/KEY: modified_base
<222> LOCATION: (386)
<223> OTHER INFORMATION: Where n is a, c, g or t
<220> FEATURE:
<221> NAME/KEY: modified_base
<222> LOCATION: (420)
<223> OTHER INFORMATION: Where n is a, c, g or t
<220> FEATURE:
<221> NAME/KEY: modified_base
<222> LOCATION: (452)
<223> OTHER INFORMATION: Where n is a, c, g or t
<220> FEATURE:
<221> NAME/KEY: modified_base
<222> LOCATION: (457)
<223> OTHER INFORMATION: Where n is a, c, g or t
<220> FEATURE:
<221> NAME/KEY: modified_base
<222> LOCATION: (461)
<223> OTHER INFORMATION: Where n is a, c, g or t
<220> FEATURE:
<221> NAME/KEY: modified_base
<222> LOCATION: (466)
<223> OTHER INFORMATION: Where n is a, c, g or t
<220> FEATURE:
<221> NAME/KEY: modified_base
<222> LOCATION: (482)
<223> OTHER INFORMATION: Where n is a, c, g or t
<220> FEATURE:
<221> NAME/KEY: modified_base
<222> LOCATION: (486)
<223> OTHER INFORMATION: Where n is a, c, g or t

<400> SEQUENCE: 53
tgaagatcct ggtgtcgcca tgggccgccg ccccgcccgt tgttaccggt attgtaagaa      60
caagccgtac ccaaagtctc gcttctgccg aggtgtccct gatgccaaaa ttcgcatttt     120
tgacctgggg cggaaaaang caaaantgga tgagtctccg ctttgtggcc acatggtgtc     180
agatcaatat gagcagctgt cctctgaagc cctgnangct gcccgaattt gtgccaataa     240
gtacatggta aaaagtngtg gcnaagatgc ttccatatcc gggtgcggnt ccacccttc     300 cacgtcatcc gcatcaacaa gatgttgtcc tgtgctgggg ctgacaggct cccaacaggc     360
atgcgaagtg cctttggaaa acccanggca ctgtggccag ggttcacatt gggccaattn     420
atcatgttca tccgcaccaa ctgcagaaca angaacntgt naattnaagc cctgcccagg     480
gncaanttca aatttcccgg cc                                              502

<210> SEQ ID NO 54
<211> LENGTH: 494
<212> TYPE: DNA
<213> ORGANISM: Homo sapiens
<220> FEATURE:
<221> NAME/KEY: modified_base
<222> LOCATION: (431)
<223> OTHER INFORMATION: Where n is a, c, g or t
<220> FEATURE:
<221> NAME/KEY: modified_base
<222> LOCATION: (442)
<223> OTHER INFORMATION: Where n is a, c, g or t
<220> FEATURE:
<221> NAME/KEY: modified_base
<222> LOCATION: (445)
<223> OTHER INFORMATION: Where n is a, c, g or t

<400> SEQUENCE: 54
actagtccaa gaaaaatatg cttaatgtat attacaaagg ctttgtatat gttaacctgt      60
tttaatgcca aaagtttgct tgtccacaa tttccttaag acctcttcag aaagggattt      120
gtttgcctta atgaatactg ttgggaaaaa acacagtata atgagtgaaa agggcagaag     180
```

```
caagaaattt ctacatctta gcgactccaa gaagaatgag tatccacatt tagatggcac      240
attatgagga cttttaatctt tccttaaaca caataatgtt ttcttttttc ttttattcac     300
atgatttcta agtatatttt tcatgcagga cagttttttca accttgatgt acagtgactg     360
tgttaaattt ttctttcagt ggcaacctct ataatcttta aaatatggtg agcatcttgt     420
ctgttttgaa ngggatatga cnatnaatct atcagatggg aaatcctgtt tccaagttag     480
aaaaaaaaaa aaaa                                                        494
```

<210> SEQ ID NO 55
<211> LENGTH: 606
<212> TYPE: DNA
<213> ORGANISM: Homo sapiens
<220> FEATURE:
<221> NAME/KEY: modified_base
<222> LOCATION: (375)
<223> OTHER INFORMATION: Where n is a, c, g or t
<220> FEATURE:
<221> NAME/KEY: modified_base
<222> LOCATION: (395)
<223> OTHER INFORMATION: Where n is a, c, g or t
<220> FEATURE:
<221> NAME/KEY: modified_base
<222> LOCATION: (511)
<223> OTHER INFORMATION: Where n is a, c, g or t
<220> FEATURE:
<221> NAME/KEY: modified_base
<222> LOCATION: (542)
<223> OTHER INFORMATION: Where n is a, c, g or t
<220> FEATURE:
<221> NAME/KEY: modified_base
<222> LOCATION: (559)
<223> OTHER INFORMATION: Where n is a, c, g or t
<220> FEATURE:
<221> NAME/KEY: modified_base
<222> LOCATION: (569)
<223> OTHER INFORMATION: Where n is a, c, g or t
<220> FEATURE:
<221> NAME/KEY: modified_base
<222> LOCATION: (578)
<223> OTHER INFORMATION: Where n is a, c, g or t
<220> FEATURE:
<221> NAME/KEY: modified_base
<222> LOCATION: (581)
<223> OTHER INFORMATION: Where n is a, c, g or t

<400> SEQUENCE: 55

```
actagtaaaa agcagcattg ccaaataatc cctaattttc cactaaaaat ataatgaaat      60
gatgttaagc ttttttgaaaa gtttaggtta aacctactgt tgttagatta atgtatttgt    120 tgcttcccctt tatctggaat gtggcattag ctttttttatt ttaaccctct ttaattctta   180
ttcaattcca tgacttaagg ttggagagct aaacactggg attttttggat aacagactga    240 cagttttgca taattataat cggcattgta catagaaagg atatggctac cttttgttaa     300
atctgcactt tctaaatatc aaaaaggga aatgaagtat aaatcaattt ttgtataatc      360
tgtttgaaac atganttta tttgcttaat attanggctt tgccctttct tgttagtctc      420
ttgggatcct gtgtaaaact gttctcatta aacaccaaac agttaagtcc attctctggt    480
actagctaca aattccgttt catattctac ntaacaattt aaattaactg aaatatttct    540
anatggtcta cttctgtcnt ataaaaacna aacttgantt nccaaaaaaa aaaaaaaaa     600 aaaaaa                                                                606
```

<210> SEQ ID NO 56
<211> LENGTH: 183
<212> TYPE: DNA

<213> ORGANISM: Homo sapiens

<400> SEQUENCE: 56

```
actagtatat ttaaacttac aggcttattt gtaatgtaaa ccaccatttt aatgtactgt      60
aattaacatg gttataatac gtacaatcct tccctcatcc catcacacaa cttttttttgt     120
gtgtgataaa ctgattttgg tttgcaataa aaccttgaaa aataaaaaaa aaaaaaaaa       180
aaa                                                                    183
```

```
<210> SEQ ID NO 57
<211> LENGTH: 622
<212> TYPE: DNA
<213> ORGANISM: Homo sapiens
<220> FEATURE:
<221> NAME/KEY: modified_base
<222> LOCATION: (358)
<223> OTHER INFORMATION: Where n is a, c, g or t
<220> FEATURE:
<221> NAME/KEY: modified_base
<222> LOCATION: (368)
<223> OTHER INFORMATION: Where n is a, c, g or t
<220> FEATURE:
<221> NAME/KEY: modified_base
<222> LOCATION: (412)
<223> OTHER INFORMATION: Where n is a, c, g or t
<220> FEATURE:
<221> NAME/KEY: modified_base
<222> LOCATION: (414)
<223> OTHER INFORMATION: Where n is a, c, g or t
<220> FEATURE:
<221> NAME/KEY: modified_base
<222> LOCATION: (425)
<223> OTHER INFORMATION: Where n is a, c, g or t
<220> FEATURE:
<221> NAME/KEY: modified_base
<222> LOCATION: (430)
<223> OTHER INFORMATION: Where n is a, c, g or t
<220> FEATURE:
<221> NAME/KEY: modified_base
<222> LOCATION: (453)
<223> OTHER INFORMATION: Where n is a, c, g or t
<220> FEATURE:
<221> NAME/KEY: modified_base
<222> LOCATION: (455)
<223> OTHER INFORMATION: Where n is a, c, g or t
<220> FEATURE:
<221> NAME/KEY: modified_base
<222> LOCATION: (469)
<223> OTHER INFORMATION: Where n is a, c, g or t
<220> FEATURE:
<221> NAME/KEY: modified_base
<222> LOCATION: (475)
<223> OTHER INFORMATION: Where n is a, c, g or t
<220> FEATURE:
<221> NAME/KEY: modified_base
<222> LOCATION: (495)
<223> OTHER INFORMATION: Where n is a, c, g or t
<220> FEATURE:
<221> NAME/KEY: modified_base
<222> LOCATION: (499)
<223> OTHER INFORMATION: Where n is a, c, g or t
<220> FEATURE:
<221> NAME/KEY: modified_base
<222> LOCATION: (529)
<223> OTHER INFORMATION: Where n is a, c, g or t
<220> FEATURE:
<221> NAME/KEY: modified_base
<222> LOCATION: (540)
<223> OTHER INFORMATION: Where n is a, c, g or t
<220> FEATURE:
<221> NAME/KEY: modified_base
<222> LOCATION: (564)
<223> OTHER INFORMATION: Where n is a, c, g or t
<220> FEATURE:
<221> NAME/KEY: modified_base
```

```
<222> LOCATION: (575)
<223> OTHER INFORMATION: Where n is a, c, g or t
<220> FEATURE:
<221> NAME/KEY: modified_base
<222> LOCATION: (590)
<223> OTHER INFORMATION: Where n is a, c, g or t

<400> SEQUENCE: 57
actagtcact actgtcttct ccttgtagct aatcaatcaa tattcttccc ttgcctgtgg      60
gcagtggaga gtgctgctgg gtgtacgctg cacctgccca ctgagttggg gaaagaggat    120
aatcagtgag cactgttctg ctcagagctc ctgatctacc ccaccccta ggatccagga     180 ctgggtcaaa gctgcatgaa accaggccct ggcagcaacc tgggaatggc tggaggtggg    240
agagaacctg acttctcttt ccctctccct cctccaacat tactggaact ctatcctgtt    300
agggatcttc tgagcttgtt tccctgctgg gtgggacaga agacaaagga gaagggangg    360
tctacaanaa gcagcccttc tttgtcctct ggggttaatg agcttgacct ananttcatg    420
gaganaccan aagcctctga tttttaattt ccntnaaatg tttgaagtnt atatntacat    480
atatatattt ctttnaatnt ttgagtcttt gatatgtctt aaaatccant ccctctgccn    540
gaaacctgaa ttaaaaccat gaanaaaaat gtttnccttta aagatgttan taattaattg    600
aaacttgaaa aaaaaaaaaa aa                                              622

<210> SEQ ID NO 58
<211> LENGTH: 433
<212> TYPE: DNA
<213> ORGANISM: Homo sapiens

<400> SEQUENCE: 58
gaacaaattc tgattggtta tgtaccgtca aaagacttga agaaatttca tgattttgca     60
gtgtggaagc gttgaaaatt gaaagttact gcttttccac ttgctcatat agtaaaggga    120
tcctttcagc tgccagtgtt gaataatgta tcatccagag tgatgttatc tgtgacagtc    180
accagcttta agctgaacca ttttatgaat accaaataaa tagacctctt gtactgaaaa    240
catatttgtg actttaatcg tgctgcttgg atagaaatat ttttactggt tcttctgaat    300
tgacagtaaa cctgtccatt atgaatggcc tactgttcta ttatttgttt tgacttgaat    360
ttatccacca aagacttcat ttgtgtatca tcaataaagt tgtatgtttc aactgaaaaa    420
aaaaaaaaaa aaa                                                        433

<210> SEQ ID NO 59
<211> LENGTH: 649
<212> TYPE: DNA
<213> ORGANISM: Homo sapiens
<220> FEATURE:
<221> NAME/KEY: modified_base
<222> LOCATION: (22)
<223> OTHER INFORMATION: Where n is a, c, g or t
<220> FEATURE:
<221> NAME/KEY: modified_base
<222> LOCATION: (190)
<223> OTHER INFORMATION: Where n is a, c, g or t
<220> FEATURE:
<221> NAME/KEY: modified_base
<222> LOCATION: (217)
<223> OTHER INFORMATION: Where n is a, c, g or t
<220> FEATURE:
<221> NAME/KEY: modified_base
<222> LOCATION: (430)
<223> OTHER INFORMATION: Where n is a, c, g or t
<220> FEATURE:
<221> NAME/KEY: modified_base
<222> LOCATION: (433)
```

```
<223> OTHER INFORMATION: Where n is a, c, g or t
<220> FEATURE:
<221> NAME/KEY: modified_base
<222> LOCATION: (484)
<223> OTHER INFORMATION: Where n is a, c, g or t
<220> FEATURE:
<221> NAME/KEY: modified_base
<222> LOCATION: (544)
<223> OTHER INFORMATION: Where n is a, c, g or t
<220> FEATURE:
<221> NAME/KEY: modified_base
<222> LOCATION: (550)
<223> OTHER INFORMATION: Where n is a, c, g or t
<220> FEATURE:
<221> NAME/KEY: modified_base
<222> LOCATION: (577)
<223> OTHER INFORMATION: Where n is a, c, g or t
<220> FEATURE:
<221> NAME/KEY: modified_base
<222> LOCATION: (583)
<223> OTHER INFORMATION: Where n is a, c, g or t
<220> FEATURE:
<221> NAME/KEY: modified_base
<222> LOCATION: (594)
<223> OTHER INFORMATION: Where n is a, c, g or t

<400> SEQUENCE: 59
actagttatt atctgacttt cnggttataa tcattctaat gagtgtgaag tagcctctgg      60
tgtcatttgg atttgcattt ctctgatgag tgatgctatc aagcacctttt gctggtgctg    120 ttggccatat gtgtatgttc cctggagaag tgtctgtgct gagccttggc ccactttta     180 attaggcgtn tgtcttttta ttactgagtt gtaaganttc tttatatatt ctggattcta    240
gacccttatc agatacatgg tttgcaaata ttttctccca ttctgtgggt tgtgttttca    300
ctttatcgat aatgtcctta gacatataat aaatttgtat tttaaaagtg acttgatttg    360
ggctgtgcaa ggtgggctca cgcttgtaat cccagcactt tgggagactg aggtgggtgg    420
atcatatgan gangctagga gttcgaggtc agcctggcca gcatagcgaa aacttgtctc    480
tacnaaaaat acaaaaatta gtcaggcatg gtggtgcacg tctgtaatac cagcttctca    540
ggangctgan gcacaaggat cacttgaacc ccagaangaa gangttgcag tganctgaag    600
atcatgccag ggcaacaaaa atgagaactt gtttaaaaaa aaaaaaaa                 649

<210> SEQ ID NO 60
<211> LENGTH: 423
<212> TYPE: DNA
<213> ORGANISM: Homo sapiens
<220> FEATURE:
<221> NAME/KEY: modified_base
<222> LOCATION: (209)
<223> OTHER INFORMATION: Where n is a, c, g or t
<220> FEATURE:
<221> NAME/KEY: modified_base
<222> LOCATION: (222)
<223> OTHER INFORMATION: Where n is a, c, g or t
<220> FEATURE:
<221> NAME/KEY: modified_base
<222> LOCATION: (277)
<223> OTHER INFORMATION: Where n is a, c, g or t
<220> FEATURE:
<221> NAME/KEY: modified_base
<222> LOCATION: (389)
<223> OTHER INFORMATION: Where n is a, c, g or t
<220> FEATURE:
<221> NAME/KEY: modified_base
<222> LOCATION: (398)
<223> OTHER INFORMATION: Where n is a, c, g or t

<400> SEQUENCE: 60
actagttcag gccttccagt tcactgacaa acatggggaa gtgtgcccag ctggctggaa      60
```

-continued

```
acctggcagt gataccatca agcctgatgt ccaaaagagc aaagaatatt tctccaagca      120
gaagtgagcg ctgggctgtt ttagtgccag gctgcggtgg gcagccatga gaacaaaacc      180
tcttctgtat ttttttttc cattagtana acacaagact cngattcagc cgaattgtgg       240
tgtcttacaa ggcagggctt tcctacaggg ggtgganaaa acagcctttc ttcctttggt      300
aggaatggcc tgagttggcg ttgtgggcag gctactggtt tgtatgatgt attagtagag      360
caacccatta atcttttgta gtttgtatna aacttganct gagaccttaa acaaaaaaaa      420
aaa                                                                     423
```

<210> SEQ ID NO 61
<211> LENGTH: 423
<212> TYPE: DNA
<213> ORGANISM: Homo sapiens
<220> FEATURE:
<221> NAME/KEY: modified_base
<222> LOCATION: (195)
<223> OTHER INFORMATION: Where n is a, c, g or t
<220> FEATURE:
<221> NAME/KEY: modified_base
<222> LOCATION: (285)
<223> OTHER INFORMATION: Where n is a, c, g or t
<220> FEATURE:
<221> NAME/KEY: modified_base
<222> LOCATION: (295)
<223> OTHER INFORMATION: Where n is a, c, g or t
<220> FEATURE:
<221> NAME/KEY: modified_base
<222> LOCATION: (329)
<223> OTHER INFORMATION: Where n is a, c, g or t
<220> FEATURE:
<221> NAME/KEY: modified_base
<222> LOCATION: (335)
<223> OTHER INFORMATION: Where n is a, c, g or t
<220> FEATURE:
<221> NAME/KEY: modified_base
<222> LOCATION: (340)
<223> OTHER INFORMATION: Where n is a, c, g or t
<220> FEATURE:
<221> NAME/KEY: modified_base
<222> LOCATION: (347)
<223> OTHER INFORMATION: Where n is a, c, g or t
<220> FEATURE:
<221> NAME/KEY: modified_base
<222> LOCATION: (367)
<223> OTHER INFORMATION: Where n is a, c, g or t
<220> FEATURE:
<221> NAME/KEY: modified_base
<222> LOCATION: (382)
<223> OTHER INFORMATION: Where n is a, c, g or t
<220> FEATURE:
<221> NAME/KEY: modified_base
<222> LOCATION: (383)
<223> OTHER INFORMATION: Where n is a, c, g or t
<220> FEATURE:
<221> NAME/KEY: modified_base
<222> LOCATION: (391)
<223> OTHER INFORMATION: Where n is a, c, g or t
<220> FEATURE:
<221> NAME/KEY: modified_base
<222> LOCATION: (396)
<223> OTHER INFORMATION: Where n is a, c, g or t
<220> FEATURE:
<221> NAME/KEY: modified_base
<222> LOCATION: (418)
<223> OTHER INFORMATION: Where n is a, c, g or t

<400> SEQUENCE: 61

```
cgggactgga atgtaaagtg aagttcggag ctctgagcac gggctcttcc cgccgggtcc       60
tccctcccca gacccagag ggagaggccc accccgccca gccccgcccc agcccctgct       120
```

```
caggtctgag tatggctggg agtcgggggc cacaggcctc tagctgtgct gctcaagaag      180
actggatcag ggtanctaca agtggccggg ccttgccttt gggattctac cctgttccta      240
atttggtgtt ggggtgcggg gtccctggcc cccttttcca cactncctcc ctccngacag      300
caacctccct tggggcaatt gggcctggnt ctccncccgn tgttgcnacc ctttgttggt      360 ttaaggncttt taaaaatgtt annttttccc ntgccngggt taaaaaagga aaaaactnaa     420
aaa                                                                   423
```

<210> SEQ ID NO 62
<211> LENGTH: 683
<212> TYPE: DNA
<213> ORGANISM: Homo sapiens
<220> FEATURE:
<221> NAME/KEY: modified_base
<222> LOCATION: (218)
<223> OTHER INFORMATION: Where n is a, c, g or t
<220> FEATURE:
<221> NAME/KEY: modified_base
<222> LOCATION: (291)
<223> OTHER INFORMATION: Where n is a, c, g or t
<220> FEATURE:
<221> NAME/KEY: modified_base
<222> LOCATION: (305)
<223> OTHER INFORMATION: Where n is a, c, g or t
<220> FEATURE:
<221> NAME/KEY: modified_base
<222> LOCATION: (411)
<223> OTHER INFORMATION: Where n is a, c, g or t
<220> FEATURE:
<221> NAME/KEY: modified_base
<222> LOCATION: (416)
<223> OTHER INFORMATION: Where n is a, c, g or t
<220> FEATURE:
<221> NAME/KEY: modified_base
<222> LOCATION: (441)
<223> OTHER INFORMATION: Where n is a, c, g or t
<220> FEATURE:
<221> NAME/KEY: modified_base
<222> LOCATION: (443)
<223> OTHER INFORMATION: Where n is a, c, g or t
<220> FEATURE:
<221> NAME/KEY: modified_base
<222> LOCATION: (453)
<223> OTHER INFORMATION: Where n is a, c, g or t
<220> FEATURE:
<221> NAME/KEY: modified_base
<222> LOCATION: (522)
<223> OTHER INFORMATION: Where n is a, c, g or t
<220> FEATURE:
<221> NAME/KEY: modified_base
<222> LOCATION: (523)
<223> OTHER INFORMATION: Where n is a, c, g or t
<220> FEATURE:
<221> NAME/KEY: modified_base
<222> LOCATION: (536)
<223> OTHER INFORMATION: Where n is a, c, g or t
<220> FEATURE:
<221> NAME/KEY: modified_base
<222> LOCATION: (542)
<223> OTHER INFORMATION: Where n is a, c, g or t
<220> FEATURE:
<221> NAME/KEY: modified_base
<222> LOCATION: (547)
<223> OTHER INFORMATION: Where n is a, c, g or t
<220> FEATURE:
<221> NAME/KEY: modified_base
<222> LOCATION: (566)
<223> OTHER INFORMATION: Where n is a, c, g or t
<220> FEATURE:
<221> NAME/KEY: modified_base
<222> LOCATION: (588)
<223> OTHER INFORMATION: Where n is a, c, g or t
<220> FEATURE:
<221> NAME/KEY: modified_base
<222> LOCATION: (592)
<223> OTHER INFORMATION: Where n is a, c, g or t
<220> FEATURE:
<221> NAME/KEY: modified_base
<222> LOCATION: (595)
<223> OTHER INFORMATION: Where n is a, c, g or t
<220> FEATURE:
<221> NAME/KEY: modified_base
<222> LOCATION: (603)
<223> OTHER INFORMATION: Where n is a, c, g or t
<220> FEATURE:
<221> NAME/KEY: modified_base
<222> LOCATION: (621)
<223> OTHER INFORMATION: Where n is a, c, g or t
<220> FEATURE:
<221> NAME/KEY: modified_base
<222> LOCATION: (628)
<223> OTHER INFORMATION: Where n is a, c, g or t
<220> FEATURE:
<221> NAME/KEY: modified_base
<222> LOCATION: (630)
<223> OTHER INFORMATION: Where n is a, c, g or t
<220> FEATURE:
<221> NAME/KEY: modified_base
<222> LOCATION: (632)
<223> OTHER INFORMATION: Where n is a, c, g or t
<220> FEATURE:
<221> NAME/KEY: modified_base
<222> LOCATION: (644)
<223> OTHER INFORMATION: Where n is a, c, g or t
<220> FEATURE:
<221> NAME/KEY: modified_base
<222> LOCATION: (645)
<223> OTHER INFORMATION: Where n is a, c, g or t
<220> FEATURE:
<221> NAME/KEY: modified_base
<222> LOCATION: (648)
<223> OTHER INFORMATION: Where n is a, c, g or t
<220> FEATURE:
<221> NAME/KEY: modified_base
<222> LOCATION: (655)
<223> OTHER INFORMATION: Where n is a, c, g or t
<220> FEATURE:
<221> NAME/KEY: modified_base
<222> LOCATION: (660)
<223> OTHER INFORMATION: Where n is a, c, g or t
<220> FEATURE:
<221> NAME/KEY: modified_base
<222> LOCATION: (672)
<223> OTHER INFORMATION: Where n is a, c, g or t
<220> FEATURE:
<221> NAME/KEY: modified_base
<222> LOCATION: (674)
<223> OTHER INFORMATION: Where n is a, c, g or t
<220> FEATURE:
<221> NAME/KEY: modified_base
<222> LOCATION: (676)
<223> OTHER INFORMATION: Where n is a, c, g or t
<220> FEATURE:
<221> NAME/KEY: modified_base
<222> LOCATION: (677)
<223> OTHER INFORMATION: Where n is a, c, g or t
<220> FEATURE:
<221> NAME/KEY: modified_base
<222> LOCATION: (683)
<223> OTHER INFORMATION: Where n is a, c, g or t

<400> SEQUENCE: 62
gctggagagg ggtacggact ttcttggagt tgtcccaggt tggaatgaga ctgaactcaa     60 gaagaccc taagagactg gggaatggtt cctgccttca ggaaagtgaa agacgcttag    120
gctgtcaaca cttaaaggaa gtccccttga agcccagagt ggacagacta gacccattga    180
tggggccact ggccatggtc cgtggacaag acattccngt gggccatggc acaccggggg    240
ggatcaaaat gtgtacttgt ggggtctcgc cccttgccaa aaccaaacca ntcccactcc    300

```
tgtcnttgga ctttcttccc attccctcct ccccaaatgc acttccctc ctccctctgc    360 ccctcctgtg tttttggaat tctgtttccc tcaaaattgt taattttta nttttngacc    420 atgaacttat gtttggggtc nangttcccc ttnccaatgc atactaatat attaatggtt   480
atttattttt gaaatatttt ttaatgaact tggaaaaaat tnntggaatt tccttncttc   540
cnttttnttt gggggggtg gggggntggg ttaaaatttt tttggaancc cnatnggaaa    600
ttnttacttg gggcccccct naaaaaantn anttccaatt cttnnatngc ccctnttccn   660
ctaaaaaaaa ananannaaa aan                                           683
```

```
<210> SEQ ID NO 63
<211> LENGTH: 731
<212> TYPE: DNA
<213> ORGANISM: Homo sapiens
<220> FEATURE:
<221> NAME/KEY: modified_base
<222> LOCATION: (236)
<223> OTHER INFORMATION: Where n is a, c, g or t
<220> FEATURE:
<221> NAME/KEY: modified_base
<222> LOCATION: (249)
<223> OTHER INFORMATION: Where n is a, c, g or t
<220> FEATURE:
<221> NAME/KEY: modified_base
<222> LOCATION: (263)
<223> OTHER INFORMATION: Where n is a, c, g or t
<220> FEATURE:
<221> NAME/KEY: modified_base
<222> LOCATION: (288)
<223> OTHER INFORMATION: Where n is a, c, g or t
<220> FEATURE:
<221> NAME/KEY: modified_base
<222> LOCATION: (312)
<223> OTHER INFORMATION: Where n is a, c, g or t
<220> FEATURE:
<221> NAME/KEY: modified_base
<222> LOCATION: (317)
<223> OTHER INFORMATION: Where n is a, c, g or t
<220> FEATURE:
<221> NAME/KEY: modified_base
<222> LOCATION: (323)
<223> OTHER INFORMATION: Where n is a, c, g or t
<220> FEATURE:
<221> NAME/KEY: modified_base
<222> LOCATION: (326)
<223> OTHER INFORMATION: Where n is a, c, g or t
<220> FEATURE:
<221> NAME/KEY: modified_base
<222> LOCATION: (337)
<223> OTHER INFORMATION: Where n is a, c, g or t
<220> FEATURE:
<221> NAME/KEY: modified_base
<222> LOCATION: (352)
<223> OTHER INFORMATION: Where n is a, c, g or t
<220> FEATURE:
<221> NAME/KEY: modified_base
<222> LOCATION: (362)
<223> OTHER INFORMATION: Where n is a, c, g or t
<220> FEATURE:
<221> NAME/KEY: modified_base
<222> LOCATION: (370)
<223> OTHER INFORMATION: Where n is a, c, g or t
<220> FEATURE:
<221> NAME/KEY: modified_base
<222> LOCATION: (376)
<223> OTHER INFORMATION: Where n is a, c, g or t
<220> FEATURE:
<221> NAME/KEY: modified_base
<222> LOCATION: (400)
<223> OTHER INFORMATION: Where n is a, c, g or t
<220> FEATURE:
<221> NAME/KEY: modified_base
<222> LOCATION: (411)
<223> OTHER INFORMATION: Where n is a, c, g or t
```

-continued

```
<220> FEATURE:
<221> NAME/KEY: modified_base
<222> LOCATION: (414)
<223> OTHER INFORMATION: Where n is a, c, g or t
<220> FEATURE:
<221> NAME/KEY: modified_base
<222> LOCATION: (434)
<223> OTHER INFORMATION: Where n is a, c, g or t
<220> FEATURE:
<221> NAME/KEY: modified_base
<222> LOCATION: (436)
<223> OTHER INFORMATION: Where n is a, c, g or t
<220> FEATURE:
<221> NAME/KEY: modified_base
<222> LOCATION: (446)
<223> OTHER INFORMATION: Where n is a, c, g or t
<220> FEATURE:
<221> NAME/KEY: modified_base
<222> LOCATION: (457)
<223> OTHER INFORMATION: Where n is a, c, g or t
<220> FEATURE:
<221> NAME/KEY: modified_base
<222> LOCATION: (473)
<223> OTHER INFORMATION: Where n is a, c, g or t
<220> FEATURE:
<221> NAME/KEY: modified_base
<222> LOCATION: (486)
<223> OTHER INFORMATION: Where n is a, c, g or t
<220> FEATURE:
<221> NAME/KEY: modified_base
<222> LOCATION: (497)
<223> OTHER INFORMATION: Where n is a, c, g or t
<220> FEATURE:
<221> NAME/KEY: modified_base
<222> LOCATION: (498)
<223> OTHER INFORMATION: Where n is a, c, g or t
<220> FEATURE:
<221> NAME/KEY: modified_base
<222> LOCATION: (502)
<223> OTHER INFORMATION: Where n is a, c, g or t
<220> FEATURE:
<221> NAME/KEY: modified_base
<222> LOCATION: (512)
<223> OTHER INFORMATION: Where n is a, c, g or t
<220> FEATURE:
<221> NAME/KEY: modified_base
<222> LOCATION: (531)
<223> OTHER INFORMATION: Where n is a, c, g or t
<220> FEATURE:
<221> NAME/KEY: modified_base
<222> LOCATION: (546)
<223> OTHER INFORMATION: Where n is a, c, g or t
<220> FEATURE:
<221> NAME/KEY: modified_base
<222> LOCATION: (554)
<223> OTHER INFORMATION: Where n is a, c, g or t
<220> FEATURE:
<221> NAME/KEY: modified_base
<222> LOCATION: (563)
<223> OTHER INFORMATION: Where n is a, c, g or t
<220> FEATURE:
<221> NAME/KEY: modified_base
<222> LOCATION: (565)
<223> OTHER INFORMATION: Where n is a, c, g or t
<220> FEATURE:
<221> NAME/KEY: modified_base
<222> LOCATION: (566)
<223> OTHER INFORMATION: Where n is a, c, g or t
<220> FEATURE:
<221> NAME/KEY: modified_base
<222> LOCATION: (588)
<223> OTHER INFORMATION: Where n is a, c, g or t
<220> FEATURE:
<221> NAME/KEY: modified_base
<222> LOCATION: (597)
<223> OTHER INFORMATION: Where n is a, c, g or t
<220> FEATURE:
<221> NAME/KEY: modified_base
<222> LOCATION: (608)
```

```
-continued

<223> OTHER INFORMATION: Where n is a, c, g or t
<220> FEATURE:
<221> NAME/KEY: modified_base
<222> LOCATION: (611)
<223> OTHER INFORMATION: Where n is a, c, g or t
<220> FEATURE:
<221> NAME/KEY: modified_base
<222> LOCATION: (613)
<223> OTHER INFORMATION: Where n is a, c, g or t
<220> FEATURE:
<221> NAME/KEY: modified_base
<222> LOCATION: (615)
<223> OTHER INFORMATION: Where n is a, c, g or t
<220> FEATURE:
<221> NAME/KEY: modified_base
<222> LOCATION: (627)
<223> OTHER INFORMATION: Where n is a, c, g or t
<220> FEATURE:
<221> NAME/KEY: modified_base
<222> LOCATION: (632)
<223> OTHER INFORMATION: Where n is a, c, g or t
<220> FEATURE:
<221> NAME/KEY: modified_base
<222> LOCATION: (640)
<223> OTHER INFORMATION: Where n is a, c, g or t
<220> FEATURE:
<221> NAME/KEY: modified_base
<222> LOCATION: (641)
<223> OTHER INFORMATION: Where n is a, c, g or t
<220> FEATURE:
<221> NAME/KEY: modified_base
<222> LOCATION: (644)
<223> OTHER INFORMATION: Where n is a, c, g or t
<220> FEATURE:
<221> NAME/KEY: modified_base
<222> LOCATION: (654)
<223> OTHER INFORMATION: Where n is a, c, g or t
<220> FEATURE:
<221> NAME/KEY: modified_base
<222> LOCATION: (660)
<223> OTHER INFORMATION: Where n is a, c, g or t
<220> FEATURE:
<221> NAME/KEY: modified_base
<222> LOCATION: (663)
<223> OTHER INFORMATION: Where n is a, c, g or t
<220> FEATURE:
<221> NAME/KEY: modified_base
<222> LOCATION: (665)
<223> OTHER INFORMATION: Where n is a, c, g or t
<220> FEATURE:
<221> NAME/KEY: modified_base
<222> LOCATION: (671)
<223> OTHER INFORMATION: Where n is a, c, g or t
<220> FEATURE:
<221> NAME/KEY: modified_base
<222> LOCATION: (678)
<223> OTHER INFORMATION: Where n is a, c, g or t
<220> FEATURE:
<221> NAME/KEY: modified_base
<222> LOCATION: (692)
<223> OTHER INFORMATION: Where n is a, c, g or t
<220> FEATURE:
<221> NAME/KEY: modified_base
<222> LOCATION: (697)
<223> OTHER INFORMATION: Where n is a, c, g or t
<220> FEATURE:
<221> NAME/KEY: modified_base
<222> LOCATION: (698)
<223> OTHER INFORMATION: Where n is a, c, g or t
<220> FEATURE:
<221> NAME/KEY: modified_base
<222> LOCATION: (699)
<223> OTHER INFORMATION: Where n is a, c, g or t
<220> FEATURE:
<221> NAME/KEY: modified_base
<222> LOCATION: (704)
<223> OTHER INFORMATION: Where n is a, c, g or t
<220> FEATURE:
<221> NAME/KEY: modified_base
```

<222> LOCATION: (705)
<223> OTHER INFORMATION: Where n is a, c, g or t
<220> FEATURE:
<221> NAME/KEY: modified_base
<222> LOCATION: (712)
<223> OTHER INFORMATION: Where n is a, c, g or t
<220> FEATURE:
<221> NAME/KEY: modified_base
<222> LOCATION: (714)
<223> OTHER INFORMATION: Where n is a, c, g or t
<220> FEATURE:
<221> NAME/KEY: modified_base
<222> LOCATION: (717)
<223> OTHER INFORMATION: Where n is a, c, g or t
<220> FEATURE:
<221> NAME/KEY: modified_base
<222> LOCATION: (718)
<223> OTHER INFORMATION: Where n is a, c, g or t
<220> FEATURE:
<221> NAME/KEY: modified_base
<222> LOCATION: (719)
<223> OTHER INFORMATION: Where n is a, c, g or t
<220> FEATURE:
<221> NAME/KEY: modified_base
<222> LOCATION: (723)
<223> OTHER INFORMATION: Where n is a, c, g or t
<220> FEATURE:
<221> NAME/KEY: modified_base
<222> LOCATION: (725)
<223> OTHER INFORMATION: Where n is a, c, g or t
<220> FEATURE:
<221> NAME/KEY: modified_base
<222> LOCATION: (730)
<223> OTHER INFORMATION: Where n is a, c, g or t
<220> FEATURE:
<221> NAME/KEY: modified_base
<222> LOCATION: (731)
<223> OTHER INFORMATION: Where n is a, c, g or t

<400> SEQUENCE: 63

```
actagtcata aagggtgtgc gcgtcttcga cgtggcggtc ttggcgccac tgctgcgaga     60
cccggccctg gacctcaagg tcatccactt ggtgcgtgat ccccgcgcgg tggcgagttc    120
acggatccgc tcgcgccacg gcctcatccg tgagagccta caggtggtgc gcagccgaga   180
ccgcgagctc accgcatgcc cttcttggag gccgcgggcc acaagcttgg cgcccanaaa   240
gaaggcgtng ggggcccgca aantaccacg ctctgggcgc tatggaangt cctcttgcaa   300
taatattggt tnaaaanctg canaanagcc cctgcanccc cctgaactgg gntgcagggc   360
cncttacctn gtttggntgc ggttacaaag aacctgttn ggaaaaccct nccnaaaacc   420
ttccgggaaa attntncaaa ttttttnttgg ggaattnttg ggtaaacccc ccnaaaatgg   480
gaaacntttt tgccctnnaa antaaaccat tnggttccgg gggcccccc ncaaaaccct   540
tttttntttt tttntgcccc cantnnccc ccggggcccc ttttttttngg ggaaaanccc   600
cccccctncc nananttta aaagggnggg anaattttn nttnccccc gggncccccn   660
ggngntaaaa nggtttcncc cccccgaggg gnggggnnnc ctcnnaaacc cntntcnna   720
ccncnttttn n                                                        731
```

<210> SEQ ID NO 64
<211> LENGTH: 313
<212> TYPE: DNA
<213> ORGANISM: Homo sapiens
<220> FEATURE:
<221> NAME/KEY: modified_base
<222> LOCATION: (240)
<223> OTHER INFORMATION: Where n is a, c, g or t

<400> SEQUENCE: 64

```
actagttgtg caaaccacga ctgaagaaag acgaaaagtg ggaaataact tgcaacgtct      60
gttagagatg gttgctacac atgttgggtc tgtagagaaa catcttgagg agcagattgc     120
taaagttgat agagaatatg aagaatgcat gtcagagaat ctctcggaaa atattaaaga     180
gattagagat aagtatgaga agaaagctac tctaattaag tcttctgaag aatgaagatn     240
aaatgttgat catgtatata tatccatagt gaataaaatt gtctcagtaa agttgtaaaa     300
aaaaaaaaaa aaa                                                        313
```

<210> SEQ ID NO 65
<211> LENGTH: 420
<212> TYPE: DNA
<213> ORGANISM: Homo sapiens
<220> FEATURE:
<221> NAME/KEY: modified_base
<222> LOCATION: (400)
<223> OTHER INFORMATION: Where n is a, c, g or t
<220> FEATURE:
<221> NAME/KEY: modified_base
<222> LOCATION: (402)
<223> OTHER INFORMATION: Where n is a, c, g or t
<220> FEATURE:
<221> NAME/KEY: modified_base
<222> LOCATION: (403)
<223> OTHER INFORMATION: Where n is a, c, g or t
<220> FEATURE:
<221> NAME/KEY: modified_base
<222> LOCATION: (404)
<223> OTHER INFORMATION: Where n is a, c, g or t
<220> FEATURE:
<221> NAME/KEY: modified_base
<222> LOCATION: (405)
<223> OTHER INFORMATION: Where n is a, c, g or t
<220> FEATURE:
<221> NAME/KEY: modified_base
<222> LOCATION: (406)
<223> OTHER INFORMATION: Where n is a, c, g or t
<220> FEATURE:
<221> NAME/KEY: modified_base
<222> LOCATION: (409)
<223> OTHER INFORMATION: Where n is a, c, g or t
<220> FEATURE:
<221> NAME/KEY: modified_base
<222> LOCATION: (411)
<223> OTHER INFORMATION: Where n is a, c, g or t
<220> FEATURE:
<221> NAME/KEY: modified_base
<222> LOCATION: (412)
<223> OTHER INFORMATION: Where n is a, c, g or t
<220> FEATURE:
<221> NAME/KEY: modified_base
<222> LOCATION: (414)
<223> OTHER INFORMATION: Where n is a, c, g or t
<220> FEATURE:
<221> NAME/KEY: modified_base
<222> LOCATION: (415)
<223> OTHER INFORMATION: Where n is a, c, g or t
<220> FEATURE:
<221> NAME/KEY: modified_base
<222> LOCATION: (416)
<223> OTHER INFORMATION: Where n is a, c, g or t

<400> SEQUENCE: 65

```
actagttccc tggcaggcaa gggcttccaa ctgaggcagt gcatgtgtgg cagagagagg      60
caggaagctg gcagtggcag cttctgtgtc tagggagggg tgtggctccc tccttccctg     120
tctgggaggt tggagggaag aatctaggcc ttagcttgcc ctcctgccac ccttcccctt     180
gtagatactg ccttaacact ccctcctctc tcagctgtgg ctgccaccca agccaggttt     240
ctccgtgctc actaatttat ttccaggaaa ggtgtgtgga agacatgagc cgtgtataat     300
atttgtttta acattttcat tgcaagtatt gaccatcatc cttggttgtg tatcgttgta     360
```
acacaaatta atgatattaa aaagcatcca aacaaagccn annnnnaana nnannngaaa    420

<210> SEQ ID NO 66
<211> LENGTH: 676
<212> TYPE: DNA
<213> ORGANISM: Homo sapiens
<220> FEATURE:
<221> NAME/KEY: modified_base
<222> LOCATION: (328)
<223> OTHER INFORMATION: Where n is a, c, g or t
<220> FEATURE:
<221> NAME/KEY: modified_base
<222> LOCATION: (454)
<223> OTHER INFORMATION: Where n is a, c, g or t
<220> FEATURE:
<221> NAME/KEY: modified_base
<222> LOCATION: (505)
<223> OTHER INFORMATION: Where n is a, c, g or t
<220> FEATURE:
<221> NAME/KEY: modified_base
<222> LOCATION: (555)
<223> OTHER INFORMATION: Where n is a, c, g or t
<220> FEATURE:
<221> NAME/KEY: modified_base
<222> LOCATION: (586)
<223> OTHER INFORMATION: Where n is a, c, g or t
<220> FEATURE:
<221> NAME/KEY: modified_base
<222> LOCATION: (612)
<223> OTHER INFORMATION: Where n is a, c, g or t
<220> FEATURE:
<221> NAME/KEY: modified_base
<222> LOCATION: (636)
<223> OTHER INFORMATION: Where n is a, c, g or t
<220> FEATURE:
<221> NAME/KEY: modified_base
<222> LOCATION: (641)
<223> OTHER INFORMATION: Where n is a, c, g or t

<400> SEQUENCE: 66 actagttttcc tatgatcatt aaactcattc tcagggttaa gaaaggaatg taaatttctg    60
cctcaatttg tacttcatca ataagttttt gaagagtgca gatttttagt caggtcttaa    120
aaataaactc acaaatctgg atgcatttct aaattctgca aatgtttcct ggggtgactt    180
aacaaggaat aatcccacaa tatacctagc tacctaatac atggagctgg ggctcaaccc    240
actgttttta aggatttgcg cttacttgtg gctgaggaaa aataagtagt tccgagggaa    300
gtagttttta aatgtgagct tatagatngg aaacagaata tcaacttaat tatgaaatt    360 gttagaaacc tgttctcttg ttatctgaat cttgattgca attactattg tactggatag    420
actccagccc attgcaaagt ctcagatatc ttanctgtgt agttgaattc cttgaaatt    480 ctttttaaga aaaattgga gtttnaaaga ataaacccc tttgttaaat gaagcttggc    540
tttttggtga aaanaatca tcccgcaggg cttattgttt aaaaanggaa ttttaagcct    600
ccctggaaaa anttgttaat taaatgggga aaatgntggg naaaaattat ccgttagggt    660
ttaaagggaa aactta    676

<210> SEQ ID NO 67
<211> LENGTH: 620
<212> TYPE: DNA
<213> ORGANISM: Homo sapiens
<220> FEATURE:
<221> NAME/KEY: modified_base
<222> LOCATION: (419)
<223> OTHER INFORMATION: Where n is a, c, g or t
<220> FEATURE:
<221> NAME/KEY: modified_base
<222> LOCATION: (493)

```
<223> OTHER INFORMATION: Where n is a, c, g or t
<220> FEATURE:
<221> NAME/KEY: modified_base
<222> LOCATION: (519)
<223> OTHER INFORMATION: Where n is a, c, g or t
<220> FEATURE:
<221> NAME/KEY: modified_base
<222> LOCATION: (568)
<223> OTHER INFORMATION: Where n is a, c, g or t
<220> FEATURE:
<221> NAME/KEY: modified_base
<222> LOCATION: (605)
<223> OTHER INFORMATION: Where n is a, c, g or t
<220> FEATURE:
<221> NAME/KEY: modified_base
<222> LOCATION: (610)
<223> OTHER INFORMATION: Where n is a, c, g or t

<400> SEQUENCE: 67
caccattaaa gctgcttacc aagaacttcc ccagcatttt gacttccttg tttgatagct      60
gaattgtgag caggtgatag aagagccttt ctagttgaac atacagataa tttgctgaat     120
acattccatt taatgaaggg gttacatctg ttacgaagct actaagaagg agcaagagca     180 tagggaaaa aaatctgatc agaacgcatc aaactcacat gtgcccctc tactacaaac      240 agattgtagt gctgtggtgg tttattccgt tgtgcagaac ttgcaagctg agtcactaaa     300
cccaaagaga ggaaattata ggttagttaa acattgtaat cccaggaact aagtttaatt     360 cactttgaa gtgttttgtt ttttatttt ggtttgtctg atttactttg ggggaaaang      420
ctaaaaaaaa agggatatca atctctaatt cagtgcccac taaagttgt ccctaaaaag     480 tctttactgg aanttatggg acttttaag ctccaggtnt tttggtcctc caaattaacc     540
ttgcatgggc cccttaaaat tgttgaangg cattcctgcc tctaagtttg gggaaaattc     600 ccccntttn aaaatttgga                                                620

<210> SEQ ID NO 68
<211> LENGTH: 551
<212> TYPE: DNA
<213> ORGANISM: Homo sapiens
<220> FEATURE:
<221> NAME/KEY: modified_base
<222> LOCATION: (286)
<223> OTHER INFORMATION: Where n is a, c, g or t
<220> FEATURE:
<221> NAME/KEY: modified_base
<222> LOCATION: (464)
<223> OTHER INFORMATION: Where n is a, c, g or t
<220> FEATURE:
<221> NAME/KEY: modified_base
<222> LOCATION: (480)
<223> OTHER INFORMATION: Where n is a, c, g or t
<220> FEATURE:
<221> NAME/KEY: modified_base
<222> LOCATION: (501)
<223> OTHER INFORMATION: Where n is a, c, g or t
<220> FEATURE:
<221> NAME/KEY: modified_base
<222> LOCATION: (502)
<223> OTHER INFORMATION: Where n is a, c, g or t
<220> FEATURE:
<221> NAME/KEY: modified_base
<222> LOCATION: (518)
<223> OTHER INFORMATION: Where n is a, c, g or t
<220> FEATURE:
<221> NAME/KEY: modified_base
<222> LOCATION: (528)
<223> OTHER INFORMATION: Where n is a, c, g or t
<220> FEATURE:
<221> NAME/KEY: modified_base
<222> LOCATION: (533)
<223> OTHER INFORMATION: Where n is a, c, g or t
```

<220> FEATURE:
<221> NAME/KEY: modified_base
<222> LOCATION: (536)
<223> OTHER INFORMATION: Where n is a, c, g or t
<220> FEATURE:
<221> NAME/KEY: modified_base
<222> LOCATION: (537)
<223> OTHER INFORMATION: Where n is a, c, g or t
<220> FEATURE:
<221> NAME/KEY: modified_base
<222> LOCATION: (538)
<223> OTHER INFORMATION: Where n is a, c, g or t
<220> FEATURE:
<221> NAME/KEY: modified_base
<222> LOCATION: (539)
<223> OTHER INFORMATION: Where n is a, c, g or t
<220> FEATURE:
<221> NAME/KEY: modified_base
<222> LOCATION: (540)
<223> OTHER INFORMATION: Where n is a, c, g or t
<220> FEATURE:
<221> NAME/KEY: modified_base
<222> LOCATION: (541)
<223> OTHER INFORMATION: Where n is a, c, g or t
<220> FEATURE:
<221> NAME/KEY: modified_base
<222> LOCATION: (543)
<223> OTHER INFORMATION: Where n is a, c, g or t
<220> FEATURE:
<221> NAME/KEY: modified_base
<222> LOCATION: (544)
<223> OTHER INFORMATION: Where n is a, c, g or t
<220> FEATURE:
<221> NAME/KEY: modified_base
<222> LOCATION: (545)
<223> OTHER INFORMATION: Where n is a, c, g or t
<220> FEATURE:
<221> NAME/KEY: modified_base
<222> LOCATION: (547)
<223> OTHER INFORMATION: Where n is a, c, g or t
<220> FEATURE:
<221> NAME/KEY: modified_base
<222> LOCATION: (548)
<223> OTHER INFORMATION: Where n is a, c, g or t
<220> FEATURE:
<221> NAME/KEY: modified_base
<222> LOCATION: (549)
<223> OTHER INFORMATION: Where n is a, c, g or t

<400> SEQUENCE: 68

```
actagtagct ggtacataat cactgaggag ctatttctta acatgctttt atagaccatg    60
ctaatgctag accagtattt aagggctaat ctcacacctc cttagctgta agagtctggc   120
ttagaacaga cctctctgtg caataacttg tggccactgg aaatccctgg gccggcattt   180
gtattgggt tgcaatgact cccaagggcc aaaagagtta aaggcacgac tgggatttct    240
tctgagactg tggtgaaact ccttccaagg ctgaggggt cagtangtgc tctgggaggg   300
actcggcacc actttgatat tcaacaagcc acttgaagcc caattataaa attgttattt   360
tacagctgat ggaactcaat ttgaaccttc aaaactttgt tagtttatcc tattatattg   420
ttaaacctaa ttacatttgt ctagcattgg atttggttcc tgtngcatat gtttttttcn   480
cctatgtgct cccctccccc nnatcttaat ttaaaccnca attttgcnat tcnccnnnnn   540
nannnannna a                                                        551
```

<210> SEQ ID NO 69
<211> LENGTH: 396
<212> TYPE: DNA
<213> ORGANISM: Homo sapiens
<220> FEATURE:
<221> NAME/KEY: modified_base
<222> LOCATION: (255)

```
<223> OTHER INFORMATION: Where n is a, c, g or t
<220> FEATURE:
<221> NAME/KEY: modified_base
<222> LOCATION: (310)
<223> OTHER INFORMATION: Where n is a, c, g or t
<220> FEATURE:
<221> NAME/KEY: modified_base
<222> LOCATION: (322)
<223> OTHER INFORMATION: Where n is a, c, g or t
<220> FEATURE:
<221> NAME/KEY: modified_base
<222> LOCATION: (381)
<223> OTHER INFORMATION: Where n is a, c, g or t

<400> SEQUENCE: 69
cagaaatgga aagcagagtt ttcatttctg tttataaacg tctccaaaca aaaatggaaa      60
gcagagtttt cattaaatcc ttttaccttt ttttttttctt ggtaatcccc tcaaataaca    120
gtatgtggga tattgaatgt taaagggata ttttttttcta ttatttttat aattgtacaa    180
aattaagcaa atgttaaaag tttatatgc tttattaatg ttttcaaaag gtatnataca     240
tgtgatacat tttttaagct tcagttgctt gtcttctggt actttctgtt atgggctttt    300
ggggagccan aaccaatct acnatctctt tttgtttgcc aggacatgca ataaaattta     360
aaaaataaat aaaaactatt nagaaattga aaaaa                                396

<210> SEQ ID NO 70
<211> LENGTH: 536
<212> TYPE: DNA
<213> ORGANISM: Homo sapiens
<220> FEATURE:
<221> NAME/KEY: modified_base
<222> LOCATION: (388)
<223> OTHER INFORMATION: Where n is a, c, g or t
<220> FEATURE:
<221> NAME/KEY: modified_base
<222> LOCATION: (446)
<223> OTHER INFORMATION: Where n is a, c, g or t
<220> FEATURE:
<221> NAME/KEY: modified_base
<222> LOCATION: (455)
<223> OTHER INFORMATION: Where n is a, c, g or t

<400> SEQUENCE: 70
actagtgcaa aagcaaatat aaacatcgaa aaggcgttcc tcacgttagc tgaagatatc      60
cttcgaaaga cccctgtaaa agagcccaac agtgaaaatg tagatatcag cagtggagga    120
ggcgtgacag gctggaagag caaatgctgc tgagcattct cctgttccat cagttgccat    180
ccactacccc gttttctctt cttgctgcaa ataaaccac tctgtccatt tttaactcta     240
aacagatatt tttgtttctc atcttaacta tccaagccac ctattttatt tgttctttca    300
tctgtgactg cttgctgact ttatcataat tttcttcaaa caaaaaaatg tatagaaaaa    360
tcatgtctgt gacttcattt ttaaatgnta cttgctcagc tcaactgcat ttcagttgtt    420
ttatagtcca gttcttatca acattnaaac ctatngcaat catttcaaat ctattctgca    480
aattgtataa gaataaaagt tagaatttaa caattaaaaa aaaaaaaaaa aaaaaa         536

<210> SEQ ID NO 71
<211> LENGTH: 865
<212> TYPE: DNA
<213> ORGANISM: Homo sapiens
<220> FEATURE:
<221> NAME/KEY: modified_base
<222> LOCATION: (22)
<223> OTHER INFORMATION: Where n is a, c, g or t
<220> FEATURE:
<221> NAME/KEY: modified_base
```

-continued

```
<222> LOCATION: (35)
<223> OTHER INFORMATION: Where n is a, c, g or t
<220> FEATURE:
<221> NAME/KEY: modified_base
<222> LOCATION: (39)
<223> OTHER INFORMATION: Where n is a, c, g or t
<220> FEATURE:
<221> NAME/KEY: modified_base
<222> LOCATION: (56)
<223> OTHER INFORMATION: Where n is a, c, g or t
<220> FEATURE:
<221> NAME/KEY: modified_base
<222> LOCATION: (131)
<223> OTHER INFORMATION: Where n is a, c, g or t
<220> FEATURE:
<221> NAME/KEY: modified_base
<222> LOCATION: (138)
<223> OTHER INFORMATION: Where n is a, c, g or t
<220> FEATURE:
<221> NAME/KEY: modified_base
<222> LOCATION: (146)
<223> OTHER INFORMATION: Where n is a, c, g or t
<220> FEATURE:
<221> NAME/KEY: modified_base
<222> LOCATION: (183)
<223> OTHER INFORMATION: Where n is a, c, g or t
<220> FEATURE:
<221> NAME/KEY: modified_base
<222> LOCATION: (194)
<223> OTHER INFORMATION: Where n is a, c, g or t
<220> FEATURE:
<221> NAME/KEY: modified_base
<222> LOCATION: (197)
<223> OTHER INFORMATION: Where n is a, c, g or t
<220> FEATURE:
<221> NAME/KEY: modified_base
<222> LOCATION: (238)
<223> OTHER INFORMATION: Where n is a, c, g or t
<220> FEATURE:
<221> NAME/KEY: modified_base
<222> LOCATION: (269)
<223> OTHER INFORMATION: Where n is a, c, g or t
<220> FEATURE:
<221> NAME/KEY: modified_base
<222> LOCATION: (277)
<223> OTHER INFORMATION: Where n is a, c, g or t
<220> FEATURE:
<221> NAME/KEY: modified_base
<222> LOCATION: (282)
<223> OTHER INFORMATION: Where n is a, c, g or t
<220> FEATURE:
<221> NAME/KEY: modified_base
<222> LOCATION: (297)
<223> OTHER INFORMATION: Where n is a, c, g or t
<220> FEATURE:
<221> NAME/KEY: modified_base
<222> LOCATION: (316)
<223> OTHER INFORMATION: Where n is a, c, g or t
<220> FEATURE:
<221> NAME/KEY: modified_base
<222> LOCATION: (331)
<223> OTHER INFORMATION: Where n is a, c, g or t
<220> FEATURE:
<221> NAME/KEY: modified_base
<222> LOCATION: (336)
<223> OTHER INFORMATION: Where n is a, c, g or t
<220> FEATURE:
<221> NAME/KEY: modified_base
<222> LOCATION: (340)
<223> OTHER INFORMATION: Where n is a, c, g or t
<220> FEATURE:
<221> NAME/KEY: modified_base
<222> LOCATION: (341)
<223> OTHER INFORMATION: Where n is a, c, g or t
<220> FEATURE:
<221> NAME/KEY: modified_base
<222> LOCATION: (346)
<223> OTHER INFORMATION: Where n is a, c, g or t
<220> FEATURE:
```

-continued

```
<221> NAME/KEY: modified_base
<222> LOCATION: (349)
<223> OTHER INFORMATION: Where n is a, c, g or t
<220> FEATURE:
<221> NAME/KEY: modified_base
<222> LOCATION: (370)
<223> OTHER INFORMATION: Where n is a, c, g or t
<220> FEATURE:
<221> NAME/KEY: modified_base
<222> LOCATION: (376)
<223> OTHER INFORMATION: Where n is a, c, g or t
<220> FEATURE:
<221> NAME/KEY: modified_base
<222> LOCATION: (381)
<223> OTHER INFORMATION: Where n is a, c, g or t
<220> FEATURE:
<221> NAME/KEY: modified_base
<222> LOCATION: (382)
<223> OTHER INFORMATION: Where n is a, c, g or t
<220> FEATURE:
<221> NAME/KEY: modified_base
<222> LOCATION: (392)
<223> OTHER INFORMATION: Where n is a, c, g or t
<220> FEATURE:
<221> NAME/KEY: modified_base
<222> LOCATION: (396)
<223> OTHER INFORMATION: Where n is a, c, g or t
<220> FEATURE:
<221> NAME/KEY: modified_base
<222> LOCATION: (397)
<223> OTHER INFORMATION: Where n is a, c, g or t
<220> FEATURE:
<221> NAME/KEY: modified_base
<222> LOCATION: (401)
<223> OTHER INFORMATION: Where n is a, c, g or t
<220> FEATURE:
<221> NAME/KEY: modified_base
<222> LOCATION: (433)
<223> OTHER INFORMATION: Where n is a, c, g or t
<220> FEATURE:
<221> NAME/KEY: modified_base
<222> LOCATION: (444)
<223> OTHER INFORMATION: Where n is a, c, g or t
<220> FEATURE:
<221> NAME/KEY: modified_base
<222> LOCATION: (445)
<223> OTHER INFORMATION: Where n is a, c, g or t
<220> FEATURE:
<221> NAME/KEY: modified_base
<222> LOCATION: (454)
<223> OTHER INFORMATION: Where n is a, c, g or t
<220> FEATURE:
<221> NAME/KEY: modified_base
<222> LOCATION: (455)
<223> OTHER INFORMATION: Where n is a, c, g or t
<220> FEATURE:
<221> NAME/KEY: modified_base
<222> LOCATION: (469)
<223> OTHER INFORMATION: Where n is a, c, g or t
<220> FEATURE:
<221> NAME/KEY: modified_base
<222> LOCATION: (472)
<223> OTHER INFORMATION: Where n is a, c, g or t
<220> FEATURE:
<221> NAME/KEY: modified_base
<222> LOCATION: (477)
<223> OTHER INFORMATION: Where n is a, c, g or t
<220> FEATURE:
<221> NAME/KEY: modified_base
<222> LOCATION: (480)
<223> OTHER INFORMATION: Where n is a, c, g or t
<220> FEATURE:
<221> NAME/KEY: modified_base
<222> LOCATION: (482)
<223> OTHER INFORMATION: Where n is a, c, g or t
<220> FEATURE:
<221> NAME/KEY: modified_base
<222> LOCATION: (489)
<223> OTHER INFORMATION: Where n is a, c, g or t
```

-continued

```
<220> FEATURE:
<221> NAME/KEY: modified_base
<222> LOCATION: (497)
<223> OTHER INFORMATION: Where n is a, c, g or t
<220> FEATURE:
<221> NAME/KEY: modified_base
<222> LOCATION: (499)
<223> OTHER INFORMATION: Where n is a, c, g or t
<220> FEATURE:
<221> NAME/KEY: modified_base
<222> LOCATION: (511)
<223> OTHER INFORMATION: Where n is a, c, g or t
<220> FEATURE:
<221> NAME/KEY: modified_base
<222> LOCATION: (522)
<223> OTHER INFORMATION: Where n is a, c, g or t
<220> FEATURE:
<221> NAME/KEY: modified_base
<222> LOCATION: (526)
<223> OTHER INFORMATION: Where n is a, c, g or t
<220> FEATURE:
<221> NAME/KEY: modified_base
<222> LOCATION: (527)
<223> OTHER INFORMATION: Where n is a, c, g or t
<220> FEATURE:
<221> NAME/KEY: modified_base
<222> LOCATION: (545)
<223> OTHER INFORMATION: Where n is a, c, g or t
<220> FEATURE:
<221> NAME/KEY: modified_base
<222> LOCATION: (553)
<223> OTHER INFORMATION: Where n is a, c, g or t
<220> FEATURE:
<221> NAME/KEY: modified_base
<222> LOCATION: (556)
<223> OTHER INFORMATION: Where n is a, c, g or t
<220> FEATURE:
<221> NAME/KEY: modified_base
<222> LOCATION: (567)
<223> OTHER INFORMATION: Where n is a, c, g or t
<220> FEATURE:
<221> NAME/KEY: modified_base
<222> LOCATION: (574)
<223> OTHER INFORMATION: Where n is a, c, g or t
<220> FEATURE:
<221> NAME/KEY: modified_base
<222> LOCATION: (580)
<223> OTHER INFORMATION: Where n is a, c, g or t
<220> FEATURE:
<221> NAME/KEY: modified_base
<222> LOCATION: (610)
<223> OTHER INFORMATION: Where n is a, c, g or t
<220> FEATURE:
<221> NAME/KEY: modified_base
<222> LOCATION: (613)
<223> OTHER INFORMATION: Where n is a, c, g or t
<220> FEATURE:
<221> NAME/KEY: modified_base
<222> LOCATION: (634)
<223> OTHER INFORMATION: Where n is a, c, g or t
<220> FEATURE:
<221> NAME/KEY: modified_base
<222> LOCATION: (638)
<223> OTHER INFORMATION: Where n is a, c, g or t
<220> FEATURE:
<221> NAME/KEY: modified_base
<222> LOCATION: (639)
<223> OTHER INFORMATION: Where n is a, c, g or t
<220> FEATURE:
<221> NAME/KEY: modified_base
<222> LOCATION: (663)
<223> OTHER INFORMATION: Where n is a, c, g or t
<220> FEATURE:
<221> NAME/KEY: modified_base
<222> LOCATION: (672)
<223> OTHER INFORMATION: Where n is a, c, g or t
<220> FEATURE:
<221> NAME/KEY: modified_base
<222> LOCATION: (689)
```

-continued

```
<223> OTHER INFORMATION: Where n is a, c, g or t
<220> FEATURE:
<221> NAME/KEY: modified_base
<222> LOCATION: (693)
<223> OTHER INFORMATION: Where n is a, c, g or t
<220> FEATURE:
<221> NAME/KEY: modified_base
<222> LOCATION: (694)
<223> OTHER INFORMATION: Where n is a, c, g or t
<220> FEATURE:
<221> NAME/KEY: modified_base
<222> LOCATION: (701)
<223> OTHER INFORMATION: Where n is a, c, g or t
<220> FEATURE:
<221> NAME/KEY: modified_base
<222> LOCATION: (704)
<223> OTHER INFORMATION: Where n is a, c, g or t
<220> FEATURE:
<221> NAME/KEY: modified_base
<222> LOCATION: (713)
<223> OTHER INFORMATION: Where n is a, c, g or t
<220> FEATURE:
<221> NAME/KEY: modified_base
<222> LOCATION: (723)
<223> OTHER INFORMATION: Where n is a, c, g or t
<220> FEATURE:
<221> NAME/KEY: modified_base
<222> LOCATION: (729)
<223> OTHER INFORMATION: Where n is a, c, g or t
<220> FEATURE:
<221> NAME/KEY: modified_base
<222> LOCATION: (732)
<223> OTHER INFORMATION: Where n is a, c, g or t
<220> FEATURE:
<221> NAME/KEY: modified_base
<222> LOCATION: (743)
<223> OTHER INFORMATION: Where n is a, c, g or t
<220> FEATURE:
<221> NAME/KEY: modified_base
<222> LOCATION: (744)
<223> OTHER INFORMATION: Where n is a, c, g or t
<220> FEATURE:
<221> NAME/KEY: modified_base
<222> LOCATION: (749)
<223> OTHER INFORMATION: Where n is a, c, g or t
<220> FEATURE:
<221> NAME/KEY: modified_base
<222> LOCATION: (761)
<223> OTHER INFORMATION: Where n is a, c, g or t
<220> FEATURE:
<221> NAME/KEY: modified_base
<222> LOCATION: (765)
<223> OTHER INFORMATION: Where n is a, c, g or t
<220> FEATURE:
<221> NAME/KEY: modified_base
<222> LOCATION: (767)
<223> OTHER INFORMATION: Where n is a, c, g or t
<220> FEATURE:
<221> NAME/KEY: modified_base
<222> LOCATION: (769)
<223> OTHER INFORMATION: Where n is a, c, g or t
<220> FEATURE:
<221> NAME/KEY: modified_base
<222> LOCATION: (772)
<223> OTHER INFORMATION: Where n is a, c, g or t
<220> FEATURE:
<221> NAME/KEY: modified_base
<222> LOCATION: (774)
<223> OTHER INFORMATION: Where n is a, c, g or t
<220> FEATURE:
<221> NAME/KEY: modified_base
<222> LOCATION: (780)
<223> OTHER INFORMATION: Where n is a, c, g or t
<220> FEATURE:
<221> NAME/KEY: modified_base
<222> LOCATION: (783)
<223> OTHER INFORMATION: Where n is a, c, g or t
<220> FEATURE:
<221> NAME/KEY: modified_base
```

<222> LOCATION: (788)
<223> OTHER INFORMATION: Where n is a, c, g or t
<220> FEATURE:
<221> NAME/KEY: modified_base
<222> LOCATION: (792)
<223> OTHER INFORMATION: Where n is a, c, g or t
<220> FEATURE:
<221> NAME/KEY: modified_base
<222> LOCATION: (803)
<223> OTHER INFORMATION: Where n is a, c, g or t
<220> FEATURE:
<221> NAME/KEY: modified_base
<222> LOCATION: (810)
<223> OTHER INFORMATION: Where n is a, c, g or t
<220> FEATURE:
<221> NAME/KEY: modified_base
<222> LOCATION: (824)
<223> OTHER INFORMATION: Where n is a, c, g or t
<220> FEATURE:
<221> NAME/KEY: modified_base
<222> LOCATION: (840)
<223> OTHER INFORMATION: Where n is a, c, g or t
<220> FEATURE:
<221> NAME/KEY: modified_base
<222> LOCATION: (848)
<223> OTHER INFORMATION: Where n is a, c, g or t

<400> SEQUENCE: 71

| | | | | | | |
|---|---|---|---|---|---|---|
| gacaaagcgt | taggagaaga | anagaggcag | ggaanactnc | ccaggcacga | tggccncctt | 60 |
| cccaccagca | accagcgccc | cccaccagcc | cccaggcccg | gacgacgaag | actccatcct | 120 |
| ggattaatct | nacctctntc | gcctgnccca | ttcctacctc | ggaggtggag | gccggaaagg | 180 |
| tcncaccaag | aganaanctg | ctgccaacac | caaccgcccc | agccctggcg | ggcacganag | 240 |
| gaaactggtg | accaatctgc | agaattctna | gaggaanaag | cnggggcccc | cgcgctnaga | 300 |
| cagagctgga | tatgangcca | gaccatggac | nctacncccn | ncaatncana | cgggactgcg | 360 |
| gaagatggan | gacccncgac | nngatcaggc | cngctnncca | nccccccacc | cctatgaatt | 420 |
| attcccgctg | aangaatctc | tganngcctt | ccannaaagc | gcctcccnc | cnaacgnaan | 480 |
| tncaacatng | ggattananng | ctgggaactg | naaggggcaa | ancctnnaat | atccccagaa | 540 |
| acaanctctc | ccnaanaaac | tgggcncct | catnggtggn | accaactatt | aactaaaccg | 600 |
| cacgccaagn | aantataaaa | ggggggcccc | tccncggnng | acccccttt | gtcccttaat | 660 |
| ganggttatc | cnccttgcgt | accatggtnc | ccnnttctgt | ntgnatgttt | ccnctcccct | 720 |
| ccncctatnt | cnagccgaac | tcnnatttnc | ccggggtgc | natcnantng | tncnccttn | 780 |
| ttngttgncc | cngcccttc | cgncggaacn | cgtttccccg | ttantaacgg | cacccggggn | 840 |
| aagggtgntt | ggccccctcc | ctccc | | | | 865 |

<210> SEQ ID NO 72
<211> LENGTH: 560
<212> TYPE: DNA
<213> ORGANISM: Homo sapiens
<220> FEATURE:
<221> NAME/KEY: modified_base
<222> LOCATION: (83)
<223> OTHER INFORMATION: Where n is a, c, g or t
<220> FEATURE:
<221> NAME/KEY: modified_base
<222> LOCATION: (173)
<223> OTHER INFORMATION: Where n is a, c, g or t
<220> FEATURE:
<221> NAME/KEY: modified_base
<222> LOCATION: (183)
<223> OTHER INFORMATION: Where n is a, c, g or t
<220> FEATURE:
<221> NAME/KEY: modified_base
<222> LOCATION: (186)

```
-continued

<223> OTHER INFORMATION: Where n is a, c, g or t
<220> FEATURE:
<221> NAME/KEY: modified_base
<222> LOCATION: (209)
<223> OTHER INFORMATION: Where n is a, c, g or t
<220> FEATURE:
<221> NAME/KEY: modified_base
<222> LOCATION: (211)
<223> OTHER INFORMATION: Where n is a, c, g or t
<220> FEATURE:
<221> NAME/KEY: modified_base
<222> LOCATION: (215)
<223> OTHER INFORMATION: Where n is a, c, g or t
<220> FEATURE:
<221> NAME/KEY: modified_base
<222> LOCATION: (255)
<223> OTHER INFORMATION: Where n is a, c, g or t
<220> FEATURE:
<221> NAME/KEY: modified_base
<222> LOCATION: (321)
<223> OTHER INFORMATION: Where n is a, c, g or t
<220> FEATURE:
<221> NAME/KEY: modified_base
<222> LOCATION: (322)
<223> OTHER INFORMATION: Where n is a, c, g or t
<220> FEATURE:
<221> NAME/KEY: modified_base
<222> LOCATION: (323)
<223> OTHER INFORMATION: Where n is a, c, g or t
<220> FEATURE:
<221> NAME/KEY: modified_base
<222> LOCATION: (335)
<223> OTHER INFORMATION: Where n is a, c, g or t
<220> FEATURE:
<221> NAME/KEY: modified_base
<222> LOCATION: (344)
<223> OTHER INFORMATION: Where n is a, c, g or t
<220> FEATURE:
<221> NAME/KEY: modified_base
<222> LOCATION: (357)
<223> OTHER INFORMATION: Where n is a, c, g or t
<220> FEATURE:
<221> NAME/KEY: modified_base
<222> LOCATION: (361)
<223> OTHER INFORMATION: Where n is a, c, g or t
<220> FEATURE:
<221> NAME/KEY: modified_base
<222> LOCATION: (368)
<223> OTHER INFORMATION: Where n is a, c, g or t
<220> FEATURE:
<221> NAME/KEY: modified_base
<222> LOCATION: (394)
<223> OTHER INFORMATION: Where n is a, c, g or t
<220> FEATURE:
<221> NAME/KEY: modified_base
<222> LOCATION: (412)
<223> OTHER INFORMATION: Where n is a, c, g or t
<220> FEATURE:
<221> NAME/KEY: modified_base
<222> LOCATION: (415)
<223> OTHER INFORMATION: Where n is a, c, g or t
<220> FEATURE:
<221> NAME/KEY: modified_base
<222> LOCATION: (442)
<223> OTHER INFORMATION: Where n is a, c, g or t
<220> FEATURE:
<221> NAME/KEY: modified_base
<222> LOCATION: (455)
<223> OTHER INFORMATION: Where n is a, c, g or t
<220> FEATURE:
<221> NAME/KEY: modified_base
<222> LOCATION: (469)
<223> OTHER INFORMATION: Where n is a, c, g or t
<220> FEATURE:
<221> NAME/KEY: modified_base
<222> LOCATION: (472)
<223> OTHER INFORMATION: Where n is a, c, g or t
<220> FEATURE:
<221> NAME/KEY: modified_base
```

```
<222> LOCATION: (475)
<223> OTHER INFORMATION: Where n is a, c, g or t
<220> FEATURE:
<221> NAME/KEY: modified_base
<222> LOCATION: (487)
<223> OTHER INFORMATION: Where n is a, c, g or t
<220> FEATURE:
<221> NAME/KEY: modified_base
<222> LOCATION: (513)
<223> OTHER INFORMATION: Where n is a, c, g or t
<220> FEATURE:
<221> NAME/KEY: modified_base
<222> LOCATION: (522)
<223> OTHER INFORMATION: Where n is a, c, g or t
<220> FEATURE:
<221> NAME/KEY: modified_base
<222> LOCATION: (528)
<223> OTHER INFORMATION: Where n is a, c, g or t
<220> FEATURE:
<221> NAME/KEY: modified_base
<222> LOCATION: (531)
<223> OTHER INFORMATION: Where n is a, c, g or t
<220> FEATURE:
<221> NAME/KEY: modified_base
<222> LOCATION: (534)
<223> OTHER INFORMATION: Where n is a, c, g or t
<220> FEATURE:
<221> NAME/KEY: modified_base
<222> LOCATION: (546)
<223> OTHER INFORMATION: Where n is a, c, g or t

<400> SEQUENCE: 72
cctggacttg tcttggttcc agaacctgac gacccggcga cggcgacgtc tcttttgact      60
aaaagacagt gtccagtgct ccngcctagg agtctacggg gaccgcctcc cgcgccgcca    120
ccatgcccaa cttctctggc aactggaaaa tcatccgatc ggaaaacttc gangaattgc    180
tcnaantgct gggggtgaat gtgatgctna ngaanattgc tgtggctgca gcgtccaagc    240
cagcagtgga gatcnaacag gagggagaca ctttctacat caaaacctcc accaccgtgc    300
gcaccacaaa gattaacttc nnngttgggg agganttga ggancaaact gtggatngga     360
ngcctgtnaa aacctggtga aatgggagaa tganaataaa atggtctgtg ancanaaact    420
cctgaaagga gaaggccccc anaactcctg gaccngaaaa actgacccnc cnatnggga     480 actgatnctt gaaccctgaa cgggcgggat gancctttt tnttgccncc naangggttc     540
tttccntttc cccaaaaaaa                                                 560

<210> SEQ ID NO 73
<211> LENGTH: 379
<212> TYPE: DNA
<213> ORGANISM: Homo sapiens
<220> FEATURE:
<221> NAME/KEY: modified_base
<222> LOCATION: (8)
<223> OTHER INFORMATION: Where n is a, c, g or t
<220> FEATURE:
<221> NAME/KEY: modified_base
<222> LOCATION: (17)
<223> OTHER INFORMATION: Where n is a, c, g or t
<220> FEATURE:
<221> NAME/KEY: modified_base
<222> LOCATION: (18)
<223> OTHER INFORMATION: Where n is a, c, g or t
<220> FEATURE:
<221> NAME/KEY: modified_base
<222> LOCATION: (21)
<223> OTHER INFORMATION: Where n is a, c, g or t
<220> FEATURE:
<221> NAME/KEY: modified_base
<222> LOCATION: (26)
<223> OTHER INFORMATION: Where n is a, c, g or t
<220> FEATURE:
```

-continued

```
<221> NAME/KEY: modified_base
<222> LOCATION: (29)
<223> OTHER INFORMATION: Where n is a, c, g or t
<220> FEATURE:
<221> NAME/KEY: modified_base
<222> LOCATION: (30)
<223> OTHER INFORMATION: Where n is a, c, g or t
<220> FEATURE:
<221> NAME/KEY: modified_base
<222> LOCATION: (32)
<223> OTHER INFORMATION: Where n is a, c, g or t
<220> FEATURE:
<221> NAME/KEY: modified_base
<222> LOCATION: (53)
<223> OTHER INFORMATION: Where n is a, c, g or t
<220> FEATURE:
<221> NAME/KEY: modified_base
<222> LOCATION: (56)
<223> OTHER INFORMATION: Where n is a, c, g or t
<220> FEATURE:
<221> NAME/KEY: modified_base
<222> LOCATION: (67)
<223> OTHER INFORMATION: Where n is a, c, g or t
<220> FEATURE:
<221> NAME/KEY: modified_base
<222> LOCATION: (71)
<223> OTHER INFORMATION: Where n is a, c, g or t
<220> FEATURE:
<221> NAME/KEY: modified_base
<222> LOCATION: (81)
<223> OTHER INFORMATION: Where n is a, c, g or t
<220> FEATURE:
<221> NAME/KEY: modified_base
<222> LOCATION: (102)
<223> OTHER INFORMATION: Where n is a, c, g or t
<220> FEATURE:
<221> NAME/KEY: modified_base
<222> LOCATION: (104)
<223> OTHER INFORMATION: Where n is a, c, g or t
<220> FEATURE:
<221> NAME/KEY: modified_base
<222> LOCATION: (111)
<223> OTHER INFORMATION: Where n is a, c, g or t
<220> FEATURE:
<221> NAME/KEY: modified_base
<222> LOCATION: (112)
<223> OTHER INFORMATION: Where n is a, c, g or t
<220> FEATURE:
<221> NAME/KEY: modified_base
<222> LOCATION: (114)
<223> OTHER INFORMATION: Where n is a, c, g or t
<220> FEATURE:
<221> NAME/KEY: modified_base
<222> LOCATION: (119)
<223> OTHER INFORMATION: Where n is a, c, g or t
<220> FEATURE:
<221> NAME/KEY: modified_base
<222> LOCATION: (122)
<223> OTHER INFORMATION: Where n is a, c, g or t
<220> FEATURE:
<221> NAME/KEY: modified_base
<222> LOCATION: (124)
<223> OTHER INFORMATION: Where n is a, c, g or t
<220> FEATURE:
<221> NAME/KEY: modified_base
<222> LOCATION: (125)
<223> OTHER INFORMATION: Where n is a, c, g or t
<220> FEATURE:
<221> NAME/KEY: modified_base
<222> LOCATION: (134)
<223> OTHER INFORMATION: Where n is a, c, g or t
<220> FEATURE:
<221> NAME/KEY: modified_base
<222> LOCATION: (144)
<223> OTHER INFORMATION: Where n is a, c, g or t
<220> FEATURE:
<221> NAME/KEY: modified_base
<222> LOCATION: (146)
<223> OTHER INFORMATION: Where n is a, c, g or t
```

```
<220> FEATURE:
<221> NAME/KEY: modified_base
<222> LOCATION: (189)
<223> OTHER INFORMATION: Where n is a, c, g or t
<220> FEATURE:
<221> NAME/KEY: modified_base
<222> LOCATION: (190)
<223> OTHER INFORMATION: Where n is a, c, g or t
<220> FEATURE:
<221> NAME/KEY: modified_base
<222> LOCATION: (214)
<223> OTHER INFORMATION: Where n is a, c, g or t
<220> FEATURE:
<221> NAME/KEY: modified_base
<222> LOCATION: (215)
<223> OTHER INFORMATION: Where n is a, c, g or t
<220> FEATURE:
<221> NAME/KEY: modified_base
<222> LOCATION: (219)
<223> OTHER INFORMATION: Where n is a, c, g or t
<220> FEATURE:
<221> NAME/KEY: modified_base
<222> LOCATION: (222)
<223> OTHER INFORMATION: Where n is a, c, g or t
<220> FEATURE:
<221> NAME/KEY: modified_base
<222> LOCATION: (235)
<223> OTHER INFORMATION: Where n is a, c, g or t
<220> FEATURE:
<221> NAME/KEY: modified_base
<222> LOCATION: (237)
<223> OTHER INFORMATION: Where n is a, c, g or t
<220> FEATURE:
<221> NAME/KEY: modified_base
<222> LOCATION: (246)
<223> OTHER INFORMATION: Where n is a, c, g or t
<220> FEATURE:
<221> NAME/KEY: modified_base
<222> LOCATION: (280)
<223> OTHER INFORMATION: Where n is a, c, g or t
<220> FEATURE:
<221> NAME/KEY: modified_base
<222> LOCATION: (288)
<223> OTHER INFORMATION: Where n is a, c, g or t
<220> FEATURE:
<221> NAME/KEY: modified_base
<222> LOCATION: (302)
<223> OTHER INFORMATION: Where n is a, c, g or t
<220> FEATURE:
<221> NAME/KEY: modified_base
<222> LOCATION: (310)
<223> OTHER INFORMATION: Where n is a, c, g or t
<220> FEATURE:
<221> NAME/KEY: modified_base
<222> LOCATION: (313)
<223> OTHER INFORMATION: Where n is a, c, g or t
<220> FEATURE:
<221> NAME/KEY: modified_base
<222> LOCATION: (319)
<223> OTHER INFORMATION: Where n is a, c, g or t
<220> FEATURE:
<221> NAME/KEY: modified_base
<222> LOCATION: (322)
<223> OTHER INFORMATION: Where n is a, c, g or t
<220> FEATURE:
<221> NAME/KEY: modified_base
<222> LOCATION: (343)
<223> OTHER INFORMATION: Where n is a, c, g or t
<220> FEATURE:
<221> NAME/KEY: modified_base
<222> LOCATION: (353)
<223> OTHER INFORMATION: Where n is a, c, g or t
<220> FEATURE:
<221> NAME/KEY: modified_base
<222> LOCATION: (354)
<223> OTHER INFORMATION: Where n is a, c, g or t

<400> SEQUENCE: 73
```

```
ctggggancc ggcggtnngc nccatntcnn gncgcgaagg tggcaataaa aanccnctga      60
aaccgcncaa naaacatgcc naagatatgg acgaggaaga tngngctttc nngnacaanc     120
gnanngagga acanaacaaa ctcnangagc tctcaagcta atgccgcggg gaagggggccc    180 ttggccacnn gtggaattaa gaaatctggc aaanngtann tgttccttgt gcctnangag     240
ataagngacc ctttatttca tctgtattta aacctctctn ttccctgnca taacttcttt    300
tnccacgtan agntggaant anttgttgtc ttggactgtt gtncatttta gannaaactt    360
ttgttcaaaa aaaaaataa                                                 379
```

<210> SEQ ID NO 74
<211> LENGTH: 437
<212> TYPE: DNA
<213> ORGANISM: Homo sapiens
<220> FEATURE:
<221> NAME/KEY: modified_base
<222> LOCATION: (145)
<223> OTHER INFORMATION: Where n is a, c, g or t
<220> FEATURE:
<221> NAME/KEY: modified_base
<222> LOCATION: (355)
<223> OTHER INFORMATION: Where n is a, c, g or t

<400> SEQUENCE: 74

```
actagttcag actgccacgc caaccccaga aaataccccca catgccagaa aagtgaagtc     60
ctaggtgttt ccatctatgt ttcaatctgt ccatctacca ggcctcgcga taaaaacaaa    120
acaaaaaaac gctgccaggt tttanaagca gttctggtct caaaaccatc aggatcctgc    180
caccagggtt cttttgaaat agtaccacat gtaaaggga atttggcttt cacttcatct     240
aatcactgaa ttgtcaggct ttgattgata attgtagaaa taagtagcct tctgttgtgg    300
gaataagtta taatcagtat tcatctcttt gtttttttgtc actcttttct ctctnattgt   360
gtcatttgta ctgtttgaaa aatatttctt ctataaaatt aaactaacct gccttaaaaa    420
aaaaaaaaaa aaaaaaa                                                   437
```

<210> SEQ ID NO 75
<211> LENGTH: 579
<212> TYPE: DNA
<213> ORGANISM: Homo sapiens
<220> FEATURE:
<221> NAME/KEY: modified_base
<222> LOCATION: (440)
<223> OTHER INFORMATION: Where n is a, c, g or t
<220> FEATURE:
<221> NAME/KEY: modified_base
<222> LOCATION: (513)
<223> OTHER INFORMATION: Where n is a, c, g or t
<220> FEATURE:
<221> NAME/KEY: modified_base
<222> LOCATION: (539)
<223> OTHER INFORMATION: Where n is a, c, g or t
<220> FEATURE:
<221> NAME/KEY: modified_base
<222> LOCATION: (551)
<223> OTHER INFORMATION: Where n is a, c, g or t

<400> SEQUENCE: 75

```
ctccgtcgcc gccaagatga tgtgcggggc gccctccgcc acgcagccgg ccaccgccga     60
gacccagcac atcgccgacc aggtgaggtc ccagcttgaa gagaaagaaa acaagaagtt    120
ccctgtgttt aaggccgtgt cattcaagag ccaggtggtc gcggggacaa actacttcat    180
caaggtgcac gtcggcgacg aggacttcgt acacctgcga gtgttccaat ctctccctca    240
tgaaaacaag cccttgacct tatctaacta ccagaccaac aaagccaagc atgatgagct    300
```

-continued

```
gacctatttc tgatcctgac tttggacaag gcccttcagc cagaagactg acaaagtcat    360
cctccgtcta ccagagcgtg cacttgtgat cctaaaataa gcttcatctc cgggctgtgc    420
ccttggggtg aaggggcan gatctgcact gcttttgcat ttctcttcct aaatttcatt    480
gtgttgattc tttccttcca ataggtgatc ttnattactt tcagaatatt ttccaaatna    540
gatatatttt naaaatcctt aaaaaaaaaa aaaaaaaa                            579
```

<210> SEQ ID NO 76
<211> LENGTH: 666
<212> TYPE: DNA
<213> ORGANISM: Homo sapiens
<220> FEATURE:
<221> NAME/KEY: modified_base
<222> LOCATION: (411)
<223> OTHER INFORMATION: Where n is a, c, g or t
<220> FEATURE:
<221> NAME/KEY: modified_base
<222> LOCATION: (470)
<223> OTHER INFORMATION: Where n is a, c, g or t
<220> FEATURE:
<221> NAME/KEY: modified_base
<222> LOCATION: (476)
<223> OTHER INFORMATION: Where n is a, c, g or t
<220> FEATURE:
<221> NAME/KEY: modified_base
<222> LOCATION: (491)
<223> OTHER INFORMATION: Where n is a, c, g or t
<220> FEATURE:
<221> NAME/KEY: modified_base
<222> LOCATION: (506)
<223> OTHER INFORMATION: Where n is a, c, g or t
<220> FEATURE:
<221> NAME/KEY: modified_base
<222> LOCATION: (527)
<223> OTHER INFORMATION: Where n is a, c, g or t
<220> FEATURE:
<221> NAME/KEY: modified_base
<222> LOCATION: (560)
<223> OTHER INFORMATION: Where n is a, c, g or t
<220> FEATURE:
<221> NAME/KEY: modified_base
<222> LOCATION: (570)
<223> OTHER INFORMATION: Where n is a, c, g or t
<220> FEATURE:
<221> NAME/KEY: modified_base
<222> LOCATION: (632)
<223> OTHER INFORMATION: Where n is a, c, g or t
<220> FEATURE:
<221> NAME/KEY: modified_base
<222> LOCATION: (636)
<223> OTHER INFORMATION: Where n is a, c, g or t
<220> FEATURE:
<221> NAME/KEY: modified_base
<222> LOCATION: (643)
<223> OTHER INFORMATION: Where n is a, c, g or t
<220> FEATURE:
<221> NAME/KEY: modified_base
<222> LOCATION: (650)
<223> OTHER INFORMATION: Where n is a, c, g or t
<220> FEATURE:
<221> NAME/KEY: modified_base
<222> LOCATION: (654)
<223> OTHER INFORMATION: Where n is a, c, g or t
<220> FEATURE:
<221> NAME/KEY: modified_base
<222> LOCATION: (658)
<223> OTHER INFORMATION: Where n is a, c, g or t

<400> SEQUENCE: 76

```
gtttatccta tctctccaac cagattgtca gctccttgag ggcaagagcc acagtatatt    60
tccctgtttc ttccacagtg cctaataata ctgtggaact aggttttaat aattttttaa    120
```

-continued

```
ttgatgttgt tatgggcagg atggcaacca gaccattgtc tcagagcagg tgctggctct    180
ttcctggcta ctccatgttg gctagcctct ggtaacctct tacttattat cttcaggaca    240
ctcactacag ggaccaggga tgatgcaaca tccttgtctt tttatgacag gatgtttgct    300
cagcttctcc aacaataaaa agcacgtggt aaaacacttg cggatattct ggactgtttt    360
taaaaaatat acagtttacc gaaaatcata ttatcttaca atgaaaagga ntttatagat    420
cagccagtga acaaccttt cccaccatac aaaaattcct tttcccgaan gaaaanggct     480
ttctcaataa ncctcacttt cttaanatct tacaagatag ccccganatc ttatcgaaac    540
tcattttagg caaatatgan ttttattgtn cgttacttgt ttcaaaattt ggtattgtga    600
atatcaatta ccaccccat ctcccatgaa anaaanggga aanggtgaan ttcntaancg     660
cttaaa                                                               666
```

```
<210> SEQ ID NO 77
<211> LENGTH: 396
<212> TYPE: DNA
<213> ORGANISM: Homo sapiens
<220> FEATURE:
<221> NAME/KEY: modified_base
<222> LOCATION: (31)
<223> OTHER INFORMATION: Where n is a, c, g or t
<220> FEATURE:
<221> NAME/KEY: modified_base
<222> LOCATION: (54)
<223> OTHER INFORMATION: Where n is a, c, g or t
<220> FEATURE:
<221> NAME/KEY: modified_base
<222> LOCATION: (125)
<223> OTHER INFORMATION: Where n is a, c, g or t
<220> FEATURE:
<221> NAME/KEY: modified_base
<222> LOCATION: (128)
<223> OTHER INFORMATION: Where n is a, c, g or t
<220> FEATURE:
<221> NAME/KEY: modified_base
<222> LOCATION: (136)
<223> OTHER INFORMATION: Where n is a, c, g or t
<220> FEATURE:
<221> NAME/KEY: modified_base
<222> LOCATION: (163)
<223> OTHER INFORMATION: Where n is a, c, g or t
<220> FEATURE:
<221> NAME/KEY: modified_base
<222> LOCATION: (168)
<223> OTHER INFORMATION: Where n is a, c, g or t
<220> FEATURE:
<221> NAME/KEY: modified_base
<222> LOCATION: (198)
<223> OTHER INFORMATION: Where n is a, c, g or t
```

<400> SEQUENCE: 77

```
ctgcagcccg ggggatccac taatctacca nggttatttg gcagctaatt ctanatttgg    60
atcattgccc aaagttgcac ttgctggtct cttgggattt ggccttggaa aggtatcata   120
catanganta tgccanaata aattccattt ttttgaaaat canctccntg gggctggttt   180
tggtccacag cataacangc actgcctcct tacctgtgag gaatgcaaaa taaagcatgg   240
attaagtgag aagggagact ctcagccttc agcttcctaa attctgtgtc tgtgactttc   300 gaagttttt aaacctctga atttgtacac atttaaaatt tcaagtgtac tttaaaataa   360
aatacttcta atgggaacaa aaaaaaaaaa aaaaaa                             396
```

```
<210> SEQ ID NO 78
<211> LENGTH: 793
<212> TYPE: DNA
<213> ORGANISM: Homo sapiens
```

```
<220> FEATURE:
<221> NAME/KEY: modified_base
<222> LOCATION: (309)
<223> OTHER INFORMATION: Where n is a, c, g or t
<220> FEATURE:
<221> NAME/KEY: modified_base
<222> LOCATION: (492)
<223> OTHER INFORMATION: Where n is a, c, g or t
<220> FEATURE:
<221> NAME/KEY: modified_base
<222> LOCATION: (563)
<223> OTHER INFORMATION: Where n is a, c, g or t
<220> FEATURE:
<221> NAME/KEY: modified_base
<222> LOCATION: (657)
<223> OTHER INFORMATION: Where n is a, c, g or t
<220> FEATURE:
<221> NAME/KEY: modified_base
<222> LOCATION: (660)
<223> OTHER INFORMATION: Where n is a, c, g or t
<220> FEATURE:
<221> NAME/KEY: modified_base
<222> LOCATION: (703)
<223> OTHER INFORMATION: Where n is a, c, g or t
<220> FEATURE:
<221> NAME/KEY: modified_base
<222> LOCATION: (708)
<223> OTHER INFORMATION: Where n is a, c, g or t
<220> FEATURE:
<221> NAME/KEY: modified_base
<222> LOCATION: (710)
<223> OTHER INFORMATION: Where n is a, c, g or t
<220> FEATURE:
<221> NAME/KEY: modified_base
<222> LOCATION: (711)
<223> OTHER INFORMATION: Where n is a, c, g or t
<220> FEATURE:
<221> NAME/KEY: modified_base
<222> LOCATION: (732)
<223> OTHER INFORMATION: Where n is a, c, g or t
<220> FEATURE:
<221> NAME/KEY: modified_base
<222> LOCATION: (740)
<223> OTHER INFORMATION: Where n is a, c, g or t
<220> FEATURE:
<221> NAME/KEY: modified_base
<222> LOCATION: (748)
<223> OTHER INFORMATION: Where n is a, c, g or t
<220> FEATURE:
<221> NAME/KEY: modified_base
<222> LOCATION: (758)
<223> OTHER INFORMATION: Where n is a, c, g or t
<220> FEATURE:
<221> NAME/KEY: modified_base
<222> LOCATION: (762)
<223> OTHER INFORMATION: Where n is a, c, g or t
<220> FEATURE:
<221> NAME/KEY: modified_base
<222> LOCATION: (765)
<223> OTHER INFORMATION: Where n is a, c, g or t
<220> FEATURE:
<221> NAME/KEY: modified_base
<222> LOCATION: (787)
<223> OTHER INFORMATION: Where n is a, c, g or t

<400> SEQUENCE: 78
gcatcctagc cgccgactca cacaaggcag gtgggtgagg aaatccagag ttgccatgga      60
gaaaattcca gtgtcagcat tcttgctcct tgtggccctc tcctacactc tggccagaga     120
taccacagtc aaacctggag ccaaaaagga cacaaggac tctcgaccca aactgcccca     180
gaccctctcc agaggttggg gtgaccaact catctggact cagacatatg aagaagctct    240
atataaatcc aagacaagca acaaacccctt gatgattatt catcacttgg atgagtgccc    300
acacagtcna gctttaaaga aagtgtttgc tgaaaataaa gaaatccaga aattggcaga    360
```

-continued

```
gcagtttgtc ctcctcaatc tggtttatga acaactgac aaacacctttt ctcctgatgg      420
ccagtatgtc ccaggattat gtttgttgac ccatctctga cagttgaagc cgatatcctg      480
ggaagatatt cnaaccgtct ctatgcttac aaactgcaga tacgctctgt tgcttgacac      540
atgaaaaagc tctcaagttg ctnaaaatga attgtaagaa aaaaaatctc cagccttctg      600
tctgtcggct tgaaaattga aaccagaaaa atgtgaaaaa tggctattgt ggaacanatn      660
gacacctgat taggttttgg ttatgttcac cactattttt aanaaaanan nttttaaaat      720
ttggttcaat tntcttttn aaacaatntg tttctacntt ngancctgat ttctaaaaaa       780
aataatnttt ggc                                                         793
```

<210> SEQ ID NO 79
<211> LENGTH: 456
<212> TYPE: DNA
<213> ORGANISM: Homo sapiens
<220> FEATURE:
<221> NAME/KEY: modified_base
<222> LOCATION: (89)
<223> OTHER INFORMATION: Where n is a, c, g or t
<220> FEATURE:
<221> NAME/KEY: modified_base
<222> LOCATION: (195)
<223> OTHER INFORMATION: Where n is a, c, g or t
<220> FEATURE:
<221> NAME/KEY: modified_base
<222> LOCATION: (255)
<223> OTHER INFORMATION: Where n is a, c, g or t
<220> FEATURE:
<221> NAME/KEY: modified_base
<222> LOCATION: (263)
<223> OTHER INFORMATION: Where n is a, c, g or t
<220> FEATURE:
<221> NAME/KEY: modified_base
<222> LOCATION: (266)
<223> OTHER INFORMATION: Where n is a, c, g or t
<220> FEATURE:
<221> NAME/KEY: modified_base
<222> LOCATION: (286)
<223> OTHER INFORMATION: Where n is a, c, g or t
<220> FEATURE:
<221> NAME/KEY: modified_base
<222> LOCATION: (353)
<223> OTHER INFORMATION: Where n is a, c, g or t
<220> FEATURE:
<221> NAME/KEY: modified_base
<222> LOCATION: (384)
<223> OTHER INFORMATION: Where n is a, c, g or t
<220> FEATURE:
<221> NAME/KEY: modified_base
<222> LOCATION: (423)
<223> OTHER INFORMATION: Where n is a, c, g or t
<220> FEATURE:
<221> NAME/KEY: modified_base
<222> LOCATION: (425)
<223> OTHER INFORMATION: Where n is a, c, g or t
<220> FEATURE:
<221> NAME/KEY: modified_base
<222> LOCATION: (436)
<223> OTHER INFORMATION: Where n is a, c, g or t
<220> FEATURE:
<221> NAME/KEY: modified_base
<222> LOCATION: (441)
<223> OTHER INFORMATION: Where n is a, c, g or t

<400> SEQUENCE: 79

```
actagtatgg ggtgggaggc cccacccttc tcccctaggc gctgttcttg ctccaaaggg      60
ctccgtggag agggactggc agagctgang ccacctgggg ctggggatcc cactcttctt      120
gcagctgttg agcgcaccta accactggtc atgcccccac cctgctctc cgcacccgct       180
tcctcccgac cccangacca ggctacttct cccctcctct tgcctccctc ctgcccctgc      240
```

| | |
|---|---|
| tgcctctgat cgtangaatt gangantgtc ccgccttgtg gctganaatg gacagtggca | 300 |
| ggggctggaa atgggtgtgt gtgtgtgtgt gtgtgtgtgt gtgtgtgtgt gcncccccc | 360 |
| tgcaagaccg agattgaggg aaancatgtc tgctgggtgt gaccatgttt cctctccata | 420 |
| aantncccct gtgacnctca naaaaaaaaa aaaaaa | 456 |

<210> SEQ ID NO 80
<211> LENGTH: 284
<212> TYPE: DNA
<213> ORGANISM: Homo sapiens
<220> FEATURE:
<221> NAME/KEY: modified_base
<222> LOCATION: (283)
<223> OTHER INFORMATION: Where n is a, c, g or t

<400> SEQUENCE: 80

| | |
|---|---|
| ctttgtacct ctagaaaaga taggtattgt gtcatgaaac ttgagtttaa attttatata | 60 |
| taaaactaaa agtaatgctc actttagcaa cacatactaa aattggaacc atactgagaa | 120 |
| gaatagcatg acctccgtgc aaacaggaca agcaaatttg tgatgtgttg attaaaaaga | 180 |
| aataaataaa tgtgtatatg tgtaacttgt atgtttatgt ggaatacaga ttgggaaata | 240 |
| aaatgtattt cttactgtga aaaaaaaaaa aaaaaaaaaa aana | 284 |

<210> SEQ ID NO 81
<211> LENGTH: 671
<212> TYPE: DNA
<213> ORGANISM: Homo sapiens
<220> FEATURE:
<221> NAME/KEY: modified_base
<222> LOCATION: (388)
<223> OTHER INFORMATION: Where n is a, c, g or t
<220> FEATURE:
<221> NAME/KEY: modified_base
<222> LOCATION: (505)
<223> OTHER INFORMATION: Where n is a, c, g or t
<220> FEATURE:
<221> NAME/KEY: modified_base
<222> LOCATION: (600)
<223> OTHER INFORMATION: Where n is a, c, g or t
<220> FEATURE:
<221> NAME/KEY: modified_base
<222> LOCATION: (603)
<223> OTHER INFORMATION: Where n is a, c, g or t
<220> FEATURE:
<221> NAME/KEY: modified_base
<222> LOCATION: (615)
<223> OTHER INFORMATION: Where n is a, c, g or t
<220> FEATURE:
<221> NAME/KEY: modified_base
<222> LOCATION: (642)
<223> OTHER INFORMATION: Where n is a, c, g or t
<220> FEATURE:
<221> NAME/KEY: modified_base
<222> LOCATION: (644)
<223> OTHER INFORMATION: Where n is a, c, g or t
<220> FEATURE:
<221> NAME/KEY: modified_base
<222> LOCATION: (660)
<223> OTHER INFORMATION: Where n is a, c, g or t

<400> SEQUENCE: 81

| | |
|---|---|
| gccaccaaca ttccaagcta ccctgggtac ctttgtgcag tagaagctag tgagcatgtg | 60 |
| agcaagcggt gtgcacacgg agactcatcg ttataattta ctatctgcca agagtagaaa | 120 |
| gaaaggctgg ggatatttgg gttggcttgg ttttgatttt ttgcttgttt gtttgttttg | 180 |
| tactaaaaca gtattatctt ttgaatatcg tagggacata agtatataca tgttatccaa | 240 |

| | | |
|---|---|---|
| tcaagatggc tagaatggtg cctttctgag tgtctaaaac ttgacacccc tggtaaatct | 300 | |
| ttcaacacac ttccactgcc tgcgtaatga agttttgatt cattttttaac cactggaatt | 360 | |
| tttcaatgcc gtcattttca gttagatnat tttgcacttt gagattaaaa tgccatgtct | 420 | |
| atttgattag tcttattttt ttattttttac aggcttatca gtctcactgt tggctgtcat | 480 | |
| tgtgacaaag tcaaataaac ccccnaggac aacacacagt atgggatcac atattgtttg | 540 | |
| acattaagct ttggccaaaa aatgttgcat gtgttttacc tcgacttgct aaatcaatan | 600 | |
| canaaaggct ggctnataat gttggtggtg aaataattaa tnantaacca aaaaaaaaan | 660 | |
| aaaaaaaaaa a | 671 | |

<210> SEQ ID NO 82
<211> LENGTH: 217
<212> TYPE: DNA
<213> ORGANISM: Homo sapiens
<220> FEATURE:
<221> NAME/KEY: modified_base
<222> LOCATION: (35)
<223> OTHER INFORMATION: Where n is a, c, g or t

<400> SEQUENCE: 82

| | | |
|---|---|---|
| ctgcagatgt ttcttgaatg ctttgtcaaa ttaanaaagt taaagtgcaa taatgtttga | 60 | |
| agacaataag tggtggtgta tcttgtttct aataagataa acttttttgt ctttgcttta | 120 | |
| tcttattagg gagttgtatg tcagtgtata aaacatactg tgtggtataa caggcttaat | 180 | |
| aaattcttta aaaggaaaaa aaaaaaaaaa aaaaaaa | 217 | |

<210> SEQ ID NO 83
<211> LENGTH: 460
<212> TYPE: DNA
<213> ORGANISM: Homo sapiens
<220> FEATURE:
<221> NAME/KEY: modified_base
<222> LOCATION: (104)
<223> OTHER INFORMATION: Where n is a, c, g or t
<220> FEATURE:
<221> NAME/KEY: modified_base
<222> LOCATION: (118)
<223> OTHER INFORMATION: Where n is a, c, g or t
<220> FEATURE:
<221> NAME/KEY: modified_base
<222> LOCATION: (172)
<223> OTHER INFORMATION: Where n is a, c, g or t
<220> FEATURE:
<221> NAME/KEY: modified_base
<222> LOCATION: (401)
<223> OTHER INFORMATION: Where n is a, c, g or t
<220> FEATURE:
<221> NAME/KEY: modified_base
<222> LOCATION: (422)
<223> OTHER INFORMATION: Where n is a, c, g or t
<220> FEATURE:
<221> NAME/KEY: modified_base
<222> LOCATION: (423)
<223> OTHER INFORMATION: Where n is a, c, g or t
<220> FEATURE:
<221> NAME/KEY: modified_base
<222> LOCATION: (444)
<223> OTHER INFORMATION: Where n is a, c, g or t
<220> FEATURE:
<221> NAME/KEY: modified_base
<222> LOCATION: (449)
<223> OTHER INFORMATION: Where n is a, c, g or t

<400> SEQUENCE: 83

| | | |
|---|---|---|
| cgcgagtggg agcaccagga tctcgggctc ggaacgagac tgcacggatt gttttaagaa | 60 | |
| aatggcagac aaaccagaca tgggggaaat cgccagcttc gatnaggcca agctgaanaa | 120 | |

```
aacggagacg caggagaaga acaccctgcc gaccaaagag accattgagc angagaagcg      180
gagtgaaatt tcctaagatc ctggaggatt tcctaccccc gtcctcttcg agacccagt       240 cgtgatgtgg aggaagagcc acctgcaaga tggacacgag ccacaagctg cactgtgaac      300
ctgggcactc cgcgccgatg ccaccggcct gtgggtctct gaagggaccc cccccaatcg      360
gactgccaaa ttctccggtt tgccccggga tattatacaa nattatttgt atgaataatg      420
annataaaac acacctcgtg gcancaaana aaaaaaaaaa                            460
```

```
<210> SEQ ID NO 84
<211> LENGTH: 323
<212> TYPE: DNA
<213> ORGANISM: Homo sapiens
<220> FEATURE:
<221> NAME/KEY: modified_base
<222> LOCATION: (70)
<223> OTHER INFORMATION: Where n is a, c, g or t
<220> FEATURE:
<221> NAME/KEY: modified_base
<222> LOCATION: (138)
<223> OTHER INFORMATION: Where n is a, c, g or t
<220> FEATURE:
<221> NAME/KEY: modified_base
<222> LOCATION: (178)
<223> OTHER INFORMATION: Where n is a, c, g or t
<220> FEATURE:
<221> NAME/KEY: modified_base
<222> LOCATION: (197)
<223> OTHER INFORMATION: Where n is a, c, g or t
<220> FEATURE:
<221> NAME/KEY: modified_base
<222> LOCATION: (228)
<223> OTHER INFORMATION: Where n is a, c, g or t
<220> FEATURE:
<221> NAME/KEY: modified_base
<222> LOCATION: (242)
<223> OTHER INFORMATION: Where n is a, c, g or t
<220> FEATURE:
<221> NAME/KEY: modified_base
<222> LOCATION: (244)
<223> OTHER INFORMATION: Where n is a, c, g or t
<220> FEATURE:
<221> NAME/KEY: modified_base
<222> LOCATION: (287)
<223> OTHER INFORMATION: Where n is a, c, g or t
<220> FEATURE:
<221> NAME/KEY: modified_base
<222> LOCATION: (311)
<223> OTHER INFORMATION: Where n is a, c, g or t

<400> SEQUENCE: 84
tggtggatct tggctctgtg gagctgctgg gacgggatct aaaagactat tctggaagct       60
gtggtccaan gcattttgct ggcttaacgg gtcccggaac aaaggacacc agctctctaa      120
aattgaagtt tacccganat aacaatcttt tgggcagaga tgcctatttt aacaaacncc      180
gtccctgcgc aacaacnaac aatctctggg aaataccggc catgaacntg ctgtctcaat      240
cnancatctc tctagctgac cgatcatatc gtcccagatt actacanatc ataataattg      300
atttcctgta naaaaaaaaa aaa                                              323
```

```
<210> SEQ ID NO 85
<211> LENGTH: 771
<212> TYPE: DNA
<213> ORGANISM: Homo sapiens
<220> FEATURE:
<221> NAME/KEY: modified_base
<222> LOCATION: (63)
<223> OTHER INFORMATION: Where n is a, c, g or t
<220> FEATURE:
```

-continued

```
<221> NAME/KEY: modified_base
<222> LOCATION: (426)
<223> OTHER INFORMATION: Where n is a, c, g or t
<220> FEATURE:
<221> NAME/KEY: modified_base
<222> LOCATION: (471)
<223> OTHER INFORMATION: Where n is a, c, g or t
<220> FEATURE:
<221> NAME/KEY: modified_base
<222> LOCATION: (487)
<223> OTHER INFORMATION: Where n is a, c, g or t
<220> FEATURE:
<221> NAME/KEY: modified_base
<222> LOCATION: (521)
<223> OTHER INFORMATION: Where n is a, c, g or t
<220> FEATURE:
<221> NAME/KEY: modified_base
<222> LOCATION: (554)
<223> OTHER INFORMATION: Where n is a, c, g or t
<220> FEATURE:
<221> NAME/KEY: modified_base
<222> LOCATION: (583)
<223> OTHER INFORMATION: Where n is a, c, g or t
<220> FEATURE:
<221> NAME/KEY: modified_base
<222> LOCATION: (586)
<223> OTHER INFORMATION: Where n is a, c, g or t
<220> FEATURE:
<221> NAME/KEY: modified_base
<222> LOCATION: (606)
<223> OTHER INFORMATION: Where n is a, c, g or t
<220> FEATURE:
<221> NAME/KEY: modified_base
<222> LOCATION: (609)
<223> OTHER INFORMATION: Where n is a, c, g or t
<220> FEATURE:
<221> NAME/KEY: modified_base
<222> LOCATION: (615)
<223> OTHER INFORMATION: Where n is a, c, g or t
<220> FEATURE:
<221> NAME/KEY: modified_base
<222> LOCATION: (652)
<223> OTHER INFORMATION: Where n is a, c, g or t
<220> FEATURE:
<221> NAME/KEY: modified_base
<222> LOCATION: (686)
<223> OTHER INFORMATION: Where n is a, c, g or t
<220> FEATURE:
<221> NAME/KEY: modified_base
<222> LOCATION: (691)
<223> OTHER INFORMATION: Where n is a, c, g or t
<220> FEATURE:
<221> NAME/KEY: modified_base
<222> LOCATION: (694)
<223> OTHER INFORMATION: Where n is a, c, g or t
<220> FEATURE:
<221> NAME/KEY: modified_base
<222> LOCATION: (695)
<223> OTHER INFORMATION: Where n is a, c, g or t
<220> FEATURE:
<221> NAME/KEY: modified_base
<222> LOCATION: (706)
<223> OTHER INFORMATION: Where n is a, c, g or t
<220> FEATURE:
<221> NAME/KEY: modified_base
<222> LOCATION: (713)
<223> OTHER INFORMATION: Where n is a, c, g or t
<220> FEATURE:
<221> NAME/KEY: modified_base
<222> LOCATION: (730)
<223> OTHER INFORMATION: Where n is a, c, g or t
<220> FEATURE:
<221> NAME/KEY: modified_base
<222> LOCATION: (732)
<223> OTHER INFORMATION: Where n is a, c, g or t
<220> FEATURE:
<221> NAME/KEY: modified_base
<222> LOCATION: (743)
<223> OTHER INFORMATION: Where n is a, c, g or t
```

<220> FEATURE:
<221> NAME/KEY: modified_base
<222> LOCATION: (751)
<223> OTHER INFORMATION: Where n is a, c, g or t

<400> SEQUENCE: 85

```
aaactgggta ctcaacactg agcagatctg ttctttgagc taaaaaccat gtgctgtacc      60
aanagtttgc tcctggctgc tttgatgtca gtgctgctac tccacctctg cggcgaatca     120
gaagcaagca actttgactg ctgtcttgga tacacagacc gtattcttca tcctaaattt     180
attgtgggct tcacacggca gctggccaat gaaggctgtg acatcaatgc tatcatcttt     240
cacacaaaga aaaagttgtc tgtgtgcgca atccaaaac agacttgggt gaaatatatt      300
gtgcgtctcc tcagtaaaaa agtcaagaac atgtaaaaac tgtggctttt ctggaatgga     360
attggacata gcccaagaac agaaagaact tgctggggtt ggaggtttca cttgcacatc     420
atggangqtt tagtgcttat cttatttgtg cctcctggac ttgtccaatt natgaagtta     480
atcatattgc atcatantt tgctttgttta acatcacatt naaattaaac tgtattttat     540
gttatttata gctntaggtt ttctgtgttt aactttttat acnaantttc ctaaactatt     600
ttggtntant gcaanttaaa aattatattt gggggggggaa taaatattgg antttctgca    660
gccacaagct ttttttaaaa aaccantaca nccnngttaa atggtnggtc ccnaatggtt     720
tttgcttttn antagaaaat ttnttagaac natttgaaaa aaaaaaaaa a               771
```

<210> SEQ ID NO 86
<211> LENGTH: 628
<212> TYPE: DNA
<213> ORGANISM: Homo sapiens
<220> FEATURE:
<221> NAME/KEY: modified_base
<222> LOCATION: (162)
<223> OTHER INFORMATION: Where n is a, c, g or t
<220> FEATURE:
<221> NAME/KEY: modified_base
<222> LOCATION: (249)
<223> OTHER INFORMATION: Where n is a, c, g or t
<220> FEATURE:
<221> NAME/KEY: modified_base
<222> LOCATION: (266)
<223> OTHER INFORMATION: Where n is a, c, g or t
<220> FEATURE:
<221> NAME/KEY: modified_base
<222> LOCATION: (348)
<223> OTHER INFORMATION: Where n is a, c, g or t
<220> FEATURE:
<221> NAME/KEY: modified_base
<222> LOCATION: (407)
<223> OTHER INFORMATION: Where n is a, c, g or t
<220> FEATURE:
<221> NAME/KEY: modified_base
<222> LOCATION: (427)
<223> OTHER INFORMATION: Where n is a, c, g or t
<220> FEATURE:
<221> NAME/KEY: modified_base
<222> LOCATION: (488)
<223> OTHER INFORMATION: Where n is a, c, g or t
<220> FEATURE:
<221> NAME/KEY: modified_base
<222> LOCATION: (518)
<223> OTHER INFORMATION: Where n is a, c, g or t
<220> FEATURE:
<221> NAME/KEY: modified_base
<222> LOCATION: (545)
<223> OTHER INFORMATION: Where n is a, c, g or t
<220> FEATURE:
<221> NAME/KEY: modified_base
<222> LOCATION: (566)
<223> OTHER INFORMATION: Where n is a, c, g or t
<220> FEATURE:

<221> NAME/KEY: modified_base
<222> LOCATION: (569)
<223> OTHER INFORMATION: Where n is a, c, g or t
<220> FEATURE:
<221> NAME/KEY: modified_base
<222> LOCATION: (597)
<223> OTHER INFORMATION: Where n is a, c, g or t
<220> FEATURE:
<221> NAME/KEY: modified_base
<222> LOCATION: (598)
<223> OTHER INFORMATION: Where n is a, c, g or t
<220> FEATURE:
<221> NAME/KEY: modified_base
<222> LOCATION: (611)
<223> OTHER INFORMATION: Where n is a, c, g or t
<220> FEATURE:
<221> NAME/KEY: modified_base
<222> LOCATION: (617)
<223> OTHER INFORMATION: Where n is a, c, g or t
<220> FEATURE:
<221> NAME/KEY: modified_base
<222> LOCATION: (621)
<223> OTHER INFORMATION: Where n is a, c, g or t
<220> FEATURE:
<221> NAME/KEY: modified_base
<222> LOCATION: (624)
<223> OTHER INFORMATION: Where n is a, c, g or t

<400> SEQUENCE: 86

```
actagtttgc tttacatttt tgaaaagtat tattttttgtc caagtgctta tcaactaaac     60
cttgtgttag gtaagaatgg aatttattaa gtgaatcagt gtgacccttc ttgtcataag    120
attatcttaa agctgaagcc aaaatatgct tcaaaagaaa angactttat tgttcattgt    180
agttcataca ttcaaagcat ctgaactgta gtttctatag caagccaatt acatccataa    240
gtggagaaag aaatagatta atgtcnaagt atgattggtg gagggagcaa ggttgaagat    300
aatctggggt tgaaattttc tagttttcat tctgtacatt tttagttnga catcagattt    360
gaaatattaa tgtttaccct tcaatgtgtg gtatcagctg gactcantaa cacccctttc    420
ttccctngg gatggggaat ggattattgg aaaatggaaa gaaaaagta cttaaagcct    480
tcctttcnca gtttctggct cctacccac tgatttancc agaataagaa acatttttat    540
catcntctgc tttattccca ttaatnaant tttgatgaat aaatctgctt ttatgcnnac    600
ccaaggaatt nagtggnttc ntcnttgt                                        628
```

<210> SEQ ID NO 87
<211> LENGTH: 518
<212> TYPE: DNA
<213> ORGANISM: Homo sapiens
<220> FEATURE:
<221> NAME/KEY: modified_base
<222> LOCATION: (384)
<223> OTHER INFORMATION: Where n is a, c, g or t
<220> FEATURE:
<221> NAME/KEY: modified_base
<222> LOCATION: (421)
<223> OTHER INFORMATION: Where n is a, c, g or t
<220> FEATURE:
<221> NAME/KEY: modified_base
<222> LOCATION: (486)
<223> OTHER INFORMATION: Where n is a, c, g or t

<400> SEQUENCE: 87

```
tttttattt tttttagaga gtagttcagc ttttatttat aaatttattg cctgttttat     60
tataacaaca ttatactgtt tatggtttaa tacatatggt tcaaaatgta taatacatca    120
agtagtacag ttttaaaatt ttatgcttaa aacaagtttt gtgtaaaaaa tgcagataca    180
ttttacatgg caaatcaatt tttaagtcat cctaaaaatt gatttttttt tgaaatttaa    240
```

| | |
|---|---|
| aaacacattt aatttcaatt tctctcttat ataaccttta ttactatagc atggtttcca | 300 |
| ctacagttta acaatgcagc aaaattccca tttcacggta aattgggttt taagcggcaa | 360 |
| ggttaaaatg ctttgaggat cctnaatacc ctttgaactt caaatgaagg ttatggttgt | 420 |
| naatttaacc ctcatgccat aagcagaagc acaagtttag ctgcattttg ctctaaactg | 480 |
| taaaancgag cccccgttg aaaaagcaaa agggaccc | 518 |

<210> SEQ ID NO 88
<211> LENGTH: 1844
<212> TYPE: DNA
<213> ORGANISM: Homo sapiens

<400> SEQUENCE: 88

| | |
|---|---|
| gagacagtga atcctagtat caaaggattt ttggcctcag aaaaagttgt tgattatttt | 60 |
| tattttattt tattttcga gactccgtct caaaaaaaa aaaaaaaaa agaatcacaa | 120 |
| ggtatttgct aaagcatttt gagctgcttg gaaaaggga agtagttgca gtagagtttc | 180 |
| ttccatcttc ttggtgctgg gaagccatat atgtgtcttt tactcaagct aagggtata | 240 |
| agcttatgtg ttgaatttgc tacatctata tttcacatat tctcacaata agagaatttt | 300 |
| gaaatagaaa tatcatagaa catttaagaa agtttagtat aaataatatt ttgtgtgttt | 360 |
| taatcccttt gaagggatct atccaaagaa atattttac actgagctcc ttcctacacg | 420 |
| tctcagtaac agatcctgtg ttagtctttg aaaatagctc attttttaaa tgtcagtgag | 480 |
| tagatgtagc atacatatga tgtataatga cgtgtattat gttaacaatg tctgcagatt | 540 |
| ttgtaggaat acaaaacatg gccttttta taagcaaaac gggccaatga ctagaataac | 600 |
| acatagggca atctgtgaat atgtattata agcagcattc cagaaaagta gttggtgaaa | 660 |
| taattttcaa gtcaaaaagg gatatggaaa gggaattatg agtaacctct atttttaag | 720 |
| ccttgctttt aaattaaacg ctacagccat ttaagccttg aggataataa agcttgagag | 780 |
| taataatgtt aggttagcaa aggtttagat gtatcacttc atgcatgcta ccatgatagt | 840 |
| aatgcagctc ttcgagtcat ttctggtcat tcaagatatt cacccttttg cccatagaaa | 900 |
| gcaccctacc tcacctgctt actgacattg tcttagctga tcacaagatc attatcagcc | 960 |
| tccattattc cttactgtat ataaaataca gagttttata ttttcctttc ttcgtttttc | 1020 |
| accatattca aaacctaaat ttgtttttgc agatggaatg caaagtaatc aagtgttcgt | 1080 |
| gctttcacct agaagggtgt ggtcctgaag gaaagaggtc cctaaatatc ccccaccctg | 1140 |
| ggtgctcctc cttccctggt accctgacta ccagaagtca ggtgctagag cagctggaga | 1200 |
| agtgcagcag cctgtgcttc cacagatggg ggtgctgctg caacaaggct ttcaatgtgc | 1260 |
| ccatcttagg gggagaagct agatcctgtg cagcagcctg gtaagtcctg aggaggttcc | 1320 |
| attgctcttc ctgctgctgt cctttgcttc tcaacggggc tcgctctaca gtctagagca | 1380 |
| catgcagcta acttgtgcct ctgcttatgc atgagggtta aattaacaac cataaccttc | 1440 |
| atttgaagtt caaaggtgta ttcaggatcc tcaaagcatt ttaaccttgc cgcttaaaac | 1500 |
| ccaatttacc gtgaaatggg aattttgctg cattgttaaa ctgtagtgga aaccatgcta | 1560 |
| tagtaataaa ggttatataa gagagaaatt gaatttaaat gtgtтттттaa atttcaaaaa | 1620 |
| aaaatcaatc tttaggatga cttaaaaatt gatttgccat gtaaaatgta tctgcatttt | 1680 |
| ttacacaaaa cттgтттттaa gcataaaatt ttaaaactgt actacttgat gtattataca | 1740 |
| ttttgaacca tatgtattaa accataaaca gtaatatgtt gttataataa aacaggcaat | 1800 |

-continued aaatttataa ataaaagctg aaaaaaaaaa aaaaaaaaaa aaaa                          1844

<210> SEQ ID NO 89
<211> LENGTH: 523
<212> TYPE: DNA
<213> ORGANISM: Homo sapiens
<220> FEATURE:
<221> NAME/KEY: modified_base
<222> LOCATION: (288)
<223> OTHER INFORMATION: Where n is a, c, g or t
<220> FEATURE:
<221> NAME/KEY: modified_base
<222> LOCATION: (352)
<223> OTHER INFORMATION: Where n is a, c, g or t
<220> FEATURE:
<221> NAME/KEY: modified_base
<222> LOCATION: (369)
<223> OTHER INFORMATION: Where n is a, c, g or t
<220> FEATURE:
<221> NAME/KEY: modified_base
<222> LOCATION: (398)
<223> OTHER INFORMATION: Where n is a, c, g or t
<220> FEATURE:
<221> NAME/KEY: modified_base
<222> LOCATION: (475)
<223> OTHER INFORMATION: Where n is a, c, g or t
<220> FEATURE:
<221> NAME/KEY: modified_base
<222> LOCATION: (511)
<223> OTHER INFORMATION: Where n is a, c, g or t
<220> FEATURE:
<221> NAME/KEY: modified_base
<222> LOCATION: (513)
<223> OTHER INFORMATION: Where n is a, c, g or t

<400> SEQUENCE: 89
tttttttttt tttttttagt caatccacat ttattgatca cttattatgt accaggcact           60
gggataaaga tgactgttag tcactcacag taaggaagaa aactagcaaa taagacgatt          120
acaatatgat gtagaaaatg ctaagccaga gatatagaaa ggtcctattg ggtccttctg          180
tcaccttgtc tttccacatc cctacccttc acaggccttc cctccagctt cctgccccg           240 ctccccactg cagatcccct gggattttgc ctagagctaa acgagganat gggcccctg           300 gccctggcat gacttgaacc caaccacaga ctgggaaagg gagcctttcg anagtggatc          360
actttgatna gaaacacat agggaattga agagaaantc cccaaatggc cacccgtgct           420
ggtgctcaag aaaagtttgc agaatggata aatgaaggat caagggaatt aatanatgaa          480
taattgaatg gtggctcaat aagaatgact ncnttgaatg acc                            523

<210> SEQ ID NO 90
<211> LENGTH: 604
<212> TYPE: DNA
<213> ORGANISM: Homo sapiens
<220> FEATURE:
<221> NAME/KEY: modified_base
<222> LOCATION: (563)
<223> OTHER INFORMATION: Where n is a, c, g or t

<400> SEQUENCE: 90
ccagtgtggt ggaatgcaaa gattaccccg gaagctttcg agaagctggg attccctgca           60
gcaaaggaaa tagccaatat gtgtcgtttc tatgaaatga agccagaccg agatgtcaat         120
ctcacccacc aactaaatcc caaagtcaaa agcttcagcc agtttatctc agagaaccag         180
gggagccttc aagggcatgt agaaaatcag ctgttcagat aggcctctgc accacacagc         240
ctctttcctc tctgatcctt ttcctctttta cggcacaaca ttcatgtttg acagaacatg         300
ctggaatgca attgtttgca acaccgaagg atttcctgcg gtcgcctctt cagtaggaag         360

-continued

```
cactgcattg gtgataggac acggtaattt gattcacatt taacttgcta gttagtgata    420 agggtggta  cacctgtttg gtaaaatgag aagcctcgga aacttgggag cttctctcct    480
accactaatg gggagggcag attattactg ggatttctcc tggggtgaat taatttcaag    540
ccctaattgc tgaaattccc ctnggcaggc tccagttttc tcaactgcat tgcaaaattc    600
cccc                                                                604
```

```
<210> SEQ ID NO 91
<211> LENGTH: 858
<212> TYPE: DNA
<213> ORGANISM: Homo sapiens
<220> FEATURE:
<221> NAME/KEY: modified_base
<222> LOCATION: (570)
<223> OTHER INFORMATION: Where n is a, c, g or t
<220> FEATURE:
<221> NAME/KEY: modified_base
<222> LOCATION: (591)
<223> OTHER INFORMATION: Where n is a, c, g or t
<220> FEATURE:
<221> NAME/KEY: modified_base
<222> LOCATION: (655)
<223> OTHER INFORMATION: Where n is a, c, g or t
<220> FEATURE:
<221> NAME/KEY: modified_base
<222> LOCATION: (664)
<223> OTHER INFORMATION: Where n is a, c, g or t
<220> FEATURE:
<221> NAME/KEY: modified_base
<222> LOCATION: (667)
<223> OTHER INFORMATION: Where n is a, c, g or t
<220> FEATURE:
<221> NAME/KEY: modified_base
<222> LOCATION: (683)
<223> OTHER INFORMATION: Where n is a, c, g or t
<220> FEATURE:
<221> NAME/KEY: modified_base
<222> LOCATION: (711)
<223> OTHER INFORMATION: Where n is a, c, g or t
<220> FEATURE:
<221> NAME/KEY: modified_base
<222> LOCATION: (759)
<223> OTHER INFORMATION: Where n is a, c, g or t
<220> FEATURE:
<221> NAME/KEY: modified_base
<222> LOCATION: (760)
<223> OTHER INFORMATION: Where n is a, c, g or t
<220> FEATURE:
<221> NAME/KEY: modified_base
<222> LOCATION: (765)
<223> OTHER INFORMATION: Where n is a, c, g or t
<220> FEATURE:
<221> NAME/KEY: modified_base
<222> LOCATION: (777)
<223> OTHER INFORMATION: Where n is a, c, g or t
<220> FEATURE:
<221> NAME/KEY: modified_base
<222> LOCATION: (787)
<223> OTHER INFORMATION: Where n is a, c, g or t
<220> FEATURE:
<221> NAME/KEY: modified_base
<222> LOCATION: (792)
<223> OTHER INFORMATION: Where n is a, c, g or t
<220> FEATURE:
<221> NAME/KEY: modified_base
<222> LOCATION: (794)
<223> OTHER INFORMATION: Where n is a, c, g or t
<220> FEATURE:
<221> NAME/KEY: modified_base
<222> LOCATION: (801)
<223> OTHER INFORMATION: Where n is a, c, g or t
<220> FEATURE:
<221> NAME/KEY: modified_base
<222> LOCATION: (804)
```

```
<223> OTHER INFORMATION: Where n is a, c, g or t
<220> FEATURE:
<221> NAME/KEY: modified_base
<222> LOCATION: (809)
<223> OTHER INFORMATION: Where n is a, c, g or t
<220> FEATURE:
<221> NAME/KEY: modified_base
<222> LOCATION: (817)
<223> OTHER INFORMATION: Where n is a, c, g or t
<220> FEATURE:
<221> NAME/KEY: modified_base
<222> LOCATION: (820)
<223> OTHER INFORMATION: Where n is a, c, g or t

<400> SEQUENCE: 91 ttttttttt  ttttttttta  tgattattat  ttttttatt   gatctttaca  tcctcagtgt      60
tggcagagtt  tctgatgctt  aataaacatt  tgttctgatc  agataagtgg  aaaaaattgt    120
catttcctta  ttcaagccat  gcttttctgt  gatattctga  tcctagttga  acatacagaa    180
ataaatgtct  aaaacagcac  ctcgattctc  gtctataaca  ggactaagtt  cactgtgatc    240
ttaaataagc  ttggctaaaa  tgggacatga  gtggaggtag  tcacacttca  gcgaagaaag    300
agaatctcct  gtataatctc  accaggagat  tcaacgaatt  ccaccacact  ggactagtgg    360
atcccccggg  ctgcaggaat  tcgatatcaa  gcttatcgat  accgtcgacc  tcgaggggg     420 gcccggtacc  caattcgccc  tatagtgagt  cgtattacgc  gcgctcactg  gccgtcgttt    480
tacaacgtcg  tgactgggaa  aaccctggcg  ttacccaact  taatcgcctt  gcagcacatc    540
cccctttcgc  cagctggcgt  aatagcgaan  agcccgcacc  gatcgccctt  ncaacagttg    600
cgcagcctga  atggcgaatg  ggacgcgccc  tgtagcggcg  cattaaagcg  cggcngggtg    660
tggnggntcc  cccacgtgac  cgntacactt  ggcagcgcct  tacgccggtc  nttcgctttc    720
ttcccttcct  ttctcgcacc  gttcgccggg  ttttcccgn   agctnttaat  cggggnctc    780 cctttanggg  tncnaattaa  nggnttacng  gaccttngan  cccaaaaact  ttgattaggg    840
ggaaggtccc  cgaagggg                                                      858

<210> SEQ ID NO 92
<211> LENGTH: 585
<212> TYPE: DNA
<213> ORGANISM: Homo sapiens
<220> FEATURE:
<221> NAME/KEY: modified_base
<222> LOCATION: (317)
<223> OTHER INFORMATION: Where n is a, c, g or t
<220> FEATURE:
<221> NAME/KEY: modified_base
<222> LOCATION: (319)
<223> OTHER INFORMATION: Where n is a, c, g or t
<220> FEATURE:
<221> NAME/KEY: modified_base
<222> LOCATION: (320)
<223> OTHER INFORMATION: Where n is a, c, g or t
<220> FEATURE:
<221> NAME/KEY: modified_base
<222> LOCATION: (321)
<223> OTHER INFORMATION: Where n is a, c, g or t
<220> FEATURE:
<221> NAME/KEY: modified_base
<222> LOCATION: (325)
<223> OTHER INFORMATION: Where n is a, c, g or t
<220> FEATURE:
<221> NAME/KEY: modified_base
<222> LOCATION: (327)
<223> OTHER INFORMATION: Where n is a, c, g or t
<220> FEATURE:
<221> NAME/KEY: modified_base
<222> LOCATION: (328)
<223> OTHER INFORMATION: Where n is a, c, g or t
```

<220> FEATURE:
<221> NAME/KEY: modified_base
<222> LOCATION: (330)
<223> OTHER INFORMATION: Where n is a, c, g or t
<220> FEATURE:
<221> NAME/KEY: modified_base
<222> LOCATION: (331)
<223> OTHER INFORMATION: Where n is a, c, g or t
<220> FEATURE:
<221> NAME/KEY: modified_base
<222> LOCATION: (332)
<223> OTHER INFORMATION: Where n is a, c, g or t
<220> FEATURE:
<221> NAME/KEY: modified_base
<222> LOCATION: (460)
<223> OTHER INFORMATION: Where n is a, c, g or t
<220> FEATURE:
<221> NAME/KEY: modified_base
<222> LOCATION: (462)
<223> OTHER INFORMATION: Where n is a, c, g or t
<220> FEATURE:
<221> NAME/KEY: modified_base
<222> LOCATION: (483)
<223> OTHER INFORMATION: Where n is a, c, g or t
<220> FEATURE:
<221> NAME/KEY: modified_base
<222> LOCATION: (485)
<223> OTHER INFORMATION: Where n is a, c, g or t
<220> FEATURE:
<221> NAME/KEY: modified_base
<222> LOCATION: (487)
<223> OTHER INFORMATION: Where n is a, c, g or t
<220> FEATURE:
<221> NAME/KEY: modified_base
<222> LOCATION: (523)
<223> OTHER INFORMATION: Where n is a, c, g or t
<220> FEATURE:
<221> NAME/KEY: modified_base
<222> LOCATION: (538)
<223> OTHER INFORMATION: Where n is a, c, g or t
<220> FEATURE:
<221> NAME/KEY: modified_base
<222> LOCATION: (566)
<223> OTHER INFORMATION: Where n is a, c, g or t
<220> FEATURE:
<221> NAME/KEY: modified_base
<222> LOCATION: (584)
<223> OTHER INFORMATION: Where n is a, c, g or t

<400> SEQUENCE: 92

```
gttgaatctc ctggtgagat tatacaggag attctctttc ttcgctgaag tgtgactacc      60
tccactcatg tcccatttta gccaagctta tttaagatca cagtgaactt agtcctgtta     120
tagacgagaa tcgaggtgct gttttagaca tttatttctg tatgttcaac taggatcaga     180
atatcacaga aaagcatggc ttgaataagg aaatgacaat tttttccact tatctgatca     240
gaacaaatgt ttattaagca tcagaaactc tgccaacact gaggatgtaa agatcaataa     300
aaaaaataat aatcatnann naaanannan nngaagggcg gccgccaccg cggtggagct     360
ccagcttttg ttccctttag tgagggttaa ttgcgcgctt ggcgttaatc atggtcatag     420
ctgtttcctg tgtgaaattg ttatccggct cacaattccn cncaacatac gagccgggaa     480
gcntnangtg taaaagcctg ggggtgccta attgagtgag ctnactcaca ttaattgngt     540
tgcgctccac ttgcccgctt ttccantccg ggaaacctgt tcgnc                     585
```

<210> SEQ ID NO 93
<211> LENGTH: 567
<212> TYPE: DNA
<213> ORGANISM: Homo sapiens
<220> FEATURE:
<221> NAME/KEY: modified_base
<222> LOCATION: (82)

-continued

```
<223> OTHER INFORMATION: Where n is a, c, g or t
<220> FEATURE:
<221> NAME/KEY: modified_base
<222> LOCATION: (158)
<223> OTHER INFORMATION: Where n is a, c, g or t
<220> FEATURE:
<221> NAME/KEY: modified_base
<222> LOCATION: (230)
<223> OTHER INFORMATION: Where n is a, c, g or t
<220> FEATURE:
<221> NAME/KEY: modified_base
<222> LOCATION: (232)
<223> OTHER INFORMATION: Where n is a, c, g or t
<220> FEATURE:
<221> NAME/KEY: modified_base
<222> LOCATION: (253)
<223> OTHER INFORMATION: Where n is a, c, g or t
<220> FEATURE:
<221> NAME/KEY: modified_base
<222> LOCATION: (266)..(287)
<223> OTHER INFORMATION: Where n is a, c, g or t
<220> FEATURE:
<221> NAME/KEY: modified_base
<222> LOCATION: (295)
<223> OTHER INFORMATION: Where n is a, c, g or t
<220> FEATURE:
<221> NAME/KEY: modified_base
<222> LOCATION: (303)
<223> OTHER INFORMATION: Where n is a, c, g or t
<220> FEATURE:
<221> NAME/KEY: modified_base
<222> LOCATION: (307)
<223> OTHER INFORMATION: Where n is a, c, g or t
<220> FEATURE:
<221> NAME/KEY: modified_base
<222> LOCATION: (314)
<223> OTHER INFORMATION: Where n is a, c, g or t
<220> FEATURE:
<221> NAME/KEY: modified_base
<222> LOCATION: (349)
<223> OTHER INFORMATION: Where n is a, c, g or t
<220> FEATURE:
<221> NAME/KEY: modified_base
<222> LOCATION: (352)
<223> OTHER INFORMATION: Where n is a, c, g or t
<220> FEATURE:
<221> NAME/KEY: modified_base
<222> LOCATION: (354)
<223> OTHER INFORMATION: Where n is a, c, g or t
<220> FEATURE:
<221> NAME/KEY: modified_base
<222> LOCATION: (356)
<223> OTHER INFORMATION: Where n is a, c, g or t
<220> FEATURE:
<221> NAME/KEY: modified_base
<222> LOCATION: (366)
<223> OTHER INFORMATION: Where n is a, c, g or t
<220> FEATURE:
<221> NAME/KEY: modified_base
<222> LOCATION: (369)
<223> OTHER INFORMATION: Where n is a, c, g or t
<220> FEATURE:
<221> NAME/KEY: modified_base
<222> LOCATION: (379)
<223> OTHER INFORMATION: Where n is a, c, g or t
<220> FEATURE:
<221> NAME/KEY: modified_base
<222> LOCATION: (382)
<223> OTHER INFORMATION: Where n is a, c, g or t
<220> FEATURE:
<221> NAME/KEY: modified_base
<222> LOCATION: (386)
<223> OTHER INFORMATION: Where n is a, c, g or t
<220> FEATURE:
<221> NAME/KEY: modified_base
<222> LOCATION: (393)
<223> OTHER INFORMATION: Where n is a, c, g or t
<220> FEATURE:
<221> NAME/KEY: modified_base
```

-continued

```
<222> LOCATION: (404)
<223> OTHER INFORMATION: Where n is a, c, g or t
<220> FEATURE:
<221> NAME/KEY: modified_base
<222> LOCATION: (427)
<223> OTHER INFORMATION: Where n is a, c, g or t
<220> FEATURE:
<221> NAME/KEY: modified_base
<222> LOCATION: (428)
<223> OTHER INFORMATION: Where n is a, c, g or t
<220> FEATURE:
<221> NAME/KEY: modified_base
<222> LOCATION: (446)
<223> OTHER INFORMATION: Where n is a, c, g or t
<220> FEATURE:
<221> NAME/KEY: modified_base
<222> LOCATION: (450)
<223> OTHER INFORMATION: Where n is a, c, g or t
<220> FEATURE:
<221> NAME/KEY: modified_base
<222> LOCATION: (452)
<223> OTHER INFORMATION: Where n is a, c, g or t
<220> FEATURE:
<221> NAME/KEY: modified_base
<222> LOCATION: (453)
<223> OTHER INFORMATION: Where n is a, c, g or t
<220> FEATURE:
<221> NAME/KEY: modified_base
<222> LOCATION: (454)
<223> OTHER INFORMATION: Where n is a, c, g or t
<220> FEATURE:
<221> NAME/KEY: modified_base
<222> LOCATION: (459)
<223> OTHER INFORMATION: Where n is a, c, g or t
<220> FEATURE:
<221> NAME/KEY: modified_base
<222> LOCATION: (462)
<223> OTHER INFORMATION: Where n is a, c, g or t
<220> FEATURE:
<221> NAME/KEY: modified_base
<222> LOCATION: (480)
<223> OTHER INFORMATION: Where n is a, c, g or t
<220> FEATURE:
<221> NAME/KEY: modified_base
<222> LOCATION: (481)
<223> OTHER INFORMATION: Where n is a, c, g or t
<220> FEATURE:
<221> NAME/KEY: modified_base
<222> LOCATION: (483)
<223> OTHER INFORMATION: Where n is a, c, g or t
<220> FEATURE:
<221> NAME/KEY: modified_base
<222> LOCATION: (488)
<223> OTHER INFORMATION: Where n is a, c, g or t
<220> FEATURE:
<221> NAME/KEY: modified_base
<222> LOCATION: (493)
<223> OTHER INFORMATION: Where n is a, c, g or t
<220> FEATURE:
<221> NAME/KEY: modified_base
<222> LOCATION: (501)
<223> OTHER INFORMATION: Where n is a, c, g or t
<220> FEATURE:
<221> NAME/KEY: modified_base
<222> LOCATION: (509)
<223> OTHER INFORMATION: Where n is a, c, g or t
<220> FEATURE:
<221> NAME/KEY: modified_base
<222> LOCATION: (511)
<223> OTHER INFORMATION: Where n is a, c, g or t
<220> FEATURE:
<221> NAME/KEY: modified_base
<222> LOCATION: (512)
<223> OTHER INFORMATION: Where n is a, c, g or t
<220> FEATURE:
<221> NAME/KEY: modified_base
<222> LOCATION: (518)
<223> OTHER INFORMATION: Where n is a, c, g or t
<220> FEATURE:
```

<221> NAME/KEY: modified_base
<222> LOCATION: (520)
<223> OTHER INFORMATION: Where n is a, c, g or t
<220> FEATURE:
<221> NAME/KEY: modified_base
<222> LOCATION: (525)
<223> OTHER INFORMATION: Where n is a, c, g or t
<220> FEATURE:
<221> NAME/KEY: modified_base
<222> LOCATION: (526)
<223> OTHER INFORMATION: Where n is a, c, g or t
<220> FEATURE:
<221> NAME/KEY: modified_base
<222> LOCATION: (532)
<223> OTHER INFORMATION: Where n is a, c, g or t
<220> FEATURE:
<221> NAME/KEY: modified_base
<222> LOCATION: (541)
<223> OTHER INFORMATION: Where n is a, c, g or t
<220> FEATURE:
<221> NAME/KEY: modified_base
<222> LOCATION: (557)
<223> OTHER INFORMATION: Where n is a, c, g or t

<400> SEQUENCE: 93

```
cggcagtgtt gctgtctgcg tgtccacctt ggaatctggc tgaactggct gggaggacca      60
agactgcggc tggggtgggc anggaaggga accgggggct gctgtgaagg atcttggaac     120
ttccctgtac ccaccttccc cttgcttcat gtttgtanag gaaccttgtg ccggccaagc     180
ccagtttcct tgtgtgatac actaatgtat ttgcttttt tgggaaatan anaaaaatca     240
attaaattgc tantgtttct ttgaannnnn nnnnnnnnnn nnnnnnnggg ggggncgccc     300
ccncggngga aacnccccct tttgttccct ttaattgaaa ggttaattng cncncntggc     360
gttaanccnt gggccaaanc tngttncccg tgntgaaatt gttnatcccc tcccaaattc     420
ccccccnncc ttccaaaccc ggaaancctn annntgttna anccggggg gttgcctaan     480
ngnaattnaa ccnaaccccc ntttaaatng nntttgcncn ccacnngccc cnctttccca     540
nttcggggaa aaccctntcc gtgccca                                         567
```

<210> SEQ ID NO 94
<211> LENGTH: 620
<212> TYPE: DNA
<213> ORGANISM: Homo sapiens
<220> FEATURE:
<221> NAME/KEY: modified_base
<222> LOCATION: (169)
<223> OTHER INFORMATION: Where n is a, c, g or t
<220> FEATURE:
<221> NAME/KEY: modified_base
<222> LOCATION: (171)
<223> OTHER INFORMATION: Where n is a, c, g or t
<220> FEATURE:
<221> NAME/KEY: modified_base
<222> LOCATION: (222)
<223> OTHER INFORMATION: Where n is a, c, g or t
<220> FEATURE:
<221> NAME/KEY: modified_base
<222> LOCATION: (472)
<223> OTHER INFORMATION: Where n is a, c, g or t
<220> FEATURE:
<221> NAME/KEY: modified_base
<222> LOCATION: (528)
<223> OTHER INFORMATION: Where n is a, c, g or t
<220> FEATURE:
<221> NAME/KEY: modified_base
<222> LOCATION: (559)
<223> OTHER INFORMATION: Where n is a, c, g or t
<220> FEATURE:
<221> NAME/KEY: modified_base
<222> LOCATION: (599)
<223> OTHER INFORMATION: Where n is a, c, g or t

<400> SEQUENCE: 94

```
actagtcaaa aatgctaaaa taatttggga gaaaatattt tttaagtagt gttatagttt      60
catgtttatc ttttattatg ttttgtgaag ttgtgtcttt tcactaatta cctatactat     120
gccaatattt ccttatatct atccataaca tttatactac atttgtaana naatatgcac     180
gtgaaactta acactttata agtaaaaat gaggtttcca anatttaata atctgatcaa      240
gttcttgtta tttccaaata gaatggactt ggtctgttaa gggctaagga gaagaggaag     300
ataaggttaa aagttgttaa tgaccaaaca ttctaaaaga aatgcaaaaa aaagttat       360
tttcaagcct tcgaactatt taaggaaagc aaaatcattt cctaaatgca tatcatttgt     420
gagaatttct cattaatatc ctgaatcatt catttcacta aggctcatgt tnactccgat     480
atgtctctaa gaaagtacta tttcatggtc caaacctggt tgccatantt gggtaaaggc     540
tttcccttaa gtgtgaaant atttaaaatg aaattttcct cttttaaaa attctttana      600
agggttaagg gtgttgggga                                                 620
```

<210> SEQ ID NO 95
<211> LENGTH: 470
<212> TYPE: DNA
<213> ORGANISM: Homo sapiens
<220> FEATURE:
<221> NAME/KEY: modified_base
<222> LOCATION: (61)
<223> OTHER INFORMATION: Where n is a, c, g or t
<220> FEATURE:
<221> NAME/KEY: modified_base
<222> LOCATION: (67)
<223> OTHER INFORMATION: Where n is a, c, g or t
<220> FEATURE:
<221> NAME/KEY: modified_base
<222> LOCATION: (79)
<223> OTHER INFORMATION: Where n is a, c, g or t
<220> FEATURE:
<221> NAME/KEY: modified_base
<222> LOCATION: (89)
<223> OTHER INFORMATION: Where n is a, c, g or t
<220> FEATURE:
<221> NAME/KEY: modified_base
<222> LOCATION: (106)
<223> OTHER INFORMATION: Where n is a, c, g or t
<220> FEATURE:
<221> NAME/KEY: modified_base
<222> LOCATION: (213)
<223> OTHER INFORMATION: Where n is a, c, g or t
<220> FEATURE:
<221> NAME/KEY: modified_base
<222> LOCATION: (271)
<223> OTHER INFORMATION: Where n is a, c, g or t
<220> FEATURE:
<221> NAME/KEY: modified_base
<222> LOCATION: (281)
<223> OTHER INFORMATION: Where n is a, c, g or t
<220> FEATURE:
<221> NAME/KEY: modified_base
<222> LOCATION: (330)
<223> OTHER INFORMATION: Where n is a, c, g or t
<220> FEATURE:
<221> NAME/KEY: modified_base
<222> LOCATION: (356)
<223> OTHER INFORMATION: Where n is a, c, g or t
<220> FEATURE:
<221> NAME/KEY: modified_base
<222> LOCATION: (387)
<223> OTHER INFORMATION: Where n is a, c, g or t
<220> FEATURE:
<221> NAME/KEY: modified_base
<222> LOCATION: (432)
<223> OTHER INFORMATION: Where n is a, c, g or t
<220> FEATURE:

<221> NAME/KEY: modified_base
<222> LOCATION: (448)
<223> OTHER INFORMATION: Where n is a, c, g or t

<400> SEQUENCE: 95
ctcgaccttc tctgcacagc ggatgaaccc tgagcagctg aagaccagaa aagccactat    60
nactttntgc ttaattcang agcttacang attcttcaaa gagtgngtcc agcatcctttt   120 gaaacatgag ttcttaccag cagaagcaga cctttacccc accacctcag cttcaacagc   180
agcaggtgaa acaacccatc cagcctccac ctnaggaaat atttgttccc acaaccaagg   240
agccatgcca ctcaaaggtt ccacaacctg naaacacaaa nattccagag ccaggctgta   300
ccaaggtccc tgagccaggg ctgtaccaan gtccctgagc caggttgtac caangtccct   360
gagccaggat gtaccaaggt ccctgancca ggttgtccaa ggtccctgag ccaggctaca   420
ccaagggcct gngccaggca gcatcaangt ccctgaccaa ggcttatcaa              470

<210> SEQ ID NO 96
<211> LENGTH: 718
<212> TYPE: DNA
<213> ORGANISM: Homo sapiens
<220> FEATURE:
<221> NAME/KEY: modified_base
<222> LOCATION: (299)
<223> OTHER INFORMATION: Where n is a, c, g or t
<220> FEATURE:
<221> NAME/KEY: modified_base
<222> LOCATION: (311)
<223> OTHER INFORMATION: Where n is a, c, g or t
<220> FEATURE:
<221> NAME/KEY: modified_base
<222> LOCATION: (360)
<223> OTHER INFORMATION: Where n is a, c, g or t
<220> FEATURE:
<221> NAME/KEY: modified_base
<222> LOCATION: (426)
<223> OTHER INFORMATION: Where n is a, c, g or t
<220> FEATURE:
<221> NAME/KEY: modified_base
<222> LOCATION: (538)
<223> OTHER INFORMATION: Where n is a, c, g or t
<220> FEATURE:
<221> NAME/KEY: modified_base
<222> LOCATION: (540)
<223> OTHER INFORMATION: Where n is a, c, g or t
<220> FEATURE:
<221> NAME/KEY: modified_base
<222> LOCATION: (542)
<223> OTHER INFORMATION: Where n is a, c, g or t
<220> FEATURE:
<221> NAME/KEY: modified_base
<222> LOCATION: (553)
<223> OTHER INFORMATION: Where n is a, c, g or t
<220> FEATURE:
<221> NAME/KEY: modified_base
<222> LOCATION: (563)
<223> OTHER INFORMATION: Where n is a, c, g or t
<220> FEATURE:
<221> NAME/KEY: modified_base
<222> LOCATION: (565)
<223> OTHER INFORMATION: Where n is a, c, g or t
<220> FEATURE:
<221> NAME/KEY: modified_base
<222> LOCATION: (592)
<223> OTHER INFORMATION: Where n is a, c, g or t
<220> FEATURE:
<221> NAME/KEY: modified_base
<222> LOCATION: (603)
<223> OTHER INFORMATION: Where n is a, c, g or t
<220> FEATURE:
<221> NAME/KEY: modified_base
<222> LOCATION: (604)
<223> OTHER INFORMATION: Where n is a, c, g or t

```
<220> FEATURE:
<221> NAME/KEY: modified_base
<222> LOCATION: (618)
<223> OTHER INFORMATION: Where n is a, c, g or t
<220> FEATURE:
<221> NAME/KEY: modified_base
<222> LOCATION: (633)
<223> OTHER INFORMATION: Where n is a, c, g or t
<220> FEATURE:
<221> NAME/KEY: modified_base
<222> LOCATION: (647)
<223> OTHER INFORMATION: Where n is a, c, g or t
<220> FEATURE:
<221> NAME/KEY: modified_base
<222> LOCATION: (649)
<223> OTHER INFORMATION: Where n is a, c, g or t
<220> FEATURE:
<221> NAME/KEY: modified_base
<222> LOCATION: (651)
<223> OTHER INFORMATION: Where n is a, c, g or t
<220> FEATURE:
<221> NAME/KEY: modified_base
<222> LOCATION: (653)
<223> OTHER INFORMATION: Where n is a, c, g or t
<220> FEATURE:
<221> NAME/KEY: modified_base
<222> LOCATION: (662)
<223> OTHER INFORMATION: Where n is a, c, g or t
<220> FEATURE:
<221> NAME/KEY: modified_base
<222> LOCATION: (668)
<223> OTHER INFORMATION: Where n is a, c, g or t
<220> FEATURE:
<221> NAME/KEY: modified_base
<222> LOCATION: (682)
<223> OTHER INFORMATION: Where n is a, c, g or t
<220> FEATURE:
<221> NAME/KEY: modified_base
<222> LOCATION: (691)
<223> OTHER INFORMATION: Where n is a, c, g or t
<220> FEATURE:
<221> NAME/KEY: modified_base
<222> LOCATION: (710)
<223> OTHER INFORMATION: Where n is a, c, g or t
<220> FEATURE:
<221> NAME/KEY: modified_base
<222> LOCATION: (715)
<223> OTHER INFORMATION: Where n is a, c, g or t

<400> SEQUENCE: 96
tttttttttt tttttttttt ggaattaaaa gcaatttaat gagggcagag caggaaacat      60
gcatttcttt tcattcgaat cttcagatga accctgagca gccgaagacc agaaaagcca     120
tgaagacttt ctgcttaatt caggggctta caggattctt cagagtgtgt gtgaacaaaa     180
gctttatagt acgtattttt aggatacaaa taagagagag actatggctt ggggtgagaa     240
tgtactgatt acaaggtcta cagacaatta agacacagaa acagatggga agagggtgnc     300
cagcatctgg nggttggctt ctcaagggct tgtctgtgca ccaaattact tctgcttggn     360
cttctgctga gctgggcctg gagtgaccgt tgaaggacat ggctctggta cctttgtgta     420
gcctgncaca ggaactttgg tgtatccttg ctcaggaact ttgatggcac ctggctcagg     480
aaacttgatg aagccttggt caagggacct tgatgcttgc tggctcaggg accttggngn     540
ancctgggct canggacctt tgncncaacc ttggcttcaa gggacccttg gnacatcctg     600
gcnnagggac ccttgggncc aaccctgggc ttnaggnacc ctttggntnc nanccttggc     660
tnaagggnac ccttggcaac anccctggct ntggaaaatc ttttggggtn ccccnggg       718

<210> SEQ ID NO 97
<211> LENGTH: 441
<212> TYPE: DNA
```

<213> ORGANISM: Homo sapiens
<220> FEATURE:
<221> NAME/KEY: modified_base
<222> LOCATION: (12)
<223> OTHER INFORMATION: Where n is a, c, g or t
<220> FEATURE:
<221> NAME/KEY: modified_base
<222> LOCATION: (308)
<223> OTHER INFORMATION: Where n is a, c, g or t

<400> SEQUENCE: 97

```
gggaccatac anagtattcc tctcttcaca ccaggaccag ccactgttgc agcatgagtt      60
cccagcagca gaagcagccc tgcatcccac cccctcagct tcagcagcag caggtgaaac     120
agccttgcca gcctccacct caggaaccat gcatccccaa aaccaaggag ccctgccacc     180
ccaaggtgcc tgagccctgc caccccaaag tgcctgagcc ctgccagccc aaggttccag     240
agccatgcca ccccaaggtg cctgagccct gcccttcaat agtcactcca gcaccagccc     300
agcagaanac caagcagaag taatgtggtc cacagccatg cccttgagga gccggccacc     360
agatgctgaa tcccctatcc cattctgtgt atgagtccca tttgccttgc aattagcatt     420
ctgtctcccc caaaaaaaaa a                                                441
```

<210> SEQ ID NO 98
<211> LENGTH: 600
<212> TYPE: DNA
<213> ORGANISM: Homo sapiens
<220> FEATURE:
<221> NAME/KEY: modified_base
<222> LOCATION: (285)
<223> OTHER INFORMATION: Where n is a, c, g or t
<220> FEATURE:
<221> NAME/KEY: modified_base
<222> LOCATION: (349)
<223> OTHER INFORMATION: Where n is a, c, g or t
<220> FEATURE:
<221> NAME/KEY: modified_base
<222> LOCATION: (489)
<223> OTHER INFORMATION: Where n is a, c, g or t
<220> FEATURE:
<221> NAME/KEY: modified_base
<222> LOCATION: (496)
<223> OTHER INFORMATION: Where n is a, c, g or t
<220> FEATURE:
<221> NAME/KEY: modified_base
<222> LOCATION: (583)
<223> OTHER INFORMATION: Where n is a, c, g or t

<400> SEQUENCE: 98

```
gtattcctct cttcacacca ggaccagcca ctgttgcagc atgagttccc agcagcagaa      60
gcagccctgc atcccacccc ctcagcttca gcagcagcag gtgaaacagc cttgccagcc     120
tccacctcag gaaccatgca tccccaaaac caaggagccc tgccacccca aggtgcctga     180
gccctgccac cccaaagtgc ctgagccctg ccagcccaag gttccagagc catgccaccc     240
caaggtgcct gagccctgcc cttcaatagt cactccagca ccagcccagc agaanaccaa     300
gcagaagtaa tgtggtccac agccatgccc ttgaggagcc ggccaccana tgctgaatcc     360
cctatcccat tctgtgtatg agtcccattt gccttgcaat tagcattctg tctcccccaa     420
aaaagaatgt gctatgaagc tttctttcct acacactctg agtctctgaa tgaagctgaa     480
ggtcttaant acaganctag ttttcagctg ctcagaattc tctgaagaaa agatttaaga     540
tgaaaggcaa atgattcagc tccttattac cccattaaat tcnctttcaa ttccaaaaaa     600
```

<210> SEQ ID NO 99
<211> LENGTH: 667

<212> TYPE: DNA
<213> ORGANISM: Homo sapiens
<220> FEATURE:
<221> NAME/KEY: modified_base
<222> LOCATION: (345)
<223> OTHER INFORMATION: Where n is a, c, g or t
<220> FEATURE:
<221> NAME/KEY: modified_base
<222> LOCATION: (562)
<223> OTHER INFORMATION: Where n is a, c, g or t
<220> FEATURE:
<221> NAME/KEY: modified_base
<222> LOCATION: (635)
<223> OTHER INFORMATION: Where n is a, c, g or t

<400> SEQUENCE: 99

```
actagtgact gagttcctgg caaagaaatt tgacctggac cagttgataa ctcatgtttt    60
accatttaaa aaaatcagtg aaggatttga gctgctcaat tcaggacaaa gcattcgaac   120
ggtcctgacg ttttgagatc caaagtggca ggaggtctgt gttgtcatgg tgaactggag   180
tttctcttgt gagagttccc tcatctgaaa tcatgtatct gtctcacaaa tacaagcata   240
agtagaagat ttgttgaaga catagaaccc ttataaagaa ttattaacct ttataaacat   300
ttaaagtctt gtgagcacct gggaattagt ataataacaa tgttnatatt tttgatttac   360
attttgtaag gctataattg tatcttttaa gaaaacatac cttggatttc tatgttgaaa   420
tggagatttt taagagtttt aaccagctgc tgcagatata ttactcaaaa cagatatagc   480
gtataaagat atagtaaatg catctcctag agtaatattc acttaacaca ttggaaacta   540
ttatttttta gatttgaata tnaatgttat tttttaaaca cttgttatga gttacttggg   600
attacatttt gaaatcagtt cattccatga tgcanattac tgggattaga ttaagaaaga   660
cggaaaa                                                             667
```

<210> SEQ ID NO 100
<211> LENGTH: 583
<212> TYPE: DNA
<213> ORGANISM: Homo sapiens
<220> FEATURE:
<221> NAME/KEY: modified_base
<222> LOCATION: (404)
<223> OTHER INFORMATION: Where n is a, c, g or t
<220> FEATURE:
<221> NAME/KEY: modified_base
<222> LOCATION: (506)
<223> OTHER INFORMATION: Where n is a, c, g or t
<220> FEATURE:
<221> NAME/KEY: modified_base
<222> LOCATION: (514)
<223> OTHER INFORMATION: Where n is a, c, g or t
<220> FEATURE:
<221> NAME/KEY: modified_base
<222> LOCATION: (527)
<223> OTHER INFORMATION: Where n is a, c, g or t
<220> FEATURE:
<221> NAME/KEY: modified_base
<222> LOCATION: (528)
<223> OTHER INFORMATION: Where n is a, c, g or t
<220> FEATURE:
<221> NAME/KEY: modified_base
<222> LOCATION: (538)
<223> OTHER INFORMATION: Where n is a, c, g or t
<220> FEATURE:
<221> NAME/KEY: modified_base
<222> LOCATION: (548)
<223> OTHER INFORMATION: Where n is a, c, g or t
<220> FEATURE:
<221> NAME/KEY: modified_base
<222> LOCATION: (556)
<223> OTHER INFORMATION: Where n is a, c, g or t
<220> FEATURE:

<221> NAME/KEY: modified_base
<222> LOCATION: (568)
<223> OTHER INFORMATION: Where n is a, c, g or t
<220> FEATURE:
<221> NAME/KEY: modified_base
<222> LOCATION: (569)
<223> OTHER INFORMATION: Where n is a, c, g or t

<400> SEQUENCE: 100

```
gttttgtttg taagatgatc acagtcatgt tacactgatc taaaggacat atatataacc      60
ctttaaaaaa aaaatcactg cctcattctt atttcaagat gaatttctat acagactaga     120
tgttttctg aagatcaatt agacattttg aaaatgattt aaagtgtttt ccttaatgtt      180
ctctgaaaac aagtttcttt tgtagtttta accaaaaaag tgccctttt gtcactggat      240
tctcctagca ttcatgattt ttttttcata caatgaaatt aaaattgcta aaatcatgga     300
ctggctttct ggttggattt caggtaagat gtgtttaagg ccagagcttt tctcagtatt     360
tgatttttt ccccaatatt tgatttttta aaaatataca catnggtgct gcatttatat      420
ctgctggttt aaaattctgt catatttcac ttctagcctt ttagttatgg caaatcatat     480
tttacttta cttaaagcat ttggtnattt ggantatctg gttctannct aaaaaaanta     540
attctatnaa ttgaantttt ggtactcnnc catatttgga tcc                      583
```

<210> SEQ ID NO 101
<211> LENGTH: 592
<212> TYPE: DNA
<213> ORGANISM: Homo sapiens
<220> FEATURE:
<221> NAME/KEY: modified_base
<222> LOCATION: (218)
<223> OTHER INFORMATION: Where n is a, c, g or t
<220> FEATURE:
<221> NAME/KEY: modified_base
<222> LOCATION: (497)
<223> OTHER INFORMATION: Where n is a, c, g or t
<220> FEATURE:
<221> NAME/KEY: modified_base
<222> LOCATION: (502)
<223> OTHER INFORMATION: Where n is a, c, g or t
<220> FEATURE:
<221> NAME/KEY: modified_base
<222> LOCATION: (533)
<223> OTHER INFORMATION: Where n is a, c, g or t
<220> FEATURE:
<221> NAME/KEY: modified_base
<222> LOCATION: (544)
<223> OTHER INFORMATION: Where n is a, c, g or t
<220> FEATURE:
<221> NAME/KEY: modified_base
<222> LOCATION: (546)
<223> OTHER INFORMATION: Where n is a, c, g or t
<220> FEATURE:
<221> NAME/KEY: modified_base
<222> LOCATION: (548)
<223> OTHER INFORMATION: Where n is a, c, g or t
<220> FEATURE:
<221> NAME/KEY: modified_base
<222> LOCATION: (550)
<223> OTHER INFORMATION: Where n is a, c, g or t
<220> FEATURE:
<221> NAME/KEY: modified_base
<222> LOCATION: (555)
<223> OTHER INFORMATION: Where n is a, c, g or t

<400> SEQUENCE: 101

```
gtggagacgt acaaagagca gccgctcaag cacctggga agaaaagaa aggcaagccc       60
gggaaacgca aggagcagga aaagaaaaaa cggcgaactc gctctgcctg gttagactct    120
ggagtgactg ggagtgggct agaaggggac cacctgtctg acacctccac aacgtcgctg    180
```

```
gagctcgatt cacggaggca ttgaaatttt cagcaganac cttccaagga catattgcag    240
gattctgtaa tagtgaacat atggaaagta ttagaaatat ttattgtctg taaatactgt    300
aaatgcattg gaataaaact gtctccccca ttgctctatg aaactgcaca ttggtcattg    360
tgaatatttt ttttttttgcc aaggctaatc caattattat tatcacattt accataattt    420
attttgtcca ttgatgtatt tattttgtaa atgtatcttg gtgctgctga atttctatat    480
tttttgtaca taatgcnttt anatataccct atcaagtttg ttgataaatg acncaatgaa    540
gtgncncnan ttggnggttg aatttaatga atgcctaatt ttattatccc aa            592
```

```
<210> SEQ ID NO 102
<211> LENGTH: 587
<212> TYPE: DNA
<213> ORGANISM: Homo sapiens
<220> FEATURE:
<221> NAME/KEY: modified_base
<222> LOCATION: (91)
<223> OTHER INFORMATION: Where n is a, c, g or t
<220> FEATURE:
<221> NAME/KEY: modified_base
<222> LOCATION: (131)
<223> OTHER INFORMATION: Where n is a, c, g or t
<220> FEATURE:
<221> NAME/KEY: modified_base
<222> LOCATION: (256)
<223> OTHER INFORMATION: Where n is a, c, g or t
<220> FEATURE:
<221> NAME/KEY: modified_base
<222> LOCATION: (263)
<223> OTHER INFORMATION: Where n is a, c, g or t
<220> FEATURE:
<221> NAME/KEY: modified_base
<222> LOCATION: (332)
<223> OTHER INFORMATION: Where n is a, c, g or t
<220> FEATURE:
<221> NAME/KEY: modified_base
<222> LOCATION: (392)
<223> OTHER INFORMATION: Where n is a, c, g or t
<220> FEATURE:
<221> NAME/KEY: modified_base
<222> LOCATION: (400)
<223> OTHER INFORMATION: Where n is a, c, g or t
<220> FEATURE:
<221> NAME/KEY: modified_base
<222> LOCATION: (403)
<223> OTHER INFORMATION: Where n is a, c, g or t
<220> FEATURE:
<221> NAME/KEY: modified_base
<222> LOCATION: (441)
<223> OTHER INFORMATION: Where n is a, c, g or t
<220> FEATURE:
<221> NAME/KEY: modified_base
<222> LOCATION: (496)
<223> OTHER INFORMATION: Where n is a, c, g or t
<220> FEATURE:
<221> NAME/KEY: modified_base
<222> LOCATION: (497)
<223> OTHER INFORMATION: Where n is a, c, g or t
<220> FEATURE:
<221> NAME/KEY: modified_base
<222> LOCATION: (499)
<223> OTHER INFORMATION: Where n is a, c, g or t
<220> FEATURE:
<221> NAME/KEY: modified_base
<222> LOCATION: (510)
<223> OTHER INFORMATION: Where n is a, c, g or t
<220> FEATURE:
<221> NAME/KEY: modified_base
<222> LOCATION: (511)
<223> OTHER INFORMATION: Where n is a, c, g or t
<220> FEATURE:
<221> NAME/KEY: modified_base
<222> LOCATION: (518)
```

<223> OTHER INFORMATION: Where n is a, c, g or t
<220> FEATURE:
<221> NAME/KEY: modified_base
<222> LOCATION: (519)
<223> OTHER INFORMATION: Where n is a, c, g or t
<220> FEATURE:
<221> NAME/KEY: modified_base
<222> LOCATION: (539)
<223> OTHER INFORMATION: Where n is a, c, g or t
<220> FEATURE:
<221> NAME/KEY: modified_base
<222> LOCATION: (554)
<223> OTHER INFORMATION: Where n is a, c, g or t
<220> FEATURE:
<221> NAME/KEY: modified_base
<222> LOCATION: (560)
<223> OTHER INFORMATION: Where n is a, c, g or t
<220> FEATURE:
<221> NAME/KEY: modified_base
<222> LOCATION: (566)
<223> OTHER INFORMATION: Where n is a, c, g or t

<400> SEQUENCE: 102

```
cgtcctaagc acttagacta catcagggaa gaacacagac cacatccctg tcctcatgcg      60
gcttatgttt tctggaagaa agtggagacc nagtccttgg ctttagggct ccccggctgg     120
gggctgtgca ntccggtcag ggcgggaagg gaaatgcacc gctgcatgtg aacttacagc     180
ccaggcggat gcccctttccc ttagcactac ctggcctcct gcatcccctc gcctcatgtt    240
cctcccacct tcaaanaatg aanaacccca tgggcccagc cccttgccct ggggaaccaa     300
ggcagccttc caaaactcag gggctgaagc anactattag ggcaggggct gactttgggt     360
gacactgccc attccctctc agggcagctc angtcacccn ggnctcttga acccagcctg     420
ttcctttgaa aaagggcaaa actgaaaagg gcttttccta naaaagaaa aaccaggaa       480 ctttgccagg gcttcnntnt taccaaaacn ncttctcnng gatttttaat tccccattng     540
gcctccactt accnggggcn atgccccaaa attaanaatt tcccatc                  587
```

<210> SEQ ID NO 103
<211> LENGTH: 496
<212> TYPE: DNA
<213> ORGANISM: Homo sapiens
<220> FEATURE:
<221> NAME/KEY: modified_base
<222> LOCATION: (2)
<223> OTHER INFORMATION: Where n is a, c, g or t
<220> FEATURE:
<221> NAME/KEY: modified_base
<222> LOCATION: (17)
<223> OTHER INFORMATION: Where n is a, c, g or t
<220> FEATURE:
<221> NAME/KEY: modified_base
<222> LOCATION: (66)
<223> OTHER INFORMATION: Where n is a, c, g or t
<220> FEATURE:
<221> NAME/KEY: modified_base
<222> LOCATION: (74)
<223> OTHER INFORMATION: Where n is a, c, g or t
<220> FEATURE:
<221> NAME/KEY: modified_base
<222> LOCATION: (82)
<223> OTHER INFORMATION: Where n is a, c, g or t
<220> FEATURE:
<221> NAME/KEY: modified_base
<222> LOCATION: (119)
<223> OTHER INFORMATION: Where n is a, c, g or t
<220> FEATURE:
<221> NAME/KEY: modified_base
<222> LOCATION: (164)
<223> OTHER INFORMATION: Where n is a, c, g or t
<220> FEATURE:
<221> NAME/KEY: modified_base
<222> LOCATION: (166)
<223> OTHER INFORMATION: Where n is a, c, g or t
<220> FEATURE:
<221> NAME/KEY: modified_base
<222> LOCATION: (172)
<223> OTHER INFORMATION: Where n is a, c, g or t
<220> FEATURE:
<221> NAME/KEY: modified_base
<222> LOCATION: (200)
<223> OTHER INFORMATION: Where n is a, c, g or t
<220> FEATURE:
<221> NAME/KEY: modified_base
<222> LOCATION: (203)
<223> OTHER INFORMATION: Where n is a, c, g or t
<220> FEATURE:
<221> NAME/KEY: modified_base
<222> LOCATION: (228)
<223> OTHER INFORMATION: Where n is a, c, g or t
<220> FEATURE:
<221> NAME/KEY: modified_base
<222> LOCATION: (232)
<223> OTHER INFORMATION: Where n is a, c, g or t
<220> FEATURE:
<221> NAME/KEY: modified_base
<222> LOCATION: (271)
<223> OTHER INFORMATION: Where n is a, c, g or t
<220> FEATURE:
<221> NAME/KEY: modified_base
<222> LOCATION: (273)
<223> OTHER INFORMATION: Where n is a, c, g or t
<220> FEATURE:
<221> NAME/KEY: modified_base
<222> LOCATION: (415)
<223> OTHER INFORMATION: Where n is a, c, g or t
<220> FEATURE:
<221> NAME/KEY: modified_base
<222> LOCATION: (423)
<223> OTHER INFORMATION: Where n is a, c, g or t
<220> FEATURE:
<221> NAME/KEY: modified_base
<222> LOCATION: (445)
<223> OTHER INFORMATION: Where n is a, c, g or t
<220> FEATURE:
<221> NAME/KEY: modified_base
<222> LOCATION: (446)
<223> OTHER INFORMATION: Where n is a, c, g or t
<220> FEATURE:
<221> NAME/KEY: modified_base
<222> LOCATION: (473)
<223> OTHER INFORMATION: Where n is a, c, g or t

<400> SEQUENCE: 103

```
anaggactgg ccctacntgc tctctctcgt cctacctatc aatgcccaac atggcagaac     60
ctgcanccct tggncactgc anatggaaac ctctcagtgt cttgacatca ccctaccent   120
gcggtgggtc tccaccacaa ccactttgac tctgtggtcc ctgnanggtg gnttctcctg   180
actggcagga tggaccttan ccacatatc cctctgttcc ctctgctnag anaaagaatt    240
cccttaacat gatataatcc acccatgcaa ntngctactg gcccagctac catttaccat   300
ttgcctacag aatttcattc agtctacact ttggcattct ctctggcgat agagtgtggc   360
tgggctgacc gcaaaaggtg ccttacacac tggcccccac cctcaaccgt tgacncatca   420
gangcttgcc tcctccttct gattnncccc catgttggat atcagggtgc tcnagggatt   480
ggaaaagaaa caaaac                                                   496
```

<210> SEQ ID NO 104
<211> LENGTH: 575
<212> TYPE: DNA
<213> ORGANISM: Homo sapiens
<220> FEATURE:
<221> NAME/KEY: modified_base
<222> LOCATION: (18)

-continued

```
<223> OTHER INFORMATION: Where n is a, c, g or t
<220> FEATURE:
<221> NAME/KEY: modified_base
<222> LOCATION: (19)
<223> OTHER INFORMATION: Where n is a, c, g or t
<220> FEATURE:
<221> NAME/KEY: modified_base
<222> LOCATION: (45)
<223> OTHER INFORMATION: Where n is a, c, g or t
<220> FEATURE:
<221> NAME/KEY: modified_base
<222> LOCATION: (68)
<223> OTHER INFORMATION: Where n is a, c, g or t
<220> FEATURE:
<221> NAME/KEY: modified_base
<222> LOCATION: (77)
<223> OTHER INFORMATION: Where n is a, c, g or t
<220> FEATURE:
<221> NAME/KEY: modified_base
<222> LOCATION: (132)
<223> OTHER INFORMATION: Where n is a, c, g or t
<220> FEATURE:
<221> NAME/KEY: modified_base
<222> LOCATION: (155)
<223> OTHER INFORMATION: Where n is a, c, g or t
<220> FEATURE:
<221> NAME/KEY: modified_base
<222> LOCATION: (174)
<223> OTHER INFORMATION: Where n is a, c, g or t
<220> FEATURE:
<221> NAME/KEY: modified_base
<222> LOCATION: (218)
<223> OTHER INFORMATION: Where n is a, c, g or t
<220> FEATURE:
<221> NAME/KEY: modified_base
<222> LOCATION: (226)
<223> OTHER INFORMATION: Where n is a, c, g or t
<220> FEATURE:
<221> NAME/KEY: modified_base
<222> LOCATION: (238)
<223> OTHER INFORMATION: Where n is a, c, g or t
<220> FEATURE:
<221> NAME/KEY: modified_base
<222> LOCATION: (259)
<223> OTHER INFORMATION: Where n is a, c, g or t
<220> FEATURE:
<221> NAME/KEY: modified_base
<222> LOCATION: (263)
<223> OTHER INFORMATION: Where n is a, c, g or t
<220> FEATURE:
<221> NAME/KEY: modified_base
<222> LOCATION: (271)
<223> OTHER INFORMATION: Where n is a, c, g or t
<220> FEATURE:
<221> NAME/KEY: modified_base
<222> LOCATION: (273)
<223> OTHER INFORMATION: Where n is a, c, g or t
<220> FEATURE:
<221> NAME/KEY: modified_base
<222> LOCATION: (306)
<223> OTHER INFORMATION: Where n is a, c, g or t
<220> FEATURE:
<221> NAME/KEY: modified_base
<222> LOCATION: (323)
<223> OTHER INFORMATION: Where n is a, c, g or t
<220> FEATURE:
<221> NAME/KEY: modified_base
<222> LOCATION: (339)
<223> OTHER INFORMATION: Where n is a, c, g or t
<220> FEATURE:
<221> NAME/KEY: modified_base
<222> LOCATION: (363)
<223> OTHER INFORMATION: Where n is a, c, g or t
<220> FEATURE:
<221> NAME/KEY: modified_base
<222> LOCATION: (368)
<223> OTHER INFORMATION: Where n is a, c, g or t
<220> FEATURE:
<221> NAME/KEY: modified_base
```

```
<222> LOCATION: (370)
<223> OTHER INFORMATION: Where n is a, c, g or t
<220> FEATURE:
<221> NAME/KEY: modified_base
<222> LOCATION: (378)
<223> OTHER INFORMATION: Where n is a, c, g or t
<220> FEATURE:
<221> NAME/KEY: modified_base
<222> LOCATION: (381)
<223> OTHER INFORMATION: Where n is a, c, g or t
<220> FEATURE:
<221> NAME/KEY: modified_base
<222> LOCATION: (382)
<223> OTHER INFORMATION: Where n is a, c, g or t
<220> FEATURE:
<221> NAME/KEY: modified_base
<222> LOCATION: (436)
<223> OTHER INFORMATION: Where n is a, c, g or t
<220> FEATURE:
<221> NAME/KEY: modified_base
<222> LOCATION: (450)
<223> OTHER INFORMATION: Where n is a, c, g or t
<220> FEATURE:
<221> NAME/KEY: modified_base
<222> LOCATION: (459)
<223> OTHER INFORMATION: Where n is a, c, g or t
<220> FEATURE:
<221> NAME/KEY: modified_base
<222> LOCATION: (460)
<223> OTHER INFORMATION: Where n is a, c, g or t
<220> FEATURE:
<221> NAME/KEY: modified_base
<222> LOCATION: (466)
<223> OTHER INFORMATION: Where n is a, c, g or t
<220> FEATURE:
<221> NAME/KEY: modified_base
<222> LOCATION: (481)
<223> OTHER INFORMATION: Where n is a, c, g or t
<220> FEATURE:
<221> NAME/KEY: modified_base
<222> LOCATION: (485)
<223> OTHER INFORMATION: Where n is a, c, g or t
<220> FEATURE:
<221> NAME/KEY: modified_base
<222> LOCATION: (496)
<223> OTHER INFORMATION: Where n is a, c, g or t
<220> FEATURE:
<221> NAME/KEY: modified_base
<222> LOCATION: (503)
<223> OTHER INFORMATION: Where n is a, c, g or t
<220> FEATURE:
<221> NAME/KEY: modified_base
<222> LOCATION: (510)
<223> OTHER INFORMATION: Where n is a, c, g or t
<220> FEATURE:
<221> NAME/KEY: modified_base
<222> LOCATION: (512)
<223> OTHER INFORMATION: Where n is a, c, g or t
<220> FEATURE:
<221> NAME/KEY: modified_base
<222> LOCATION: (515)
<223> OTHER INFORMATION: Where n is a, c, g or t
<220> FEATURE:
<221> NAME/KEY: modified_base
<222> LOCATION: (528)
<223> OTHER INFORMATION: Where n is a, c, g or t
<220> FEATURE:
<221> NAME/KEY: modified_base
<222> LOCATION: (542)
<223> OTHER INFORMATION: Where n is a, c, g or t
<220> FEATURE:
<221> NAME/KEY: modified_base
<222> LOCATION: (552)
<223> OTHER INFORMATION: Where n is a, c, g or t

<400> SEQUENCE: 104
gcacctgctc tcaatccnnc tctcaccatg atcctccgcc tgcanaaact cctctgccaa      60
```

| | | | |
|---|---|---|---|
| ctatggangt | ggtttcnggg | gtggctcttg ccaactggga agaagccgtg gtgtctctac | 120 |
| ctgttcaact | cngtttgtgt | ctgggggatc aactngggc tatggaagcg gctnaactgt | 180 |
| tgttttggtg | gaagggctgg | taattggctt tgggaagtng cttatngaag ttggcctngg | 240 |
| gaagttgcta | ttgaaagtng | ccntggaagt ngntttggtg ggggttttg ctggtggcct | 300 |
| ttgttnaatt | tgggtgcttt | gtnaatggcg gcccctcnc ctgggcaatg aaaaaaatca | 360 |
| ccnatgcngn | aaacctcnac | nnaacagcct gggcttccct cacctcgaaa aagttgctc | 420 |
| ccccccaaa | aaaggncaan | ccctcaann tggaangttg aaaaaatcct cgaatgggga | 480 |
| ncccnaaaac | aaaancccc | ccntttcccn gnaanggggg aaataccncc cccccactta | 540 |
| cnaaaaccct | tntaaaaaac | ccccgggaa aaaa | 575 |

<210> SEQ ID NO 105
<211> LENGTH: 619
<212> TYPE: DNA
<213> ORGANISM: Homo sapiens
<220> FEATURE:
<221> NAME/KEY: modified_base
<222> LOCATION: (260)
<223> OTHER INFORMATION: Where n is a, c, g or t
<220> FEATURE:
<221> NAME/KEY: modified_base
<222> LOCATION: (527)
<223> OTHER INFORMATION: Where n is a, c, g or t
<220> FEATURE:
<221> NAME/KEY: modified_base
<222> LOCATION: (560)
<223> OTHER INFORMATION: Where n is a, c, g or t
<220> FEATURE:
<221> NAME/KEY: modified_base
<222> LOCATION: (564)
<223> OTHER INFORMATION: Where n is a, c, g or t
<220> FEATURE:
<221> NAME/KEY: modified_base
<222> LOCATION: (566)
<223> OTHER INFORMATION: Where n is a, c, g or t
<220> FEATURE:
<221> NAME/KEY: modified_base
<222> LOCATION: (575)
<223> OTHER INFORMATION: Where n is a, c, g or t
<220> FEATURE:
<221> NAME/KEY: modified_base
<222> LOCATION: (599)
<223> OTHER INFORMATION: Where n is a, c, g or t

<400> SEQUENCE: 105

| | | | |
|---|---|---|---|
| cactagtagg | atagaaacac | tgtgtcccga gagtaaggag agaagctact attgattaga | 60 |
| gcctaaccca | ggttaactgc | aagaagaggc gggatacttt cagcttttcca tgtaactgta | 120 |
| tgcataaagc | caatgtagtc | cagtttctaa gatcatgttc caagctaact gaatcccact | 180 |
| tcaatacaca | ctcatgaact | cctgatggaa caataacagg cccaagcctg tggtatgatg | 240 |
| tgcacacttg | ctagactcan | aaaaaatact actctcataa atgggtggga gtattttggt | 300 |
| gacaacctac | tttgcttggc | tgagtgaagg aatgatattc atatattcat ttattccatg | 360 |
| gacatttagt | tagtgctttt | tatataccag gcatgatgct gagtgacact cttgtgtata | 420 |
| tttccaaatt | tttgtacagt | cgctgcacat atttgaaatc atatattaag acttccaaaa | 480 |
| aatgaagtcc | ctggttttc | atggcaactt gatcagtaaa ggattcncct ctgtttggta | 540 |
| cttaaaacat | ctactatatn | gttnanatga aattcctttt ccccnctcc cgaaaaaana | 600 |
| aagtggtggg | gaaaaaaaa | | 619 |

<210> SEQ ID NO 106
<211> LENGTH: 506

```
<212> TYPE: DNA
<213> ORGANISM: Homo sapiens
<220> FEATURE:
<221> NAME/KEY: modified_base
<222> LOCATION: (8)
<223> OTHER INFORMATION: Where n is a, c, g or t
<220> FEATURE:
<221> NAME/KEY: modified_base
<222> LOCATION: (21)
<223> OTHER INFORMATION: Where n is a, c, g or t
<220> FEATURE:
<221> NAME/KEY: modified_base
<222> LOCATION: (31)
<223> OTHER INFORMATION: Where n is a, c, g or t
<220> FEATURE:
<221> NAME/KEY: modified_base
<222> LOCATION: (32)
<223> OTHER INFORMATION: Where n is a, c, g or t
<220> FEATURE:
<221> NAME/KEY: modified_base
<222> LOCATION: (58)
<223> OTHER INFORMATION: Where n is a, c, g or t
<220> FEATURE:
<221> NAME/KEY: modified_base
<222> LOCATION: (75)
<223> OTHER INFORMATION: Where n is a, c, g or t
<220> FEATURE:
<221> NAME/KEY: modified_base
<222> LOCATION: (89)
<223> OTHER INFORMATION: Where n is a, c, g or t
<220> FEATURE:
<221> NAME/KEY: modified_base
<222> LOCATION: (96)
<223> OTHER INFORMATION: Where n is a, c, g or t
<220> FEATURE:
<221> NAME/KEY: modified_base
<222> LOCATION: (99)
<223> OTHER INFORMATION: Where n is a, c, g or t
<220> FEATURE:
<221> NAME/KEY: modified_base
<222> LOCATION: (103)
<223> OTHER INFORMATION: Where n is a, c, g or t
<220> FEATURE:
<221> NAME/KEY: modified_base
<222> LOCATION: (122)
<223> OTHER INFORMATION: Where n is a, c, g or t
<220> FEATURE:
<221> NAME/KEY: modified_base
<222> LOCATION: (126)
<223> OTHER INFORMATION: Where n is a, c, g or t
<220> FEATURE:
<221> NAME/KEY: modified_base
<222> LOCATION: (147)
<223> OTHER INFORMATION: Where n is a, c, g or t
<220> FEATURE:
<221> NAME/KEY: modified_base
<222> LOCATION: (150)
<223> OTHER INFORMATION: Where n is a, c, g or t
<220> FEATURE:
<221> NAME/KEY: modified_base
<222> LOCATION: (158)
<223> OTHER INFORMATION: Where n is a, c, g or t
<220> FEATURE:
<221> NAME/KEY: modified_base
<222> LOCATION: (195)
<223> OTHER INFORMATION: Where n is a, c, g or t
<220> FEATURE:
<221> NAME/KEY: modified_base
<222> LOCATION: (210)
<223> OTHER INFORMATION: Where n is a, c, g or t
<220> FEATURE:
<221> NAME/KEY: modified_base
<222> LOCATION: (212)
<223> OTHER INFORMATION: Where n is a, c, g or t
<220> FEATURE:
<221> NAME/KEY: modified_base
<222> LOCATION: (219)
<223> OTHER INFORMATION: Where n is a, c, g or t
<220> FEATURE:
```

```
<221> NAME/KEY: modified_base
<222> LOCATION: (226)
<223> OTHER INFORMATION: Where n is a, c, g or t
<220> FEATURE:
<221> NAME/KEY: modified_base
<222> LOCATION: (246)
<223> OTHER INFORMATION: Where n is a, c, g or t
<220> FEATURE:
<221> NAME/KEY: modified_base
<222> LOCATION: (248)
<223> OTHER INFORMATION: Where n is a, c, g or t
<220> FEATURE:
<221> NAME/KEY: modified_base
<222> LOCATION: (249)
<223> OTHER INFORMATION: Where n is a, c, g or t
<220> FEATURE:
<221> NAME/KEY: modified_base
<222> LOCATION: (255)
<223> OTHER INFORMATION: Where n is a, c, g or t
<220> FEATURE:
<221> NAME/KEY: modified_base
<222> LOCATION: (258)
<223> OTHER INFORMATION: Where n is a, c, g or t
<220> FEATURE:
<221> NAME/KEY: modified_base
<222> LOCATION: (261)
<223> OTHER INFORMATION: Where n is a, c, g or t
<220> FEATURE:
<221> NAME/KEY: modified_base
<222> LOCATION: (263)
<223> OTHER INFORMATION: Where n is a, c, g or t
<220> FEATURE:
<221> NAME/KEY: modified_base
<222> LOCATION: (265)
<223> OTHER INFORMATION: Where n is a, c, g or t
<220> FEATURE:
<221> NAME/KEY: modified_base
<222> LOCATION: (275)
<223> OTHER INFORMATION: Where n is a, c, g or t
<220> FEATURE:
<221> NAME/KEY: modified_base
<222> LOCATION: (304)
<223> OTHER INFORMATION: Where n is a, c, g or t
<220> FEATURE:
<221> NAME/KEY: modified_base
<222> LOCATION: (317)
<223> OTHER INFORMATION: Where n is a, c, g or t
<220> FEATURE:
<221> NAME/KEY: modified_base
<222> LOCATION: (321)
<223> OTHER INFORMATION: Where n is a, c, g or t
<220> FEATURE:
<221> NAME/KEY: modified_base
<222> LOCATION: (331)
<223> OTHER INFORMATION: Where n is a, c, g or t
<220> FEATURE:
<221> NAME/KEY: modified_base
<222> LOCATION: (337)
<223> OTHER INFORMATION: Where n is a, c, g or t
<220> FEATURE:
<221> NAME/KEY: modified_base
<222> LOCATION: (340)
<223> OTHER INFORMATION: Where n is a, c, g or t
<220> FEATURE:
<221> NAME/KEY: modified_base
<222> LOCATION: (358)
<223> OTHER INFORMATION: Where n is a, c, g or t
<220> FEATURE:
<221> NAME/KEY: modified_base
<222> LOCATION: (371)
<223> OTHER INFORMATION: Where n is a, c, g or t
<220> FEATURE:
<221> NAME/KEY: modified_base
<222> LOCATION: (377)
<223> OTHER INFORMATION: Where n is a, c, g or t
<220> FEATURE:
<221> NAME/KEY: modified_base
<222> LOCATION: (380)
<223> OTHER INFORMATION: Where n is a, c, g or t
```

```
<220> FEATURE:
<221> NAME/KEY: modified_base
<222> LOCATION: (396)
<223> OTHER INFORMATION: Where n is a, c, g or t
<220> FEATURE:
<221> NAME/KEY: modified_base
<222> LOCATION: (450)
<223> OTHER INFORMATION: Where n is a, c, g or t
<220> FEATURE:
<221> NAME/KEY: modified_base
<222> LOCATION: (491)
<223> OTHER INFORMATION: Where n is a, c, g or t

<400> SEQUENCE: 106
cattggtnct ttcatttgct ntggaagtgt nnatctctaa cagtggacaa agttcccngt      60
gccttaaact ctgtnacact tttgggaant gaaaanttng tantatgata ggttattctg     120
angtanagat gttctggata ccattanatn tgcccccngt gtcagaggct catattgtgt     180
tatgtaaatg gtatntcatt cgctactatn antcaattng aaatanggtc tttgggttat     240
gaatantnng cagcncanct nanangctgt ctgtngtatt cattgtggtc atagcacctc     300
acancattgt aacctcnatc nagtgagaca nactagnaan ttcctagtga tggctcanga     360
ttccaaatgg nctcatntcn aatgtttaaa agttanttaa gtgtaagaaa tacagactgg     420
atgttccacc aactagtacc tgtaatgacn ggcctgtccc aacacatctc ccttttccat     480
gactgtggta ncccgcatcg gaaaaa                                          506

<210> SEQ ID NO 107
<211> LENGTH: 452
<212> TYPE: DNA
<213> ORGANISM: Homo sapiens
<220> FEATURE:
<221> NAME/KEY: modified_base
<222> LOCATION: (289)
<223> OTHER INFORMATION: Where n is a, c, g or t
<220> FEATURE:
<221> NAME/KEY: modified_base
<222> LOCATION: (317)
<223> OTHER INFORMATION: Where n is a, c, g or t
<220> FEATURE:
<221> NAME/KEY: modified_base
<222> LOCATION: (378)
<223> OTHER INFORMATION: Where n is a, c, g or t

<400> SEQUENCE: 107
gttgagtctg tactaaacag taagatatct caatgaacca taaattcaac tttgtaaaaa      60
tcttttgaag catagataat attgtttggt aaatgtttct tttgtttggt aaatgtttct     120
tttaaagacc ctcctattct ataaaactct gcatgtagag gcttgtttac ctttctctct     180
ctaaggttta caataggagt ggtgatttga aaaatataaa attatgagat tggttttcct     240
gtggcataaa ttgcatcact gtatcatttt ctttttttaac cggtaagant ttcagtttgt     300
tggaaagtaa ctgtganaac ccagtttccc gtccatctcc cttagggact acccatagaa     360
catgaaaagg tccccacnga agcaagaaga taagtctttc atggctgctg gttgcttaaa     420
ccactttaaa accaaaaaat tccccttgga aa                                   452

<210> SEQ ID NO 108
<211> LENGTH: 502
<212> TYPE: DNA
<213> ORGANISM: Homo sapiens
<220> FEATURE:
<221> NAME/KEY: modified_base
<222> LOCATION: (22)
<223> OTHER INFORMATION: Where n is a, c, g or t
<220> FEATURE:
```

-continued

```
<221> NAME/KEY: modified_base
<222> LOCATION: (31)
<223> OTHER INFORMATION: Where n is a, c, g or t
<220> FEATURE:
<221> NAME/KEY: modified_base
<222> LOCATION: (126)
<223> OTHER INFORMATION: Where n is a, c, g or t
<220> FEATURE:
<221> NAME/KEY: modified_base
<222> LOCATION: (168)
<223> OTHER INFORMATION: Where n is a, c, g or t
<220> FEATURE:
<221> NAME/KEY: modified_base
<222> LOCATION: (183)
<223> OTHER INFORMATION: Where n is a, c, g or t
<220> FEATURE:
<221> NAME/KEY: modified_base
<222> LOCATION: (205)
<223> OTHER INFORMATION: Where n is a, c, g or t
<220> FEATURE:
<221> NAME/KEY: modified_base
<222> LOCATION: (219)
<223> OTHER INFORMATION: Where n is a, c, g or t
<220> FEATURE:
<221> NAME/KEY: modified_base
<222> LOCATION: (231)
<223> OTHER INFORMATION: Where n is a, c, g or t
<220> FEATURE:
<221> NAME/KEY: modified_base
<222> LOCATION: (236)
<223> OTHER INFORMATION: Where n is a, c, g or t
<220> FEATURE:
<221> NAME/KEY: modified_base
<222> LOCATION: (259)
<223> OTHER INFORMATION: Where n is a, c, g or t
<220> FEATURE:
<221> NAME/KEY: modified_base
<222> LOCATION: (283)
<223> OTHER INFORMATION: Where n is a, c, g or t
<220> FEATURE:
<221> NAME/KEY: modified_base
<222> LOCATION: (295)
<223> OTHER INFORMATION: Where n is a, c, g or t
<220> FEATURE:
<221> NAME/KEY: modified_base
<222> LOCATION: (296)
<223> OTHER INFORMATION: Where n is a, c, g or t
<220> FEATURE:
<221> NAME/KEY: modified_base
<222> LOCATION: (298)
<223> OTHER INFORMATION: Where n is a, c, g or t
<220> FEATURE:
<221> NAME/KEY: modified_base
<222> LOCATION: (301)
<223> OTHER INFORMATION: Where n is a, c, g or t
<220> FEATURE:
<221> NAME/KEY: modified_base
<222> LOCATION: (340)
<223> OTHER INFORMATION: Where n is a, c, g or t
<220> FEATURE:
<221> NAME/KEY: modified_base
<222> LOCATION: (354)
<223> OTHER INFORMATION: Where n is a, c, g or t
<220> FEATURE:
<221> NAME/KEY: modified_base
<222> LOCATION: (378)
<223> OTHER INFORMATION: Where n is a, c, g or t
<220> FEATURE:
<221> NAME/KEY: modified_base
<222> LOCATION: (383)
<223> OTHER INFORMATION: Where n is a, c, g or t
<220> FEATURE:
<221> NAME/KEY: modified_base
<222> LOCATION: (409)
<223> OTHER INFORMATION: Where n is a, c, g or t
<220> FEATURE:
<221> NAME/KEY: modified_base
<222> LOCATION: (433)
<223> OTHER INFORMATION: Where n is a, c, g or t
```

<220> FEATURE:
<221> NAME/KEY: modified_base
<222> LOCATION: (446)
<223> OTHER INFORMATION: Where n is a, c, g or t
<220> FEATURE:
<221> NAME/KEY: modified_base
<222> LOCATION: (455)
<223> OTHER INFORMATION: Where n is a, c, g or t
<220> FEATURE:
<221> NAME/KEY: modified_base
<222> LOCATION: (466)
<223> OTHER INFORMATION: Where n is a, c, g or t
<220> FEATURE:
<221> NAME/KEY: modified_base
<222> LOCATION: (488)
<223> OTHER INFORMATION: Where n is a, c, g or t

<400> SEQUENCE: 108

| | | | | | |
|---|---|---|---|---|---|
| atcttcttcc | cttaattagt | tnttatttat | ntattaaatt | ttattgcatg | tcctggcaaa | 60 |
| caaaaagaga | ttgtagattg | gcttctggct | ccccaaaagc | ccataacaga | aagtaccaca | 120 |
| agaccncaac | tgaagcttaa | aaaatctatc | acatgtataa | tacctttnga | agaacattaa | 180 |
| tanagcatat | aaaactttta | acatntgctt | aatgttgtnc | aattataaaa | ntaatngaaa | 240 |
| aaaatgtccc | tttaacatnc | aatatcccac | atagtgttat | ttnaggggat | taccnngnaa | 300 |
| naaaaaaagg | gtagaaggga | tttaatgaaa | actctgcttn | ccatttctgt | ttanaaacgt | 360 |
| ctccagaaca | aaaacttntc | aantctttca | gctaaccgca | tttgagctna | ggccactcaa | 420 |
| aaactccatt | agncccactt | tctaanggtc | tctanagctt | actaancctt | ttgacccctt | 480 |
| accctggnta | ctcctgccct | ca | | | | 502 |

<210> SEQ ID NO 109
<211> LENGTH: 1308
<212> TYPE: DNA
<213> ORGANISM: Homo sapiens

<400> SEQUENCE: 109

| | | | | | |
|---|---|---|---|---|---|
| acccgaggtc | tcgctaaaat | catcatggat | tcacttggcg | ccgtcagcac | tcgacttggg | 60 |
| tttgatcttt | tcaaagagct | gaagaaaaca | aatgatggca | acatcttctt | ttcccctgtg | 120 |
| ggcatcttga | ctgcaattgg | catggtcctc | ctggggaccc | gaggagccac | cgcttcccag | 180 |
| ttggaggagg | tgtttcactc | tgaaaaagag | acgaagagct | caagaataaa | ggctgaagaa | 240 |
| aagaggtga | ttgagaacac | agaagcagta | catcaacaat | tccaaaagtt | tttgactgaa | 300 |
| ataagcaaac | tcactaatga | ttatgaactg | aacataacca | acaggctgtt | tggagaaaaa | 360 |
| acatacctct | tccttcaaaa | atacttagat | tatgttgaaa | aatattatca | tgcatctctg | 420 |
| gaacctgttg | attttgtaaa | tgcagccgat | gaaagtcgaa | agaagattaa | ttcctgggtt | 480 |
| gaaagcaaaa | caaatgaaaa | aatcaaggac | ttgttcccag | atggctctat | tagtagctct | 540 |
| accaagctgg | tgctggtgaa | catggtttat | tttaaagggc | aatgggacag | ggagtttaag | 600 |
| aaagaaaata | ctaaggaaga | gaaattttgg | atgaataaga | gcacaagtaa | atctgtacag | 660 |
| atgatgacac | agagccattc | ctttagcttc | actttcctgg | aggacttgca | ggccaaaatt | 720 |
| ctagggattc | catataaaaa | caacgaccta | agcatgtttg | tgcttctgcc | caacgacatc | 780 |
| gatggcctgg | agaagataat | agataaaata | agtcctgaga | aattggtaga | gtggactagt | 840 |
| ccagggcata | tggaagaaag | aaaggtgaat | ctgcacttgc | cccggtttga | ggtggaggac | 900 |
| agttacgatc | tagaggcggt | cctggctgcc | atggggatgg | gcgatgcctt | cagtgagcac | 960 |
| aaagccgact | actcgggaat | gtcgtcaggc | tccgggttgt | acgcccagaa | gttcctgcac | 1020 |

```
agttcctttg tggcagtaac tgaggaaggc accgaggctg cagctgccac tggcataggc    1080
tttactgtca catccgcccc aggtcatgaa aatgttcact gcaatcatcc cttcctgttc    1140
ttcatcaggc acaatgaatc caacagcatc ctcttcttcg gcagattttc ttctccttaa    1200
gatgatcgtt gccatggcat tgctgctttt agcaaaaaac aactaccagt gttactcata    1260
tgattatgaa aatcgtccat tcttttaaat ggtggctcac ttgcattt                 1308
```

<210> SEQ ID NO 110
<211> LENGTH: 391
<212> TYPE: PRT
<213> ORGANISM: Homo sapiens

<400> SEQUENCE: 110

```
Met Asp Ser Leu Gly Ala Val Ser Thr Arg Leu Gly Phe Asp Leu Phe
 1               5                  10                  15

Lys Glu Leu Lys Lys Thr Asn Asp Gly Asn Ile Phe Phe Ser Pro Val
             20                  25                  30

Gly Ile Leu Thr Ala Ile Gly Met Val Leu Leu Gly Thr Arg Gly Ala
         35                  40                  45

Thr Ala Ser Gln Leu Glu Glu Val Phe His Ser Glu Lys Glu Thr Lys
     50                  55                  60

Ser Ser Arg Ile Lys Ala Glu Glu Lys Glu Val Ile Glu Asn Thr Glu
 65                  70                  75                  80

Ala Val His Gln Gln Phe Gln Lys Phe Leu Thr Glu Ile Ser Lys Leu
                 85                  90                  95

Thr Asn Asp Tyr Glu Leu Asn Ile Thr Asn Arg Leu Phe Gly Glu Lys
            100                 105                 110

Thr Tyr Leu Phe Leu Gln Lys Tyr Leu Asp Tyr Val Glu Lys Tyr Tyr
        115                 120                 125

His Ala Ser Leu Glu Pro Val Asp Phe Val Asn Ala Ala Asp Glu Ser
    130                 135                 140

Arg Lys Lys Ile Asn Ser Trp Val Glu Ser Lys Thr Asn Glu Lys Ile
145                 150                 155                 160

Lys Asp Leu Phe Pro Asp Gly Ser Ile Ser Ser Ser Thr Lys Leu Val
                165                 170                 175

Leu Val Asn Met Val Tyr Phe Lys Gly Gln Trp Asp Arg Glu Phe Lys
            180                 185                 190

Lys Glu Asn Thr Lys Glu Glu Lys Phe Trp Met Asn Lys Ser Thr Ser
        195                 200                 205

Lys Ser Val Gln Met Met Thr Gln Ser His Ser Phe Ser Phe Thr Phe
    210                 215                 220

Leu Glu Asp Leu Gln Ala Lys Ile Leu Gly Ile Pro Tyr Lys Asn Asn
225                 230                 235                 240

Asp Leu Ser Met Phe Val Leu Leu Pro Asn Asp Ile Asp Gly Leu Glu
                245                 250                 255

Lys Ile Ile Asp Lys Ile Ser Pro Glu Lys Leu Val Glu Trp Thr Ser
            260                 265                 270

Pro Gly His Met Glu Glu Arg Lys Val Asn Leu His Leu Pro Arg Phe
        275                 280                 285

Glu Val Glu Asp Ser Tyr Asp Leu Glu Ala Val Leu Ala Ala Met Gly
    290                 295                 300

Met Gly Asp Ala Phe Ser Glu His Lys Ala Asp Tyr Ser Gly Met Ser
305                 310                 315                 320

Ser Gly Ser Gly Leu Tyr Ala Gln Lys Phe Leu His Ser Ser Phe Val
```

```
                    325                 330                 335
Ala Val Thr Glu Glu Gly Thr Glu Ala Ala Ala Thr Gly Ile Gly
                340                 345                 350

Phe Thr Val Thr Ser Ala Pro Gly His Glu Asn Val His Cys Asn His
            355                 360                 365

Pro Phe Leu Phe Phe Ile Arg His Asn Glu Ser Asn Ser Ile Leu Phe
        370                 375                 380

Phe Gly Arg Phe Ser Ser Pro
385                 390

<210> SEQ ID NO 111
<211> LENGTH: 1419
<212> TYPE: DNA
<213> ORGANISM: Homo sapiens

<400> SEQUENCE: 111
ggagaactat aaattaagga tcccagctac ttaattgact tatgcttcct agttcgttgc      60
ccagccacca ccgtctctcc aaaaacccga ggtctcgcta aaatcatcat ggattcactt     120
ggcgccgtca gcactcgact tgggtttgat cttttcaaag agctgaagaa aacaaatgat     180
ggcaacatct tcttttcccc tgtgggcatc ttgactgcaa ttggcatggt cctcctgggg     240
acccgaggag ccaccgcttc ccagttggag gaggtgtttc actctgaaaa agagacgaag     300
agctcaagaa taaaggctga agaaaaagag gtggtaagaa taaaggctga aggaaaagag     360
attgagaaca cagaagcagt acatcaacaa ttccaaaagt ttttgactga ataagcaaa     420 ctcactaatg attatgaact gaacataacc aacaggctgt ttggagaaaa acatacctc     480 ttccttcaaa aatacttaga ttatgttgaa aaatattatc atgcatctct ggaacctgtt     540
gattttgtaa atgcagccga tgaaagtcga aagaagatta attcctgggt tgaaagcaaa     600
acaaatgaaa aaatcaagga cttgttccca gatggctcta ttagtagctc taccaagctg     660
gtgctggtga acatggttta ttttaaaggg caatgggaca gggagtttaa gaaagaaaat     720
actaaggaag agaaattttg gatgaataag agcacaagta aatctgtaca gatgatgaca     780
cagagccatt cctttagctt cactttcctg gaggacttgc aggccaaaat tctagggatt     840
ccatataaaa acaacgacct aagcatgttt gtgcttctgc ccaacgacat cgatggcctg     900
gagaagataa tagataaaat aagtcctgag aaattggtag agtggactag tccagggcat     960
atggaagaaa gaaggtgaa tctgcacttg ccccggtttg aggtggagga cagttacgat    1020
ctagaggcgg tcctggctgc catggggatg ggcgatgcct tcagtgagca caaagccgac    1080
tactcgggaa tgtcgtcagg ctccggggtg tacgcccaga gttcctgca cagttccttt    1140 gtggcagtaa ctgaggaagg caccgaggct gcagctgcca ctggcatagg ctttactgtc    1200
acatccgccc caggtcatga aaatgttcac tgcaatcatc ccttcctgtt cttcatcagg    1260
cacaatgaat ccaacagcat cctcttcttc ggcagatttt cttctcctta agatgatcgt    1320
tgccatggca ttgctgcttt tagcaaaaaa caactaccag tgttactcat atgattatga    1380
aaatcgtcca ttctttaaa tggtggctca cttgcattt                            1419

<210> SEQ ID NO 112
<211> LENGTH: 400
<212> TYPE: PRT
<213> ORGANISM: Homo sapiens

<400> SEQUENCE: 112

Met Asp Ser Leu Gly Ala Val Ser Thr Arg Leu Gly Phe Asp Leu Phe
```

```
            1               5                   10                  15
Lys Glu Leu Lys Lys Thr Asn Asp Gly Asn Ile Phe Phe Ser Pro Val
                    20                  25                  30

Gly Ile Leu Thr Ala Ile Gly Met Val Leu Leu Gly Thr Arg Gly Ala
            35                  40                  45

Thr Ala Ser Gln Leu Glu Glu Val Phe His Ser Glu Lys Glu Thr Lys
        50                  55                  60

Ser Ser Arg Ile Lys Ala Glu Glu Lys Glu Val Val Arg Ile Lys Ala
65                  70                  75                  80

Glu Gly Lys Glu Ile Glu Asn Thr Glu Ala Val His Gln Gln Phe Gln
                        85                  90                  95

Lys Phe Leu Thr Glu Ile Ser Lys Leu Thr Asn Asp Tyr Glu Leu Asn
                100                 105                 110

Ile Thr Asn Arg Leu Phe Gly Glu Lys Thr Tyr Leu Phe Leu Gln Lys
            115                 120                 125

Tyr Leu Asp Tyr Val Glu Lys Tyr Tyr His Ala Ser Leu Glu Pro Val
        130                 135                 140

Asp Phe Val Asn Ala Ala Asp Glu Ser Arg Lys Lys Ile Asn Ser Trp
145                 150                 155                 160

Val Glu Ser Lys Thr Asn Glu Lys Ile Lys Asp Leu Phe Pro Asp Gly
                    165                 170                 175

Ser Ile Ser Ser Thr Lys Leu Val Leu Val Asn Met Val Tyr Phe
                180                 185                 190

Lys Gly Gln Trp Asp Arg Glu Phe Lys Lys Glu Asn Thr Lys Glu Glu
            195                 200                 205

Lys Phe Trp Met Asn Lys Ser Thr Ser Lys Ser Val Gln Met Met Thr
        210                 215                 220

Gln Ser His Ser Phe Ser Phe Thr Phe Leu Glu Asp Leu Gln Ala Lys
225                 230                 235                 240

Ile Leu Gly Ile Pro Tyr Lys Asn Asn Asp Leu Ser Met Phe Val Leu
                    245                 250                 255

Leu Pro Asn Asp Ile Asp Gly Leu Glu Lys Ile Ile Asp Lys Ile Ser
                260                 265                 270

Pro Glu Lys Leu Val Glu Trp Thr Ser Pro Gly His Met Glu Glu Arg
            275                 280                 285

Lys Val Asn Leu His Leu Pro Arg Phe Glu Val Glu Asp Ser Tyr Asp
        290                 295                 300

Leu Glu Ala Val Leu Ala Ala Met Gly Met Gly Asp Ala Phe Ser Glu
305                 310                 315                 320

His Lys Ala Asp Tyr Ser Gly Met Ser Ser Gly Ser Gly Leu Tyr Ala
                    325                 330                 335

Gln Lys Phe Leu His Ser Ser Phe Val Ala Val Thr Glu Glu Gly Thr
                340                 345                 350

Glu Ala Ala Ala Ala Thr Gly Ile Gly Phe Thr Val Thr Ser Ala Pro
            355                 360                 365

Gly His Glu Asn Val His Cys Asn His Pro Phe Leu Phe Phe Ile Arg
        370                 375                 380

His Asn Glu Ser Asn Ser Ile Leu Phe Phe Gly Arg Phe Ser Ser Pro
385                 390                 395                 400
```

<210> SEQ ID NO 113
<211> LENGTH: 957
<212> TYPE: DNA
<213> ORGANISM: Homo sapiens

<400> SEQUENCE: 113

```
ctcgaccttc tctgcacagc ggatgaaccc tgagcagctg aagaccagaa aagccactat      60
gactttctgc ttaattcagg agcttacagg attcttcaaa gagtgtgtcc agcatccttt     120
gaaacatgag ttcttaccag cagaagcaga cctttacccc accacctcag cttcaacagc     180
agcaggtgaa acaacccagc cagcctccac ctcaggaaat atttgttccc acaaccaagg     240
agccatgcca ctcaaaggtt ccacaacctg gaaacacaaa gattccagag ccaggctgta     300
ccaaggtccc tgagccaggc tgtaccaagg tccctgagcc aggttgtacc aaggtccctg     360
agccaggatg taccaaggtc cctgagccag gttgtaccaa ggtccctgag ccaggctaca     420
ccaaggtccc tgagccaggc agcatcaagg tccctgacca aggcttcatc aagtttcctg     480
agccaggtgc catcaaagtt cctgagcaag gatacaccaa agttcctgtg ccaggctaca     540
caaaggtacc agagccatgt ccttcaacgg tcactccagg cccagctcag cagaagacca     600
agcagaagta atttggtgca cagacaagcc cttgagaagc caaccaccag atgctggaca     660
ccctcttccc atctgtttct gtgtcttaat tgtctgtaga ccttgtaatc agtacattct     720
cacccaagc  atagtctct  ctcttatttg tatcctaaaa atacggtact ataaagcttt     780
tgttcacaca cactctgaag aatcctgtaa gcccctgaat taagcagaaa gtcttcatgg     840
cttttctggt cttcggctgc tcagggttca tctgaagatt cgaatgaaaa gaaatgcatg     900
tttcctgctc tgccctcatt aaattgcttt taattccaaa aaaaaaaaaa aaaaaaa       957
```

<210> SEQ ID NO 114
<211> LENGTH: 161
<212> TYPE: PRT
<213> ORGANISM: Homo sapiens

<400> SEQUENCE: 114

```
Met Ser Ser Tyr Gln Gln Lys Gln Thr Phe Thr Pro Pro Gln Leu
 1               5                  10                  15
Gln Gln Gln Val Lys Gln Pro Ser Gln Pro Pro Gln Glu Ile
            20                  25                  30
Phe Val Pro Thr Thr Lys Glu Pro Cys His Ser Lys Val Pro Gln Pro
        35                  40                  45
Gly Asn Thr Lys Ile Pro Glu Pro Gly Cys Thr Lys Val Pro Glu Pro
    50                  55                  60
Gly Cys Thr Lys Val Pro Glu Pro Gly Cys Thr Lys Val Pro Glu Pro
65                  70                  75                  80
Gly Cys Thr Lys Val Pro Glu Pro Gly Cys Thr Lys Val Pro Glu Pro
                85                  90                  95
Gly Tyr Thr Lys Val Pro Glu Pro Gly Ser Ile Lys Val Pro Asp Gln
            100                 105                 110
Gly Phe Ile Lys Phe Pro Glu Pro Gly Ala Ile Lys Val Pro Glu Gln
        115                 120                 125
Gly Tyr Thr Lys Val Pro Val Pro Gly Tyr Thr Lys Val Pro Glu Pro
    130                 135                 140
Cys Pro Ser Thr Val Thr Pro Gly Pro Ala Gln Gln Lys Thr Lys Gln
145                 150                 155                 160
Lys
```

<210> SEQ ID NO 115
<211> LENGTH: 506
<212> TYPE: DNA

-continued

```
<213> ORGANISM: Human
<220> FEATURE:
<221> NAME/KEY: modified_base
<222> LOCATION: (8)
<223> OTHER INFORMATION: Where n is a, c, g or t
<220> FEATURE:
<221> NAME/KEY: modified_base
<222> LOCATION: (21)
<223> OTHER INFORMATION: Where n is a, c, g or t
<220> FEATURE:
<221> NAME/KEY: modified_base
<222> LOCATION: (31)
<223> OTHER INFORMATION: Where n is a, c, g or t
<220> FEATURE:
<221> NAME/KEY: modified_base
<222> LOCATION: (32)
<223> OTHER INFORMATION: Where n is a, c, g or t
<220> FEATURE:
<221> NAME/KEY: modified_base
<222> LOCATION: (58)
<223> OTHER INFORMATION: Where n is a, c, g or t
<220> FEATURE:
<221> NAME/KEY: modified_base
<222> LOCATION: (75)
<223> OTHER INFORMATION: Where n is a, c, g or t
<220> FEATURE:
<221> NAME/KEY: modified_base
<222> LOCATION: (89)
<223> OTHER INFORMATION: Where n is a, c, g or t
<220> FEATURE:
<221> NAME/KEY: modified_base
<222> LOCATION: (96)
<223> OTHER INFORMATION: Where n is a, c, g or t
<220> FEATURE:
<221> NAME/KEY: modified_base
<222> LOCATION: (99)
<223> OTHER INFORMATION: Where n is a, c, g or t
<220> FEATURE:
<221> NAME/KEY: modified_base
<222> LOCATION: (103)
<223> OTHER INFORMATION: Where n is a, c, g or t
<220> FEATURE:
<221> NAME/KEY: modified_base
<222> LOCATION: (122)
<223> OTHER INFORMATION: Where n is a, c, g or t
<220> FEATURE:
<221> NAME/KEY: modified_base
<222> LOCATION: (126)
<223> OTHER INFORMATION: Where n is a, c, g or t
<220> FEATURE:
<221> NAME/KEY: modified_base
<222> LOCATION: (147)
<223> OTHER INFORMATION: Where n is a, c, g or t
<220> FEATURE:
<221> NAME/KEY: modified_base
<222> LOCATION: (150)
<223> OTHER INFORMATION: Where n is a, c, g or t
<220> FEATURE:
<221> NAME/KEY: modified_base
<222> LOCATION: (158)
<223> OTHER INFORMATION: Where n is a, c, g or t
<220> FEATURE:
<221> NAME/KEY: modified_base
<222> LOCATION: (195)
<223> OTHER INFORMATION: Where n is a, c, g or t
<220> FEATURE:
<221> NAME/KEY: modified_base
<222> LOCATION: (210)
<223> OTHER INFORMATION: Where n is a, c, g or t
<220> FEATURE:
<221> NAME/KEY: modified_base
<222> LOCATION: (212)
<223> OTHER INFORMATION: Where n is a, c, g or t
<220> FEATURE:
<221> NAME/KEY: modified_base
<222> LOCATION: (219)
<223> OTHER INFORMATION: Where n is a, c, g or t
<220> FEATURE:
<221> NAME/KEY: modified_base
```

-continued

```
<222> LOCATION: (226)
<223> OTHER INFORMATION: Where n is a, c, g or t
<220> FEATURE:
<221> NAME/KEY: modified_base
<222> LOCATION: (246)
<223> OTHER INFORMATION: Where n is a, c, g or t
<220> FEATURE:
<221> NAME/KEY: modified_base
<222> LOCATION: (248)
<223> OTHER INFORMATION: Where n is a, c, g or t
<220> FEATURE:
<221> NAME/KEY: modified_base
<222> LOCATION: (249)
<223> OTHER INFORMATION: Where n is a, c, g or t
<220> FEATURE:
<221> NAME/KEY: modified_base
<222> LOCATION: (255)
<223> OTHER INFORMATION: Where n is a, c, g or t
<220> FEATURE:
<221> NAME/KEY: modified_base
<222> LOCATION: (258)
<223> OTHER INFORMATION: Where n is a, c, g or t
<220> FEATURE:
<221> NAME/KEY: modified_base
<222> LOCATION: (261)
<223> OTHER INFORMATION: Where n is a, c, g or t
<220> FEATURE:
<221> NAME/KEY: modified_base
<222> LOCATION: (263)
<223> OTHER INFORMATION: Where n is a, c, g or t
<220> FEATURE:
<221> NAME/KEY: modified_base
<222> LOCATION: (265)
<223> OTHER INFORMATION: Where n is a, c, g or t
<220> FEATURE:
<221> NAME/KEY: modified_base
<222> LOCATION: (275)
<223> OTHER INFORMATION: Where n is a, c, g or t
<220> FEATURE:
<221> NAME/KEY: modified_base
<222> LOCATION: (304)
<223> OTHER INFORMATION: Where n is a, c, g or t
<220> FEATURE:
<221> NAME/KEY: modified_base
<222> LOCATION: (317)
<223> OTHER INFORMATION: Where n is a, c, g or t
<220> FEATURE:
<221> NAME/KEY: modified_base
<222> LOCATION: (321)
<223> OTHER INFORMATION: Where n is a, c, g or t
<220> FEATURE:
<221> NAME/KEY: modified_base
<222> LOCATION: (331)
<223> OTHER INFORMATION: Where n is a, c, g or t
<220> FEATURE:
<221> NAME/KEY: modified_base
<222> LOCATION: (337)
<223> OTHER INFORMATION: Where n is a, c, g or t
<220> FEATURE:
<221> NAME/KEY: modified_base
<222> LOCATION: (340)
<223> OTHER INFORMATION: Where n is a, c, g or t
<220> FEATURE:
<221> NAME/KEY: modified_base
<222> LOCATION: (358)
<223> OTHER INFORMATION: Where n is a, c, g or t
<220> FEATURE:
<221> NAME/KEY: modified_base
<222> LOCATION: (371)
<223> OTHER INFORMATION: Where n is a, c, g or t
<220> FEATURE:
<221> NAME/KEY: modified_base
<222> LOCATION: (377)
<223> OTHER INFORMATION: Where n is a, c, g or t
<220> FEATURE:
<221> NAME/KEY: modified_base
<222> LOCATION: (380)
<223> OTHER INFORMATION: Where n is a, c, g or t
<220> FEATURE:
```

<221> NAME/KEY: modified_base
<222> LOCATION: (396)
<223> OTHER INFORMATION: Where n is a, c, g or t
<220> FEATURE:
<221> NAME/KEY: modified_base
<222> LOCATION: (450)
<223> OTHER INFORMATION: Where n is a, c, g or t
<220> FEATURE:
<221> NAME/KEY: modified_base
<222> LOCATION: (491)
<223> OTHER INFORMATION: Where n is a, c, g or t

<400> SEQUENCE: 115

| | | | | | |
|---|---|---|---|---|---|
| cattggtnct | ttcatttgct | ntggaagtgt | nnatctctaa | cagtggacaa | agttcccngt | 60 |
| gccttaaact | ctgtnacact | tttgggaant | gaaaanttng | tantatgata | ggttattctg | 120 |
| angtanagat | gttctggata | ccattanatn | tgccccccngt | gtcagaggct | catattgtgt | 180 |
| tatgtaaatg | gtatntcatt | cgctactatn | antcaattng | aaatanggtc | tttgggttat | 240 |
| gaatantnng | cagcncanct | nanangctgt | ctgtngtatt | cattgtggtc | atagcacctc | 300 |
| acancattgt | aacctcnatc | nagtgagaca | nactagnaan | ttcctagtga | tggctcanga | 360 |
| ttccaaatgg | nctcatntcn | aatgtttaaa | agttanttaa | gtgtaagaaa | tacagactgg | 420 |
| atgttccacc | aactagtacc | tgtaatgacn | ggcctgtccc | aacacatctc | ccttttccat | 480 |
| gactgtggta | ncccgcatcg | gaaaaa | | | | 506 |

<210> SEQ ID NO 116
<211> LENGTH: 3079
<212> TYPE: DNA
<213> ORGANISM: Human

<400> SEQUENCE: 116

| | | | | | |
|---|---|---|---|---|---|
| ggatccccgg | gtttcctaaa | ccccccacag | agtcctgccc | aggccaaaga | gcaaggaaaa | 60 |
| ggtcaaaggg | cagaaaaaat | gctgagttag | gaggagctat | ggaaggataa | acctggcctt | 120 |
| aaagaggtca | agtggtttta | taggggggcgc | tgagggcttc | ccacattctc | tggcctaaac | 180 |
| cttgcaggca | gatctgccca | gtgggctctg | ggatagctgt | gccttcccta | acaaaaaaat | 240 |
| tgtgcacaaa | aggatgaaac | tctattttcc | ctctagcaca | taaccaagaa | tataaggcta | 300 |
| cagattgcct | ttcccagagg | gaaaaccctg | cagcaacctg | ctgcctggaa | aagtgtaaga | 360 |
| gcagatcact | ggggaatcgt | ttgccccccg | ctgatggaca | gcttccccaa | gctccaaggg | 420 |
| caggtgctca | gcatgtaccg | tactgggatg | gttgtcaata | ctcctggtcc | tgtaagagtc | 480 |
| ccaggacact | gccatgccaa | tgccccctca | gttcctggca | tccttttttgg | gctgctcaca | 540 |
| gccccagcct | ctatggtgaa | gacatacttg | ctagcagcgt | caccaacttg | ttgccaagag | 600 |
| atcagtgctc | gaaggcaagg | ttatttctaa | ctgagcagag | cctgccagga | agaaagcgtt | 660 |
| tgcaccccac | accactgtgc | aggtgtgacc | ggtgagctca | cagctgcccc | ccaggcatgc | 720 |
| ccagcccact | taatcatcac | agctcgacag | ctctctcgcc | cagcccagtt | ctggaaggga | 780 |
| taaaagggg | catcaccgtt | cctgggtaac | agagccacct | tctgcgtcct | gctgagctct | 840 |
| gttctctcca | gcacctccca | acccactagt | gcctggttct | cttgctccac | caggaacaag | 900 |
| ccaccatgtc | tcgccagtca | agtgtgtctt | ccggagcggg | gggcagtcgt | agcttcagca | 960 |
| ccgcctctgc | catcacccccg | tctgtctccc | gcaccagctt | cacctccgtg | tcccggtccg | 1020 |
| ggggtggcgg | tggtggtggc | ttcggcaggg | tcagccttgc | gggtgcttgt | ggagtgggtg | 1080 |
| gctatggcag | ccggagcctc | tacaacctgg | ggggctccaa | gaggatatcc | atcagcacta | 1140 |
| gtggtggcag | cttcaggaac | cggtttggtg | ctggtgctgg | aggcggctat | ggctttggag | 1200 |

-continued

```
gtggtgccgg tagtggattt ggtttcggcg gtggagctgg tggtggcttt gggctcggtg      1260
gcggagctgg ctttggaggt ggcttcggtg gccctggctt tcctgtctgc cctcctggag      1320
gtatccaaga ggtcactgtc aaccagagtc tcctgactcc cctcaacctg caaatcgacc      1380
ccagcatcca gagggtgagg accgaggagc gcgagcagat caagaccctc aacaataagt      1440
ttgcctcctt catcgacaag gtgcggttcc tggagcagca gaacaaggtt ctggaaacaa      1500
agtggaccct gctgcaggag cagggcacca agactgtgag gcagaacctg gagccgttgt      1560
tcgagcagta catcaacaac ctcaggaggc agctggacag catcgtgggg gaacggggcc      1620
gcctggactc agagctgaga aacatgcagg acctggtgga agacttcaag aacaagtatg      1680
aggatgaaat caacaagcgt accactgctg agaatgagtt tgtgatgctg aagaaggatg      1740
tagatgctgc ctacatgaac aaggtggagc tggaggccaa ggttgatgca ctgatggatg      1800
agattaactt catgaagatg ttctttgatg cggagctgtc ccagatgcag acgcatgtct      1860
ctgacacctc agtggtcctc tccatggaca caaccgcaa cctggacctg atagcatca       1920 tcgctgaggt caaggcccag tatgaggaga ttgccaaccg cagccggaca gaagccgagt      1980
cctggtatca gaccaagtat gaggagctgc agcagacagc tggccggcat ggcgatgacc      2040
tccgcaacac caagcatgag atctctgaga tgaaccggat gatccagagg ctgagagccg      2100
agattgacaa tgtcaagaaa cagtgcgcca atctgcagaa cgccattgcg gatgccgagc      2160
agcgtgggga gctggccctc aaggatgcca ggaacaagct ggccgagctg gaggaggccc      2220
tgcagaaggc caagcaggac atggcccggc tgctgcgtga gtaccaggag ctcatgaaca      2280
ccaagctggc cctggacgtg gagatcgcca cttaccgcaa gctgctggag ggcgaggaat      2340
gcagactcag tggagaagga gttggaccag tcaacatctc tgttgtcaca agcagtgttt      2400
cctctggata tggcagtggc agtggctatg cggtggccct cggtgaggt cttggcggcg      2460 gcctcggtgg aggtcttgcc ggaggtagca gtggaagcta ctactccagc agcagtgggg      2520
gtgtcggcct agtggtggg ctcagtgtgg ggggctctgg cttcagtgca agcagtagcc      2580
gagggctggg ggtgggcttt ggcagtggcg ggggtagcag ctccagcgtc aaatttgtct      2640
ccaccacctc ctcctcccgg aagagcttca gagctaagaa acctgctgca agtcactgcc      2700
ttccaagtgc agcaacccag cccatggaga ttgcctcttc taggcagttg ctcaagccat      2760
gttttatcct tttctggaga gtagtctaga ccaagccaat tgcagaacca cattctttgg      2820
ttcccaggag agccccattc ccagcccctg gtctcccgtg ccgcagttct atattctgct      2880
tcaaatcagc cttcaggttt cccacagcat ggccctgct gacacgagaa cccaaagttt      2940
tcccaaatct aaatcatcaa aacagaatcc ccaccccaat cccaaatttt gtttggttc       3000 taactacctc cagaatgtgt tcaataaaat gttttataat ataagctggt gtgcagaatt      3060
gttttttttt tctacccaa                                                  3079
```

<210> SEQ ID NO 117
<211> LENGTH: 6921
<212> TYPE: DNA
<213> ORGANISM: Human

<400> SEQUENCE: 117

```
gaattctgac tgtccactca aaacttctat tccgatcaaa gctatctgtg actacagaca        60
aattgagata accatttaca aagacgatga atgtgttttg gcgaataact ctcatcgtgc       120
taaatggaag gtcattagtc ctactgggaa tgaggctatg gtcccatctg tgtgcttcac       180
```

-continued

```
cgttcctcca ccaaacaaag aagcggtgga ccttgccaac agaattgagc aacagtatca    240
gaatgtcctg actctttggc atgagtctca cataaacatg aagagtgtag tatcctggca    300
ttatctcatc aatgaaattg atagaattcg agctagcaat gtggcttcaa taaagacaat    360
gctacctggt gaacatcagc aagttctaag taatctacaa tctcgttttg aagattttct    420
ggaagatagc caggaatccc aagtcttttc aggctcagat ataacacaac tggaaaagga    480
ggttaatgta tgtaagcagt attatcaaga acttcttaaa tctgcagaaa gagaggagca    540
agaggaatca gtttataatc tctacatctc tgaagttcga acattagac ttcggttaga     600 gaactgtgaa gatcggctga ttagacagat tcgaactccc ctggaaagag atgatttgca    660
tgaaagtgtg ttcagaatca cagaacagga gaaactaaag aaagagctgg aacgacttaa    720
agatgatttg ggaacaatca caaataagtg tgaggagttt ttcagtcaag cagcagcctc    780
ttcatcagtc cctaccctac gatcagagct taatgtggtc cttcagaaca tgaaccaagt    840
ctattctatg tcttccactt acatagataa gttgaaaact gttaacttgg tgttaaaaaa    900
cactcaagct gcagaagccc tcgtaaaact ctatgaaact aaactgtgtg aagaagaagc    960
agttatagct gacaagaata atattgagaa tctaataagt actttaaagc aatggagatc   1020
tgaagtagat gaaagagac aggtattcca tgccttagag gatgagttgc agaaagctaa    1080
agccatcagt gatgaaatgt ttaaaacgta taaagaacgg gaccttgatt ttgactggca   1140
caaagaaaaa gcagatcaat tagttgaaag gtggcaaaat gttcatgtgc agattgacaa   1200
caggttacgg gacttagagg gcattggcaa atcactgaag tactacagag acacttacca   1260
tcctttagat gattggatcc agcaggttga aactactcag agaaagattc aggaaaatca   1320
gcctgaaaat agtaaaaccc tagccacaca gttgaatcaa cagaagatgc tggtgtccga   1380
aatagaaatg aaacagagca aaatggacga gtgtcaaaaa tatgcagaac agtactcagc   1440
tacagtgaag gactatgaat tacaaacaat gacctaccgg gccatggtag attcacaaca   1500
aaaatctcca gtgaaacgcc gaagaatgca gagttcagca gatctcatta ttcaagagtt   1560
catggaccta aggactcgat atactgccct ggtcactctc atgacacaat atattaaatt   1620
tgctggtgat tcattgaaga ggctggaaga ggaggagatt aaaaggtgta aggagacttc   1680
tgaacatggg gcatattcag atctgcttca gcgtcagaag gcaacagtgc ttgagaatag   1740
caaacttaca ggaaagataa gtgagttgga agaatggta gctgaactaa agaaacaaaa    1800
gtcccgagta gaggaagaac ttccgaaggt cagggaggct gcagaaaatg aattgagaaa   1860
gcagcagaga aatgtagaag atatctctct gcagaagata agggctgaaa gtgaagccaa   1920
gcagtaccgc agggaacttg aaaccattgt gagagagaag gaagccgctg aaagagaact   1980
ggagcgggtg aggcagctca ccatagaggc cgaggctaaa agagctgccg tggaagagaa   2040
cctcctgaat tttcgcaatc agttggagga aaacaccttt accagacgaa cactggaaga   2100
tcatcttaaa agaaagatt taagtctcaa tgatttggag caacaaaaaa ataaattaat    2160
ggaagaatta agaagaaaga gagacaatga ggaagaactc ttgaagctga taagcagat    2220 ggaaaaagac cttgcatttc agaaacaggt agcagagaaa cagttgaaag aaaagcagaa   2280
aattgaattg gaagcaagaa gaaaaataac tgaaattcag tatacatgta gagaaaatgc   2340
attgccagtg tgtccgatca cacaggctac atcatgcagg gcagtaacgg gtctccagca   2400
agaacatgac aagcagaaag cagaagaact caaacagcag gtagatgaac taacagctgc   2460
caatagaaag gctgaacaag acatgagaga gctgacatat gaacttaatg ccctccagct   2520
tgaaaaaacg tcatctgagg aaaaggctcg tttgctaaaa gataaactag atgaaacaaa   2580
```

```
taatacactc agatgcctta agttggagct ggaaaggaag gatcaggcgg agaaagggta    2640
ttctcaacaa ctcagagagc ttggtaggca attgaatcaa accacaggta aagctgaaga    2700
agccatgcaa gaagctagtg atctcaagaa aataaagcgc aattatcagt tagaattaga    2760
atctcttaat catgaaaaag ggaaactaca aagagaagta gacagaatca caagggcaca    2820
tgctgtagct gagaagaata ttcagcattt aaattcacaa attcattctt ttcgagatga    2880
gaaagaatta gaaagactac aaatctgcca gagaaaatca gatcatctaa aagaacaatt    2940
tgagaaaagc catgagcagt tgcttcaaaa tatcaaagct gaaaagaaaa ataatgataa    3000
aatccaaagg ctcaatgaag aattggagaa aagtaatgag tgtgcagaga tgctaaaaca    3060
aaaagtagag gagcttacta ggcagaataa tgaaaccaaa ttaatgatgc agagaattca    3120
ggcagaatca gagaatatag ttttagagaa acaaactatc cagcaaagat gtgaagcact    3180
gaaaattcag gcagatggtt ttaaagatca gctacgcagc acaaatgaac acttgcataa    3240
acagacaaaa acagagcagg attttcaaag aaaaattaaa tgcctagaag aagacctggc    3300
gaaaagtcaa aatttggtaa gtgaatttaa gcaaagtgt gaccaacaga acattatcat    3360
ccagaatacc aagaaagaag ttagaaatct gaatgcggaa ctgaatgctt ccaaagaaga    3420
gaagcgacgc ggggagcaga aagttcagct acaacaagct caggtgcaag agttaaataa    3480
caggttgaaa aaagtacaag acgaattaca cttaaagacc atagaggagc agatgaccca    3540
cagaaagatg gttctgtttc aggaagaatc tggtaaattc aaacaatcag cagaggagtt    3600
tcggaagaag atggaaaaat taatggagtc caaagtcatc actgaaaatg atatttcagg    3660
cattaggctt gactttgtgt ctcttcaaca agaaaactct agagcccaag aaaatgctaa    3720
gctttgtgaa acaaacatta aagaacttga agacagctt caacagtatc gtgaacaaat    3780
gcagcaaggg cagcacatgg aagcaaatca ttaccaaaaa tgtcagaaac ttgaggatga    3840
gctgatagcc cagaagcgtg aggttgaaaa cctgaagcaa aaaatggacc aacagatcaa    3900
agagcatgaa catcaattag ttttgctcca gtgtgaaatt caaaaaaga gcacagccaa    3960 agactgtacc ttcaaaccag attttgagat gacagtgaag gagtgccagc actctggaga    4020
gctgtcctct agaaacactg gacaccttca cccaacaccc agatcccctc tgttgagatg    4080
gactcaagaa ccacagccat ggaagagaa gtggcagcat cgggttgttg aacagatacc    4140
caaagaagtc caattccagc caccaggggc tccactcgag aaagagaaaa gccagcagtg    4200
ttactctgag tacttttctc agacaagcac cgagttacag ataacttttg atgagacaaa    4260
ccccattaca agactgtctg aaattgagaa gataagagac caagccctga caattctag    4320 accacctgtt aggtatcaag ataacgcatg tgaaatggaa ctggtgaagg ttttgacacc    4380
cttagagata gctaagaaca agcagtatga tatgcataca gaagtcacaa cattaaaaca    4440
agaaaagaac ccagttccca gtgctgaaga atggatgctt gaagggtgca gagcatctgg    4500
tggactcaag aaagggggatt tccttaagaa gggcttagaa ccagagacct tccagaactt    4560
tgatggtgat catgcatgtt cagtcaggga tgatgaattt aaattccaag gcttaggca    4620 cactgtgact gccaggcagt tggtggaagc taagcttctg gacatgagaa caattgagca    4680
gctgcgactc ggtcttaaga ctgttgaaga agttcagaaa actcttaaca gtttctgac    4740 gaaagccacc tcaattgcag ggctttacct agaatctaca aagaaaaga tttcatttgc    4800 ctcagcggcc gagagaatca taatagacaa aatggtggct ttggcatttt tagaagctca    4860
ggctgcaaca ggttttataa ttgatcccat ttcaggtcag acatattctg ttgaagatgc    4920
```

```
agttcttaaa ggagttgttg accccgaatt cagaattagg cttcttgagg cagagaaggc      4980
agctgtggga tattcttatt cttctaagac attgtcagtg tttcaagcta tggaaaatag      5040
aatgcttgac agacaaaaag gtaaacatat cttggaagcc cagattgcca gtgggggtgt      5100
cattgaccct gtgagaggca ttcgtgttcc tccagaaatt gctctgcagc aggggttgtt      5160
gaataatgcc atcttacagt ttttacatga gccatccagc aacacaagag ttttccctaa      5220
tcccaataac aagcaagctc tgtattactc agaattactg cgaatgtgtg tatttgatgt      5280
agagtcccaa tgctttctgt ttccatttgg ggagaggaac atttccaatc tcaatgtcaa      5340
gaaaacacat agaatttctg tagtagatac taaaacagga tcagaattga ccgtgtatga      5400
ggctttccag agaaacctga ttgagaaaag tatatatctt gaactttcag ggcagcaata      5460
tcagtggaag gaagctatgt ttttttgaatc ctatgggcat tcttctcata tgctgactga      5520
tactaaaaca ggattacact tcaatattaa tgaggctata gagcagggaa caattgacaa      5580
agccttggtc aaaaagtatc aggaaggcct catcacactt acagaacttg ctgattcttt      5640
gctgagccgg ttagtcccca agaaagattt gcacagtcct gttgcagggt attggctgac      5700
tgctagtggg gaaaggatct ctgtactaaa agcctcccgt agaaatttgg ttgatcggat      5760
tactgccctc cgatgccttg aagcccaagt cagtacaggg ggcataattg atcctcttac      5820
tggcaaaaag taccgggtgg ccgaagcttt gcatagaggc ctggttgatg aggggttttgc     5880 ccagcagctg cgacagtgtg aattagtaat cacaggggatt ggccatccca tcactaacaa     5940
aatgatgtca gtggtggaag ctgtgaatgc aaatattata aataaggaaa tgggaatccg      6000
atgtttggaa tttcagtact tgacaggagg gttgatagag ccacaggttc actctcggtt      6060
atcaatagaa gaggctctcc aagtaggtat tatagatgtc ctcattgcca caaaactcaa      6120
agatcaaaag tcatatgtca gaaatataat atgccctcag acaaaaagaa agttgacata      6180
taaagaagcc ttagaaaaag ctgattttga tttccacaca ggacttaaac tgttagaagt      6240
atctgagccc ctgatgacag gaatttctag cctctactat tcttcctaat gggacatgtt      6300
taaataactg tgcaagggggt gatgcaggct ggttcatgcc acttttttcag agtatgatga     6360 tatcggctac atatgcagtc tgtgaattat gtaacatact ctatttcttg agggctgcaa      6420
attgctaagt gctcaaaata gagtaagttt taaattgaaa attacataag atttaatgcc      6480
cttcaaatgg tttcatttag ccttgagaat ggttttttga aacttggcca cactaaaatg      6540 ttttttttttt tttacgtaga atgtgggata aacttgatga actccaagtt cacagtgtca      6600
tttcttcaga actccccttc attgaatagt gatcatttat taaatgataa attgcactcg      6660
ctgaaagagc acgtcatgaa gcaccatgga atcaaagaga aagatataaa ttcgttccca      6720
cagccttcaa gctgcagtgt tttagattgc ttcaaaaaat gaaaaagttt tgccttttct      6780
gatatagtga ccttctttgc atattaaaat gtttaccaca atgtcccatt tctagttaag      6840
tcttcgcact tgaaagctaa cattatgaat attatgtgtt ggaggagggg aaggattttc      6900
ttcattctgt gtattttccg g                                                6921
```

<210> SEQ ID NO 118
<211> LENGTH: 946
<212> TYPE: DNA
<213> ORGANISM: Human

<400> SEQUENCE: 118

```
cttctgactg ggctcaggct gacaggtaga gctcaccatg gcttcttgtg tccttgtccc        60
ctccccatca cagctgtggt gcagtccacc gtctccagtg gctatggcgg tgccagtggt       120
```

```
gtcggcagtg gcttaggcct gggtggagga agcagctact cctatggcag tggtcttggc      180
gttggaggtg gcttcagttc cagcagtggc agagccattg ggggtggcct cagctctgtt      240
ggaggcggca gttccaccat caagtacacc accacctcct cctccagcag gaagagctat      300
aagcactaaa gtgcgtctgc tagctctcgg tcccacagtc ctcaggcccc tctctggctg      360
cagagccctc tcctcaggtt gcctgtcctc tcctggcctc cagtctcccc tgctgtccca      420
ggtagagctg gggatgaatg cttagtgccc tcacttcttc tctctctctc tataccatct      480
gagcacccat tgctcaccat cagatcaacc tctgatttta catcatgatg taatcaccac      540
tggagcttca ctgttactaa attattaatt tcttgcctcc agtgttctat ctctgaggct      600
gagcattata agaaaatgac ctctgctcct tttcattgca gaaaattgcc aggggcttat      660
ttcagaacaa cttccactta ctttccactg gctctcaaac tctctaactt ataagtgttg      720
tgaaccccca cccaggcagt atccatgaaa gcacaagtga ctagtcctat gatgtacaaa      780
gcctgtatct ctgtgatgat ttctgtgctc ttcactgttt gcaattgcta aataaagcag      840
atttataata catatattct tttactttgc cttgctttgg ggccaaagtt ttgggcttaa      900
acttttttat ctgataagtg aatagttgtt tttaaaagat aatcta                    946

<210> SEQ ID NO 119
<211> LENGTH: 8948
<212> TYPE: DNA
<213> ORGANISM: Human

<400> SEQUENCE: 119
tcaacagccc ctgctccttg ggcccctcca tgccatgccg taatctctcc cacccgacca       60
acaccaacac ccagctccga cgcagctcct ctgcgccctt gccgccctcc gagccacagc      120
tttcctcccg ctcctgcccc cggccgcgtc ccgtctccgc gctcgcagcg gcctcgggag      180
ggcccaggta gcgagcagcg acctcgcgag ccttccgcac tcccgcccgg ttccccggcc      240
gtccgcctat ccttggcccc ctccgctttc tccgcgccgg cccgcctcgc ttatgcctcg      300
gcgctgagcc gctctcccga ttgcccgccg acatgagctg caacggaggc tcccacccgc      360
ggatcaacac tctgggccgc atgatccgcc ccgagtctgg cccggacctg cgctacgagg      420
tgaccagcgg cggcggggc accagcagga tgtactattc tcggcgcggc gtgatcaccg      480
accagaactc ggacggctac tgtcaaaccg gcacgatgtc caggcaccag aaccagaaca      540
ccatccagga gctgctgcag aactgctccg actgcttgat gcgagcagag ctcatcgtgc      600
agcctgaatt gaagtatgga gatgaatacc aactgactcg gagtcgagaa ttggatgagt      660
gttttgccca ggccaatgac caaatggaaa tcctcgacag cttgatcaga gagatgcggc      720
agatgggcca gccctgtgat gcttaccaga aaggcttct tcagctccaa gagcaaatgc      780 gagccccttta taaagccatc agtgtccctc gagtccgcag ggccagctcc aagggtggtg      840
gaggctacac ttgtcagagt ggctctggct gggatgagtt caccaaacat gtcaccagtg      900
aatgtttggg gtgatgagg cagcaaaggg cggagatgga catggtggcc tggggtgtgg      960
acctggcctc agtggagcag cacattaaca gccaccgggg catccacaac tccatcggcg     1020
actatcgctg gcagctggac aaaatcaaag ccgacctgcg cgagaaatct gcgatctacc     1080
agttggagga ggagtatgaa aacctgctga agcgtccttt gagaggatg gatcacctgc     1140 gacagctgca gaacatcatt caggccacgt ccagggagat catgtggatc aatgactgcg     1200
aggaggagga gctgctgtac gactgagcg acaagaacac caacatcgct cagaaacagg     1260
```

-continued

```
aggccttctc catacgcatg agtcaactgg aagttaaaga aaaagagctc aataagctga   1320
aacaagaaag tgaccaactt gtcctcaatc agcatccagc ttcagacaaa attgaggcct   1380
atatggacac tctgcagacg cagtggagtt ggattcttca gatcaccaag tgcattgatg   1440
ttcatctgaa agaaaatgct gcctactttc agttttttga agaggcgcag tctactgaag   1500
catacctgaa ggggctccag gactccatca ggaagaagta cccctgcgac aagaacatgc   1560
ccctgcagca cctgctggaa cagatcaagg agctggagaa agaacgagag aaaatccttg   1620
aatacaagcg tcaggtgcag aacttggtaa acaagtctaa gaagattgta cagctgaagc   1680
ctcgtaaccc agactacaga agcaataaac ccattattct cagagctctc tgtgactaca   1740
aacaagatca gaaaatcgtg cataagggg atgagtgtat cctgaaggac aacaacgagc   1800
gcagcaagtg gtacgtgacg ggcccgggag gcgttgacat gcttgttccc tctgtggggc   1860
tgatcatccc tcctccgaac ccactggccg tggacctctc ttgcaagatt gagcagtact   1920
acgaagccat cttggctctg tggaaccagc tctacatcaa catgaagagc ctggtgtcct   1980
ggcactactg catgattgac atagagaaga tcagggccat gacaatcgcc aagctgaaaa   2040
caatgcggca ggaagattac atgaagacga tagccgacct tgagttacat taccaagagt   2100
tcatcagaaa tagccaaggc tcagagatgt ttggagatga tgacaagcgg aaaatacagt   2160
ctcagttcac cgatgcccag aagcattacc agaccctggt cattcagctc cctggctatc   2220
cccagcacca gacagtgacc acaactgaaa tcactcatca tggaacctgc caagatgtca   2280
accataataa agtaattgaa accaacgag aaaatgacaa gcaagaaaca tggatgctga   2340
tggagctgca gaagattcgc aggcagatag agcactgcga gggcaggatg actctcaaaa   2400
acctccctct agcagaccag gggtcttctc accacatcac agtgaaaatt aacgagctta   2460
agagtgtgca gaatgattca caagcaattg ctgaggttct caaccagctt aaagatatgc   2520
ttgccaactt cagaggttct gaaaagtact gctatttaca gaatgaagta tttgactat   2580 ttcagaaact ggaaaatatc aatggtgtta cagatggcta cttaaatagc ttatgcacag   2640
taagggcact gctccaggct attctccaaa cagaagacat gttaaaggtt tatgaagcca   2700
ggctcactga ggaggaaact gtctgcctgg acctggataa agtggaagct taccgctgtg   2760
gactgaagaa aataaaaaat gacttgaact tgaagaagtc gttgttggcc actatgaaga   2820
cagaactaca gaaagcccag cagatccact ctcagacttc acagcagtat ccactttatg   2880
atctggactt gggcaagttc ggtgaaaaag tcacacagct gacagaccgc tggcaaagga   2940
tagataaaca gatcgacttt agattatggg acctggagaa acaaatcaag caattgagga   3000
attatcgtga taactatcag gctttctgca agtggctcta tgatcgtaaa cgccgccagg   3060
attccttaga atccatgaaa tttggagatt ccaacacagt catgcggttt ttgaatgagc   3120
agaagaactt gcacagtgaa atatctggca acgagacaa atcagaggaa gtacaaaaaa   3180
ttgctgaact ttgcgccaat tcaattaagg attatgagct ccagctggcc tcatacacct   3240
caggactgga aactctgctg aacataccta tcaagaggac catgattcag tccccttctg   3300
gggtgattct gcaagaggct gcagatgttc atgctcggta cattgaacta cttacaagat   3360
ctggagacta ttcacaggttc ttaagtgaga tgctgaagag tttggaagat ctgaagctga   3420 aaataccaa gatcgaagtt ttggaagagg agctcagact ggcccgagat gccaactcgg   3480
aaaactgtaa taagaacaaa ttcctggatc agaacctgca gaaataccag gcagagtgtt   3540
cccagttcaa agcgaagctt gcgagcctgg aggagctgaa gagacaggct gagctggatg   3600
ggaagtcggc taagcaaaat ctagacaagt gctacggcca aataaaagaa ctcaatgaga   3660
```

```
agatcacccg actgacttat gagattgaag atgaaaagag aagaagaaaa tctgtggaag    3720
acagatttga ccaacagaag aatgactatg accaactgca gaaagcaagg caatgtgaaa    3780
aggagaacct tggttggcag aaattagagt ctgagaaagc catcaaggag aaggagtacg    3840
agattgaaag gttgagggtt ctactgcagg aagaaggcac ccggaagaga gaatatgaaa    3900
atgagctggc aaaggtaaga aaccactata atgaggagat gagtaattta aggaacaagt    3960
atgaaacaga gattaacatt acgaagacca ccatcaagga gatatccatg caaaagagg     4020 atgattccaa aaatcttaga aaccagcttg atagactttc aagggaaaat cgagatctga    4080
aggatgaaat tgtcaggctc aatgacagca tcttgcaggc cactgagcag cgaaggcgag    4140
ctgaagaaaa cgcccttcag caaaaggcct gtggctctga gataatgcag aagaagcagc    4200
atctggagat agaactgaag caggtcatgc agcagcgctc tgaggacaat gcccggcaca    4260
agcagtccct ggaggaggct gccaagacca ttcaggacaa aaataaggag atcgagagac    4320
tcaaagctga gtttcaggag gaggccaagc gccgctggga atatgaaaat gaactgagta    4380
aggtaagaaa caattatgat gaggagatca ttagcttaaa aaatcagttt gagaccgaga    4440
tcaacatcac caagaccacc atccaccagc tcaccatgca gaaggaagag gataccagtg    4500
gctaccgggc tcagatagac aatctcaccc gagaaaacag gagcttatct gaagaaataa    4560
agaggctgaa gaacactcta acccagacca cagagaatct caggagggtg aagaagaca     4620 tccaacagca aaaggccact ggctctgagg tgtctcagag gaaacagcag ctggaggttg    4680
agctgagaca agtcactcag atgcgaacag aggagagcgt aagatataag caatctcttg    4740
atgatgctgc caaaccatcc caggataaaa acaaggagat agaaaggtta aaacaactga    4800
tcgacaaaga aacaaatgac cggaaatgcc tggaagatga aaacgcgaga ttacaaaggg    4860
tccagtatga cctgcagaaa gcaaacagta gtgcgacgga gacaataaac aaactgaagg    4920
ttcaggagca agaactgaca cgcctgagga tcgactatga aagggttttcc caggagagga    4980 ctgtgaagga ccaggatatc acgcggttcc agaactctct gaaagagctg cagctgcaga    5040
agcagaaggt ggaagaggag ctgaatcggc tgaagaggac cgcgtcagaa gactcctgca    5100
agaggaagaa gctggaggaa gagctggaag gcatgaggag gtcgctgaag gagcaagcca    5160
tcaaaatcac caacctgacc cagcagctgg agcaggcatc cattgttaag aagaggagtg    5220
aggatgacct ccggcagcag agggacgtgc tggatggcca cctgagggaa aagcagagga    5280
cccaggaaga gctgaggagg ctctcttctg aggtcgaggc cctgaggcgg cagttactcc    5340
aggaacagga aagtgtcaaa caagctcact tgaggaatga gcatttccag aaggcgatag    5400
aagataaaag cagaagctta aatgaaagca aaatagaaat tgagaggctg cagtctctca    5460
cagagaacct gaccaaggag cacttgatgt tagaagaaga actgcggaac ctgaggctgg    5520
agtacgatga cctgaggaga ggacgaagcg aagcggacag tgataaaaat gcaaccatct    5580
tggaactaag gagccagctg cagatcagca acaaccggac cctggaactg caggggctga    5640
ttaatgattt acagagagag agggaaaatt tgagacagga aattgagaaa ttccaaaagc    5700
aggctttaga ggcatctaat aggattcagg aatcaaagaa tcagtgtact caggtggtac    5760
aggaaagaga gagccttctg gtgaaaatca agtcctgga gcaagacaag gcaaggctgc    5820
agaggctgga ggatgagctg aatcgtgcaa aatcaactct agaggcagaa accagggtga    5880
aacagcgcct ggagtgtgag aaacagcaaa ttcagaatga cctgaatcag tggaagactc    5940
aatattcccg caaggaggag gctattagga agatagaatc ggaaagagaa aagagtgaga    6000
```

-continued

```
gagagaagaa cagtcttagg agtgagatcg aaagactcca agcagagatc aagagaattg    6060
aagagaggtg caggcgtaag ctggaggatt ctaccaggga gacacagtca cagttagaaa    6120
cagaacgctc ccgatatcag agggagattg ataaactcag acagcgccca tatgggtccc    6180
atcgagagac ccagactgag tgtgagtgga ccgttgacac ctccaagctg gtgtttgatg    6240
ggctgaggaa gaaggtgaca gcaatgcagc tctatgagtg tcagctgatc gacaaaacaa    6300
ccttggacaa actattgaag gggaagaagt cagtggaaga agttgcttct gaaatccagc    6360
cattccttcg gggtgcagga tctatcgctg gagcatctgc ttctcctaag gaaaaatact    6420
ctttggtaga ggccaagaga aagaaattaa tcagcccaga atccacagtc atgcttctgg    6480
aggcccaggc agctacaggt ggtataattg atccccatcg gaatgagaag ctgactgtcg    6540
acagtgccat agctcgggac ctcattgact tcgatgaccg tcagcagata tatgcagcag    6600
aaaaagctat cactggtttt gatgatccat tttcaggcaa gacagtatct gtttcagaag    6660
ccatcaagaa aaatttgatt gatagagaaa ccggaatgcg cctgctggaa gcccagattg    6720
cttcaggggg tgtagtagac cctgtgaaca gtgtcttttt gccaaaagat gtcgccttgg    6780
cccgggggct gattgataga gatttgtatc gatccctgaa tgatccccga gatagtcaga    6840
aaaactttgt ggatccagtc accaaaaaga aggtcagtta cgtgcagctg aaggaacggt    6900
gcagaatcga accacatact ggtctgctct tgctttcagt acagaagaga agcatgtcct    6960
tccaaggaat cagacaacct gtgaccgtca ctgagctagt agattctggt atattgagac    7020
cgtccactgt caatgaactg gaatctggtc agatttctta tgacgaggtt ggtgagagaa    7080
ttaaggactt cctccagggt tcaagctgca tagcaggcat atacaatgag accacaaaac    7140
agaagcttgg catttatgag gccatgaaaa ttggcttagt ccgacctggt actgctctgg    7200
agttgctgga agcccaagca gctactggct ttatagtgga tcctgttagc aacttgaggt    7260
taccagtgga ggaagcctac aagagaggtc tggtgggcat tgagttcaaa gagaagctcc    7320
tgtctgcaga acgagctgtc actgggtata atgatcctga acaggaaac atcatctctt    7380
tgttccaagc catgaataag gaactcatcg aaaaggcca cggtattcgc ttattagaag    7440
cacagatcgc aaccgggggg atcattgacc caaaggagag ccatcgtttta ccagttgaca    7500
tagcatataa gagggctat ttcaatgagg aactcagtga gattctctca gatccaagtg    7560
atgataccaa aggattttt gaccccaaca ctgaagaaaa tcttacctat ctgcaactaa    7620
aagaaagatg cattaaggat gaggaaacag ggctctgtct tctgcctctg aaagaaaaga    7680
agaaacaggt gcagacatca caaaagaata ccctcaggaa gcgtagagtg gtcatagttg    7740
acccagaaac caataaagaa atgtctgttc aggaggccta caagaagggc ctaattgatt    7800
atgaaacctt caaagaactg tgtgagcagg aatgtgaatg ggaagaaata accatcacgg    7860
gatcagatgg ctccaccagg gtggtcctgg tagatagaaa gacaggcagt cagtatgata    7920
ttcaagatgc tattgacaag ggccttgttg acaggaagtt ctttgatcag taccgatccg    7980
gcagcctcag cctcactcaa tttgctgaca tgatctcctt gaaaaatggt gtcggcacca    8040
gcagcagcat gggcagtggt gtcagcgatg atgtttttag cagctcccga catgaatcag    8100
taagtaagat ttccaccata tccagcgtca ggaatttaac cataaggagc agctcttttt    8160
cagacaccct ggaagaatcg agcccattg cagccatctt tgacacagaa acctggagaa    8220
aaatctccat tacagaaggt atagagcggg gcatcgttga cagcatcacg ggtcagaggc    8280
ttctggaggc tcaggcctgc acaggtggca tcatccaccc aaccacgggc cagaagctgt    8340
cacttcagga cgcagtctcc cagggtgtga ttgaccaaga catggccacc agcgtgaagc    8400
```

```
ctgctcagaa agccttcata ggcttcgagg gtgtgaaggg aaagaagaag atgtcagcag    8460
cagaggcagt gaaagaaaaa tggctcccgt atgaggctgg ccagcgcttc ctggagttcc    8520
agtacctcac gggaggtctt gttgacccgg aagtgcatgg gaggataagc accgaagaag    8580
ccatccggaa ggggttcata gatggccgcg ccgcacagag gctgcaagac accagcagct    8640
atgccaaaat cctgacctgc cccaaaacca aattaaaaat atcctataag gatgccataa    8700
atcgctccat ggtagaagat atcactgggc tgcgccttct ggaagccgcc tccgtgtcgt    8760
ccaagggctt acccagccct tacaacatgt cttcggctcc ggggtcccgc tccggctccc    8820
gctcgggatc tcgctccgga tctcgctccg ggtcccgcag tgggtcccgg agaggaagct    8880
ttgacgccac agggaattct tcctactctt attcctactc atttagcagt agttctattg    8940
ggcactag                                                             8948
```

<210> SEQ ID NO 120
<211> LENGTH: 587
<212> TYPE: DNA
<213> ORGANISM: Human
<220> FEATURE:
<221> NAME/KEY: modified_base
<222> LOCATION: (91)
<223> OTHER INFORMATION: Where n is a, c, g or t
<220> FEATURE:
<221> NAME/KEY: modified_base
<222> LOCATION: (131)
<223> OTHER INFORMATION: Where n is a, c, g or t
<220> FEATURE:
<221> NAME/KEY: modified_base
<222> LOCATION: (256)
<223> OTHER INFORMATION: Where n is a, c, g or t
<220> FEATURE:
<221> NAME/KEY: modified_base
<222> LOCATION: (263)
<223> OTHER INFORMATION: Where n is a, c, g or t
<220> FEATURE:
<221> NAME/KEY: modified_base
<222> LOCATION: (332)
<223> OTHER INFORMATION: Where n is a, c, g or t
<220> FEATURE:
<221> NAME/KEY: modified_base
<222> LOCATION: (392)
<223> OTHER INFORMATION: Where n is a, c, g or t
<220> FEATURE:
<221> NAME/KEY: modified_base
<222> LOCATION: (400)
<223> OTHER INFORMATION: Where n is a, c, g or t
<220> FEATURE:
<221> NAME/KEY: modified_base
<222> LOCATION: (403)
<223> OTHER INFORMATION: Where n is a, c, g or t
<220> FEATURE:
<221> NAME/KEY: modified_base
<222> LOCATION: (461)
<223> OTHER INFORMATION: Where n is a, c, g or t
<220> FEATURE:
<221> NAME/KEY: modified_base
<222> LOCATION: (496)
<223> OTHER INFORMATION: Where n is a, c, g or t
<220> FEATURE:
<221> NAME/KEY: modified_base
<222> LOCATION: (497)
<223> OTHER INFORMATION: Where n is a, c, g or t
<220> FEATURE:
<221> NAME/KEY: modified_base
<222> LOCATION: (499)
<223> OTHER INFORMATION: Where n is a, c, g or t
<220> FEATURE:
<221> NAME/KEY: modified_base
<222> LOCATION: (510)
<223> OTHER INFORMATION: Where n is a, c, g or t
<220> FEATURE:

<221> NAME/KEY: modified_base
<222> LOCATION: (511)
<223> OTHER INFORMATION: Where n is a, c, g or t
<220> FEATURE:
<221> NAME/KEY: modified_base
<222> LOCATION: (518)
<223> OTHER INFORMATION: Where n is a, c, g or t
<220> FEATURE:
<221> NAME/KEY: modified_base
<222> LOCATION: (539)
<223> OTHER INFORMATION: Where n is a, c, g or t
<220> FEATURE:
<221> NAME/KEY: modified_base
<222> LOCATION: (554)
<223> OTHER INFORMATION: Where n is a, c, g or t
<220> FEATURE:
<221> NAME/KEY: modified_base
<222> LOCATION: (560)
<223> OTHER INFORMATION: Where n is a, c, g or t
<220> FEATURE:
<221> NAME/KEY: modified_base
<222> LOCATION: (576)
<223> OTHER INFORMATION: Where n is a, c, g or t

<400> SEQUENCE: 120

```
cgtcctaagc acttagacta catcagggaa gaacacagac cacatccctg tcctcatgcg      60
gcttatgttt tctggaagaa agtggagacc nagtccttgg ctttagggct ccccggctgg     120
gggctgtgca ntccggtcag ggcgggaagg gaaatgcacc gctgcatgtg aacttacagc     180
ccaggcggat gcccctttcc ttagcactac ctggcctcct gcatccctc gcctcatgtt      240
cctcccacct tcaaanaatg aanaacccca tgggcccagc cccttgccct ggggaaccaa     300
ggcagccttc caaaactcag gggctgaagc anactattag ggcaggggct gactttgggt     360
gacactgccc attccctctc agggcagctc angtcacccn ggnctcttga acccagcctg     420
ttcctttgaa aaagggcaaa actgaaaagg gcttttccta naaaagaaa aaccagggaa      480
ctttgccagg gcttcnntnt taccaaaacn ncttctcnng gatttttaat tccccattng     540
gcctccactt accngggggcn atgccccaaa attaanaatt tcccatc                  587
```

<210> SEQ ID NO 121
<211> LENGTH: 619
<212> TYPE: DNA
<213> ORGANISM: Human
<220> FEATURE:
<221> NAME/KEY: modified_base
<222> LOCATION: (260)
<223> OTHER INFORMATION: Where n is a, c, g or t
<220> FEATURE:
<221> NAME/KEY: modified_base
<222> LOCATION: (527)
<223> OTHER INFORMATION: Where n is a, c, g or t
<220> FEATURE:
<221> NAME/KEY: modified_base
<222> LOCATION: (560)
<223> OTHER INFORMATION: Where n is a, c, g or t
<220> FEATURE:
<221> NAME/KEY: modified_base
<222> LOCATION: (564)
<223> OTHER INFORMATION: Where n is a, c, g or t
<220> FEATURE:
<221> NAME/KEY: modified_base
<222> LOCATION: (566)
<223> OTHER INFORMATION: Where n is a, c, g or t
<220> FEATURE:
<221> NAME/KEY: modified_base
<222> LOCATION: (585)
<223> OTHER INFORMATION: Where n is a, c, g or t
<220> FEATURE:
<221> NAME/KEY: modified_base
<222> LOCATION: (599)
<223> OTHER INFORMATION: Where n is a, c, g or t

<400> SEQUENCE: 121

```
cactagtagg atagaaacac tgtgtcccga gagtaaggag agaagctact attgattaga      60
gcctaaccca ggttaactgc aagaagaggc gggatacttt cagctttcca tgtaactgta     120
tgcataaagc caatgtagtc cagtttctaa gatcatgttc caagctaact gaatcccact     180
tcaatacaca ctcatgaact cctgatggaa caataacagg cccaagcctg tggtatgatg     240
tgcacacttg ctagactcan aaaaaatact actctcataa atgggtggga gtattttggt     300
gacaacctac tttgcttggc tgagtgaagg aatgatattc atatattcat ttattccatg     360
gacatttagt tagtgctttt tatataccag gcatgatgct gagtgacact cttgtgtata     420
tttccaaatt tttgtacagt cgctgcacat atttgaaatc atatattaag acttccaaaa     480
aatgaagtcc ctggtttttc atggcaactt gatcagtaaa ggattcncct ctgtttggta     540
cttaaaacat ctactatatn gttnanatga aattccttttt cccncctcc cgaaaaaana     600
aagtggtggg gaaaaaaaa                                                  619
```

<210> SEQ ID NO 122
<211> LENGTH: 1475
<212> TYPE: DNA
<213> ORGANISM: Human

<400> SEQUENCE: 122

```
tccacctgtc cccgcagcgc cggctcgcgc cctcctgccg cagccaccga gccgccgtct      60
agcgccccga cctcgccacc atgagagccc tgctggcgcg cctgcttctc tgcgtcctgg     120
tcgtgagcga ctccaaaggc agcaatgaac ttcatcaagt tccatcgaac tgtgactgtc     180
taaatggagg aacatgtgtg tccaacaagt acttctccaa cattcactgg tgcaactgcc     240
caaagaaatt cggagggcag cactgtgaaa tagataagtc aaaaacctgc tatgagggga     300
atggtcactt ttaccgagga aaggccagca ctgacaccat gggccggccc tgcctgccct     360
ggaactctgc cactgtcctt cagcaaacgt accatgccca cagatctgat gctcttcagc     420
tgggcctggg gaaacataat tactgcagga acccagacaa ccggaggcga ccctggtgct     480
atgtgcaggt gggcctaaag ccgcttgtcc aagagtgcat ggtgcatgac tgcgcagatg     540
gaaaaaagcc ctcctctcct ccagaagaat taaaatttca gtgtggccaa aagactctga     600
ggccccgctt taagattatt ggggagaat tcaccaccat cgagaaccag ccctggtttg     660
cggccatcta caggaggcac cgggggggct ctgtcaccta cgtgtgtgga ggcagcctca     720
tcagcccttg ctgggtgatc agcgccacac actgcttcat tgattaccca agaaggagg     780
actacatcgt ctacctgggt cgctcaagc ttaactccaa cacgcaaggg gagatgaagt     840
ttgaggtgga aaacctcatc ctacacaagg actacagcgc tgacacgctt gctcaccaca     900
acgacattgc cttgctgaag atccgttcca aggagggcag gtgtgcgcag ccatcccgga     960
ctatacagac catctgcctg ccctcgatgt ataacgatcc ccagtttggc acaagctgtg    1020
agatcactgg ctttggaaaa gagaattcta ccgactatct ctatccggag cagctgaaga    1080
tgactgttgt gaagctgatt tcccaccggg agtgtcagca gccccactac tacggctctg    1140
aagtcaccac caaaatgctg tgtgctgctg acccacagtg gaaaacagat tcctgccagg    1200
gagactcagg ggaccccctc gtctgttccc tccaaggccg catgactttg actggaattg    1260
tgagctgggg ccgtgatgt gccctgaagg acaagccagg cgtctacacg agagtctcac    1320
acttcttacc ctggatccgc agtcacacca aggaagagaa tggcctggcc ctctgagggt    1380
```

```
cccagggag gaaacgggca ccacccgctt tcttgctggt tgtcattttt gcagtagagt    1440
catctccatc agctgtaaga agagactggg aagat                              1475

<210> SEQ ID NO 123
<211> LENGTH: 2294
<212> TYPE: DNA
<213> ORGANISM: Human

<400> SEQUENCE: 123
cagcgccggc tcgcgccctc ctgccgcagc caccgagccg ccgtctagcg ccccgacctc     60
gccaccatga gagccctgct ggcgcgcctg cttctctgcg tcctggtcgt gagcgactcc    120
aaaggcagca atgaacttca tcaagttcca tcgaactgtg actgtctaaa tggaggaaca    180
tgtgtgtcca acaagtactt ctccaacatt cactggtgca actgcccaaa gaaattcgga    240
gggcagcact gtgaaataga taagtcaaaa acctgctatg aggggaatgg tcacttttac    300
cgaggaaagg ccagcactga caccatgggc cggccctgcc tgccctggaa ctctgccact    360
gtccttcagc aaacgtacca tgcccacaga tctgatgctc ttcagctggg cctggggaaa    420
cataattact gcaggaaccc agacaaccgg aggcgaccct ggtgctatgt gcaggtgggc    480
ctaaagccgc ttgtccaaga gtgcatggtg catgactgcg cagatggaaa aaagccctcc    540
tctcctccag aagaattaaa atttcagtgt ggccaaaaga ctctgaggcc ccgctttaag    600
attattgggg gagaattcac caccatcgag aaccagccct ggtttgcggc catctacagg    660
aggcaccggg ggggctctgt cacctacgtg tgtggaggca cctcatcag cccttgctgg    720 gtgatcagcg ccacacactg cttcattgat tacccaaaga aggaggacta catcgtctac    780
ctgggtcgct caaggcttaa ctccaacacg caaggggaga tgaagtttga ggtggaaaac    840
ctaatcctac acaaggacta cagcgctgac acgcttgctc accacaacga cattgccttg    900
ctgaagatcc gttccaagga gggcaggtgt gcgcagccat cccggactat acagaccatc    960
tgcctgccct cgatgtataa cgatcccccag tttggcacaa gctgtgagat cactggcttt   1020
ggaaaagaga attctaccga ctatctctat ccggagcagc tgaaaatgac tgttgtgaag   1080
ctgatttccc accgggagtg tcagcagccc cactactacg gctctgaagt caccaccaaa   1140
atgctgtgtg ctgctgaccc acagtggaaa acagattcct gccagggaga ctcaggggga   1200
cccctcgtct gttcctcca aggccgcatg actttgactg gaattgtgag ctgggccgt    1260 ggatgtgccc tgaaggacaa gccaggcgtc tacacgagag tctcacactt cttaccctgg   1320
atccgcagtc acaccaagga agagaatggc ctggccctct gagggtcccc agggaggaaa   1380
cgggcaccac ccgctttctt gctggttgct atttttgcagt agagtcatct ccatcagctg   1440
taagaagagc tgggaatata ggctctgcac agatggattt gcctgtgcca ccaccaggc    1500 gaacgacaat agctttaccc tcaggcatag gcctgggtgc tggctgccca gacccctctg   1560
gccaggatgg aggggtggtc ctgactcaac atgttactga ccagcaactt gtcttttct   1620 ggactgaagc ctgcaggagt taaaaagggc agggcatctc ctgtgcatgg gctcgaaggg   1680
agagccagct cccccgaccg gtgggcattt gtgaggccca tggttgagaa atgaataatt   1740
tcccaattag gaagtgtaag cagctgaggt ctcttgaggg agcttagcca atgtgggagc   1800
agcggtttgg ggagcagaga cactaacgac ttcagggcag ggctctgata ttccatgaat   1860
gtatcaggaa atatatatgt gtgtgtatgt ttgcacactt gtgtgtgggc tgtgagtgta   1920
agtgtgagta agagctggtg tctgattgtt aagtctaaat atttccttaa actgtgtgga   1980
ctgtgatgcc acacagagtg gtctttctgg agaggttata ggtcactcct ggggcctctt   2040
```

```
gggtccccca cgtgacagtg cctgggaatg tattattctg cagcatgacc tgtgaccagc    2100
actgtctcag tttcactttc acatagatgt ccctttcttg ccagttatc ccttcctttt     2160 agcctagttc atccaatcct cactgggtgg ggtgaggacc actcctgtac actgaatatt    2220
tatatttcac tatttttatt tatattttg taattttaaa taaaagtgat caataaaatg     2280 tgattttct gatg                                                        2294
```

<210> SEQ ID NO 124
<211> LENGTH: 956
<212> TYPE: DNA
<213> ORGANISM: Human

<400> SEQUENCE: 124

```
gatgagttcc gcaccaagtt tgagacagac caggccctgc cctgagtgt ggaggccgac      60 atcaatggcc tgcgcagggt gctggatgag ctgaccctgg ccagagccga cctggagatg    120
cagattgaga acctcaagga ggagctggcc tacctgaaga agaaccacga ggaggagatg    180
aacgccctgc gaggccaggt gggtggtgag atcaatgtgg agatggacgc tgccccaggc    240
gtggacctga gccgcatcct caacgagatg cgtgaccagt atgagaagat ggcagagaag    300
aaccgcaagg atgccgagga ttggttcttc agcaagacag aggaactgaa ccgcgaggtg    360
gccaccaaca gtgagctggt gcagagtggc aagagtgaga tctcggagct ccggcgcacc    420
atgcaggcct ggagataga gctgcagtcc cagctcagca tgaaagcatc cctggagggc    480
aacctggcgg agacagagaa ccgctactgc gtgcagctgt cccagatcca ggggctgatt    540
ggcagcgtgg aggagcagct ggcccagctt cgctgcgaga tggagcagca gaaccaggaa    600
tacaaaatcc tgctggatgt gaagacgcgg ctggagcagg agattgccac ctaccgccgc    660
ctgctggagg gagaggatgc ccacctgact cagtacaaga agaaccggt gaccacccgt     720 caggtgcgta ccattgtgga agaggtccag gatggcaagg tcatctcctc ccgcgagcag    780
gtccaccaga ccacccgctg aggactcagc taccccggcc ggccacccag gaggcaggga    840
cgcagccgcc ccatctgccc cacagtctcc ggcctctcca gcctcagccc cctgcttcag    900
tcccttcccc atgcttcctt gcctgatgac aataaaagct tgttgactca gctatg        956
```

<210> SEQ ID NO 125
<211> LENGTH: 486
<212> TYPE: DNA
<213> ORGANISM: Human
<220> FEATURE:
<221> NAME/KEY: unsure
<222> LOCATION: (16)...(16)

<400> SEQUENCE: 125

```
aaattatata tagtgnttca gctcccattg tggtgttcat agtcttctag gaacagataa     60
acttaagtat tcaattcact cttggcattt tttctttaat ataggctttt tagcctattt    120
ttggaaaact gcttttcttc tgagaacctt attctgaatg tcatcaactt taccaaacct    180
tctaagtcca gagctaactt agtactgttt aagttactat tgactgaatt tcttcatttt    240
tctgtttagc cagtgttacc aaggtaagct ggggaatgaa gtataccaac ttctttcaga    300
gcattttagg acattatggc agctttagaa ggctgtcttg tttctagcca agggagagcc    360
agcgcaggtt ttggatacta gagaaagtca tttgcttgta ctattgccat tttagaaagc    420
tctgatgtga attcaaattt tacctctgtt acttaaagcc aacaattta aggcagtagt     480 tttact                                                                486
```

<210> SEQ ID NO 126
<211> LENGTH: 3552
<212> TYPE: DNA
<213> ORGANISM: Human

<400> SEQUENCE: 126

| | | | | | |
|---|---|---|---|---|---|
| cggcaggcag | gtctcgtctc | ggcaccctcc | cggcgcccgc | gttctcctgg | ccctgcccgg | 60 |
| catcccgatg | gccgccgctg | ggccccggcg | ctccgtgcgc | ggagccgtct | gcctgcatct | 120 |
| gctgctgacc | ctcgtgatct | tcagtcgtgc | tggtgaagcc | tgcaaaaagg | tgatacttaa | 180 |
| tgtaccttct | aaactagagg | cagacaaaat | aattggcaga | gttaatttgg | aagagtgctt | 240 |
| caggtctgca | gacctcatcc | ggtcaagtga | tcctgatttc | agagttctaa | atgatgggtc | 300 |
| agtgtacaca | gccagggctg | ttgcgctgtc | tgataagaaa | agatcattta | ccatatggct | 360 |
| ttctgacaaa | aggaaacaga | cacagaaaga | ggttactgtg | ctgctagaac | atcagaagaa | 420 |
| ggtatcgaag | acaagacaca | ctagagaaac | tgttctcagg | cgtgccaaga | ggagatgggc | 480 |
| acctattcct | tgctctatgc | aagagaattc | cttgggccct | ttcccattgt | ttcttcaaca | 540 |
| agttgaatct | gatgcagcac | agaactatac | tgtcttctac | tcaataagtg | acgtggagt | 600 |
| tgataaagaa | cctttaaatt | tgttttatat | agaaagagac | actggaaatc | tattttgcac | 660 |
| tcggcctgtg | gatcgtgaag | aatatgatgt | ttttgatttg | attgcttatg | cgtcaactgc | 720 |
| agatggatat | tcagcagatc | tgccctccc | actacccatc | agggtagagg | atgaaaatga | 780 |
| caaccaccct | gttttcacag | aagcaattta | taattttgaa | gttttggaaa | gtagtagacc | 840 |
| tggtactaca | gtgggggtgg | tttgtgccac | agacagagat | gaaccggaca | caatgcatac | 900 |
| gcgcctgaaa | tacagcattt | tgcagcagac | accaaggtca | cctgggctct | ttctgtgca | 960 |
| tcccagcaca | ggcgtaatca | ccacagtctc | tcattatttg | gacagagagg | ttgtagacaa | 1020 |
| gtactcattg | ataatgaaag | tacaagacat | ggatggccag | ttttttggat | tgataggcac | 1080 |
| atcaacttgt | atcataacag | taacagattc | aaatgataat | gcacccactt | tcagacaaaa | 1140 |
| tgcttatgaa | gcatttgtag | aggaaaatgc | attcaatgtg | gaaatcttac | gaatacctat | 1200 |
| agaagataag | gatttaatta | acactgccaa | ttggagagtc | aatttttacca | ttttaaaggg | 1260 |
| aaatgaaaat | ggacatttca | aaatcagcac | agacaaagaa | actaatgaag | gtgttctttc | 1320 |
| tgttgtaaag | ccactgaatt | atgaagaaaa | ccgtcaagtg | aacctggaaa | ttggagtaaa | 1380 |
| caatgaagcg | ccatttgcta | gagatattcc | cagagtgaca | gccttgaaca | gagccttggt | 1440 |
| tacagttcat | gtgagggatc | tggatgaggg | gcctgaatgc | actcctgcag | cccaatatgt | 1500 |
| gcggattaaa | gaaaacttag | cagtgggtc | aaagatcaac | ggctataagg | catatgaccc | 1560 |
| cgaaaataga | aatggcaatg | gtttaaggta | caaaaaattg | catgatccta | aggttggat | 1620 |
| caccattgat | gaaatttcag | ggtcaatcat | aacttccaaa | atcctggata | gggaggttga | 1680 |
| aactcccaaa | aatgagttgt | ataatattac | agtcctggca | atagacaaag | atgatagatc | 1740 |
| atgtactgga | acacttgctg | tgaacattga | agatgtaaat | gataatccac | cagaaatact | 1800 |
| tcaagaatat | gtagtcattt | gcaaaccaaa | aatggggtat | accgacattt | tagctgttga | 1860 |
| tcctgatgaa | cctgtccatg | gagctccatt | ttatttcagt | ttgcccaata | cttctccaga | 1920 |
| aatcagtaga | ctgtggagcc | tcaccaaagt | taatgataca | gctgccgtc | tttcatatca | 1980 |
| gaaaaatgct | ggatttcaag | aatataccat | tcctattact | gtaaaagaca | gggccggcca | 2040 |
| agctgcaaca | aaattattga | gagttaatct | gtgtgaatgt | actcatccaa | ctcagtgtcg | 2100 |

-continued

```
tgcgacttca aggagtacag gagtaatact tggaaaatgg gcaatccttg caatattact      2160
gggtatagca ctgctctttt ctgtattgct aactttagta tgtggagttt ttggtgcaac      2220
taaagggaaa cgttttcctg aagatttagc acagcaaaac ttaattatat caaacacaga      2280
agcacctgga gacgatagag tgtgctctgc caatggattt atgacccaaa ctaccaacaa      2340
ctctagccaa ggttttgtg gtactatggg atcaggaatg aaaaatggag ggcaggaaac       2400
cattgaaatg atgaaaggag gaaaccagac cttggaatcc tgccgggggg ctgggcatca      2460 tcatacccctg gactcctgca ggggaggaca cacgagggtg gacaactgca gatacactta    2520
ctcggagtgg cacagttta ctcaaccccg tctcggtgaa aaattgcatc gatgtaatca      2580
gaatgaagac cgcatgccat cccaagatta tgtcctcact ataactatg agggaagagg      2640 atctccagct ggttctgtgg gctgctgcag tgaaaagcag gaagaagatg gccttgactt      2700
tttaaataat ttggaaccca aatttattac attagcagaa gcatgcacaa agagataatg      2760
tcacagtgct acaattaggt ctttgtcaga cattctggag gtttccaaaa ataatattgt      2820
aaagttcaat ttcaacatgt atgtatatga tgatttttt ctcaattttg aattatgcta       2880
ctcaccaatt tatattttta aagcaagttg ttgcttatct tttccaaaaa gtgaaaaatg      2940
ttaaaacaga caactggtaa atctcaaact ccagcactgg aattaaggtc tctaaagcat     3000
ctgctctttt tttttttac agatattta gtaataaata tgctggataa atattagtcc       3060
aacaatagct aagttatgct aatatcacat tattatgtat tcactttaag tgatagttta     3120
aaaaataaac aagaaatatt gagtatcact atgtgaagaa agttttggaa aagaaacaat     3180
gaagactgaa ttaaattaaa aatgttgcag ctcataaaga attggactca ccctactgc      3240 actaccaaat tcatttgact ttggaggcaa aatgtgttga agtgccctat gaagtagcaa     3300
ttttctatag gaatatagtt ggaaataaat gtgtgtgtgt atattattat taatcaatgc     3360
aatatttaaa tgaaatgaga acaaagagga aaatggtaaa aacttgaaat gaggctgggg     3420
tatagtttgt cctacaatag aaaaaagaga gagcttccta ggcctgggct cttaaatgct     3480
gcattataac tgagtctatg aggaaatagt tcctgtccaa tttgtgtaat ttgtttaaaa     3540
ttgtaaataa at                                                         3552
```

<210> SEQ ID NO 127
<211> LENGTH: 754
<212> TYPE: DNA
<213> ORGANISM: Human

<400> SEQUENCE: 127

```
ttttttttt ttgtcattgt tcattgattt taatgagaaa gctaagagag gaaataagta       60
gcctttcaaa ggtcacacag aagtaagtga cagatccagg attcatatcc aagcattctg      120
gctctagtgt ccatgcttct caaccattat gacccaatat tcaaccaaat caatactgaa     180
ggacacgtga atgtatccg gtattttact attacaaaca aaatccaat gaacattctt       240 gaagacatac acaaaaataa tggttacaat agaagttact ggaattgaaa ttttggttca     300
acctatatta aaatgtaagg cttttgatat agctaataga tttttgaaat gatcagtctt     360
aacgtttgta ggggagcaca ctcctgcatg gggaaaagat tcactgtgaa gcacagagca     420 ccttatggt tggatcatct tgtcattaaa gttcaggcgt tatctatcct gtaagtggca      480
gaatcaagac tgcaatatcg cctgcttttc tttttaactc atgttttccc ttgactacac     540
tggtcctcaa agtaaaaccc ctgtgtcagt gtactattca tggaatactc tgcaattata     600
accaccttct aatactttta atacccaatc aaaatttatt atacatatgt atcatagata     660
```

```
ctcatctgta aagctgtgct tcaaaatagt gatctcttcc caacattaca atatatatta    720
atgatgtcga acctgcccgg gcggccgctc gaag                                754
```

<210> SEQ ID NO 128
<211> LENGTH: 374
<212> TYPE: DNA
<213> ORGANISM: Human

<400> SEQUENCE: 128

```
aggttttgat taaaaaggca aatgatttta ttgttcgata atcttttaaa aaaataagag     60
gaaggagtaa aattaaagat gaaagatgat ttttatttcc ttgtgacctc tatatccccc    120
ttcccctgcc cttggtaagt aactcttgat ggagaaagga ttaaagactc ttatttaacc    180
aaaaaacaga gccagctaat catttccaaa ggttagtatc tccctgctga cctcttcttt    240
ggtttaattg aataaaacta tatgttcata tatgttattaa aacaactcag aataacatct    300
tttcttcctt agttaaggca ttataagggc tatactatca tccataataa ccaaggcaat    360
aacttaaaaa gctg                                                      374
```

<210> SEQ ID NO 129
<211> LENGTH: 546
<212> TYPE: DNA
<213> ORGANISM: Human

<400> SEQUENCE: 129

```
agtgtgatgg atatctgcag aattcgggct aagcgtggtc gcggcccgag gtctggaact     60
tcccagcacy tgaaaaggag cctcctgagc tgactcggct aaagccccac tttcgctcct    120
cctcatttct gcctactgat ttccttggag cattcatctg aatattaccg tttgctgtgt    180
aacctggtac atacatagca tgactccctg gaatagagtg ggctggggtg cttatgctgg    240
gagagtgatt gacatgcact ttcaagctat atctaccatt tgcagcaaag gagaaaaaat    300
acctcgagta aattccatca ttttttataa catcagcacc tgctccatca tcaaggagtc    360
tcagcgtaac aggatctcca gtctctggct caactgtggc agtgacagtg cattaagaa    420 tgggataaaa tccctgtttc acattggcat aaatcatcac aggatgagga aaatggaggc    480
tgtctctttc cacaaaggct tccacagtgg ctgggggcac agacctgccc gggcggccgc    540
tcgaaa                                                               546
```

<210> SEQ ID NO 130
<211> LENGTH: 5156
<212> TYPE: DNA
<213> ORGANISM: Human

<400> SEQUENCE: 130

```
accaaccgag gcgccgggca gcgacccctg cagcggagac agagactgag cggcccggca     60
ccgccatgcc tgcgctctgg ctgggctgct gcctctgctt gtcgctcctc ctgcccgcag    120
cccgggccac ctccaggagg gaagtctgtg attgcaatgg gaagtccagg cagtgtatct    180
ttgatcggga acttcacaga caaactggta atggattccg ctgcctcaac tgcaatgaca    240
acactgatgg cattcactgc gagaagtgca agaatggctt ttaccggcac agagaaaggg    300
accgctgttt gccctgcaat tgtaactcca aggttctct tagtgctcga tgtgacaact    360
ccggacggtc cagctgtaaa ccaggtgtga caggagccga atgcgaccga tgtctgccag    420
gcttccacat gctcacggat gcggggtgca cccaagacca gagactgcta gactccaagt    480
```

-continued

```
gtgactgtga cccagctggc atcgcagggc cctgtgacgc gggccgctgt gtctgcaagc      540
cagctgtcac tggagaacgc tgtgataggt gtcgatcagg ttactataat ctggatgggg      600
ggaaccctga gggctgtacc cagtgtttct gctatgggca ttcagccagc tgccgcagct      660
ctgcagaata cagtgtccat aagatcacct ctacctttca tcaagatgtt gatggctgga      720
aggctgtcca acgaaatggg tctcctgcaa agctccaatg gtcacagcgc catcaagatg      780
tgtttagctc agcccaacga ctagaccctg tctattttgt ggctcctgcc aaatttcttg      840
ggaatcaaca ggtgagctat ggtcaaagcc tgtcctttga ctaccgtgtg acagaggag       900
gcagacaccc atctgcccat gatgtgattc tggaaggtgc tggtctacgg atcacagctc      960
ccttgatgcc acttggcaag acactgcctt gtgggctcac caagacttac acattcaggt     1020
taaatgagca tccaagcaat aattggagcc cccagctgag ttactttgag tatcgaaggt     1080
tactgcggaa tctcacagcc ctccgcatcc gagctacata tggagaatac agtactgggt     1140
acattgacaa tgtgaccctg atttcagccc gccctgtctc tggagcccca gcaccctggg     1200
ttgaacagtg tatatgtcct gttgggtaca agggcaatt ctgccaggat tgtgcttctg      1260
gctacaagag agattcagcg agactggggc cttttggcac ctgtattcct tgtaactgtc     1320
aaggggagg ggcctgtgat ccagacacag gagattgtta ttcagggat gagaatcctg       1380
acattgagtg tgctgactgc ccaattggtt tctacaacga tccgcacgac ccccgcagct     1440
gcaagccatg tccctgtcat aacgggttca gctgctcagt gatgccggag acggaggagg     1500
tggtgtgcaa taactgccct cccggggtca ccggtgcccg ctgtgagctc tgtgctgatg     1560
gctactttgg ggacccctt ggtgaacatg cccagtgag gccttgtcag ccctgtcaat       1620
gcaacaacaa tgtggacccc agtgcctctg ggaattgtga ccggctgaca ggcaggtgtt     1680
tgaagtgtat ccacaacaca gccggcatct actgcgacca gtgcaaagca ggctacttcg     1740
gggacccatt ggctcccaac ccagcagaca agtgtcgagc ttgcaactgt aaccccatgg     1800
gctcagagcc tgtaggatgt cgaagtgatg gcacctgtgt ttgcaagcca ggatttggtg     1860
gccccaactg tgagcatgga gcattcagct gtccagcttg ctataatcaa gtgaagattc     1920
agatggatca gtttatgcag cagcttcaga gaatggaggc cctgatttca aaggctcagg     1980
gtggtgatgg agtagtacct gatacagagc tggaaggcag gatgcagcag gctgagcagg     2040
cccttcagga cattctgaga gatgcccaga tttcagaagg tgctagcaga tcccttggtc     2100
tccagttggc caaggtgagg agccaagaga acagctacca gagccgcctg gatgacctca     2160
agatgactgt ggaaagagtt cgggctctgg gaagtcagta ccagaaccga gttcgggata     2220
ctcacaggct catcactcag atgcagctga gcctggcaga aagtgaagct tccttgggaa     2280
acactaacat tcctgcctca gaccactacg tggggccaaa tggctttaaa gtctggctc      2340
aggaggccac aagattagca gaaagccacg ttgagtcagc cagtaacatg gagcaactga     2400
caagggaaac tgaggactat tccaaacaag ccctctcact ggtgcgcaag gccctgcatg     2460
aaggagtcgg aagcggaagc ggtagcccgg acggtgctgt ggtgcaaggg cttgtggaaa     2520
aattggagaa accaagtcc ctggcccagc agttgacaag ggaggccact caagcggaaa      2580
ttgaagcaga taggtcttat cagcacagtc tccgcctcct ggattcagtg tctcggcttc     2640
agggagtcag tgatcagtcc tttcaggtgg aagaagcaaa gaggatcaaa caaaaagcgg     2700
attcactctc aagcctggta accaggcata tggatgagtt caagcgtaca cagaagaatc     2760
tgggaaactg gaaagaagaa gcacagcagc tcttacagaa tggaaaaagt gggagagaga     2820
aatcagatca gctgctttcc cgtgccaatc ttgctaaaag cagagcacaa gaagcactga     2880
```

```
gtatgggcaa tgccactttt tatgaagttg agagcatcct taaaaacctc agagagtttg      2940
acctgcaggt ggacaacaga aaagcagaag ctgaagaagc catgaagaga ctctcctaca      3000
tcagccagaa ggtttcagat gccagtgaca agacccagca agcagaaaga gccctgggga      3060
gcgctgctgc tgatgcacag agggcaaaga atggggccgg ggaggccctg gaaatctcca      3120
gtgagattga acaggagatt gggagtctga acttggaagc caatgtgaca gcagatggag      3180
ccttggccat ggaaaaggga ctggcctctc tgaagagtga gatgagggaa gtggaaggag      3240
agctggaaag gaaggagctg gagtttgaca cgaatatgga tgcagtacag atggtgatta      3300
cagaagccca aaggttgat accagagcca agaacgctgg ggttacaatc caagacacac      3360
tcaacacatt agacggcctc ctgcatctga tggaccagcc tctcagtgta gatgaagagg      3420
ggctggtctt actggagcag aagctttccc gagccaagac ccagatcaac agccaactgc      3480
ggcccatgat gtcagagctg aagagaggg cacgtcagca gagggccac ctccatttgc       3540 tggagacaag catagatggg attctggctg atgtgaagaa cttggagaac attagggaca      3600
acctgccccc aggctgctac aatacccagg ctccttgagca cagtgaagc tgccataaat      3660 atttctcaac tgaggttctt gggatacaga tctcaggget cgggagccat gtcatgtgag      3720
tgggtgggat gggacatttt gaacatgttt aatgggtatg ctcaggtcaa ctgacctgac      3780
cccattcctg atcccatggc caggtggttg tcttattgca ccatactcct tgcttcctga      3840
tgctgggcaa tgaggcagat agcactgggt gtgagaatga tcaaggatct ggaccccaaa      3900
gaatagactg gatggaaaga caaactgcac aggcagatgt ttgcctcata atagtcgtaa      3960
gtggagtcct ggaatttgga caagtgctgt tgggatatag tcaacttatt ctttgagtaa      4020
tgtgactaaa ggaaaaaact ttgactttgc ccaggcatga aattcttcct aatgtcagaa      4080
cagagtgcaa cccagtcaca ctgtggccag taaaatacta ttgcctcata ttgtcctctg      4140
caagcttctt gctgatcaga gttcctccta cttacaaccc agggtgtgaa catgttctcc      4200
attttcaagc tggaagaagt gagcagtgtt ggagtgagga cctgtaaggc aggcccattc      4260
agagctatgg tgcttgctgg tgcctgccac cttcaagttc tggacctggg catgacatcc      4320
tttcttttaa tgatgccatg gcaacttaga gattgcattt ttattaaagc atttcctacc      4380
agcaaagcaa atgttgggaa agtatttact ttttcggttt caaagtgata gaaaagtgtg      4440
gcttgggcat tgaaagaggt aaaattctct agatttatta gtcctaattc aatcctactt      4500
ttagaacacc aaaaatgatg cgcatcaatg tattttatct tattttctca atctcctctc      4560
tctttcctcc acccataata agagaatgtt cctactcaca cttcagctgg gtcacatcca      4620
tccctccatt catccttcca tccatctttc catccattac ctccatccat ccttccaaca      4680 tatattta gagtacctac tgtgtgccag gggctggtgg gacagtggtg acatagtctc        4740
tgccctcata gagttgattg tctagtgagg aagacaagca ttttaaaaa ataaatttaa        4800 acttacaaac tttgtttgtc acaagtggtg tttattgcaa taccgcttg gtttgcaacc       4860 tctttgctca acagaacata tgttgcaaga ccctcccatg ggggcacttg agttttggca      4920
aggctgacag agctctgggt tgtgcacatt tctttgcatt ccagctgtca ctctgtgcct      4980
ttctacaact gattgcaaca gactgttgag ttatgataac accagtggga attgctggag      5040
gaaccagagg cacttccacc ttggctggga agactatggt gctgccttgc ttctgtattt      5100
ccttggattt tcctgaaagt gttttaaat aagaacaat tgttagaaaa aaaaaa         5156
```

<210> SEQ ID NO 131

<211> LENGTH: 671
<212> TYPE: DNA
<213> ORGANISM: Human

<400> SEQUENCE: 131

| | | | | | |
|---|---|---|---|---|---|
| aggtctggag | ggcccacagc | cggatgtggg | acaccgggaa | aaagtggtca | tagcacacat | 60 |
| ttttgcatcc | cggttgcagt | gtgttgcaga | cgaagtcctc | ttgctcgtca | ccccacactt | 120 |
| cctgggcagc | caycacgagg | atcatgactc | ggaaaataaa | gatgactgtg | atccacacct | 180 |
| tcccgatgct | ggtggagtgt | tgttgacac | ccccgatgaa | agtgtgcagc | gtcccccaat | 240 |
| ccattgcgct | ggtttatccc | tgagtcctgt | ttccaacgac | tgccagtgtt | tcagacccaa | 300 |
| agaatgaggg | caagatccct | ctgcgagggt | ttcagacctc | cttctcctac | cccactggag | 360 |
| tgcctagaag | ccaatgggtg | cacagtgatg | atacgaatgt | caatctttgc | tcggtcagtg | 420 |
| aggatgtcgc | ctggaatatt | caaattgaat | tacagatgca | tgaagagggc | gtacaagtta | 480 |
| gaattttcct | ttcgccatac | agaaattgtt | tagccagatc | ttctgtactt | cttttccttc | 540 |
| cctgacccct | tcctgctccc | aggaagggag | gtcagccccg | tttgcaaaac | acaggatgcc | 600 |
| cgtgacaccg | gagacaggtc | ttcttcaccg | acaggaagtg | ccttctggtg | cctgcacgtt | 660 |
| ttaactgcta | t | | | | | 671 |

<210> SEQ ID NO 132
<211> LENGTH: 590
<212> TYPE: DNA
<213> ORGANISM: Human

<400> SEQUENCE: 132

| | | | | | |
|---|---|---|---|---|---|
| ctgaatggaa | aagcttatgg | ctctgtgatg | atattagtga | ccagcggaga | tgataagctt | 60 |
| cttggcaatt | gcttacccac | tgtgctcagc | agtggttcaa | caattcactc | cattgccctg | 120 |
| ggttcatctg | cagccccaaa | tctggaggaa | ttatcacgtc | ttacaggagg | tttaaagttc | 180 |
| tttgttccag | atatatcaaa | ctccaatagc | atgattgatg | ctttcagtag | aatttcctct | 240 |
| ggaactggag | acattttcca | gcaacatatt | cagcttgaaa | gtacaggtga | aaatgtcaaa | 300 |
| cctcaccatc | aattgaaaaa | cacagtgact | gtggataata | ctgtgggcaa | cgacactatg | 360 |
| tttctagtta | cgtggcaggc | cagtggtcct | cctgagatta | tattatttga | tcctgatgga | 420 |
| cgaaaatact | acacaaataa | ttttatcacc | aatctaactt | ttcggacagc | tagtctttgg | 480 |
| attccaggaa | cagctaagcc | tgggcactgg | acttacaccc | tgaacaatac | ccatcattct | 540 |
| ctgcaagccc | tgaaagtgac | agtgacctct | cgcgcctcca | actcagacct | | 590 |

<210> SEQ ID NO 133
<211> LENGTH: 581
<212> TYPE: DNA
<213> ORGANISM: Human

<400> SEQUENCE: 133

| | | | | | |
|---|---|---|---|---|---|
| aggtcctgtc | cgggggcact | gagaactccc | tctggaattc | ttgggggtg | ttggggagag | 60 |
| actgtgggcc | tggagataaa | acttgtctcc | tctaccacca | ccctgtaccc | tagcctgcac | 120 |
| ctgtcctcat | ctctgcaaag | ttcagcttcc | ttccccaggt | ctctgtgcac | tctgtcttgg | 180 |
| atgctctggg | gagctcatgg | gtggaggagt | ctccaccaga | gggaggctca | ggggactggt | 240 |
| tgggccaggg | atgaatattt | gagggataaa | aattgtgtaa | gagccaaaga | attggtagta | 300 |
| ggggagaac | agagaggagc | tgggctatgg | gaaatgattt | gaataatgga | gctgggaata | 360 |
| tggctggata | tctggtacta | aaaagggtc | tttaagaacc | tacttcctaa | tctcttcccc | 420 |

```
aatccaaacc atagctgtct gtccagtgct ctcttcctgc ctccagctct gccccaggct      480
cctcctagac tctgtccctg ggctagggca ggggaggagg gagagcaggg ttgggggaga      540
ggctgaggag agtgtgacat gtggggagag gaccagacct c                          581

<210> SEQ ID NO 134
<211> LENGTH: 4797
<212> TYPE: DNA
<213> ORGANISM: Human
<220> FEATURE:
<221> NAME/KEY: modified_base
<222> LOCATION: (135)
<223> OTHER INFORMATION: Where n is a, c, g or t
<220> FEATURE:
<221> NAME/KEY: modified_base
<222> LOCATION: (501)
<223> OTHER INFORMATION: Where n is a, c, g or t
<220> FEATURE:
<221> NAME/KEY: modified_base
<222> LOCATION: (4421)
<223> OTHER INFORMATION: Where n is a, c, g or t
<220> FEATURE:
<221> NAME/KEY: modified_base
<222> LOCATION: (4467)
<223> OTHER INFORMATION: Where n is a, c, g or t
<220> FEATURE:
<221> NAME/KEY: modified_base
<222> LOCATION: (4468)
<223> OTHER INFORMATION: Where n is a, c, g or t
<220> FEATURE:
<221> NAME/KEY: modified_base
<222> LOCATION: (4698)
<223> OTHER INFORMATION: Where n is a, c, g or t

<400> SEQUENCE: 134
cctgggacca aagtgctgcc cagagctgag ggtcctggag ccacatgaga aggcttctcc       60
ctgtgtacct gtgcagcaca gggtagggtg agtccactca gctgtctagg agaggaccca     120
ggagcagcag agacncgcca agcctttact cataccatat tctgatcctt ttccagcaaa     180
ttgtggctac taatttgccc cctgaagatc aagatggctc tggggatgac tctgacaact     240
tctccggctc aggtgcaggt gaggttgtca tgggggcccc ccccacccaa gacggcaaca     300
ggtcatgcct gggggcagtg gtcaggcagt ctcctgtgtt tactgagcat gtactgagtg     360
caccctgcct gccctgtctc cacccagctg gctccaaagg gcaatgctga ggagaggaat     420
ggggtcgtga gctgctgtta aggagagctc atgcttggag gtgaggtgaa ggctgtgagc     480
tccagaaggc cccagggcgc nctgctgcac gcaggctcat attcactagg aatagcttta     540
ctcactaaga aacctctgga accccttca gaaggttatt tgactcctga gcctctattt      600
tctcatctgc aaaatgggaa taatacccttg acctgataag cttgtggagc tgtaaggcag    660
cacagagcca gctggggtgt agctcttcca tccaagctcc cttccttact tccccttcc     720 tgtggggact gggggagaga agtccctgag ctggaggtgg tcaggaaagc ttcacagagg     780
aggtggctct tgagtggacc tcaggaagag gggtgagaga gctaaggaag gaggctgagg     840
tcatccctgg ggaagtgacc tagcggaggc ctgagctg caaggtagga tatctgttgt       900
tggaagtgtc tgttgttgga agtgggggcc tttttttcag ggagggtggg gccagagaag     960
tgtgtgccct gggataagta ggataaccac agtagttatg cccctaaggg atgcccaccc    1020 caccctgtg gtcacagaaa agctttccca ggtggcctag gcacctgtct cgtggctcca     1080
gagacaggct gcacctgaca cacacaatgg aaggacagct ctccttgtcc attttccaag    1140
gagcttagcc tcagctgcct tgtccaggta ctagcctcc tcatagcctg agcttggcca     1200
```

```
                                              -continued gcccaggtgc tctggagcct cccccgaccc acccaacaca ctctgcttct ggtcctcccc      1260 acccccccacc tccccaacac actctgcttc tggtcctgca ggtgctttgc aagatatcac     1320
cttgtcacag cagaccccct ccacttggaa ggacacgcag ctcctgacgg ctattcccac     1380
gtctccagaa cccaccggcc tggaggctac agctgcctcc acctccaccc tgccggctgg     1440
agagggcccc aaggagggag aggctgtagt cctgccagaa gtggagcctg gcctcaccgc     1500
ccgggagcag gaggccaccc cccgacccag ggagaccaca cagctcccga ccactcatca     1560
ggcctcaacg accacagcca ccacggccca ggagcccgcc acctcccacc ccacagggga     1620
catgcagcct ggccaccatg agacctcaac ccctgcagga cccagccaag ctgaccttca     1680
cactccccac acagaggatg gaggtccttc tgccaccgag agggctgctg aggatggagc     1740
ctccagtcag ctcccagcag cagagggctc tggggagcag gtgagtggcc tctgcattcc     1800
ttgggaaatt gagtgggttg gtcctaatgc ctggcacttg gcaggcccta cacctgtgcc     1860
ctgcgcgatc tcgtattcct caccaggaag acagggcaca ggggccgcct tcccctaccc     1920
ccagggcctc gcagagcagg acagactaac tatgagatca gagcagaagc acccttaaag     1980
atcacccaag agagggctcc caaactcaca atccaaactt gcagccctcg tcgaagagtg     2040
aacgttatac cagtcatttt atttatagct tcgtggattt acgcttacac taaatagtct     2100
gctattcata caaaatgtgt gctttgtatc acttttttgtg atatccatgc catggtccag     2160
ccagggtccg gagttgatgt ggcaagaagg cctggctttc gggccctgtg cgatcctggt     2220
ttgggtgcat ctgagtgggt ggtggcaaag atcagggagg caggagctgc ttctgggtct     2280
gtagtggagc tggttgctgc tgctggcggt gacctggcca acccaatctg ccctgccct     2340 cccacaggac ttcacctttg aaacctcggg ggagaatacg gctgtagtgg ccgtggagcc     2400
tgaccgccgg aaccagtccc cagtggatca ggggccacg ggggcctcac agggcctcct     2460
ggacaggaaa gaggtgctgg gagtgagtt ttctttcagg ggggtagttt ggggtgaatt      2520
gctgctgtgg ggtcagggtg gggctgacca cagccaaggc cactgctttg ggagggtctg     2580
cacgagagcc caaggagccg ctgagctgag ctggccccgt ctacctgccc tagggtcat     2640 tgccggaggc ctcgtggggc tcatctttgc tgtgtgcctg gtgggtttca tgctgtaccg     2700
catgaagaag aaggacgaag gcagctactc cttggaggag ccgaaacaag ccaacggcgg     2760
ggcctaccag aagcccacca acaggagga attctatgcc tgacgcggga gccatgcgcc     2820
ccctccgccc tgccactcac taggccccca cttgcctctt ccttgaagaa ctgcaggccc     2880
tggcctcccc tgccaccagg ccacctcccc agcattccag cccctctggt cgctcctgcc     2940
cacggagtcg tgggtgtgct gggagctcca ctctgcttct ctgacttctg cctggagact     3000
tagggcacca ggggtttctc gcataggacc tttccaccac agccagcacc tggcatcgca     3060
ccattctgac tcggtttctc caaactgaag cagcctctcc ccaggtccag ctctggaggg     3120
gagggggatc cgactgcttt ggacctaaat ggcctcatgt ggctggaaga tcctgcgggt     3180
ggggcttggg gctcacacac ctgtagcact tactggtagg accaagcatc ttgggggggt     3240
ggccgctgag tggcagggga caggagtcac tttgtttcgt ggggaggtct aatctagata     3300
tcgacttgtt tttgcacatg tttcctctag ttctttgttc atagcccagt agaccttgtt     3360
acttctgagg taagttaagt aagttgattc ggtatccccc catcttgctt ccctaatcta     3420
tggtcgggag acagcatcag ggttaagaag acttttttttt tttttttaa actaggagaa     3480 ccaaatctgg aagccaaaat gtaggcttag tttgtgtgtt gtctcttgag tttgtcgctc     3540
atgtgtgcaa cagggtatgg actatctgtc tggtggcccc gttctggtgg tctgttggca     3600
```

```
ggctggccag tccaggctgc cgtggggccg ccgcctcttt caagcagtcg tgcctgtgtc    3660
catgcgctca gggccatgct gaggcctggg ccgctgccac gttggagaag cccgtgtgag    3720
aagtgaatgc tgggactcag ccttcagaca gagaggactg tagggagggc ggcaggggcc    3780
tggagatcct cctgcaggct cacgcccgtc ctcctgtggc gccgtctcca ggggctgctt    3840
cctcctggaa attgacgagg ggtgtcttgg gcagagctgg ctctgagcgc ctccatccaa    3900
ggccaggttc tccgttagct cctgtggccc caccctgggc cctgggctgg aatcaggaat    3960
attttccaaa gagtgatagt cttttgcttt tggcaaaact ctacttaatc caatgggttt    4020
ttccctgtac agtagatttt ccaaatgtaa taaactttaa tataaagtag tctgtgaatg    4080
ccactgcctt cgcttcttgc ctctgtgctg tgtgtgacgt gaccggactt ttctgcaaac    4140
accaacatgt tgggaaactt ggctcgaatc tctgtgcctt cgtctttccc atggggaggg    4200
attctggttc cagggtccct ctgtgtattt gcttttttgt tttggctgaa attctcctgg    4260
aggtcggtag gttcagccaa ggttttataa ggctgatgtc aatttctgtg ttgccaagct    4320
ccaagcccat cttctaaatg gcaaaggaag gtggatggcc ccagcacagc ttgacctgag    4380
gctgtggtca cagcggaggt gtggagccga ggcctacccc ncagacacct tggacatcct    4440
cctcccaccc ggctgcagag gccagannec agcccagggt cctgcactta cttgcttatt    4500
tgacaacgtt tcagcgactc cgttggccac tccgagagtg ggccagtctg tggatcagag    4560
atgcaccacc aagccaaggg aacctgtgtc cggtattcga tactgcgact ttctgcctgg    4620
agtgtatgac tgcacatgac tcggggggtgg ggaaaggggt cggctgacca tgctcatctg    4680
ctggtccgtg ggacggttcc caagccagag gtgggttcat ttgtgtaacg acaataaacg    4740
gtacttgtca tttcgggcaa cggctgctgt ggtggtggtt gagtctcttc ttggcct       4797
```

<210> SEQ ID NO 135
<211> LENGTH: 2856
<212> TYPE: DNA
<213> ORGANISM: Human

<400> SEQUENCE: 135

```
tagtcgcggg tccccgagtg agcacgccag ggagcaggag accaaacgac gggggtcgga     60
gtcagagtcg cagtgggagt ccccggaccg gagcacgagc ctgagcggga gagcgccgct    120
cgcacgcccg tcgccacccg cgtacccggc gcagccagag ccaccagcgc agcgctgcca    180
tggagcccag cagcaagaag ctgacgggtc gcctcatgct ggctgtggga ggagcagtgc    240
ttggctccct gcagtttggc tacaacactg gagtcatcaa tgcccccag aaggtgatcg    300 aggagttcta caaccagaca tgggtccacc gctatgggga gagcatcctg cccaccacgc    360
tcaccacgct ctggtccctc tcagtggcca tcttttctgt tgggggcatg attggctcct    420
tctctgtggg ccttttcgtt aaccgctttg gccggcggaa ttcaatgctg atgatgaacc    480
tgctggcctt cgtgtccgcc gtgctcatgg gcttctcgaa actgggcaag tcctttgaga    540
tgctgatcct gggccgcttc atcatcggtg tgtactgcgg cctgaccaca ggcttcgtgc    600
ccatgtatgt gggtgaagtg tcacccacag cctttcgtgg ggccctgggc accctgcacc    660
agctgggcat cgtcgtcggc atcctcatcg cccaggtgtt cggcctggac tccatcatgg    720
gcaacaagga cctgtggccc ctgctgctga gcatcatctt catcccggcc ctgctgcagt    780
gcatcgtgct gcccttctgc cccgagagtc cccgcttcct gctcatcaac cgcaacgagg    840
agaaccgggc caagagtgtg ctaaagaagc tgcgcgggac agctgacgtg acccatgacc    900
```

```
tgcaggagat gaaggaagag agtcggcaga tgatgcggga gaagaaggtc accatcctgg      960
agctgttccg ctcccccgcc taccgccagc ccatcctcat cgctgtggtg ctgcagctgt     1020
cccagcagct gtctggcatc aacgctgtct tctattactc cacgagcatc ttcgagaagg     1080
cgggggtgca gcagcctgtg tatgccacca ttggctccgg tatcgtcaac acggccttca     1140
ctgtcgtgtc gctgtttgtg gtggagcgag caggccggcg gaccctgcac tcataggcc      1200
tcgctggcat ggcgggttgt gccatactca tgaccatcgc gctagcactg ctggagcagc     1260
taccctggat gtcctatctg agcatcgtgg ccatctttgg ctttgtggcc ttctttgaag     1320
tgggtcctgg ccccatccca tggttcatcg tggctgaact cttcagccag ggtccacgtc     1380
cagctgccat tgccgttgca ggcttctcca actggacctc aaatttcatt gtgggcatgt     1440
gcttccagta tgtggagcaa ctgtgtggtc cctacgtctt catcatcttc actgtgctcc     1500
tggttctgtt cttcatcttc acctacttca agttcctga gactaaaggc cggaccttcg      1560
atgagatcgc ttccggcttc cggcaggggg gagccagcca aagtgataag acacccgagg     1620
agctgttcca tcccctgggg gctgattccc aagtgtgagt cgccccagat caccagcccg     1680
gcctgctccc agcagcccta aggatctctc aggagcacag gcagctggat gagacttcca     1740
aacctgacag atgtcagccg agccgggcct ggggctcctt tctccagcca gcaatgatgt     1800
ccagaagaat attcaggact taacggctcc aggattttaa caaaagcaag actgttgctc     1860
aaatctattc agacaagcaa caggttttat aattttttta ttactgattt tgttattttt     1920
atatcagcct gagtctcctg tgcccacatc ccaggcttca ccctgaatgg ttccatgcct     1980
gagggtggag actaagccct gtcgagacac ttgccttctt cacccagcta atctgtaggg     2040
ctggacctat gtcctaagga cacactaatc gaactatgaa ctacaaagct tctatcccag     2100
gaggtggcta tggccaccg ttctgctggc ctggatctcc ccactctagg ggtcaggctc     2160
cattaggatt tgcccttcc catctcttcc tacccaacca ctcaaattaa tctttctta      2220
cctgagacca gttgggagca ctggagtgca gggaggagag gggaagggcc agtctgggct     2280
gccgggttct agtctccttt gcactgaggg ccacactatt accatgagaa gagggcctgt     2340
gggagcctgc aaactcactg ctcaagaaga catggagact cctgccctgt tgtgtataga     2400
tgcaagatat ttatatatat ttttggttgt caatattaaa tacagacact aagttatagt     2460
atatctggac aagccaactt gtaaatacac cacctcactc ctgttactta cctaaacaga     2520
tataaatggc tggtttttag aaacatggtt ttgaaatgct tgtggattga gggtaggagg     2580
tttggatggg agtgagacag aagtaagtgg ggttgcaacc actgcaacgg cttagacttc     2640
gactcaggat ccagtccctt acacgtacct ctcatcagtg tcctcttgct caaaaatctg     2700
tttgatccct gttacccaga gaatatatac attctttatc ttgacattca aggcatttct     2760
atcacatatt tgatagttgg tgttcaaaaa aacactagtt ttgtgccagc cgtgatgctc     2820
aggcttgaaa tcgcattatt ttgaatgtga agggaa                               2856

<210> SEQ ID NO 136
<211> LENGTH: 356
<212> TYPE: DNA
<213> ORGANISM: Human

<400> SEQUENCE: 136
ggtggagcca aatgaagaaa atgaagatga aagagacaga cacctcagtt tttctggatc       60
aggcattgat gatgatgaag attttatctc cagcaccatt tcaaccacac cacgggcttt      120
tgaccacaca aaacagaacc aggactggac tcagtggaac ccaagccatt caaatccgga      180
```
agtgctactt cagacaacca caaggatgac tgatgtagac agaaatggca ccactgctta    240
tgaaggaaac tggaacccag aagcacaccc tcccctcatt caccatgagc atcatgagga    300
agaagagacc ccacattcta caagcacaat ccaggcaact cctagtagta caacgg        356

<210> SEQ ID NO 137
<211> LENGTH: 356
<212> TYPE: DNA
<213> ORGANISM: Human
<220> FEATURE:
<221> NAME/KEY: modified_base
<222> LOCATION: (254)
<223> OTHER INFORMATION: Where n is a, c, g or t
<220> FEATURE:
<221> NAME/KEY: modified_base
<222> LOCATION: (264)
<223> OTHER INFORMATION: Where n is a, c, g or t
<220> FEATURE:
<221> NAME/KEY: modified_base
<222> LOCATION: (279)
<223> OTHER INFORMATION: Where n is a, c, g or t
<220> FEATURE:
<221> NAME/KEY: modified_base
<222> LOCATION: (281)
<223> OTHER INFORMATION: Where n is a, c, g or t
<220> FEATURE:
<221> NAME/KEY: modified_base
<222> LOCATION: (290)
<223> OTHER INFORMATION: Where n is a, c, g or t
<220> FEATURE:
<221> NAME/KEY: modified_base
<222> LOCATION: (328)
<223> OTHER INFORMATION: Where n is a, c, g or t
<220> FEATURE:
<221> NAME/KEY: modified_base
<222> LOCATION: (342)
<223> OTHER INFORMATION: Where n is a, c, g or t

<400> SEQUENCE: 137
gcaggtggag aagacatttt attgttcctg gggtctctgg aggcccattg gtggggctgg    60
gtcactggct gcccccggaa cagggcgctg ctccatggct ctgcttgtgg tagtctgtgg   120
ctatgtctcc cagcaaggac agaaactcag aaaaatcaat cttcttatcc tcattcttgt   180
cctttttctc aaagacatcg gcgaggtaat ttgtgcccct tttacctcgg cccgcgacca   240
cgctaaggcc aaanttccag acanayggcc gggccggtnc natagggggan cccaacttgg   300 ggacccaaac tctggcgcgg aaacacangg gcataagctt gnttcctgtg gggaaa        356

<210> SEQ ID NO 138
<211> LENGTH: 353
<212> TYPE: DNA
<213> ORGANISM: Human

<400> SEQUENCE: 138
aggtccagtc ctccacttgg cctgatgaga gtggggagtg gcaagggacg tttctcctgc    60
aatagacact tagatttctc tcttgtggga agaaaccacc tgtccatcca ctgactcttc   120
tacattgatg tggaaattgc tgctgctacc accacctcct gaagaggctt ccctgatgcc   180
aatgccagcc atcttggcat cctggccctc gagcaggctg cggtaagtag cgatctcctg   240
ctccagccgt gtctttatgt caagcagcat cttgtactcc tggttctgag cctccatctc   300
gcatcggagc tcactcagac ctcgsccgsg mssmcgctam gccgaattcc agc           353

<210> SEQ ID NO 139
<211> LENGTH: 371
<212> TYPE: DNA

<213> ORGANISM: Human

<400> SEQUENCE: 139

| | | | | | |
|---|---|---|---|---|---|
| agcgtggtcg | cggccgaggt | ccatccgaag | caagattgca | gatggcagtg | tgaagagaga | 60 |
| agacatattc | tacacttcaa | agctttggtg | caattcccat | cgaccagagt | tggtccgacc | 120 |
| agccttggaa | aggtcactga | aaaatcttca | attggattat | gttgacctct | accttattca | 180 |
| ttttccagtg | tctgtaaagc | caggtgagga | agtgatccca | aaagatgaaa | atggaaaaat | 240 |
| actatttgac | acagtggatc | tctgtgccac | gtgggaggcc | gtggagaagt | gtaaagatgc | 300 |
| aggattggac | ctgcccgggc | ggccgctcga | aagccgaatt | ccagcacact | ggcggccgtt | 360 |
| actagtggat | c | | | | | 371 |

<210> SEQ ID NO 140
<211> LENGTH: 370
<212> TYPE: DNA
<213> ORGANISM: Human

<400> SEQUENCE: 140

| | | | | | |
|---|---|---|---|---|---|
| tagcgtggtc | gcggccgagg | tccatctccc | tttgggaact | aggggctgc | tggtgggaaa | 60 |
| tgggagccag | ggcagatgtt | gcattccttt | gtgtccctgt | aaatgtggga | ctacaagaag | 120 |
| aggagctgcc | tgagtggtac | tttctcttcc | tggtaatcct | ctggcccagc | ctcatggcag | 180 |
| aatagaggta | tttttaggct | attttttgtaa | tatggcttct | ggtcaaaatc | cctgtgtagc | 240 |
| tgaattccca | agccctgcat | tgtacagccc | cccactcccc | tcaccaccta | ataaggaat | 300 |
| agttaacact | caaaaaaaaa | aaaaaacctg | cccgggcggc | cgctcgaaag | ccgaattcca | 360 |
| gcacactggc | | | | | | 370 |

<210> SEQ ID NO 141
<211> LENGTH: 371
<212> TYPE: DNA
<213> ORGANISM: Human

<400> SEQUENCE: 141

| | | | | | |
|---|---|---|---|---|---|
| tagcgtggtc | gcggccgagg | tcctctgtgc | tgcctgtcac | agcccgatgg | taccagcgca | 60 |
| gggtgtaggc | agtgcaggag | ccctcatcca | gtggcaggga | acaggggtca | tcactatccc | 120 |
| aaggagcttc | agggtcctgg | tactcctcca | cagaatactc | ggagtattca | gagtactcat | 180 |
| catcctcagg | gggtacccgc | tcttcctcct | ctgcatgaga | gacgcggagc | acaggcacag | 240 |
| catggagctg | ggagccggca | gtgtctgcag | cataactagg | gagggtcgt | gatccagatg | 300 |
| cgatgaactg | gccctggcag | gcacagtgct | gactcatctc | ttggcgacct | gcccgggcgg | 360 |
| ccgctcgaag | c | | | | | 371 |

<210> SEQ ID NO 142
<211> LENGTH: 343
<212> TYPE: DNA
<213> ORGANISM: Human

<400> SEQUENCE: 142

| | | | | | |
|---|---|---|---|---|---|
| gcgttttgag | gccaatggtg | taaaggaaa | tatcttcaca | taaaaactag | atggaagcat | 60 |
| tgtcagaaac | ctctttgtga | tgtttgcttt | caactcacag | agttgaacat | tcctttcat | 120 |
| agagcagttt | tgaaacactc | ttttgtagaa | tttgcaagcg | gatgattgga | tcgctatgag | 180 |
| gtcttcattg | gaaacgggat | accttttacat | aaaaactaga | cagtagcatt | ctcagaaatt | 240 |
| tctttgggat | gtgggcattc | aacccacaga | ggagaacttc | atttgataga | gcagttttga | 300 |

```
aacacccttt ttgtagaatc tacaggtgga catttagagt gct              343

<210> SEQ ID NO 143
<211> LENGTH: 354
<212> TYPE: DNA
<213> ORGANISM: Human

<400> SEQUENCE: 143
aggtctgatg gcagaaaaac tcagactgtc tgcaacttta cagatggtgc attggttcag    60
catcaggagt gggatgggaa ggaaagcaca ataacaagaa aattgaaaga tgggaaatta   120
gtggtggagt gtgtcatgaa caatgtcacc tgtactcgga tctatgaaaa agtagaataa   180
aaattccatc atcactttgg acaggagtta attaagagaa tgaccaagct cagttcaatg   240
agcaaatctc catactgttt ctttcttttt tttttcatta ctgtgttcaa ttatctttat   300
cataaacatt ttacatgcag ctatttcaaa gtgtgttgga ttaattagga tcat         354

<210> SEQ ID NO 144
<211> LENGTH: 353
<212> TYPE: DNA
<213> ORGANISM: Human

<400> SEQUENCE: 144
ggtcaaggac ctgggggacc cccaggtcca gcagccacat gattctgcag cagacaggga    60
cctagagcac atctggatct cagccccacc cctggcaacc tgcctgccta gagaactccc   120
aagatgacag actaagtagg attctgccat ttagaataat tctggtatcc tgggcgttgc   180
gttaagttgc ttaactttca ttctgtctta cgatagtctt cagaggtggg aacagatgaa   240
gaaaccatgc cccagagaag gttaagtgac ttcctcttta tggagccagt gttccaacct   300
aggtttgcct gataccagac ctgtggcccc acctcccatg caggtctctg tgg          353

<210> SEQ ID NO 145
<211> LENGTH: 371
<212> TYPE: DNA
<213> ORGANISM: Human

<400> SEQUENCE: 145
caggtctgtc ataaactggt ctggagtttc tgacgactcc ttgttcacca aatgcaccat    60
ttcctgagac ttgctggcct ctccgttgag tccacttggc tttctgtcct ccacagctcc   120
attgccactg ttgatcacta gctttttctt ctgcccacac cttcttcgac tgttgactgc   180
aatgcaaact gcaagaatca agccaaggc caagagggat gccaagatga tcagccattc   240
tggaatttgg ggtgtcctta taggaccaga ggttgtgttt gctccacctt cttgactccc   300
atgtgagacc tcggccgcga ccacgctaag ccgaattcca gcacactggc ggcccgttac   360
tagtggatcc g                                                        371

<210> SEQ ID NO 146
<211> LENGTH: 355
<212> TYPE: DNA
<213> ORGANISM: Human

<400> SEQUENCE: 146
ggtcctccgt cctcttccca gaggtgtcgg ggcttggccc cagcctccat cttcgtctct    60
caggatggcg agtagcagcg gctccaaggc tgaattcatt gtcggaggga atataaaact   120
ggtacggaag atcgggtctg gctccttcgg ggacatctat ttggcgatca acatcaccaa   180
```

```
cggcgaggaa gtggcagtga agctagaatc tcagaaggcc aggcatcccc agttgctgta      240
cgagagcaag ctctataaga ttcttcaagg tggggttggc atcccccaca tacggtggta      300
tggtcaggaa aaagactaca atgtactagt catggatctt ctgggaccta gcctc          355
```

<210> SEQ ID NO 147
<211> LENGTH: 355
<212> TYPE: DNA
<213> ORGANISM: Human

<400> SEQUENCE: 147

```
ggtctgttac aaaatgaaga cagacaacac aacatttact ctgtggagat atcctactca      60
tactatgcac gtgctgtgat tttgaacata actcgtccca aaaacttgtc acgatcatcc     120
tgacttttta ggttggctga tccatcaatc ttgcactcaa ctgttacttc tttcccagtg     180
ttgttaggag caaagctgac ctgaacagca accaatggct gtagatacccc aacatgcagt    240 tttttcccat aatatgggaa atattttaag tctatcattc cattatgagg ataaactgct     300
acatttggta tatcttcatt ctttgaaaca caatctatcc ttggcactcc ttcag          355
```

<210> SEQ ID NO 148
<211> LENGTH: 369
<212> TYPE: DNA
<213> ORGANISM: Human

<400> SEQUENCE: 148

```
aggtctctct cccctctcc ctctcctgcc agccaagtga agacatgctt acttcccctt       60
caccttcctt catgatgtgg gaagagtgct gcaacccagc cctagccaac accgcatgag     120
agggagtgtg ccgagggctt ctgagaaggt ttctctcaca tctagaaaga agcgcttaag     180
atgtggcagc ccctcttctt caagtggctc ttgtcctgtt gccctgggag ttctcaaatt     240
gctgcagcag cctccatcca gcctgaggat gacatcaata cacagaggaa gaagagtcag     300
gaaaagatga gagaagttac agactctcct gggcgacccc gagagcttac cattcctcag     360
acttcttca                                                              369
```

<210> SEQ ID NO 149
<211> LENGTH: 620
<212> TYPE: DNA
<213> ORGANISM: Human
<220> FEATURE:
<221> NAME/KEY: modified_base
<222> LOCATION: (169)
<223> OTHER INFORMATION: Where n is a, c, g or t
<220> FEATURE:
<221> NAME/KEY: modified_base
<222> LOCATION: (171)
<223> OTHER INFORMATION: Where n is a, c, g or t
<220> FEATURE:
<221> NAME/KEY: modified_base
<222> LOCATION: (222)
<223> OTHER INFORMATION: Where n is a, c, g or t
<220> FEATURE:
<221> NAME/KEY: modified_base
<222> LOCATION: (472)
<223> OTHER INFORMATION: Where n is a, c, g or t
<220> FEATURE:
<221> NAME/KEY: modified_base
<222> LOCATION: (528)
<223> OTHER INFORMATION: Where n is a, c, g or t
<220> FEATURE:
<221> NAME/KEY: modified_base
<222> LOCATION: (559)
<223> OTHER INFORMATION: Where n is a, c, g or t
<220> FEATURE:
<221> NAME/KEY: modified_base
<222> LOCATION: (599)
<223> OTHER INFORMATION: Where n is a, c, g or t

<400> SEQUENCE: 149

```
actagtcaaa aatgctaaaa taatttggga gaaaatattt tttaagtagt gttatagttt    60
catgtttatc ttttattatg ttttgtgaag ttgtgtcttt tcactaatta cctatactat   120
gccaatattt ccttatatct atccataaca tttatactac atttgtaana naatatgcac   180
gtgaaactta cactttata aggtaaaaat gaggtttcca anatttaata atctgatcaa    240
gttcttgtta tttccaaata gaatggactt ggtctgttaa gggctaagga gaagaggaag   300
ataaggttaa aagttgttaa tgaccaaaca ttctaaaaga aatgcaaaaa aaagtttat    360
tttcaagcct tcgaactatt taaggaaagc aaaatcattt cctaaatgca tatcatttgt   420
gagaatttct cattaatatc ctgaatcatt catttcacta aggctcatgt tnactccgat   480
atgtctctaa gaaagtacta tttcatggtc caaacctggt tgccatantt gggtaaaggc   540
tttcccttaa gtgtgaaant atttaaaatg aaattttcct cttttttaaaa attctttana   600
agggttaagg gtgttgggga                                               620
```

<210> SEQ ID NO 150
<211> LENGTH: 371
<212> TYPE: DNA
<213> ORGANISM: Human

<400> SEQUENCE: 150

```
ggtccgatca aaacctgcta cctccccaag actttactag tgccgataaa ctttctcaaa    60
gagcaaccag tatcacttcc ctgtttataa aacctctaac catctctttg ttctttgaac   120
atgctgaaaa ccacctggtc tgcatgtatg cccgaatttg yaattctttt ctctcaaatg   180
aaaatttaat tttagggatt catttctata ttttcacata tgtagtatta ttatttcctt   240
atatgtgtaa ggtgaaattt atggtatttg agtgtgcaag aaaatatatt tttaaagctt   300
tcatttttcc cccagtgaat gatttagaat ttttatgta aatatacaga atgttttttc   360
ttacttttat a                                                       371
```

<210> SEQ ID NO 151
<211> LENGTH: 4655
<212> TYPE: DNA
<213> ORGANISM: Human

<400> SEQUENCE: 151

```
gggacttgag ttctgttatc ttcttaagta gattcatatt gtaagggtct cggggtgggg    60
gggttggcaa atcctggag ccagaagaaa ggacagcagc attgatcaat cttacagcta   120
acatgttgta cctggaaaac aatgcccaga ctcaatttag tgagccacag tacacgaacc   180
tggggctcct gaacagcatg gaccagcaga ttcagaacgg ctcctcgtcc accagtccc    240
ataacacaga ccacgcgcag aacagcgtca cggcgccctc gccctacgca cagcccagct   300
ccaccttcga tgctctctct ccatcacccg ccatcccctc caacaccgac tacccaggcc   360
cgcacagttt cgacgtgtcc ttccagcagt cgagcaccgc caagtcggcc acctggacgt   420
attccactga actgaagaaa ctctactgcc aaattgcaaa acatgccccc atccagatca   480
aggtgatgac cccacctcct cagggagctg ttatccgcgc catgcctgtc tacaaaaaag   540
ctgagcacgt cacggaggtg gtgaagcggg cccccaacca tgagctgagc cgtgaattca   600
acgagggaca gattgcccct yctagtcatt tgattcgagt agagggaac agccatgccc   660
```

-continued

```
agtatgtaga agatcccatc acaggaagac agagtgtgct ggtaccttat gagccacccc   720
aggttggcac tgaattcacg acagtcttgt acaatttcat gtgtaacagc agttgtgttg   780
gagggatgaa ccgccgtcca attttaatca ttgttactct ggaaaccaga gatgggcaag   840
tcctgggccg acgctgcttt gaggcccgga tctgtgcttg cccaggaaga gacaggaagg   900
cggatgaaga tagcatcaga aagcagcaag tttcggacag tacaaagaac ggtgatggta   960
cgaagcgccc gtttcgtcag aacacacatg gtatccagat gacatccatc aagaaacgaa  1020
gatccccaga tgatgaactg gtatacttac cagtgagggg ccgtgagact tatgaaatgc  1080
tggtgaagat caaagagtcc ctggaactca tgcagtacct tcttcagcac acaattgaaa  1140
cgtacaggca acagcaacag cagcagcacc agcacttact tcagaaacag acctcaatac  1200
agtctccatc ttcatatggt aacagctccc cacctctgaa caaaatgaac agcatgaaca  1260
agctgccttc tgtgagccag cttatcaacc ctcagcagcg caacgccctc actcctacaa  1320
ccattcctga tggcatggga gccaacattc ccatgatggg cacccacatg ccaatggctg  1380
gagacatgaa tggactcagc cccacccagg cactccctcc cccactctcc atgccatcca  1440
cctcccactg cacacccca cctccgtatc ccacagattg cagcattgtc agtttcttag  1500
cgaggttggg ctgttcatca tgtctggact atttcacgac ccaggggctg accaccatct  1560
atcagattga gcattactcc atggatgatc tgcaagtct gaaaatccct gagcaatttc  1620
gacatgcgat ctggaagggc atcctggacc accggcagct ccacgaattc tcctcccctt  1680
ctcatctcct gcggacccca agcagtgcct ctacagtcag tgtgggctcc agtgagaccc  1740
ggggtgagcg tgttattgat gctgtgcgat tcaccctccg ccagaccatc tctttcccac  1800
cccgagatga gtggaatgac ttcaactttg acatggatgc tcgccgcaat aagcaacagc  1860
gcatcaaaga ggagggggag tgagcctcac catgtgagct cttcctatcc ctctcctaac  1920
tgccagcccc ctaaaagcac tcctgcttaa tcttcaaagc cttctcccta gctcctcccc  1980
ttcctcttgt ctgatttctt aggggaagga gaagtaagag cttacttct taccctaacc  2040 atctgacctg gcatctaatt ctgattctgg ctttaagcct tcaaaactat agcttgcaga  2100
actgtagctt gccatggcta ggtagaagtg agcaaaaaag agttgggtgt ctccttaagc  2160
tgcagagatt tctcattgac ttttataaag catgttcacc cttatagtct aagactatat  2220
atataaatgt ataaatatac agtatagatt tttgggtggg gggcattgag tattgtttaa  2280
aatgtaattt aaatgaaaga aaattgagtt gcacttattg accattttt aatttacttg  2340 ttttggatgg cttgtctata ctccttccct taaggggtat catgtatggt gataggtatc  2400
tagagcttaa tgctacatgt gagtgacgat gatgtacaga ttctttcagt tctttggatt  2460
ctaaatacat gccacatcaa acctttgagt agatccattt ccattgctta ttatgtaggt  2520
aagactgtag atatgtattc ttttctcagt gttggtatat tttatattac tgacatttct  2580
tctagtgatg atggttcacg ttgggtgat ttaatccagt tataagaaga agttcatgtc  2640
caaacgtcct ctttagtttt tggttgggaa tgaggaaaat tcttaaaagg cccatagcag  2700
ccagttcaaa acacccgac gtcatgtatt tgagcatatc agtaaccccc ttaaatttaa  2760
taccagatac cttatcttac aatattgatt gggaaaacat ttgctgccat tacagaggta  2820
ttaaaactaa atttcactac tagattgact aactcaaata cacatttgct actgttgtaa  2880
gaattctgat tgatttgatt gggatgaatg ccatctatct agttctaaca gtgaagtttt  2940
actgtctatt aatattcagg gtaaatagga atcattcaga aatgttgagt ctgtactaaa  3000
cagtaagata tctcaatgaa ccataaattc aactttgtaa aaatctttg aagcatagat  3060
```

-continued

```
aatattgttt ggtaaatgtt tcttttgttt ggtaaatgtt tcytttaaag accctcctat    3120
tctataaaac tctgcatgta gaggcttgtt tacctttctc tctctaaggt ttacaatagg    3180
agtggtgatt tgaaaaatat aaaattatga gattggtttt cctgtggcat aaattgcatc    3240
actgtatcat tttctttttt aaccggtaag agtttcagtt tgttggaaag taactgtgag    3300
aacccagttt cccgtccatc tcccttaggg actacccata gacatgaaag gtccccacag    3360
agcaagagat aagtctttca tggctgctgt tgcttaaacc acttaaacga agagttccct    3420
tgaaactttg ggaaaacatg ttaatgacaa tattccagat ctttcagaaa tataacacat    3480
ttttttgcat gcatgcaaat gagctctgaa atcttcccat gcattctggt caagggctgt    3540
cattgcacat aagcttccat tttaatttta aagtgcaaaa gggccagcgt ggctctaaaa    3600
ggtaatgtgt ggattgcctc tgaaaagtgt gtatatattt tgtgtgaaat tgcatacttt    3660
gtattttgat tatttttttt ttcttcttgg gatagtggga tttccagaac cacacttgaa    3720 acctttttt atcgttttg tattttcatg aaaataccat ttagtaagaa taccacatca    3780
aataagaaat aatgctacaa ttttaagagg ggagggaagg gaaagttttt ttttttatta    3840
tttttttaaa attttgtatg ttaaagagaa tgagtccttg atttcaaagt tttgttgtac    3900
ttaaatggta ataagcactg taaacttctg caacaagcat gcagctttgc aaacccatta    3960 agggggaagaa tgaaagctgt tccttggtcc tagtaagaag acaaactgct tcccttactt    4020
tgctgagggt ttgaataaac ctaggacttc cgagctatgt cagtactatt caggtaacac    4080
tagggccttg gaaatccctg tactgtgtct catggatttg gcactagcca aagcgaggca    4140 cccccttactg gcttacctcc tcatggcagc ctactctcct tgagtgtatg agtagccagg    4200
gtaaggggta aaaggatagt aagcatagaa accactagaa agtgggctta atggagttct    4260
tgtggcctca gctcaatgca gttagctgaa gaattgaaaa gtttttgttt ggagacgttt    4320
ataaacagaa atggaaagca gagttttcat taaatccttt taccttttt ttttcttggt    4380 aatcccctaa aataacagta tgtgggatat tgaatgttaa agggatattt ttttctatta    4440
tttttataat tgtacaaaat taagcaaatg ttaaaagttt tatatgcttt attaatgttt    4500
tcaaaaggta ttatacatgt gatacatttt ttaagcttca gttgcttgtc ttctggtact    4560
ttctgttatg ggctttggg gagccagaag ccaatctaca atctcttttt gtttgccagg    4620
acatgcaata aatttaaaa aataaataaa aacta                               4655
```

<210> SEQ ID NO 152
<211> LENGTH: 586
<212> TYPE: PRT
<213> ORGANISM: Human

<400> SEQUENCE: 152

```
Met Leu Tyr Leu Glu Asn Asn Ala Gln Thr Gln Phe Ser Glu Pro Gln
 1               5                  10                  15

Tyr Thr Asn Leu Gly Leu Leu Asn Ser Met Asp Gln Gln Ile Gln Asn
            20                  25                  30

Gly Ser Ser Ser Thr Ser Pro Tyr Asn Thr Asp His Ala Gln Asn Ser
        35                  40                  45

Val Thr Ala Pro Ser Pro Tyr Ala Gln Pro Ser Ser Thr Phe Asp Ala
    50                  55                  60

Leu Ser Pro Ser Pro Ala Ile Pro Ser Asn Thr Asp Tyr Pro Gly Pro
65                  70                  75                  80

His Ser Phe Asp Val Ser Phe Gln Gln Ser Ser Thr Ala Lys Ser Ala
```

-continued

```
                        85                  90                      95
Thr Trp Thr Tyr Ser Thr Glu Leu Lys Lys Leu Tyr Cys Gln Ile Ala
                100             105                 110
Lys Thr Cys Pro Ile Gln Ile Lys Val Met Thr Pro Pro Gln Gly
        115             120             125
Ala Val Ile Arg Ala Met Pro Val Tyr Lys Lys Ala Glu His Val Thr
    130             135                 140
Glu Val Val Lys Arg Cys Pro Asn His Glu Leu Ser Arg Glu Phe Asn
145             150             155                 160
Glu Gly Gln Ile Ala Pro Ser Ser His Leu Ile Arg Val Glu Gly Asn
                165             170                 175
Ser His Ala Gln Tyr Val Glu Asp Pro Ile Thr Gly Arg Gln Ser Val
            180             185                 190
Leu Val Pro Tyr Glu Pro Pro Gln Val Gly Thr Glu Phe Thr Thr Val
        195             200                 205
Leu Tyr Asn Phe Met Cys Asn Ser Ser Cys Val Gly Gly Met Asn Arg
    210             215                 220
Arg Pro Ile Leu Ile Val Thr Leu Glu Thr Arg Asp Gly Gln Val
225             230             235                 240
Leu Gly Arg Arg Cys Phe Glu Ala Arg Ile Cys Ala Cys Pro Gly Arg
            245             250                 255
Asp Arg Lys Ala Asp Glu Asp Ser Ile Arg Lys Gln Val Ser Asp
        260             265                 270
Ser Thr Lys Asn Gly Asp Gly Thr Lys Arg Pro Phe Arg Gln Asn Thr
    275             280                 285
His Gly Ile Gln Met Thr Ser Ile Lys Lys Arg Arg Ser Pro Asp Asp
    290             295                 300
Glu Leu Val Tyr Leu Pro Val Arg Gly Arg Glu Thr Tyr Glu Met Leu
305             310             315                 320
Val Lys Ile Lys Glu Ser Leu Glu Leu Met Gln Tyr Leu Leu Gln His
                325             330                 335
Thr Ile Glu Thr Tyr Arg Gln Gln Gln Gln Gln His Gln His Leu
            340             345                 350
Leu Gln Lys Gln Thr Ser Ile Gln Ser Pro Ser Ser Tyr Gly Asn Ser
        355             360                 365
Ser Pro Pro Leu Asn Lys Met Asn Ser Met Asn Lys Leu Pro Ser Val
370             375                 380
Ser Gln Leu Ile Asn Pro Gln Gln Arg Asn Ala Leu Thr Pro Thr Thr
385             390             395                 400
Ile Pro Asp Gly Met Gly Ala Asn Ile Pro Met Met Gly Thr His Met
            405             410                 415
Pro Met Ala Gly Asp Met Asn Gly Leu Ser Pro Thr Gln Ala Leu Pro
        420             425                 430
Pro Pro Leu Ser Met Pro Ser Thr His Cys Thr Pro Pro Pro Pro
    435             440                 445
Tyr Pro Thr Asp Cys Ser Ile Val Ser Phe Leu Ala Arg Leu Gly Cys
    450             455                 460
Ser Ser Cys Leu Asp Tyr Phe Thr Thr Gln Gly Leu Thr Thr Ile Tyr
465             470                 475                 480
Gln Ile Glu His Tyr Ser Met Asp Asp Leu Ala Ser Leu Lys Ile Pro
            485             490                 495
Glu Gln Phe Arg His Ala Ile Trp Lys Gly Ile Leu Asp His Arg Gln
        500             505                 510
```

```
Leu His Glu Phe Ser Ser Pro Ser His Leu Leu Arg Thr Pro Ser Ser
            515                 520                 525

Ala Ser Thr Val Ser Val Gly Ser Ser Glu Thr Arg Gly Glu Arg Val
        530                 535                 540

Ile Asp Ala Val Arg Phe Thr Leu Arg Gln Thr Ile Ser Phe Pro Pro
545                 550                 555                 560

Arg Asp Glu Trp Asn Asp Phe Asn Phe Asp Met Asp Ala Arg Arg Asn
                565                 570                 575

Lys Gln Gln Arg Ile Lys Glu Glu Gly Glu
            580                 585

<210> SEQ ID NO 153
<211> LENGTH: 2007
<212> TYPE: DNA
<213> ORGANISM: Human

<400> SEQUENCE: 153
```

| | | | | | |
|---|---|---|---|---|---|
| gaattcgtcg | ctgctccagg | gaaagttctg | ttactccact | gactctctct | tttcctgata | 60 |
| acatggccag | caagaaagta | attacagtgt | ttggagcaac | aggagctcaa | ggtggctctg | 120 |
| tggccagggc | aattttggag | agcaaaaaat | ttgcagtgag | agcagtgacc | agggatgtga | 180 |
| cttgaccaaa | tgccctggag | ctccagcgcc | ttggagctga | ggtggtcaaa | ggtgacctga | 240 |
| atgataaagc | atcggtggac | agtgccttaa | aaggtgtcta | tggggccttc | ttggtgacca | 300 |
| acttctggga | ccctctcaac | caagataagg | aagtgtgtcg | ggggaagctg | gtggcagact | 360 |
| ccgccaagca | cctgggtctg | aagcacgtgg | tgtacagcgg | cctggagaac | gtcaagcgac | 420 |
| tgacggatgg | caagctggag | gtgccgcact | ttgacagcaa | gggcgaggtg | gaggagtact | 480 |
| tctggtccat | tggcatcccc | atgaccagtg | tccgcgtggc | ggcctacttt | gaaaactttc | 540 |
| tcgcggcgtg | gcgggcccgtg | aaagcctctg | atggagatta | ctacaccttg | gctgtaccga | 600 |
| tgggagatgt | accaatggat | ggtatctctg | ttgctgatat | tggagcagcc | gtctctagca | 660 |
| tttttaattc | tccagaggaa | tttttaggca | aggccgtggg | gctcagtgca | gaagcactaa | 720 |
| caatacagca | atatgctgat | gttttgtcca | aggctttggg | gaaagaagtc | cgagatgcaa | 780 |
| agattacccc | ggaagctttc | gagaagctgg | gattccctgc | agcaaaggaa | atagccaata | 840 |
| tgtgtcgttt | ctatgaaatg | aagccagacc | gagatgtcaa | tctcacccac | caactaaatc | 900 |
| ccaaagtcaa | aagcttcagc | cagtttatct | cagagaacca | gggagccttc | aagggcatgt | 960 |
| agaaaatcag | ctgttcagat | aggcctctgc | accacacagc | ctctttcctc | tctgatcctt | 1020 |
| ttcctctttta | cggcacaaca | ttcatgttga | cagaacatgc | tggaatgcaa | ttgtttgcaa | 1080 |
| caccgaagga | tttcctgcgg | tcgcctcttc | agtaggaagc | actgcattgg | tgataggaca | 1140 |
| cggtaatttg | attcacattt | aacttgctag | ttagtgataa | gggtggtaca | actgtttggt | 1200 |
| aaaatgagaa | gcctcggaac | ttggagcttc | tctcctacca | ctaatgggag | ggcagattat | 1260 |
| actgggattt | ctcctgggtg | agtaatttca | agccctaatg | ctgaaattcc | ctaggcagc | 1320 |
| tccagttttc | tcaactgcat | tgcaaaattc | ccagtgaact | tttaagtact | tttaacttaa | 1380 |
| aaaaatgaac | atctttgtag | agaattttct | ggggaacatg | gtgttcaatg | aacaagcaca | 1440 |
| agcattggaa | atgctaaaat | tcagttttgc | ctcaagattg | gaagtttatt | ttctgactca | 1500 |
| ttcatgaagt | catctattga | gccaccattc | aattattcat | ctattaattc | cttgatcctt | 1560 |
| catttatcca | ttctgcaaac | ttttcttgag | caccagcacg | ggtggccatt | tgtggacttc | 1620 |
| tcttcattcc | tatgtgtttt | cttatcaaag | tgatccactc | tcgaaaggct | cctttccagt | 1680 |

-continued

```
ctgtggttgg gttcaagtca tgccagggcc aggggggccca tctcctcgtt tagctctagg      1740
caaaatccag gggatctgca gtggggagcg ggggcaggaa gctggaggga aggcctgtga      1800
agggtaggga tgtggaaaga caaggtgaca gaaggaccca ataggacctt tctatatctc      1860
tggcttagca ttttctacat catattgtaa tcgtcttatt tgctagtttt cttccttact      1920
gtgagtgact aacagtcatc tttatcccag tgcctggtac ataataagtg atcaataaat      1980
gttgattgac taaaaaaaaa aaaaaaa                                          2007
```

<210> SEQ ID NO 154
<211> LENGTH: 2148
<212> TYPE: DNA
<213> ORGANISM: Human

<400> SEQUENCE: 154

```
gaattcgtcg ctgctccagg gaaagttctg ttactccact gactctctct tttcctgata        60
acatggccag caagaaagta attacagtgt ttggagcaac aggagctcaa ggtggctctg       120
tggccagggc aattttggag agcaaaaaat ttgcagtgag agcagtgacc agggatgtga       180
cttgaccaaa tgccctggag ctccagcgcc ttggagctga ggtggtcaaa ggtgacctga       240
atgataaagc atcggtggac agtgccttaa aaggggaagc tggtggcaga ctccgccaag       300
cacctgggtc tgaagcacgt ggtgtacagc ggcctggaga acgtcaagcg actgacggat       360
ggcaagctgg aggtgccgca ctttgacagc aagggcgagg tggaggagta cttctggtcc       420
attggcatcc ccatgaccag tgtccgcgtg gcggcctact ttgaaaactt tctcgcggcg       480
tggcggcccg tgaaagcctc tgatggagat tactacacct tggctgtacc gatgggagat       540
gtaccaatgg atggtatctc tgttgctgat attggagcag ccgtctctag cattttaat       600
tctccagagg aatttttagg caaggccgtg gggctcagtg cagaagcact aacaatacag       660
caatatgctg atgttttgtc caaggctttg gggaaagaag tccgagatgc aaagactatc       720
tgtgctatag atgaccagaa aacagtggaa gaaggtttca tggaagacgt gggcttgagt       780
tggtccttga gggaacatga ccatgtatag acagaggagg catcaagaag gctggcctgg       840
ctaattctgg aataaacacg acaaaccaga ggcagtacgg gaaggaggca aattctggct       900
ctgcctctat ccttgattac cccggaagct ttcgagaagc tgggattccc tgcagcaaag       960
gaaatagcca atatgtgtcg tttctatgaa atgaagccag accgagatgt caatctcacc      1020
caccaactaa atcccaaagt caaaagcttc agccatttta tctcagagaa ccaggagcc      1080
ttcaagggca tgtagaaaat cagctgttca gataggcctc tgcaccacac agcctctttc      1140
ctctctgatc cttttcctct ttacggcaca acattcatgt tgcagaaca tgctggaatg      1200
caattgtttg caacaccgaa ggatttcctg cggtcgcctc ttcagtagga agcactgcat      1260
tggtgatagg acacggtaat ttgattcaca tttaacttgc tagttagtga taagggtggt      1320
acaactgttt ggtaaaatga gaagcctcgg aacttggagc ttctctccta ccactaatgg      1380
gagggcagat tatactggga tttctcctgg gtgagtaatt tcaagcccta atgctgaaat      1440
tcccctaggc agctccagtt ttctcaactg cattgcaaaa ttcccagtga acttttaagt      1500
acttttaact taaaaaaatg aacatctttg tagagaattt tctggggaac atggtgttca      1560
atgaacaagc acaagcattg gaaatgctaa aattcagttt tgcctcaaga ttggaagttt      1620
attttctgac tcattcatga agtcatctat tgagccacca ttcaattatt catctattaa      1680
ttccttgatc cttcatttat ccattctgca aacttttctt gagcaccagc acgggtggcc      1740
```

|                                                                                            |      |
|--------------------------------------------------------------------------------------------|------|
| atttgtggac ttctcttcat tcctatgtgt tttcttatca aagtgatcca ctctcgaaag                           | 1800 |
| gctcctttcc agtctgtggt tgggttcaag tcatgccagg gccagggggc ccatctcctc                           | 1860 |
| gtttagctct aggcaaaatc caggggatct gcagtgggga gcgggggcag gaagctggag                           | 1920 |
| ggaaggcctg tgaagggtag ggatgtggaa agacaaggtg acagaaggac ccaataggac                           | 1980 |
| ctttctatat ctctggctta gcattttcta catcatattg taatcgtctt atttgctagt                           | 2040 |
| tttcttcctt actgtgagtg actaacagtc atctttatcc cagtgcctgg tacataataa                           | 2100 |
| gtgatcaata aatgttgatt gactaaatga aaaaaaaaaa aaaaaaaa                                        | 2148 |

<210> SEQ ID NO 155
<211> LENGTH: 153
<212> TYPE: PRT
<213> ORGANISM: Human

<400> SEQUENCE: 155

Met Thr Ser Val Arg Val Ala Ala Tyr Phe Glu Asn Phe Leu Ala Ala
1               5                   10                  15

Trp Arg Pro Val Lys Ala Ser Asp Gly Asp Tyr Tyr Thr Leu Ala Val
            20                  25                  30

Pro Met Gly Asp Val Pro Met Asp Gly Ile Ser Val Ala Asp Ile Gly
        35                  40                  45

Ala Ala Val Ser Ser Ile Phe Asn Ser Pro Glu Glu Phe Leu Gly Lys
    50                  55                  60

Ala Val Gly Leu Ser Ala Glu Ala Leu Thr Ile Gln Gln Tyr Ala Asp
65                  70                  75                  80

Val Leu Ser Lys Ala Leu Gly Lys Glu Val Arg Asp Ala Lys Ile Thr
                85                  90                  95

Pro Glu Ala Phe Glu Lys Leu Gly Phe Pro Ala Ala Lys Glu Ile Ala
            100                 105                 110

Asn Met Cys Arg Phe Tyr Glu Met Lys Pro Asp Arg Asp Val Asn Leu
        115                 120                 125

Thr His Gln Leu Asn Pro Lys Val Lys Ser Phe Ser Gln Phe Ile Ser
    130                 135                 140

Glu Asn Gln Gly Ala Phe Lys Gly Met
145                 150

<210> SEQ ID NO 156
<211> LENGTH: 128
<212> TYPE: PRT
<213> ORGANISM: Human

<400> SEQUENCE: 156

Met Thr Ser Val Arg Val Ala Ala Tyr Phe Glu Asn Phe Leu Ala Ala
1               5                   10                  15

Trp Arg Pro Val Lys Ala Ser Asp Gly Asp Tyr Tyr Thr Leu Ala Val
            20                  25                  30

Pro Met Gly Asp Val Pro Met Asp Gly Ile Ser Val Ala Asp Ile Gly
        35                  40                  45

Ala Ala Val Ser Ser Ile Phe Asn Ser Pro Glu Glu Phe Leu Gly Lys
    50                  55                  60

Ala Val Gly Leu Ser Ala Glu Ala Leu Thr Ile Gln Gln Tyr Ala Asp
65                  70                  75                  80

Val Leu Ser Lys Ala Leu Gly Lys Glu Val Arg Asp Ala Lys Thr Ile
                85                  90                  95

Cys Ala Ile Asp Asp Gln Lys Thr Val Glu Glu Gly Phe Met Glu Asp

|   | 100 |   |   |   | 105 |   |   |   | 110 |   |   |
|---|---|---|---|---|---|---|---|---|---|---|---|
| Val | Gly | Leu | Ser | Trp | Ser | Leu | Arg | Glu | His | Asp | His | Val | Ala | Gly | Ala |
|   |   |   | 115 |   |   |   |   | 120 |   |   |   |   | 125 |   |   |

<210> SEQ ID NO 157
<211> LENGTH: 424
<212> TYPE: DNA
<213> ORGANISM: Human
<220> FEATURE:
<221> NAME/KEY: unsure
<222> LOCATION: (320)...(320)
<221> NAME/KEY: unsure
<222> LOCATION: (322)...(322)

<400> SEQUENCE: 157

| ctgcagcccg | gggatccac | tagtccagtg | tggtggaatt | cattggtctt | tacaagactt | 60 |
| ggatacatta | cagcagacat | ggaaatataa | ttttaaaaaa | tttctctcca | acctccttca | 120 |
| aattcagtca | ccactgttat | attaccttct | ccaggaaccc | tccagtgggg | aaggctgcga | 180 |
| tattagattt | ccttgtatgc | aaagttttg | ttgaaagctg | tgctcagagg | aggtgagagg | 240 |
| agaggaagga | gaaaactgca | tcataacttt | acagaattga | atctagagtc | ttccccgaaa | 300 |
| agcccagaaa | cttctctgcn | gnatctggct | tgtccatctg | gtctaaggtg | gctgcttctt | 360 |
| ccccagccat | cgagtcagtt | tgtgcccatg | aataatacac | gacctgctat | ttcccatgac | 420 |
| tgct |   |   |   |   |   | 424 |

<210> SEQ ID NO 158
<211> LENGTH: 2099
<212> TYPE: DNA
<213> ORGANISM: Human

<400> SEQUENCE: 158

| ccgcggttaa | aaggcgcagc | aggtgggagc | cggggccttc | acccgaaacc | cgacgagagc | 60 |
| ccgacagccg | gcggcgcccg | agcccgacct | gcctgcccag | ccggagcgaa | gggcgccgcc | 120 |
| ccgcgcagag | cccgcgccag | ggccgccggc | cgcagagcag | ttaaaacgtg | caggcaccag | 180 |
| aaggcacttc | ctgtcggtga | agaagacctg | tctccggtgt | cacgggcatc | ctgtgttttg | 240 |
| caaacggggc | tgacctcct | tcctggggag | caggaagggt | cagggaagga | aaagaagtac | 300 |
| agaagatctg | gctaaacaat | ttctgtatgg | cgaaagaaaa | attctaactt | gtacgccctc | 360 |
| ttcatgcatc | tttaattcaa | tttgaatatt | ccaggcgaca | tcctcactga | ccgagcaaag | 420 |
| attgacattc | gtatcatcac | tgtgcaccat | ggcttctag | gcactccagt | ggggtaggag | 480 |
| aaggaggtct | gaaccctcg | cagagggatc | ttgccctcat | tctttgggtc | tgaaacactg | 540 |
| gcagtcgttg | gaaacaggac | tcaggataa | accagcgcaa | tggattgggg | gacgctgcac | 600 |
| actttcatcg | ggggtgtcaa | caaacactcc | accagcatcg | ggaaggtgtg | gatcacagtc | 660 |
| atctttattt | tccgagtcat | gatcctcgtg | gtggctgccc | aggaagtgtg | gggtgacgag | 720 |
| caagaggact | tcgtctgcaa | cacactgcaa | ccgggatgca | aaaatgtgtg | ctatgaccac | 780 |
| ttttcccgg | tgtcccacat | ccggctgtgg | gccctccagc | tgatcttcgt | ctccacccca | 840 |
| gcgctgctgg | tggccatgca | tgtggcctac | acaggcacg | aaaccactcg | caagttcagg | 900 |
| cgaggagaga | agaggaatga | tttcaaagac | atagaggaca | ttaaaaagca | gaaggttcgg | 960 |
| atagaggggt | cgctgtggtg | gacgtacacc | agcagcatct | ttttccgaat | catctttgaa | 1020 |
| gcagccttta | tgtatgtgtt | ttacttcctt | tacaatggga | ccacctgcc | ctgggtgttg | 1080 |
| aaatgtggga | ttgacccctg | ccccaacctt | gttgactgct | ttatttctag | gccaacagag | 1140 |

-continued

```
aagaccgtgt ttaccatttt tatgatttct gcgtctgtga tttgcatgct gcttaacgtg     1200
gcagagttgt gctacctgct gctgaaagtg tgttttagga gatcaaagag agcacagacg     1260
caaaaaaatc accccaatca tgccctaaag gagagtaagc agaatgaaat gaatgagctg     1320
atttcagata gtggtcaaaa tgcaatcaca ggttcccaag ctaaacattt caaggtaaaa     1380
tgtagctgcg tcataaggag acttctgtct tctccagaag gcaataccaa cctgaaagtt     1440
ccttctgtag cctgaagagt ttgtaaatga cttcataat aaatagacac ttgagttaac      1500
tttttgtagg atacttgctc cattcataca caacgtaatc aaatatgtgg tccatctctg     1560
aaaacaagag actgcttgac aaaggagcat tgcagtcact tgacaggtt cctttaagt       1620 ggactctctg acaaagtggg tactttctga aaatttatat aactgttgtt gataaggaac     1680
atttatccag gaattgatac gttattagg aaaagatatt tttataggct tggatgtttt      1740
tagttctgac tttgaattta tataaagtat ttttataatg actggtcttc cttacctgga    1800
aaaacatgcg atgttagttt tagaattaca ccacaagtat ctaaatttgg aacttacaaa     1860
gggtctatct tgtaaatatt gttttgcatt gtctgttggc aaatttgtga actgtcatga     1920
tacgcttaag gtggaaagtg ttcattgcac aatatatttt tactgctttc tgaatgtaga     1980
cggaacagtg tggaagcaga aggctttttt aactcatccg tttgccaatc attgcaaaca     2040
actgaaatgt ggatgtgatt gcctcaataa agctcgtccc cattgcttaa aaaaaaaaa     2099
```

<210> SEQ ID NO 159
<211> LENGTH: 291
<212> TYPE: PRT
<213> ORGANISM: Human

<400> SEQUENCE: 159

```
Met Asp Trp Gly Thr Leu His Thr Phe Ile Gly Gly Val Asn Lys His
  1               5                  10                  15

Ser Thr Ser Ile Gly Lys Val Trp Ile Thr Val Ile Phe Ile Phe Arg
             20                  25                  30

Val Met Ile Leu Val Val Ala Ala Gln Glu Val Trp Gly Asp Glu Gln
         35                  40                  45

Glu Asp Phe Val Cys Asn Thr Leu Gln Pro Gly Cys Lys Asn Val Cys
 50                  55                  60

Tyr Asp His Phe Phe Pro Val Ser His Ile Arg Leu Trp Ala Leu Gln
 65                  70                  75                  80

Leu Ile Phe Val Ser Thr Pro Ala Leu Leu Val Ala Met His Val Ala
                 85                  90                  95

Tyr Tyr Arg His Glu Thr Thr Arg Lys Phe Arg Arg Gly Glu Lys Arg
            100                 105                 110

Asn Asp Phe Lys Asp Ile Glu Asp Ile Lys Lys Gln Lys Val Arg Ile
            115                 120                 125

Glu Gly Ser Leu Trp Trp Thr Tyr Thr Ser Ser Ile Phe Phe Arg Ile
        130                 135                 140

Ile Phe Glu Ala Ala Phe Met Tyr Val Phe Tyr Leu Tyr Asn Gly
145                 150                 155                 160

Tyr His Leu Pro Trp Val Leu Lys Cys Gly Ile Asp Pro Cys Pro Asn
                165                 170                 175

Leu Val Asp Cys Phe Ile Ser Arg Pro Thr Glu Lys Thr Val Phe Thr
            180                 185                 190

Ile Phe Met Ile Ser Ala Ser Val Ile Cys Met Leu Leu Asn Val Ala
        195                 200                 205
```

```
Glu Leu Cys Tyr Leu Leu Leu Lys Val Cys Phe Arg Arg Ser Lys Arg
    210                 215                 220
Ala Gln Thr Gln Lys Asn His Pro Asn His Ala Leu Lys Glu Ser Lys
225                 230                 235                 240
Gln Asn Glu Met Asn Glu Leu Ile Ser Asp Ser Gly Gln Asn Ala Ile
                245                 250                 255
Thr Gly Ser Gln Ala Lys His Phe Lys Val Lys Cys Ser Cys Val Ile
            260                 265                 270
Arg Arg Leu Leu Ser Ser Pro Glu Gly Asn Thr Asn Leu Lys Val Pro
        275                 280                 285
Ser Val Ala
    290

<210> SEQ ID NO 160
<211> LENGTH: 3951
<212> TYPE: DNA
<213> ORGANISM: Human

<400> SEQUENCE: 160
```

| | | | | | |
|---|---|---|---|---|---|
| tctgcatcca | tattgaaaac | ctgacacaat | gtatgcagca | ggctcagtgt | gagtgaactg | 60 |
| gaggcttctc | tacaacatga | cccaaaggag | cattgcaggt | cctatttgca | acctgaagtt | 120 |
| tgtgactctc | ctggttgcct | taagttcaga | actcccattc | ctgggagctg | gagtacagct | 180 |
| tcaagacaat | gggtataatg | gattgctcat | tgcaattaat | cctcaggtac | ctgagaatca | 240 |
| gaacctcatc | tcaaacatta | aggaaatgat | aactgaagct | tcatttttacc | tatttaatgc | 300 |
| taccaagaga | gagtattttt | tcagaaatat | aaagatttta | atacctgcca | catggaaagc | 360 |
| taataataac | agcaaaataa | aacaagaatc | atatgaaaag | gcaaatgtca | tagtgactga | 420 |
| ctggtatggg | gcacatggag | atgatccata | caccctacaa | tacagagggt | gtggaaaaga | 480 |
| gggaaaatac | attcatttca | cacctaattt | cctactgaat | gataacttaa | cagctggcta | 540 |
| cggatcacga | ggccgagtgt | ttgtccatga | atgggcccac | ctccgttggg | gtgtgttcga | 600 |
| tgagtataac | aatgacaaac | ctttctacat | aaatgggcaa | atcaaatta | aagtgacaag | 660 |
| gtgttcatct | gacatcacag | gcatttttgt | gtgtgaaaaa | ggtccttgcc | cccaagaaaa | 720 |
| ctgtattatt | agtaagcttt | ttaaagaagg | atgcacctttt | atctacaata | gcacccaaaa | 780 |
| tgcaactgca | tcaataatgt | tcatgcaaag | tttatcttct | gtggttgaat | tttgtaatgc | 840 |
| aagtacccac | aaccaagaag | caccaaacct | acagaaccag | atgtgcagcc | tcagaagtgc | 900 |
| atgggatgta | atcacagact | ctgctgactt | tcaccacagc | tttcccatga | acggactga | 960 |
| gcttccacct | cctcccacat | tctcgcttgt | agaggctggt | gacaaagtgg | tctgtttagt | 1020 |
| gctggatgtg | tccagcaaga | tggcagaggc | tgacagactc | cttcaactac | aacaagccgc | 1080 |
| agaattttat | ttgatgcaga | ttgttgaaat | tcataccttc | gtgggcattg | ccagtttcga | 1140 |
| cagcaaagga | gagatcagag | cccagctaca | ccaaattaac | agcaatgatg | atcgaaagtt | 1200 |
| gctggtttca | tatctgccca | ccactgtatc | agctaaaaca | gacatcagca | tttgttcagg | 1260 |
| gcttaagaaa | ggatttgagg | tggttgaaaa | actgaatgga | aaagcttatg | ctctgtgat | 1320 |
| gatattagtg | accagcggag | atgataagct | tcttggcaat | tgcttaccca | ctgtgctcag | 1380 |
| cagtggttca | acaattcact | ccattgccct | gggttcatct | gcagccccaa | atctggagga | 1440 |
| attatcacgt | cttacaggag | gtttaaagtt | ctttgttcca | gatatatcaa | actccaatag | 1500 |
| catgattgat | gctttcagta | gaatttcctc | tggaactgga | gacattttcc | agcaacatat | 1560 |

```
tcagcttgaa agtacaggtg aaaatgtcaa acctcaccat caattgaaaa acacagtgac    1620
tgtggataat actgtgggca acgacactat gtttctagtt acgtggcagg ccagtggtcc    1680
tcctgagatt atattatttg atcctgatgg acgaaaatac tacacaaata attttatcac    1740
caatctaact tttcggacag ctagtctttg gattccagga acagctaagc ctgggcactg    1800
gacttacacc ctgaacaata cccatcattc tctgcaagcc ctgaaagtga cagtgacctc    1860
tcgcgcctcc aactcagctg tgcccccagc cactgtggaa gcctttgtgg aaagagacag    1920
cctccatttt cctcatcctg tgatgattta tgccaatgtg aaacagggat tttatcccat    1980
tcttaatgcc actgtcactg ccacagttga gccagagact ggagatcctg ttacgctgag    2040
actccttgat gatggagcag gtgctgatgt tataaaaaat gatggaattt actcgaggta    2100
ttttttctcc tttgctgcaa atggtagata tagcttgaaa gtgcatgtca atcactctcc    2160
cagcataagc accccagccc actctattcc agggagtcat gctatgtatg taccaggtta    2220
cacagcaaac ggtaatattc agatgaatgc tccaaggaaa tcagtaggca gaaatgagga    2280
ggagcgaaag tggggctttta gccgagtcag ctcaggaggc tccttttcag tgctgggagt    2340
tccagctggc ccccaccctg atgtgtttcc accatgcaaa attattgacc tggaagctgt    2400
aaaagtagaa gaggaattga ccctatcttg gacagcacct ggagaagact ttgatcaggg    2460
ccaggctaca agctatgaaa taagaatgag taaaagtcta cagaatatcc aagatgactt    2520
taacaatgct attttagtaa atacatcaaa gcgaaatcct cagcaagctg gcatcaggga    2580
gatatttacg ttctcacccc aaatttccac gaatggacct gaacatcagc caaatggaga    2640
aacacatgaa agccacagaa tttatgttgc aatacgagca atggatagga actccttaca    2700
gtctgctgta tctaacattg cccaggcgcc tctgtttatt cccccaatt ctgatcctgt    2760 acctgccaga gattatctta tattgaaagg agtttaaca gcaatgggtt tgataggaat    2820
catttgcctt attatagttg tgacacatca tactttaagc aggaaaaaga gagcagacaa    2880
gaaagagaat ggaacaaaat tattataaat aaatatccaa agtgtcttcc ttcttagata    2940
taagacccat ggccttcgac tacaaaaaca tactaacaaa gtcaaattaa catcaaaact    3000 gtattaaaaat gcattgagtt tttgtacaat acagataaga ttttttacatg gtagatcaac    3060 aaattctttt tgggggtaga ttagaaaacc cttacacttt ggctatgaac aaataataaa    3120
aattattctt taaagtaatg tctttaaagg caaagggaag ggtaaagtcg gaccagtgtc    3180
aaggaaagtt tgttttattg aggtggaaaa atagccccaa gcagagaaaa ggagggtagg    3240
tctgcattat aactgtctgt gtgaagcaat catttagtta ctttgattaa ttttctttt    3300 ctccttatct gtgcagaaca ggttgcttgt ttacaactga agatcatgct atatttcata    3360
tatgaagccc ctaatgcaaa gctctttacc tcttgctatt ttgttatata tattacagat    3420
gaaatctcac tgctaatgct cagagatctt ttttcactgt aagaggtaac ctttaacaat    3480
atgggtatta cctttgtctc ttcataccgg ttttatgaca aaggtctatt gaatttattt    3540
gtttgtaagt ttctactccc atcaaagcag cttttttaagt tattgccttg gttattatgg    3600
atgatagtta tagcccttat aatgccttaa ctaaggaaga aaagatgtta ttctgagttt    3660
gttttaatac atatatgaac atatagtttt attcaattaa accaaagaag aggtcagcag    3720
ggagatacta accttttggaa atgattagct ggctctgttt tttggttaaa taagagtctt    3780
taatcctttc tccatcaaga gttacttacc aagggcaggg gaaggggggat atagaggtcc    3840 caaggaaata aaaatcatct ttcatcttta attttactcc ttcctcttat tttttaaaa    3900 gattatcgaa caataaaatc atttgccttt ttaattaaaa acataaaaaa a             3951
```

```
<210> SEQ ID NO 161
<211> LENGTH: 943
<212> TYPE: PRT
<213> ORGANISM: Human

<400> SEQUENCE: 161

Met Thr Gln Arg Ser Ile Ala Gly Pro Ile Cys Asn Leu Lys Phe Val
 1               5                  10                  15

Thr Leu Val Ala Leu Ser Ser Glu Leu Pro Phe Leu Gly Ala Gly
             20                  25                  30

Val Gln Leu Gln Asp Asn Gly Tyr Asn Gly Leu Leu Ile Ala Ile Asn
             35                  40                  45

Pro Gln Val Pro Glu Asn Gln Asn Leu Ile Ser Asn Ile Lys Glu Met
 50                  55                  60

Ile Thr Glu Ala Ser Phe Tyr Leu Phe Asn Ala Thr Lys Arg Arg Val
 65                  70                  75                  80

Phe Phe Arg Asn Ile Lys Ile Leu Ile Pro Ala Thr Trp Lys Ala Asn
                 85                  90                  95

Asn Asn Ser Lys Ile Lys Gln Glu Ser Tyr Glu Lys Ala Asn Val Ile
                100                 105                 110

Val Thr Asp Trp Tyr Gly Ala His Gly Asp Asp Pro Tyr Thr Leu Gln
            115                 120                 125

Tyr Arg Gly Cys Gly Lys Glu Gly Lys Tyr Ile His Phe Thr Pro Asn
130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
            180                 185                 190

Val Thr Arg Cys Ser Ser Asp Ile Thr Gly Ile Phe Val Cys Glu Lys
        195                 200                 205

Gly Pro Cys Pro Gln Glu Asn Cys Ile Ile Ser Lys Leu Phe Lys Glu
210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
            260                 265                 270

Arg Ser Ala Trp Asp Val Ile Thr Asp Ser Ala Asp Phe His His Ser
        275                 280                 285

Phe Pro Met Asn Gly Thr Glu Leu Pro Pro Pro Thr Phe Ser Leu
    290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Ala Ala Glu
                325                 330                 335

Phe Tyr Leu Met Gln Ile Val Glu Ile His Thr Phe Val Gly Ile Ala
            340                 345                 350

Ser Phe Asp Ser Lys Gly Glu Ile Arg Ala Gln Leu His Gln Ile Asn
        355                 360                 365

Ser Asn Asp Asp Arg Lys Leu Leu Val Ser Tyr Leu Pro Thr Thr Val
```

```
            370                 375                 380
Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
                420                 425                 430

Val Leu Ser Ser Gly Ser Thr Ile His Ser Ile Ala Leu Gly Ser Ser
                435                 440                 445

Ala Ala Pro Asn Leu Glu Glu Leu Ser Arg Leu Thr Gly Gly Leu Lys
450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys Asn
                500                 505                 510

Thr Val Thr Val Asp Asn Thr Val Gly Asn Asp Thr Met Phe Leu Val
                515                 520                 525

Thr Trp Gln Ala Ser Gly Pro Pro Glu Ile Ile Leu Phe Asp Pro Asp
530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
                565                 570                 575

Tyr Thr Leu Asn Asn Thr His His Ser Leu Gln Ala Leu Lys Val Thr
                580                 585                 590

Val Thr Ser Arg Ala Ser Asn Ser Ala Val Pro Pro Ala Thr Val Glu
                595                 600                 605

Ala Phe Val Glu Arg Asp Ser Leu His Phe Pro His Pro Val Met Ile
610                 615                 620

Tyr Ala Asn Val Lys Gln Gly Phe Tyr Pro Ile Leu Asn Ala Thr Val
625                 630                 635                 640

Thr Ala Thr Val Glu Pro Glu Thr Gly Asp Pro Val Thr Leu Arg Leu
                645                 650                 655

Leu Asp Asp Gly Ala Gly Ala Asp Val Ile Lys Asn Asp Gly Ile Tyr
                660                 665                 670

Ser Arg Tyr Phe Phe Ser Phe Ala Ala Asn Gly Arg Tyr Ser Leu Lys
                675                 680                 685

Val His Val Asn His Ser Pro Ser Ile Ser Thr Pro Ala His Ser Ile
                690                 695                 700

Pro Gly Ser His Ala Met Tyr Val Pro Gly Tyr Thr Ala Asn Gly Asn
705                 710                 715                 720

Ile Gln Met Asn Ala Pro Arg Lys Ser Val Gly Arg Asn Glu Glu Glu
                725                 730                 735

Arg Lys Trp Gly Phe Ser Arg Val Ser Ser Gly Ser Phe Ser Val
                740                 745                 750

Leu Gly Val Pro Ala Gly Pro His Pro Asp Val Phe Pro Pro Cys Lys
                755                 760                 765

Ile Ile Asp Leu Glu Ala Val Lys Val Glu Glu Leu Thr Leu Ser
                770                 775                 780

Trp Thr Ala Pro Gly Glu Asp Phe Asp Gln Gly Gln Ala Thr Ser Tyr
785                 790                 795                 800
```

-continued

```
Glu Ile Arg Met Ser Lys Ser Leu Gln Asn Ile Gln Asp Asp Phe Asn
            805             810             815
Asn Ala Ile Leu Val Asn Thr Ser Lys Arg Asn Pro Gln Gln Ala Gly
            820             825             830
Ile Arg Glu Ile Phe Thr Phe Ser Pro Gln Ile Ser Thr Asn Gly Pro
            835             840             845
Glu His Gln Pro Asn Gly Glu Thr His Glu Ser His Arg Ile Tyr Val
    850             855             860
Ala Ile Arg Ala Met Asp Arg Asn Ser Leu Gln Ser Ala Val Ser Asn
865             870             875             880
Ile Ala Gln Ala Pro Leu Phe Ile Pro Pro Asn Ser Asp Pro Val Pro
            885             890             895
Ala Arg Asp Tyr Leu Ile Leu Lys Gly Val Leu Thr Ala Met Gly Leu
            900             905             910
Ile Gly Ile Ile Cys Leu Ile Ile Val Val Thr His His Thr Leu Ser
            915             920             925
Arg Lys Lys Arg Ala Asp Lys Lys Glu Asn Gly Thr Lys Leu Leu
    930             935             940
```

COMPOUNDS AND METHODS FOR THERAPY AND DIAGNOSIS OF LUNG CANCER

REFERENCE TO RELATED APPLICATIONS

This application is a continuation-in-part of U.S. patent application No. 09/123,912, filed Jul. 27, 1998, now U.S. Pat. No. 6,312,695, which is a continuation-in-part of U.S. patent application Ser. No. 09/040,802, filed Mar. 18, 1998, now abandoned.

TECHNICAL FIELD

The present invention relates generally to compositions and methods for the treatment and diagnosis of lung cancer. The invention is more specifically related to nucleotide sequences that are preferentially expressed in lung tumor tissue, together with polypeptides encoded by such nucleotide sequences. The inventive nucleotide sequences and polypeptides may be used in vaccines and pharmaceutical compositions for the treatment and diagnosis of lung cancer.

BACKGROUND OF THE INVENTION

Lung cancer is the primary cause of cancer death among both men and women in the U.S., with an estimated 172,000 new cases being reported in 1994. The five-year survival rate among all lung cancer patients, regardless of the stage of disease at diagnosis, is only 13%. This contrasts with a five-year survival rate of 46% among cases detected while the disease is still localized. However, only 16% of lung cancers are discovered before the disease has spread.

Early detection is difficult since clinical symptoms are often not seen until the disease has reached an advanced stage. Currently, diagnosis is aided by the use of chest x-rays, analysis of the type of cells contained in sputum and fiberoptic examination of the bronchial passages. Treatment regimens are determined by the type and stage of the cancer, and include surgery, radiation therapy and/or chemotherapy. In spite of considerable research into therapies for the disease, lung cancer remains difficult to treat.

Accordingly, there remains a need in the art for improved vaccines, treatment methods and diagnostic techniques for lung cancer.

SUMMARY OF THE INVENTION

Briefly stated, the present invention provides compounds and methods for the therapy of lung cancer. In a first aspect, isolated polynucleotide molecules encoding lung tumor polypeptides are provided, such polynucleotide molecules comprising a nucleotide sequence selected from the group consisting of: (a) sequences provided in SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, and 160; (b) sequences complementary to a sequence provided in SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, and 160; and (b) sequences that hybridize to a sequence of (a) or (b) under moderately stringent conditions.

In a second aspect, isolated polypeptides are provided that comprise at least an immunogenic portion of a lung tumor protein or a variant thereof. In specific embodiments, such polypeptides comprise an amino acid sequence encoded by a polynucleotide molecule comprising a nucleotide sequence selected from the group consisting of (a) sequences recited in SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, and 160; (b) sequences complementary to a sequence provided in SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, and 160; and (c) sequences that hybridize to a sequence of (a) or (b) under moderately stringent conditions.

In related aspects, expression vectors comprising the inventive polynucleotide molecules, together with host cells transformed or transfected with such expression vectors are provided. In preferred embodiments, the host cells are selected from the group consisting of *E. Coli*, yeast and mammalian cells.

In another aspect, fusion proteins comprising a first and a second inventive polypeptide or, alternatively, an inventive polypeptide and a known lung tumor antigen, are provided.

The present invention further provides pharmaceutical compositions comprising one or more of the above polypeptides, fusion proteins or polynucleotide molecules and a physiologically acceptable carrier, together with vaccines comprising one or more such polypeptides, fusion proteins or polynucleotide molecules in combination with an immune response enhancer.

In related aspects, the present invention provides methods for inhibiting the development of lung cancer in a patient, comprising administering to a patient an effective amount of at least one of the above pharmaceutical compositions and/or vaccines.

Additionally, the present invention provides methods for immunodiagnosis of lung cancer, together with kits for use in such methods. Polypeptides are disclosed which comprise at least an immunogenic portion of a lung tumor protein or a variant of said protein that differs only in conservative substitutions and/or modifications, wherein the lung tumor protein comprises an amino acid sequence encoded by a polynucleotide molecule having a sequence selected from the group consisting of nucleotide sequences recited in SEQ ID NO: 1–109, 111, 113, 115–151, 153, 154, 157, 158, and 160, and variants thereof. Such polypeptides may be usefully employed in the diagnosis and monitoring of lung cancer.

In one specific aspect of the present invention, methods are provided for detecting lung cancer in a patient, comprising: (a) contacting a biological sample obtained from a patient with a binding agent that is capable of binding to one of the above polypeptides; and (b) detecting in the sample a protein or polypeptide that binds to the binding agent. In preferred embodiments, the binding agent is an antibody, most preferably a monoclonal antibody.

In related aspects, methods are provided for monitoring the progression of lung cancer in a patient, comprising: (a) contacting a biological sample obtained from a patient with a binding agent that is capable of binding to one of the above polypeptides; (b) determining in the sample an amount of a protein or polypeptide that binds to the binding agent; (c) repeating steps (a) and (b); and comparing the amounts of polypeptide detected in steps (b) and (c).

Within related aspects, the present invention provides antibodies, preferably monoclonal antibodies, that bind to the inventive polypeptides, as well as diagnostic kits comprising such antibodies, and methods of using such antibodies to inhibit the development of lung cancer.

The present invention further provides methods for detecting lung cancer comprising: (a) obtaining a biological sample from a patient; (b) contacting the sample with a first and a second oligonucleotide primer in a polymerase chain reaction, at least one of the oligonucleotide primers being specific for a polynucleotide molecule that encodes one of the above polypeptides; and (c) detecting in the sample a polynucleotide sequence that amplifies in the presence of the first and second oligonucleotide primers. In a preferred embodiment, at least one of the oligonucleotide primers comprises at least about 10 contiguous nucleotides of a polynucleotide molecule including a sequence selected from the group consisting of SEQ ID NO: 1–109, 111, 113, 115–151, 153, 154, 157, 158, and 160.

In a further aspect, the present invention provides a method for detecting lung cancer in a patient comprising: (a) obtaining a biological sample from the patient; (b) contacting the sample with an oligonucleotide probe specific for a polynucleotide molecule that encodes one of the above polypeptides; and (c) detecting in the sample a polynucleotide sequence that hybridizes to the oligonucleotide probe. Preferably, the oligonucleotide probe comprises at least about 15 contiguous nucleotides of a polynucleotide molecule having a partial sequence selected from the group consisting of SEQ ID NO: 1–109, 111, 113, 115–151, 153, 154, 157, 158, and 160.

In related aspects, diagnostic kits comprising the above oligonucleotide probes or primers are provided.

In yet a further aspect, methods for the treatment of lung cancer in a patient are provided, the methods comprising obtaining PBMC from the patient, incubating the PBMC with a polypeptide of the present invention (or a polynucleotide that encodes such a polypeptide) to provide incubated T cells and administering the incubated T cells to the patient. The present invention additionally provides methods for the treatment of lung cancer that comprise incubating antigen presenting cells with a polypeptide of the present invention (or a polynucleotide that encodes such a polypeptide) to provide incubated antigen presenting cells and administering the incubated antigen presenting cells to the patient. In certain embodiments, the antigen presenting cells are selected from the group consisting of dendritic cells and macrophages. Compositions for the treatment of lung cancer comprising T cells or antigen presenting cells that have been incubated with a polypeptide or polynucleotide of the present invention are also provided. These and other aspects of the present invention will become apparent upon reference to the following detailed description. All references disclosed herein are hereby incorporated by reference in their entirety as if each was incorporated individually.

DETAILED DESCRIPTION OF THE INVENTION

As noted above, the present invention is generally directed to compositions and methods for the therapy and diagnosis of lung cancer. The compositions described herein include polypeptides, fusion proteins and polynucleotide molecules. Also included within the present invention are molecules (such as an antibody or fragment thereof) that bind to the inventive polypeptides. Such molecules are referred to herein as "binding agents."

In one aspect, the subject invention discloses polypeptides comprising an immunogenic portion of a human lung tumor protein, wherein the lung tumor protein includes an amino acid sequence encoded by a polynucleotide molecule including a sequence selected from the group consisting of (a) nucleotide sequences recited in SEQ ID NO: 1–109, 111, 113 115–151, 153, 154, 157, 158, and 160, (b) the complements of said nucleotide sequences, and (c) variants of such sequences. As used herein, the term "polypeptide" encompasses amino acid chains of any length, including full length proteins, wherein the amino acid residues are linked by covalent peptide bonds. Thus, a polypeptide comprising a portion of one of the above lung tumor proteins may consist entirely of the portion, or the portion may be present within a larger polypeptide that contains additional sequences. The additional sequences may be derived from the native protein or may be heterologous, and such sequences may (but need not) be immunoreactive and/or antigenic. As detailed below, such polypeptides may be isolated from lung tumor tissue or prepared by synthetic or recombinant means.

As used herein, an "immunogenic portion" of a lung tumor protein is a portion that is capable of eliciting an immune response in a patient inflicted with lung cancer and as such binds to antibodies present within sera from a lung cancer patient. Such immunogenic portions generally comprise at least about 5 amino acid residues, more preferably at least about 10, and most preferably at least about 20 amino acid residues. Immunogenic portions of the proteins described herein may be identified in antibody binding assays. Such assays may generally be performed using any of a variety of means known to those of ordinary skill in the art, as described, for example, in Harlow and Lane, *Antibodies. A Laboratory Manual*, Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$I-labeled Protein A. Alternatively, a polypeptide may be used to generate monoclonal and polyclonal antibodies for use in detection of the polypeptide in blood or other fluids of lung cancer patients. Methods for preparing and identifying immunogenic portions of antigens of known sequence are well known in the art and include those summarized in Paul, *Fundamental Immunology*, 3$^{rd}$ ed., Raven Press, 1993, pp. 243–247.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof Operable anti-sense polynucleotides may comprise a fragment of the corresponding polynucleotide, and the definition of "polynucleotide" therefore includes all such operable anti-sense fragments.

The compositions and methods of the present invention also encompass variants of the above polypeptides and polynucleotides. A polypeptide "variant," as used herein, is a polypeptide that differs from the recited polypeptide only in conservative substitutions and/or modifications, such that the therapeutic, antigenic and/or immunogenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. Polypeptide variants preferably exhibit at least about 70%, more preferably at least about 90% and most preferably at least about 95% identity (determined as describe below) to the identified polypeptides.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity (determined as described below) to the recited sequence.

The antigens provided by the present invention include variants that are encoded by polynucleotide sequences which are substantially homologous to one or more of the polynucleotide sequences specifically recited herein. "Substantial homology," as used herein, refers to polynucleotide sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.–65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing polynucleotide sequences are also within the scope of this invention, as are nucleotide sequences that, due to code degeneracy, encode an immunogenic polypeptide that is encoded by a hybridizing polynucleotide sequence.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Resarch Foundaiton, Washington DC Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer *CABIOS* 5:151–153; Myers, E. W. and Muller W. (1988) Optimal alignments in linear space *CABIOS* 4:11–17; Robinson, E. D. (1971) *Comb. Theor* 11:105; Santou, N. Nes, M. (1987) The neighbor joining method. A new method for reconstructing phylogenetic trees *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) Rapid similarity searches of nucleic acid and protein data banks *Proc. Natl. Acad, Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Also included in the scope of the present invention are alleles of the genes encoding the nucleotide sequences recited in herein. As used herein, an "allele" or "allellic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone or in combination with the others, one or more times in a given sequence.

For lung tumor polypeptides with immunoreactive properties, variants may, alternatively, be identified by modifying the amino acid sequence of one of the above polypeptides, and evaluating the immunoreactivity of the modified polypeptide. For lung tumor polypeptides useful for the generation of diagnostic binding agents, a variant may be identified by evaluating a modified polypeptide for the ability to generate antibodies that detect the presence or absence of lung cancer. Such modified sequences may be prepared and tested using, for example, the representative procedures described herein.

The lung tumor polypeptides of the present invention, and polynucleotide molecules encoding such polypeptides, may be isolated from lung tumor tissue using any of a variety of methods well known in the art. Polynucleotide sequences corresponding to a gene (or a portion thereof) encoding one of the inventive lung tumor proteins may be isolated from a lung tumor cDNA library using a subtraction technique as described in detail below. Examples of such polynucleotide sequences are provided in SEQ ID NO: 1–109, 111, 113 115–151, 153, 154, 157, 158, and 160. Partial polynucleotide sequences thus obtained may be used to design oligonucleotide primers for the amplification of full-length polynucleotide sequences from a human genomic DNA library or from a lung tumor cDNA library in a polymerase chain reaction (PCR), using techniques well known in the art (see, for example, Mullis et al., *Cold Spring Harbor Symp. Quant. Biol.* 51:263, 1987; Erlich ed., *PCR Technology*, Stockton Press, NY, 1989). For this approach, sequence-specific primers may be designed based on the nucleotide sequences provided herein and may be purchased or synthesized.

Once a polynucleotide sequence encoding a polypeptide is obtained, the polypeptide may be produced recombinantly by inserting the polynucleotide sequence into an expression vector and expressing the polypeptide in an appropriate host. Any of a variety of expression vectors known to those of ordinary skill in the art may be employed to express recombinant polypeptides of this invention. Expression may be achieved in any appropriate host cell that has been transformed or transfected with an expression vector containing a polynucleotide molecule that encodes the recombinant polypeptide. Suitable host cells include prokaryotes, yeast, insect and higher eukaryotic cells. Preferably, the host cells employed are *E. coli*, yeast or a mammalian cell line, such as COS or CHO cells. The polynucleotide sequences expressed in this manner may encode naturally occurring polypeptides, portions of naturally occurring polypeptides, or other variants thereof. Supernatants from suitable host/vector systems which secrete the recombinant polypeptide may first be concentrated using a commercially available filter. The concentrate may then be applied to a suitable purification matrix, such as an affinity matrix or ion exchange resin. Finally, one or more reverse phase HPLC steps can be employed to further purify the recombinant polypeptide.

The lung tumor polypeptides disclosed herein may also be generated by synthetic means. In particular, synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J Am. Chem. Soc.* 85:2149–2146, 1963). Equipment for automated synthesis of polypeptides is commercially available from suppliers such as Perkin Elmer/Applied BioSystems Division (Foster City, Calif.), and may be operated according to the manufacturer's instructions.

In general, regardless of the method of preparation, the polypeptides disclosed herein are prepared in an isolated, substantially pure form (i.e., the polypeptides are homogenous as determined by amino acid composition and primary sequence analysis). Preferably, the polypeptides are at least about 90% pure, more preferably at least about 95% pure and most preferably at least about 99% pure. In certain preferred embodiments, described in more detail below, the substantially pure polypeptides are incorporated into pharmaceutical compositions or vaccines for use in one or more of the methods disclosed herein.

In a related aspect, the present invention provides fusion proteins comprising a first and a second inventive polypeptide or, alternatively, a polypeptide of the present invention and a known lung tumor antigen, together with variants of such fusion proteins. The fusion proteins of the present invention may (but need not) include a linker peptide between the first and second polypeptides.

A polynucleotide sequence encoding a fusion protein of the present invention is constructed using known recombinant DNA techniques to assemble separate polynucleotide sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad Sci. USA* 83:8258–8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated polynucleotide sequences are operably linked to suitable transcriptional or translational regulatory elements. The regulatory elements responsible for expression of polynucleotide are located only 5' to the DNA sequence encoding the first polypeptides. Similarly, stop codons require to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J Med.*, 336:86–91 (1997)).

Polypeptides of the present invention that comprise an immunogenic portion of a lung tumor protein may generally be used for therapy of lung cancer, wherein the polypeptide stimulates the patient's own immune response to lung tumor cells. The present invention thus provides methods for using one or more of the compounds described herein (which may be polypeptides, polynucleotide molecules or fusion proteins) for immunotherapy of lung cancer in a patient. As used herein, a "patient" refers to any warm-blooded animal, preferably a human. A patient may be afflicted with disease, or may be free of detectable disease. Accordingly, the compounds disclosed herein may be used to treat lung cancer or to inhibit the development of lung cancer. The compounds are preferably administered either prior to or following surgical removal of primary tumors and/or treatment by administration of radiotherapy and conventional chemotherapeutic drugs.

In these aspects, the inventive polypeptide is generally present within a pharmaceutical composition or a vaccine. Pharmaceutical compositions may comprise one or more polypeptides, each of which may contain one or more of the above sequences (or variants thereof), and a physiologically acceptable carrier. The vaccines may comprise one or more such polypeptides and a non-specific immune-response enhancer, wherein the non-specific immune response enhancer is capable of eliciting or enhancing an immune response to an exogenous antigen. Examples of non-specific-immune response enhancers include adjuvants, biodegradable microspheres (e.g., polylactic galactide) and liposomes (into which the polypeptide is incorporated). Pharmaceutical compositions and vaccines may also contain other epitopes of lung tumor antigens, either incorporated into a fusion protein as described above (i.e., a single polypeptide that contains multiple epitopes) or present within a separate polypeptide.

Alternatively, a pharmaceutical composition or vaccine may contain polynucleotide encoding one or more of the above polypeptides and/or fusion proteins, such that the polypeptide is generated in situ. In such pharmaceutical compositions and vaccines, the polynucleotide may be present within any of a variety of delivery systems known to those of ordinary skill in the art, including nucleic acid expression systems, bacteria and viral expression systems. Appropriate nucleic acid expression systems contain the necessary polynucleotide sequences for expression in the patient (such as a suitable promoter). Bacterial delivery systems involve the administration of a bacterium (such as *Bacillus-Calmette-Guerrin*) that expresses an epitope of a lung cell antigen on its cell surface. In a preferred embodiment, the polynucleotides may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad Sci.* 569:86–103, 1989; Flexner et al., *Vaccine* 8:17–21, 1990; U.S. Pat. Nos. 4,603,112, 4,769,330, and 5,017,487; WO89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., PNAS 91:215–219, 1994; Kass-Eisler et al., PNAS 90:11498–11502, 1993; Guzman et al., *Circulation* 88:2838–2848, 1993; and Guzman et al., *Cir. Res.* 73:1202–1207, 1993. Techniques for incorporating polynucleotide into such expression systems are well known to those of ordinary skill in the art. The polynucleotides may also be "naked," as described, for example, in published PCT application WO 90/11092, and Ulmer et al., *Science* 259:1745–1749, 1993, reviewed by Cohen, *Science* 259:1691–1692, 1993. The uptake of naked polynucleotides may be increased by coating the polynucleotides onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or polynucleotide that is effective to raise an immune response (cellular and/or humoral) against lung tumor cells in a treated patient. A suitable immune response is at least 10–50% above the basal (i.e., untreated) level. In general, the amount of polypeptide present in a dose (or produced in situ by the polynucleotide molecule(s) in a dose) ranges from about 1 pg to about 100 mg per kg of host, typically from about 10 $\mu$g to about 1 $\mu$g, and preferably from about 100 $\mu$g to about 1 $\mu$g. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of immune-response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in adoptive immunotherapy for the treatment of cancer. Adoptive immunotherapy may be broadly classified into either active or passive immunotherapy. In active immunotherapy, treatment relies on the in vivo stimulation of the endogenous host immune system to react against tumors with the administration of immune response-modifying agents (for example, tumor vaccines, bacterial adjuvants, and/or cytokines).

In passive immunotherapy, treatment involves the delivery of biologic reagents with established tumor-immune reactivity (such as effector cells or antibodies) that can directly or indirectly mediate antitumor effects and does not necessarily depend on an intact host immune system. Examples of effector cells include T lymphocytes (for example, CD8+ cytotoxic T-lymphocyte, CD4+ T-helper, tumor-infiltrating lymphocytes), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage or B-cells, may be pulsed with immunoreactive polypeptides or transfected with a polynucleotide sequence(s), using standard techniques well known in the art. For example, antigen presenting cells may be transfected with a polynucleotide sequence, wherein said sequence contains a promoter region appropriate for increasing expression, and can be expressed as part of a recombinant virus or other expression system. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al, "Therapy With Cultured T Cells: Principles Revisited," *Immunological Reviews*, 157:177, 1997).

The polypeptides disclosed herein may also be employed to generate and/or isolate tumor-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the polypeptides may be employed to generate tumor reactive T cell subsets by selective in vitro stimulation and expansion of autologous T cells to provide antigen-specific T cells which may be subsequently transferred to the patient as described, for example, by Chang et al. (*Crit. Rev. Oncol. Hematol.*, 22(3), 213, 1996). Cells of the immune system, such as T cells, may be isolated from the peripheral blood of a patient, using a commercially available cell separation system, such as CellPro Incorporated's (Bothell, WA) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

In another embodiment, T-cell and/or antibody receptors specific for the polypeptides can be cloned, expanded, and transferred into other vectors or effector cells for use in adoptive immunotherapy.

In a further embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate tumors in a murine model has been demonstrated by Cheever et al, *Immunological Reviews*, 157:177,1997), Additionally, vectors expressing the disclosed polynucleotides may be introduced into stem cells taken from the patient and clonally propagated in vitro for autologous transplant back into the same patient. Polypeptides and fusion proteins of the present invention may also, or alternatively, be used to generate binding agents, such as antibodies or fragments thereof, that are capable of detecting metastatic human lung tumors. Binding agents of the present invention may generally be prepared using methods known to those of ordinary skill in the art, including the representative procedures described herein. Binding agents are capable of differentiating between patients with and without lung cancer, using the representative assays described herein. In other words, antibodies or other binding agents raised against a lung tumor protein, or a suitable portion thereof, will generate a signal indicating the presence of primary or metastatic lung cancer in at least about 20% of patients afflicted with the disease, and will generate a negative signal indicating the absence of the disease in at least about 90% of individuals without primary or metastatic lung cancer. Suitable portions of such lung tumor proteins are portions that are able to generate a binding agent that indicates the presence of primary or metastatic lung cancer in substantially all (i.e., at least about 80%, and preferably at least about 90%) of the patients for which lung cancer would be indicated using the full length protein, and that indicate the absence of lung cancer in substantially all of those samples that would be negative when tested with full length protein. The representative assays described below, such as the two-antibody sandwich assay, may generally be employed for evaluating the ability of a binding agent to detect metastatic human lung tumors.

The ability of a polypeptide prepared as described herein to generate antibodies capable of detecting primary or metastatic human lung tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic lung cancer for the presence of a polypeptide that binds to the generated antibodies. Such test assays may be performed, for example, using a representative procedure described below. Polypeptides that generate antibodies capable of detecting at least 20% of primary or metastatic lung tumors by such procedures are considered to be useful in assays for detecting primary or metastatic human lung tumors. Polypeptide specific antibodies may be used alone or in combination to improve sensitivity.

Polypeptides capable of detecting primary or metastatic human lung tumors may be used as markers for diagnosing lung cancer or for monitoring disease progression in patients. In one embodiment, lung cancer in a patient may be diagnosed by evaluating a biological sample obtained from the patient for the level of one or more of the above polypeptides, relative to a predetermined cut-off value. As used herein, suitable "biological samples" include blood, sera, urine and/or lung secretions.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ Limol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies: A Laboratory Manual*, Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may. be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with lung cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of lung cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without lung cancer. In general, a sample generating a signal that is three standard deviations above the predetermined cut-off value is considered positive for lung cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for lung cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of lung cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of lung cancer. In this embodiment, assays as described above for the diagnosis of lung cancer may be performed over time, and the change in the level of reactive polypeptide(s) evaluated. For example, the assays may be performed every 24–72 hours for a period of 6 months to 1 year, and thereafter performed as needed. In general, lung cancer is progressing in those patients in whom the level of polypeptide detected by the binding agent increases over time. In contrast, lung cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate lung tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et-al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise polynucleotide sequences encoding one or more of the above polypeptides, or one or more portions thereof. For example, at least two oligonucleotide primers may be employed in a polymerase chain reaction (PCR) based assay to amplify lung tumor-specific cDNA derived from a biological sample, wherein at least one of the oligonucleotide primers is specific for a polynucleotide molecule encoding a lung tumor protein of the present invention. The presence of the amplified cDNA is then detected using techniques well known in the art, such as gel electrophoresis. Similarly, oligonucleotide probes specific for a polynucleotide molecule encoding a lung tumor protein of the present invention may be used in a hybridization assay to detect the presence of an inventive polypeptide in a biological sample.

As used herein, the term "oligonucleotide primer/probe specific for a polynucleotide molecule" means an oligonucleotide sequence that has at least about 60%, preferably at least about 75% and more preferably at least about 90%, identity to the polynucleotide molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a polynucleotide molecule comprising sequence selected from SEQ ID NO: 1–109, 111, 113 115–151, 153, 154, 157, 158, and 160. Preferably, oligonucleotide probes for use in the inventive diagnostic methods comprise at least about 15 contiguous oligonucleotides of a polynucleotide molecule comprising a sequence provided in SEQ ID NO: 1–109, 111, 113 115–151, 153, 154, 157, 158, and 160. Techniques for both PCR based assays and hybridization assays are well known in the art (see, for example, Mullis el al. Ibid; Ehrlich, Ibid).

Primers or probes may thus be used to detect lung tumor-specific sequences in biological samples, including blood, semen, lung tissue and/or lung tumor tissue.

The following Examples are offered by way of illustration and not by way of limitation.

EXAMPLES

Example 1

Isolation and Characterization of cDNA Sequences Enconding Lung Tumor Polypeptides This example illustrates the isolation of cDNA molecules encoding lung tumor-specific polypeptides from lung tumor cDNA libraries.

A. Isolation of cDNA Sequences from a Lung Squamous Cell Carcinoma Library

A human lung squamous cell carcinoma cDNA expression library was constructed from poly $A^+$ RNA from a pool of two patient tissues using a Superscript Plasmid System for cDNA Synthesis and Plasmid Cloning kit (BRL Life Technologies, Gaithersburg, Md.) following the manufacturer's protocol. Specifically, lung carcinoma tissues were homogenized with polytron (Kinematica, Switzerland) and total RNA was extracted using Trizol reagent (BRL Life Technologies) as directed by the manufacturer. The poly $A^+$ RNA was then purified using an oligo dT cellulose column as described in Sambrook et al., *Molecular Cloning: A Laboratory Manual*, Cold Spring Harbor Laboratories, Cold Spring Harbor, N.Y., 1989. First-strand cDNA was synthesized using the NotI/Oligo-dT18 primer. Double-stranded cDNA was synthesized, ligated with BstXI/EcoRI adaptors (Invitrogen, San Diego, Calif.) and digested with NotI. Following size fractionation with cDNA size fractionation columns (BRL Life Technologies), the cDNA was ligated into the BstXI/NotI site of pcDNA3.1 (Invitrogen) and transformed into ElectroMax *E. coli* DH10B cells (BRL Life Technologies) by electroporation.

Using the same procedure, a normal human lung cDNA expression library was prepared from a pool of four tissue specimens. The cDNA libraries were characterized by determining the number of independent colonies, the percentage of clones that carried insert, the average insert size and by sequence analysis. The lung squamous cell carcinoma library contained $2.7 \times 10^6$ independent colonies, with 100% of clones having an insert and the average insert size being 2100 base pairs. The normal lung cDNA library contained $1.4 \times 10^6$ independent colonies, with 90% of clones having inserts and the average insert size being 1800 base pairs. For both libraries, sequence analysis showed that the majority of clones had a full length cDNA sequence and were synthesized from mRNA.

cDNA library subtraction was performed using the above lung squamous cell carcinoma and normal lung cDNA libraries, as described by Hara et al. (*Blood*, 84:189–199, 1994) with some modifications. Specifically, a lung squamous cell carcinoma-specific subtracted cDNA library was generated as follows. Normal tissue cDNA library (80 μg) was digested with BamHI and XhoI, followed by a filling-in reaction with DNA polymerase Klenow fragment. After phenol-chloroform extraction and ethanol precipitation, the DNA was dissolved in 133 μl of $H_2O$, heat-denatured and mixed with 133 μl (133 μg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (67 μl) was added and the biotinylation reaction was repeated. After extraction with butanol five times, the DNA was ethanol-precipitated and dissolved in 23 μl $H_2O$ to form the driver DNA.

To form the tracer DNA, 10 μg lung squamous cell carcinoma cDNA library was digested with NotI and SpeI, phenol chloroform extracted and passed through Chroma spin-400 columns (Clontech, Palo Alto, Calif.). Typically, 5 μg of cDNA was recovered after the sizing column. Following ethanol precipitation, the tracer DNA was dissolved in 5 μl $H_2O$. Tracer DNA was mixed with 15 μl driver DNA and 20 μl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 μl $H_2O$, mixed with 8 μl driver DNA and 20 μl of 2×hybridization buffer, and subjected to a hybridization at 68° C. for 2 hours (short hybridization [SH]). After removal of biotinylated double-stranded DNA, subtracted cDNA was ligated into NotI/SpeI site of chloramphenicol resistant pBCSK$^+$ (Stratagene, La Jolla, Calif.) and transformed into ElectroMax *E. coli* DH10B cells by electroporation to generate a lung squamous cell carcinoma specific subtracted cDNA library (herein after referred to as "lung subtraction I").

A second lung squamous cell carcinoma specific subtracted cDNA library (referred to as "lung subtraction II") was generated in a similar way to the lung subtraction library I, except that eight frequently recovered genes from lung subtraction I were included in the driver DNA, and 24,000 independent clones were recovered.

To analyze the subtracted cDNA libraries, plasmid DNA was prepared from 320 independent clones, randomly picked from the subtracted lung squamous cell carcinoma specific libraries. Representative cDNA clones were further characterized by DNA sequencing with a Perkin Elmer/Applied Biosystems Division Automated Sequencer Model 373A and/or Model 377 (Foster City, Calif.). The cDNA sequences for sixty isolated clones are provided in SEQ ID NO: 1–60. These sequences were compared to known sequences in the gene bank using the EMBL and GenBank databases (release 96). No significant homologies were found to the sequences provided in SEQ ID NO: 2, 3, 19, 38 and 46. The sequences of SEQ ID NO: 1, 6–8, 10–13, 15, 17, 18, 20–27, 29, 30, 32, 34–37, 39–45, 47–49, 51, 52, 54, 55 and 57–59 were found to show some homology to previously identified expressed sequence tags (ESTs). The sequences of SEQ ID NO: 9, 28, 31 and 33 were found to show some homology to previously identified non-human gene sequences and the sequences of SEQ ID NO: 4, 5, 14, 50, 53, 56 and 60 were found to show some homology to gene sequences previously identified in humans.

The subtraction procedure described above was repeated using the above lung squamous cell carcinoma cDNA library as the tracer DNA, and the above normal lung tissue cDNA library and a cDNA library from normal liver and heart (constructed from a pool of one sample of each tissue as described above), plus twenty other cDNA clones that were frequently recovered in lung subtractions I and II, as the driver DNA (lung subtraction III). The normal liver and heart cDNA library contained $1.76 \times 10^6$ independent colonies, with 100% of clones having inserts and the average insert size being 1600 base pairs. Ten additional clones were isolated (SEQ ID NO: 61–70). Comparison of these cDNA sequences with those in the gene bank as described above, revealed no significant homologies to the sequences provided in SEQ ID NO: 62 and 67. The sequences of SEQ ID NO: 61, 63–66, 68 and 69 were found to show some homology to previously isolated ESTs and the sequence provided in SEQ ID NO: 70 was found to show some homology to a previously identified rat gene.

B. Isolation of cDNA Sequences From a Lung Adenocarcinoma Library

A human lung adenocarcinoma cDNA expression library was constructed as described above. The library contained 3.2×10⁶ independent colonies, with 100% of clones having an insert and the average insert size being 1500 base pairs. Library subtraction was performed as described above using the normal lung and normal liver and heart cDNA expression libraries described above as the driver DNA. Twenty-six hundred independent clones were recovered.

Initial cDNA sequence analysis from 100 independent clones revealed many ribosomal protein genes. The cDNA sequences for fifteen clones isolated in this subtraction are provided in SEQ ID NO: 71–86. Comparison of these sequences with those in the gene bank as described above revealed no significant homologies to the sequence provided in SEQ ID NO: 84. The sequences of SEQ ID NO: 71, 73, 74, 77, 78 and 80–82 were found to show some homology to previously isolated ESTs, and the sequences of SEQ ID NO: 72, 75, 76, 79, 83 and 85 were found to show some homology to previously identified human genes.

Example 2

Determination of Tissue Specificity of Lung Tumor Polypeptides

Using gene specific primers, mRNA expression levels for seven representative lung tumor polypeptides described in Example 1 were examined in a variety of normal and tumor tissues using RT-PCR.

Briefly, total RNA was extracted from a variety of normal and tumor tissues using Trizol reagent as described above. First strand synthesis was carried out using 2 μg of total RNA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. 1 μl of 1:30 dilution of cDNA was employed to enable the linear range amplification of the β-actin template and was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in five different types of tumor tissue (lung squamous cell carcinoma from 3 patients, lung adenocarcinoma, colon tumor from 2 patients, breast tumor and prostate tumor), and thirteen different normal tissues (lung from 4 donors, prostate, brain, kidney, liver, ovary, skeletal muscle, skin, small intestine, stomach, myocardium, retina and testes). Using a 10-fold amount of cDNA, the antigen LST-S1-90 (SEQ ID NO: 3) was found to be expressed at high levels in lung squamous cell carcinoma and in breast tumor, and at low to undetectable levels in the other tissues examined.

The antigen LST-S2-68 (SEQ ID NO: 15) appears to be specific to lung and breast tumor, however, expression was also detected in normal kidney. Antigens LST-S1-169 (SEQ ID NO: 6) and LST-S1-133 (SEQ ID NO: 5) appear to be very abundant in lung tissues (both normal and tumor), with the expression of these two genes being decreased in most of the normal tissues tested. Both LST-S1-169 and LST-S1-133 were also expressed in breast and colon tumors. Antigens LST-S1-6 (SEQ ID NO: 7) and LST-S2-12-5F (SEQ ID NO: 47) did not show tumor or tissue specific expression, with the expression of LST-S1-28 being rare and only detectable in a few tissues. The antigen LST-S3-7 (SEQ ID NO: 63) showed lung and breast tumor specific expression, with its message only being detected in normal testes when the PCR was performed for 30 cycles. Lower level expression was detected in some normal tissues when the cycle number was increased to 35. Antigen LST-S3-13 (SEQ ID NO: 66) was found to be expressed in 3 out of 4 lung tumors, one breast tumor and both colon tumor samples. Its expression in normal tissues was lower compared to tumors, and was only detected in 1 out of 4 normal lung tissues and in normal tissues from kidney, ovary and retina. Expression of antigens LST-S3-4 (SEQ ID NO: 62) and LST-S3-14 (SEQ ID NO: 67) was rare and did not show any tissue or tumor specificity. Consistent with Northern blot analyses, the RT-PCT results on antigen LAT-S1-A-10A (SEQ ID NO: 78) suggested that its expression is high in lung, colon, stomach and small intestine tissues, including lung and colon tumors, whereas its expression was low or undetectable in other tissues.

A total of 2002 cDNA fragments isolated in lung subtractions I, II and III, described above, were colony PCR amplified and their mRNA expression levels in lung tumor, normal lung, and various other normal and tumor tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Seventeen non-redundant cDNA clones showed over-expression in lung squamous tumors, with expression in normal tissues tested (lung, skin, lymph node, colon, liver, pancreas, breast, heart, bone marrow, large intestine, kidney, stomach, brain, small intestine, bladder and salivary gland) being either undetectable, or 10-fold less compared to lung squamous tumors. The determined partial cDNA sequences for the clone L513S are provided in SEQ ID NO: 87 and 88; those for L514S are provided in SEQ ID NO: 89 and 90; those for L516S in SEQ ID NO: 91 and 92; that for L517S in SEQ ID NO: 93; that for L519S in SEQ ID NO: 94; those for L520S in SEQ ID NO: 95 and 96; those for L521S in SEQ ID NO: 97 and 98; that for L522S in SEQ ID NO: 99; that for L523S in SEQ ID NO: 100; that for L524S in SEQ ID NO: 101; that for L525S in SEQ ID NO: 102; that for L526S in SEQ ID NO: 103; that for L527S in SEQ ID NO: 104; that for L528S in SEQ ID NO: 105; that for L529S in SEQ ID NO: 106; and those for L530S in SEQ ID NO: 107 and 108. Additionally, the full-length cDNA sequences for L503S and L514S (variants 1 and 2), are provided in SEQ ID NO: 151, 153, and 154, respectively, with the corresponding predicted amino acid sequence being provided in SEQ ID NO: 152, 155, and 156. Due to polymorphisms, the clone L531 S appears to have two forms. A first determined full-length cDNA sequence for L531S is provided in SEQ ID NO: 109, with the corresponding predicted amino acid sequence being provided in SEQ ID NO: 110. A second determined full-length cDNA sequence for L531S is provided in SEQ ID NO: 111, with the corresponding predicted amino acid sequence being provided in SEQ ID NO: 112. The sequence of SEQ ID NO: 111 is identical to that of SEQ ID NO: 109, except that it contains a 27 bp insertion. Similarly, L514S also has two alternatively spliced forms; the first variant cDNA is listed as SEQ ID NO: 153, with the corresponding amino acid sequence as SEQ ID NO: 155. The second variant form of L514S full-length cNDA is referred to as SEQ ID NO: 154, with its corresponding amino acid sequence as SEQ ID NO: 156.

Comparison of the sequences of L514S and L531 S (SEQ ID NO: 87 and 88, 89 and 90, and 109, respectively) with those in the gene bank, as described above, revealed no significant homologies to known sequences. The sequences of L513S, L516S, L517S, L519S, L520S and L530S (SEQ ID NO: 87 and 88, 91 and 92, 93, 94, 95 and 96, 107 and 108, respectively) were found to show some homology to previously identified ESTs. The sequences of L521S, L522S, L523S, L524S, L525S, L526S, L527S, L528S and L529S (SEQ ID NO: 97 and 98, 99, 99, 101, 102, 103, 104, 105, and 106, respectively) were found to represent known genes. The determined full-length cDNA sequences for L520S is provided in SEQ ID NO: 113, with the corresponding predicted amino acid sequence being provided in SEQ ID NO: 114. Subsequent microarray analysis has shown L520S to be overexpressed in breast tumors in addition to lung squamous tumors.

Example 3

Isolation and Characterization of Lung Tumor Polypeptides by PCR-based Subtraction Eight hundred and fifty seven clones from a cDNA subtraction library, containing cDNA from a pool of two human lung squamous tumors subtracted against eight normal human tissue cDNAs including lung, PBMC, brain, heart, kidney, liver, pancreas, and skin, (Clontech, Palo Alto, Calif.) were derived and submitted to a first round of PCR amplification. This library was subjected to a second round of PCR amplification, following the manufacturer's protocol. The resulting cDNA fragments were subcloned into the vector P7- Adv vector (Clontech, Palo Alto, Calif.) and transformed into DH5α E. coli (Gibco, BRL). DNA was isolated from independent clones and sequenced using a Perkin Elmer/Applied Biosystems Division Automated Sequencer Model 373A.

One hundred and sixty two positive clones were sequenced. Comparison of the DNA sequences of these clones with those in the gene bank using the EMBL and GenBank databases, as described above, revealed no significant homologies to 13 of these clones, hereinafter referred to as Contig 13, 16, 17, 19, 22, 24, 29, 47, 49, 56–59. The determined cDNA sequences for these clones are provided in SEQ ID NO: 125, 127–129, 131–133, 142, 144, 148–150, and 157, respectively. Contigs 1, 3–5, 7–10, 12, 11, 15, 20, 31, 33, 38, 39, 41, 43, 44, 45, 48, 50, 53, 54 (SEQ ID NO: 115–124, 126, 130, 134–141, 143, 145–147, respectively) were found to show some degree of homology to previously identified DNA sequences. Contig 57 (SEQ ID NO: 149) was found to represent the clone L519S (SEQ ID NO: 94) disclosed in U.S. Pat. application Ser. No. 09/123,912, filed Jul. 27, 1998. To the best of the inventors' knowledge, none of these sequences have been previously shown to be differentially over-expressed in lung tumors. mRNA expression levels for representative clones in lung tumor tissues, normal lung tissues (n=4), resting PBMC, salivary gland, heart, stomach, lymph nodes, skeletal muscle, soft palate, small intestine, large intestine, bronchial, bladder, tonsil, kidney, esophagus, bone marrow, colon, adrenal gland, pancreas, and skin, (all derived from human) were determined by RT-PCR as described above. Expression levels using microarray technology, as described above, were examined in one sample of each tissue type unless otherwise indicated.

Contig 3 (SEQ ID NO: 116) was found to be highly expressed in all head and neck squamous cell tumors tested (17/17), and expressed in the majority (8/12) of lung squamous tumors, (high expression in 7/12, moderate in 2/12, and low in 2/12), while showing negative expression for 2/4 normal lung tissues and low expression in the remaining two samples. Contig 3 showed high expression in skin and soft palate, and moderate expression levels in resting PBMC, large intestine, salivary gland, tonsil, pancreas, esophagus, and colon. Contig 11 (SEQ ID NO: 124) was found to be expressed in all head and neck squamous cell tumors tested (17/17): highly expressed in 14/17, and moderately expressed in 3/17. Additionally, expression in lung squamous tumors showed high expression in 3/12 and moderate in 4/12. Contig 11 was negative for 3/4 normal lung samples, with the remaining sample having only low expression. Contig 11 showed low to moderate reactivity to salivary gland, soft palate, bladder, tonsil, skin, esophagus, and large intestine. Contig 13 (SEQ ID NO: 125) was found to be expressed in all head and neck squamous cell tumors tested (17/17): highly expressed in 12/17, and moderately expressed in 5/17. Contig 13 was expressed in 7/12 lung squamous tumors, with high expression in 4/12 and moderate expression in three samples. Analysis of normal lung samples showed negative expression for 2/4 and low to moderate expression in the remaining two samples. Contig 13 did show low to moderate reactivity to resting PBMC, salivary gland, bladder, pancreas, tonsil, skin, esophagus, and large intestine, as well as high expression in soft palate. Contig 16 (SEQ ID NO: 127) was found to be moderately expressed in some head and neck squamous cell tumors (6/17) and one lung squamous tumor; while showing no expression in any normal lung samples tested. Contig 16 did show low to moderate reactivity to resting PBMC, large intestine, skin, salivary gland, and soft palate. Contig 17 (SEQ ID NO: 128) was shown to be expressed in all head and neck squamous cell tumors tested (17/17): highly expressed in 5/17, and moderately expressed in 12/17. Expression levels in lung squamous tumors showed one tumor sample with high expression and 3/12 with moderate levels. Contig 17 was negative for 2/4 normal lung samples, with the remaining samples having only low expression. Additionally, moderate expression was found in esophagus and soft palate, and low expression in resting PBMC, large intestine, skin, salivary gland, bladder, and pancreas. Contig 19 (SEQ ID NO: 129) was found to be expressed in most head and neck squamous cell tumors tested (11/17): with two samples having high levels, 6/17 showing moderate expression, and low expression being found in 3/17. Testing in lung squamous tumors revealed only moderate expression in 3/12 samples. Expression levels in 2/4 of normal lung samples were negative, the two other samples having only low expression. Contig 19 did show moderate expression in large intestine as well as low expression levels in esophagus, resting PBMC, salivary gland, bladder, soft palate, and pancreas.

Contig 22, (SEQ ID NO: 131) was shown to be expressed in most head and neck squamous cell tumors tested (13/17)

with high expression in four of these samples, moderate expression in 6/17, and low expression in 3/17. Expression levels in lung squamous tumors were found to be moderate to high for 3/12 tissues tested, with negative expression in two normal lung samples and low expression in two other samples (n=4). Contig 22 did show low expression in resting PBMC, bladder, large intestine, skin, salivary gland, soft palate, and pancreas. Similarly, Contig 24 (SEQ ID NO: 132) was found to be expressed in most head and neck squamous cell tumors tested (13/17) with high expression in three of these samples, moderate expression in 6/17, and low expression in 4/17. Expression levels in lung squamous tumors were found to be moderate to high for 3/12 tissues tested, with negative expression for three normal lung samples and low expression in one sample (n=4). Contig 24 did show low expression in resting PBMC, large intestine, salivary gland, soft palate, and pancreas. Contig 29 (SEQ ID NO: 133) was expressed in nearly all head and neck squamous cell tumors tested (16/17): highly expressed in 4/17, moderately expressed in 11/17, with low expression in one sample. Also, it was moderately expressed in 3/12 lung squamous tumors, while being negative for 2/4 normal lung samples. Contig 29 showed moderate expression in large intestine, skin, salivary gland, pancreas, and soft palate, and low expression in resting PBMC, bladder, tonsil, and heart. Contig 47 (SEQ ID NO: 142) was expressed in most head and neck squamous cell tumors tested (12/17): moderate expression in 10/17, and low expression in two samples. In lung squamous tumors, it was highly expressed in one sample and moderately expressed in two others (n=13). Contig 47 was negative for 2/4 normal lung samples, with the remaining two samples having moderate expression. Also, Contig 47 showed moderate expression in large intestine, and pancreas, and low expression in skin, salivary gland, soft palate, stomach, bladder, resting PBMC, and tonsil.

Contig 48 (SEQ ID NO: 143) was expressed in all head and neck squamous cell tumors tested (17/17): highly expressed in 8/17 and moderately expressed in 7/17, with low expression in two samples. Expression levels in lung squamous tumors were high to moderate in three samples (n=13). Contig 48 was negative for one out of four normal lung samples, the remaining showing low or moderate expression. Contig 48 showed moderate expression in soft palate, large intestine, pancreas, and bladder, and low expression in esophagus, salivary gland, resting PBMC, and heart. Contig 49 (SEQ ID NO: 144) was expressed at low to moderate levels in 6/17 head and neck squamous cell tumors tested. Expression levels in lung squamous tumors were moderate in three samples (n=13). Contig 49 was negative for 2/4 normal lung samples, the remaining samples showing low expression. Moderate expression levels in skin, salivary gland, large intestine, pancreas, bladder and resting PBMC were shown, as well as low expression in soft palate, lymph nodes, and tonsil. Contig 56 (SEQ ID NO: 148) was expressed in low to moderate levels in 3/17 head and neck squamous cell tumors tested, and in lung squamous tumors, showing low to moderate levels in three out of thirteen samples. Notably, low expression levels were detected in one adenocarcinoma lung tumor sample (n=2). Contig 56 was negative for 3/4 normal lung samples, and showed moderate expression levels in only large intestine, and low expression in salivary gland, soft palate, pancreas, bladder, and resting PBMC. Contig 58, also known as L769P, (SEQ ID NO: 150) was expressed at moderate levels in 11/17 head and neck squamous cell tumors tested and low expression in one additional sample. Expression in lung squamous tumors showed low to moderate levels in three out of thirteen samples. Contig 58 was negative for 3/4 normal lung samples, with one sample having low expression. Moderate expression levels in skin, large intestine, and resting PBMC were demonstrated, as well as low expression in salivary gland, soft palate, pancreas, and bladder. Contig 59 (SEQ ID NO: 157) was expressed in some head, neck, and lung squamous tumors. Low level expression of Contig 59 was also detected in salivary gland and large intestine.

Additionally, the full-length cDNA sequence for Contigs 22, referred to as L763P, is provided in SEQ ID NO: 158, with the corresponding predicted amino acid sequence being provided in SEQ ID NO: 159. Also, the full-length cDNA sequence incorporating Contigs 17, 19, and 24, referred to as L762P, is provided in SEQ ID NO: 160, with the corresponding predicted amino acid sequence being provided in SEQ ID NO: 161.

Subsequent microarray analysis has shown Contig 58, also referred to as L769S (SEQ ID NO: 150), to be overexpressed in breast tumors in addition to lung squamous tumors.

Example 4

SYNTHESIS OF POLYPEPTIDES

Polypeptides may be synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. An isolated polypeptide comprising the amino acid sequence of SEQ ID NO: 161.

2. A composition comprising a polypeptide of claim 1 and a physiologically acceptable carrier.

3. A composition comprising a polypeptide of claim 1 and a non-specific immune response enhancer.

4. The composition of claim 3 wherein the non-specific immune response enhancer is an adjuvant.

5. fusion polypeptide comprising a polypeptide of claim 1.

* * * * *

UNITED STATES PATENT AND TRADEMARK OFFICE
CERTIFICATE OF CORRECTION

PATENT NO.    : 6,660,838 B1
DATED         : December 9, 2003
INVENTOR(S)   : Tongtong Wang It is certified that error appears in the above-identified patent and that said Letters Patent is hereby corrected as shown below:

Column 394,
Line 30, "fusion" should read as -- A fusion --.

Signed and Sealed this

Twenty-second Day of June, 2004

JON W. DUDAS
*Acting Director of the United States Patent and Trademark Office*